US010561725B2

(12) United States Patent
Haynes et al.

(10) Patent No.: US 10,561,725 B2
(45) Date of Patent: Feb. 18, 2020

(54) METHOD OF INDUCING THE PRODUCTION OF PROTECTIVE ANTI-HIV-1 ANTIBODIES

(71) Applicants: DUKE UNIVERSITY, Durham, NC (US); THE UNIVERSITY OF NORTH CAROLINA AT CHAPEL HILL, Chapel Hill, NC (US); THE TRUSTEES OF THE UNIVERSITY OF PENNSYLVANIA, Philadelphia, PA (US)

(72) Inventors: Barton F. Haynes, Durham, NC (US); Hua-Xin Liao, Durham, NC (US); Li-Hua Ping, Chapel Hill, NC (US); Ronald Swanstrom, Chapel Hill, NC (US); Beatrice H. Hahn, Philadelphia, PA (US); George M. Shaw, Philadelphia, PA (US)

(73) Assignees: DUKE UNIVERSITY, Durham, NC (US); THE UNIVERSITY OF NORTH CAROLINA AT CHAPEL HILL, Chapel Hill, NC (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 401 days.

(21) Appl. No.: 14/106,461

(22) Filed: Dec. 13, 2013

(65) Prior Publication Data

US 2014/0248301 A1 Sep. 4, 2014

Related U.S. Application Data

(63) Continuation of application No. 13/581,157, filed as application No. PCT/US2011/000352 on Feb. 25, 2011, now abandoned.

(60) Provisional application No. 61/344,622, filed on Sep. 1, 2010, provisional application No. 61/344,580, filed on Aug. 25, 2010, provisional application No. 61/344,457, filed on Jul. 27, 2010, provisional application No. 61/282,526, filed on Feb. 25, 2010.

(51) Int. Cl.

| | |
|---|---|
| ***A61K 39/21*** | (2006.01) |
| ***A61K 39/12*** | (2006.01) |
| ***C07K 14/005*** | (2006.01) |
| ***A61K 39/00*** | (2006.01) |
| ***A61K 39/02*** | (2006.01) |
| ***C07K 16/10*** | (2006.01) |
| ***A61K 39/108*** | (2006.01) |

(52) U.S. Cl.

CPC .......... *A61K 39/21* (2013.01); *A61K 39/0005* (2013.01); *A61K 39/0258* (2013.01); *C07K 16/1063* (2013.01); *A61K 2039/53* (2013.01); *A61K 2039/58* (2013.01); *C12N 2740/16034* (2013.01); *C12N 2740/16134* (2013.01)

(58) Field of Classification Search

CPC ........ A61K 39/00; A61K 39/39; A61K 39/12; A61K 9/14; A61K 2039/55511

See application file for complete search history.

(56) References Cited

U.S. PATENT DOCUMENTS

| | | | | |
|---|---|---|---|---|
| 7,605,238 B2 | 10/2009 | Korman et al. | | |
| 7,611,704 B2 | 11/2009 | Thorpe et al. | | |
| 7,731,967 B2 * | 6/2010 | O'Hagan | A61K 39/39 | 424/184.1 |
| 8,048,431 B2 * | 11/2011 | Haynes | A61K 39/12 | 424/208.1 |
| 2003/0181406 A1 | 9/2003 | Schetter et al. | | |
| 2004/0006032 A1 | 1/2004 | Lopez | | |
| 2004/0006242 A1 | 1/2004 | Hawkins et al. | | |
| 2004/0053880 A1 | 3/2004 | Krieg | | |
| 2004/0067905 A1 | 4/2004 | Krieg | | |
| 2004/0092472 A1 | 5/2004 | Krieg | | |
| 2004/0152649 A1 | 8/2004 | Krieg | | |
| 2004/0171086 A1 | 9/2004 | Fink et al. | | |
| 2004/0198680 A1 | 10/2004 | Krieg | | |
| 2005/0059619 A1 | 3/2005 | Krieg et al. | | |
| 2006/0165687 A1 | 7/2006 | Haynes et al. | | |
| 2008/0031890 A1 | 2/2008 | Haynes et al. | | |
| 2008/0057075 A1 | 3/2008 | Haynes | | |
| 2010/0028415 A1 | 2/2010 | Haynes et al. | | |

FOREIGN PATENT DOCUMENTS

| | | |
|---|---|---|
| JP | 2007-505624 | 3/2007 |
| WO | 2001/082962 | 11/2001 |
| WO | 2005/028625 | 3/2005 |
| WO | 2006/110831 | 10/2006 |
| WO | 2008/127651 | 10/2008 |
| WO | 2010/037408 | 4/2010 |
| WO | 2010/072275 | 7/2010 |
| WO | 2010/114628 | 10/2010 |
| WO | 2010/114629 | 10/2010 |
| WO | 2010/115210 | 10/2010 |
| WO | 2011/106100 | 9/2011 |

OTHER PUBLICATIONS

Abrahams et al. "Abrahams", Supplemental Table 1, Journal of Virology, 2009, 83(8): PDF pp. 1-3.*

International Search Report for PCT/US2011/000352, dated Dec. 21, 2011.

Scheid, J.-F. et al., "Broad diversity of neutralizing antibodies isolated from memory B cells in HIV-infected individuals", Nature, vol. 458, (Apr. 2, 2009), pp. 636-640.

Climent, N. et al., "Generation of human monoclonal antibodies from HIV-infected individuals", Immunogia, vol. 23, No. 4, (Dec. 2004), pp. 303-312.

(Continued)

*Primary Examiner* — Barry A Chestnut

(74) *Attorney, Agent, or Firm* — Baker Donelson

(57) ABSTRACT

The present invention relates, in general, to an immunogen for HIV vaccination and, in particular, to a method of inducing the production of protective anti-HIV antibodies by targeting B cell germline and clone intermediates using a combination of HIV envelope and non-HIV immunogens. The invention also relates to compositions suitable for use in such a method.

20 Claims, 125 Drawing Sheets

Specification includes a Sequence Listing.

(56) References Cited

OTHER PUBLICATIONS

Scheid, J.-F. et al., "A method for identification of HIV gp140 binding memory B cells in human blood", Journal of Immunological Methods, vol. 343, (Dec. 25, 2008), pp. 65-67.
Bonsignori, M. et al., "P04-48. HIV-1 envelop induces memory B cell responses that correlate with plasma antibody levels after gp120 protein vaccination or chronic HIV infection", Retroviology, vol. 6, Supp. 3, (Oct. 22, 2009), pp. 76.
Doria-Rose, N-A. et al., "Antibody secreting B-cells in HIV infection", Current Opinion of HIV AIDS, vol. 4, No. 5, (Sep. 2009), pp. 426-430.
Matyas et al., "Neutralizing antibodies induced by liposomal HIV-1 glycoprotein 41 peptide simultaneously bind to both the 2F5 or 4E10 epitope and lipid epitopes" AIDS 23:2069-2077 (2009).
Pancera et al. "Crystal Structure of PG16 and Chimeric Dissection with Somatically Related PG9: Structure-Function Analysis of Two Quaternary-Specific Antibodies That Effectively Neutralize HIV-1 ." Journal of Virology 84(16) 2010: 8098-8110.
Pejchal et al. "Structure and Function of Broadly Reactive Antibody PG16 Reveal an H3 Subdomain That Mediates Potent Neutralization of HIV-1." Proceedings of the National Academy of Sciences of the United States of America 107(25) 2010: 11483-11488.
Rao et al., "Immunostimulatory CpG motifs induce CTL responses to HIV type I oligomeric gp140 envelope protein", Immunol Cell Biol, 82(5), 2004:523-530.
Rauch et al., "Phospholipid in the Hexagonal II Phase Is Immunogenic: Evidence for Immunorecognition of Nonbilayer Lipid Phases in Vivo." Proceedings of the National Academy of Sciences of the United States of America 87(11) 1990: 4112-4114.
Richards et al., "Liposomes Containing Lipid A Serve as an Adjuvant for Induction of Antibody and Cytotoxic T-Cell Responses against RTS,S Malaria Antigen", Infection and Immunity 66(6), 1998: 2859-2865.
Scanlan et al., "The carbohydrate epitope of the neutralizing anti-HIV-1 antibody 2G12", Adv Exp Med Biol, 535, 2003: 205-218.
Shen et al., "In Vivo gp41 Antibodies Targeting the 2F5 Monoclonal Antibody Epitope Mediate Human Immunodeficiency Virus Type 1 Neutralization Breadth." Journal of Virology 83(8) 2009: 3617-3625.
Smith et al., "Rapid Generation of Fully Human Monoclonal Antibodies Specific to a Vaccinating Antigen." Nature protocols 4(3) 2009: 372-384.
Smith and Waterman, "Identification of common molecular subsequences" J Mol Biol 147(1) 1981:195-197.
Stiegler and Katinger, "Therapeutic potential of neutralizing antibodies in the treatment of HIV-1 infection" J. Antimicrob. Chemother. (2003) 51 (4): 757-759.
Tomaras et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia", Journal of Virology 82(24) 2008: 12449-12463.
Tran et al., "Specificity and immunochemical properties of anti-DNA antibodies induced in normal mice by immunization with mammalian DNA with a CpG oligonucleotide as adjuvant", Clin Immunol, 109(3) 2003:278-287.
Verkoczy et al., "Autoreactivity in an HIV-1 Broadly Reactive Neutralizing Antibody Variable Region Heavy Chain Induces Immunologic Tolerance." Proceedings of the National Academy of Sciences of the United States of America 107(1) 2010: 181-186.
Walker et al., "A Limited Number of Antibody Specificities Mediate Broad and Potent Serum Neutralization in Selected HIV-1 Infected Individuals." PLoS Pathogens 6(8) 2010: e1001028.
Walker et al., "Broad and Potent Neutralizing Antibodies from an African Donor Reveal a New HIV-1 Vaccine Target." Science 326(5950) 2009: 285-289.
Wrammert et al., "Rapid cloning of high affinity human monoclonal antibodies against influenza virus", Nature 453(7195) 2008:667-671.
Xiao et al. "Germline-like Predecessors of Broadly Neutralizing Antibodies Lack Measurable Binding to HIV-1 Envelope Glycoproteins: Implications for Evasion of Immune Responses and Design of Vaccine Immunogens." Biochemical and biophysical research communications 390(3) 2009: 404-409.
Yoon et al., "Mutations in the N Termini of Herpes Simplex Virus Type 1 and 2 gDs Alter Functional Interactions with the Entry/Fusion Receptors HVEM, Nectin-2, and 3-O-Sulfated Heparan Sulfate but Not with Nectin-1." Journal of Virology 77(17) 2003: 9221-9231.
Zhang and Darst. "Structure of the *Escherichia coli* RNA polymerase alpha subunit amino-terminal domain." Science, 281(5374), 1998:262-266.
Zwick et al., "Molecular Features of the Broadly Neutralizing Immunoglobulin G1 b12 Required for Recognition of Human Immunodeficiency Virus Type 1 gp120." Journal of Virology 77(10) 2003: 5863-5876.
Zwick et al. "Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1." Journal of Virology 79(2) 2005: 1252-1261.
Zwick et al., "The Long Third Complementarity-Determining Region of the Heavy Chain Is Important in the Activity of the Broadly Neutralizing Anti-Human Immunodeficiency Virus Type 1 Antibody 2F5." Journal of Virology 78(6) 2004: 3155-3161.
Rossner et al., "Intracerebroventricular infusion of CHO5, a rat monoclonal antibody directed against mouse low-affinity nerve growth factor receptor (p75NTR), specifically labels basal forebrain cholinergic neurons in mouse brain," Metab Brain Dis. Mar. 2000;15(1):17-27.
European extended search report dated Feb. 20, 2015.
Japanese Office Action dated Mar. 2, 2015.
NCBI Protein Accession No. NP_289856.1.
NCBI Protein Accession No. YP_404940.1.
NCBI Protein Accession No. NP_438962.1.
NCBI Protein Accession No. NP_P37382.2.
NCBI Protein Accession No. NP_116558.1.
Japanese Patent Office communication dated Jan. 29, 2016.
Chinese Patent Office communication dated Dec. 16, 2015.
European Patent Office communication dated Apr. 12, 2015.
Australian Patent Examination Report dated Nov. 5, 2015.
Abrahams et al., "Quantitating the multiplicity of infection with human immunodeficiency virus type 1 subtype C reveals a non-poisson distribution of transmitted variants" Journal of Virology 83(8) 2009: 3556-3567.
Aguilar et al., "Phospholipid membranes form specific nonbilayer molecular arrangements that are antigenic." J Biol Chem 274(36) 1999:25193-25196.
Alam et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes." Journal of immunology 178(7) 2007: 4424-4435.
Alam et al., "Role of HIV Membrane in Neutralization by Two Broadly Neutralizing Antibodies." Proceedings of the National Academy of Sciences of the United States of America 106(48) 2009: 20234-20239.
Alving et al., Liposome technology 2nd Ed., vol. 3, Edited by G. Gregoriadis, CRC Press (1993).
Armbruster et al., "Passive immunization with the anti-HIV-1 human monoclonal antibody (hMAb) 4E10 and the hMAb combination 4E10/2F5/2G12." J Antimicrob Chemother 54(5) 2004: 915-920.
Binley et al., "Enhancing the proteolytic maturation of human immunodeficiency virus type 1 envelope glycoproteins." Journal of Virology 76(6) 2002: 2606-2616.
Burton et al., "HIV vaccine design and the neutralizing antibody problem", Nat Immunol. 5(3), 2004:233-236.
Cardoso et al, "Broadly Neutralizing Anti-HIV Antibody 4E10 Recognizes a Helical Conformation of a Highly Conserved Fusion-Associated Motif in gp41" Immunity 22, 2005:163-172.

(56) References Cited

OTHER PUBLICATIONS

Cerutti and Rescigno., "The Biology of Intestinal Immunoglobulin A Responses", Immunity 28(6) 2008: 740-750.
Chakrabarti et al., "Modifications of the Human Immunodeficiency Virus Envelope Glycoprotein Enhance Immunogenicity for Genetic Immunization", Journal of Virology 76(11) 2002: 5357-5368.
Chen et al., "Structural Basis of Immune Evasion at the Site of CD4 Attachment on HIV-1 gp120." Science 326(5956) 2009: 1123-1127.
Connolly et al,. "Potential Nectin-1 Binding Site on Herpes Simplex Virus Glycoprotein D." Journal of Virology 79(2) 2005: 1282-1295.
Dennison et al., "Stable Docking of Neutralizing Human Immunodeficiency Virus Type 1 gp41 Membrane-Proximal External Region Monoclonal Antibodies 2F5 and 4E10 Is Dependent on the Membrane Immersion Depth of Their Epitope Regions." Journal of Virology 83(19) 2009: 10211-10223.
Ewing et al., "Base-calling of automated sequencer traces using phred. I. Accuracy assessment" Genome Res 8(3) 1998:175-185.
Ewing and Green, "Base-calling of automated sequencer traces using phred. II Error probabilities" Genome Res 8(3) 1998:186-194.
Felsenstein, "Evolutionary trees from DNA sequences: a maximum likelihood approach" J Mol Evol 17(6) 1981:368-376.
Felsenstein, "Using the Quantitative Genetic Threshold Model for Inferences between and within Species." Philosophical Transactions of the Royal Society B: Biological Sciences 360(1459) 2005: 1427-1434.
Fiebig et al., "Dynamics of HIV viremia and antibody seroconversion in plasma donors: implications for diagnosis and staging of primary HIV infection", AIDS, 17(13), 2330:1871-1879.
Frey et al., "A Fusion-Intermediate State of HIV-1 gp41 Targeted by Broadly Neutralizing Antibodies", Proceedings of the National Academy of Sciences of the United States of America 105(10) 2008: 3739-3744.
Gao et al., "Antigenicity and immunogenicity of a synthetic human immunodeficiency virus type 1 group M consensus envelope glycoprotein", Journal of Virology 79(2) 2005: 1154-1163.
Go et al., "Charaterization of glycosylation profiles of HIV-1 transmitted/founder envelopes by Mass Spectrometry", Journal of Virology 85(16) 2011: 8270-8284.
Gurgo et al., "Envelope sequences of two new United States HIV-1 isolates", Virology, 164(2), 1988:531-536.
Haynes et al., "Antibody Polyspecificity and Neutralization of HIV-1: A Hypothesis." Human antibodies 14(3-4) 2005: 59-67.
Haynes et al., "Cardiolipin polyspecific autoreactivity in two broadly neutralizing HIV-1 antibodies", Science, 308(5730), 2005:1906-1908.
He et al., "Intestinal bacteria trigger T cell-independent immunoglobulin A(2) class switching by inducing epithelial-cell secretion of the cytokine APRIL", Immunity, 26(6) 2007:812-826.
Holl. "The Influence of B-cell Tolerance on Humoral Immunity to HIV-1." Diss. Duke University, 2010.
Huang et al. "Structural Basis of Tyrosine Sulfation and VH-Gene Usage in Antibodies That Recognize the HIV Type 1 Coreceptor-Binding Site on gp120." Proceedings of the National Academy of Sciences of the United States of America 101(9) 2004: 2706-2711.
Kawatsu et al., "Development and Evaluation of Immunochromatographic Assay for Simple and Rapid Detection of Campylobacter Jejuni and Campylobacter Coli in Human Stool Specimens", Journal of Clinical Microbiology 46(4) 2008: 1226-1231.
Keele et al., "Identification and Characterization of Transmitted and Early Founder Virus Envelopes in Primary HIV-1 Infection." Proceedings of the National Academy of Sciences of the United States of America 105(21) 2008: 7552-7557.
Kwong et al. "Mining the B Cell Repertoire for Broadly Neutralizing Monoclonal Antibodies to HIV-1." Cell Host and Microbe 6(4) 2009: 292-294.
Liao et al., "A Group M Consensus Envelope Glycoprotein Induces Antibodies That Neutralize Subsets of Subtype B and C HIV-1 Primary Viruses." Virology 353(2) 2006: 268-282.
Liao et al., "High-Throughput Isolation of Immunoglobulin Genes from Single Human B Cells and Expression as Monoclonal Antibodies." Journal of virological methods 158(1-2) 2009: 171-179.
Lima et al., "Crystal Structure of *Homo sapiens* Kynureninase." Biochemistry 46(10) 2007: 2735-2744.
Maksyutov et al., "Exclusion of HIV epitopes shared with human proteins is prerequisite for designing safer AIDS vaccines", J Clin Virol, 2004:S26-S38.
McMichael et al., "The Immune Response during Acute HIV-1 Infection: Clues for Vaccine Development." Nature reviews. Immunology 10(1) 2010: 11-23.
Mietzner et al., "Autoreactive IgG Memory Antibodies in Patients with Systemic Lupus Erythematosus Arise from Nonreactive and Polyreactive Precursors." Proceedings of the National Academy of Sciences of the United States of America 105(28) 2008: 9727-9732.
Ofek et al., "Structure and Mechanistic Analysis of the Anti-Human Immunodeficiency Virus Type 1 Antibody 2F5 in Complex with Its gp41 Epitope." Journal of Virology 78(19) 2004: 10724-10737.
Li et al., "Control of Expression, Glycosylation, and Secretion of HIV-1 gp120 by Homologous and Heterologous Signal Sequences" Virology 204, 266-278 (1994).
Li et al., "Effects of inefficient cleavage of the signal sequence of HIV-1 gp120 on its association with calnexin, folding, and intracellular transport" Proc. Natl. Acad. Sci. USA, vol. 93, pp. 9606-9611, Sep. 1996, Cell Biology.
Bosch et al. "Mutational Analysis of the Human Immunodeficiency Virus Type 1 env Gene Product Proteolytic Cleavage Site" Virology 65(5): 2337-2344 (1990).
Guo et al. "Characterterization of an HIV-1 Point Mutant Blocked in Envelope Glycoprotein Cleavage"; Virology 174: 217-224 (1990).
Liao et al. "Antigenicity and Immunogenicity of Transmitted/Founder, Consensus, and Chronic Envelope Glycoproteins of Human Immunodeficiency Virus Type 1" J. Virol. 87(8):4185-4201 (2013).
McCune et al. "Endoproteolytic Cleavage of gp160 Is Required for the Activation of Human Immunodeficiency Virus" Cell vol. 53; p. 55-67 (1998).

* cited by examiner

HA Clone from 7 days after influenza vaccination – all 14 sequences are positive for HA

Heavy – VH3-49, DH2, JH4, IgG1,
Kappa – VK1-51, JK2

Of clones studied in 8 patients with influenza vaccination or Influenza infection, 94% of antibodies in clones reacted with influenza antigens

Plasma Cell Antibody Repertoire
in Pt. 684-6, ~20 days after HIV
transmission
217 VH+VL total pairs; PCs=19.7%
-52 antibodies in this clone
-heavily mutated Heavy – VH3-7, DH1-26, JH5, IgG3
Kappa – VK1-39 JK4

Of clones studied in 5 patients with acute
HIV infection, only 37% of antibodies in
clones reacted with HIV antigens

Is There Evidence of Antigen Drive In This Clone By gp41?

301, 307

Produced Additional Inferred Intermediate Clone Antibodies: ELISA, Luminex, SPR, Autoreactive IF

All Inferred and actual isolated clone MAbs were expressed in mg quantities and assayed at a wide concentration range

Circles = inferred intermediate antibodies
Boxes = actual isolated clone antibodies

Polyreactivity of 6846 Clone 52 Germline and Inferred Intermediate gp41 Antibodies

BlueNative-PAGE and Western Blot Images of Gut Extract vs Mojo Antibody (12/10/2009, test on HV00276)

Coomassie Blue Image

Samples: 5-20 ug Gut Extract / Lane

Gel: NativePAGE Novex 4-16% Bis-Tris gel

Western Blot Image

Primary Ab: HV00276 (20 ug/ml)

Secondary Ab: AP-conjugated Goat anti-Human IgG

Gel: NativePAGE Novex 4-16% Bis-Tris gel

Western Blot Images of Gut Extract vs Mojo Antibody

Non-reducing, vs HV00276

Primary Ab: HV00276 (20 ug/ml)

2nd Ab: AP-conjugated Goat anti-Human IgG

Samples: 100 ug Gut extract / Lane

Gel: NuPAGE Novex 4-12% Bis-Tris gel

Reducing, vs HV00276

Primary Ab: HV00276 (20 ug/ml)

2nd Ab: AP-conjugated Goat anti-Human IgG

Samples: 100 ug Gut extract / Lane

Gel: NuPAGE Novex 4-12% Bis-Tris gel

A large fraction of B cells expressing 4E10 $V_H$ are deleted in the bone marrow at the pre-B to immature B cell stage in 4E10 $V_H$ knock-in mice

8 wk mice, singlet, live, CD19+ gate:

SDS-PAGE Images of Apoferritin

SDS-PAGE ( Non-reducing )

Samples: 10 ug Apoferrin/Lane,
5ul Native Marker/ Lane
Gel: NuPAGE Novex 4-12% Bis-Tris gel SDS-PAGE ( Reducing )

Samples: 10 ug Apoferrin/Lane,
5ul Native Marker/ Lane
Gel: NuPAGE Novex 4-12% Bis-Tris gel Note: Native Marker for BN-PAGE was used as a sample control of Apoferrin, since Apoferritin was identified from Native Marker.

Immunogenicity of Group M Consensus HIV-1 Env, CON-S and Subtype C Acute HIV-1 Env, 1086C, Subtype B Chronic HIV-1 Env, JRFL

| | Geometric Mean IC50 Neutralization Titers | | |
|---|---|---|---|
| HIV-1 Isolate | CON-S 140CFI (n=8 animals) | C.1086C 140CF (n=8 animals) | B.JRFL 140CF (n=7 animals) |
| B.SF162.LS | 19,425 | 1,875 | 1,084 |
| B. BaL.26 | 630 | 203 | 1,380 |
| B.SS1196.1 | 1,043 | 84 | 931 |
| B.6535.3 | 648 | 34 | <20 |
| B.QH0692.42 | 47 | 47 | <20 |
| B.PVO.4 | <20 | <20 | <20 |
| C.TV-1.21 | 1,621 | 209 | <20 |
| C.DU172.17 | 169 | 28 | <20 |

Figure 19A

Methods

- Mutation of CD4 binding site

345 CD4BS
374

JRFL WT

E*NKT*IVF*NHS*SGGDPEIVMHSFNCGGEFFY

C3

- Deglycosylation

JRFL APA

<u>E*NKT*IVF*NHS*SGGAPAIVMHSFNCGGEFFY</u>

- Analyses and Immunization

Antigenicity of JRFL gp140 Env in SPR
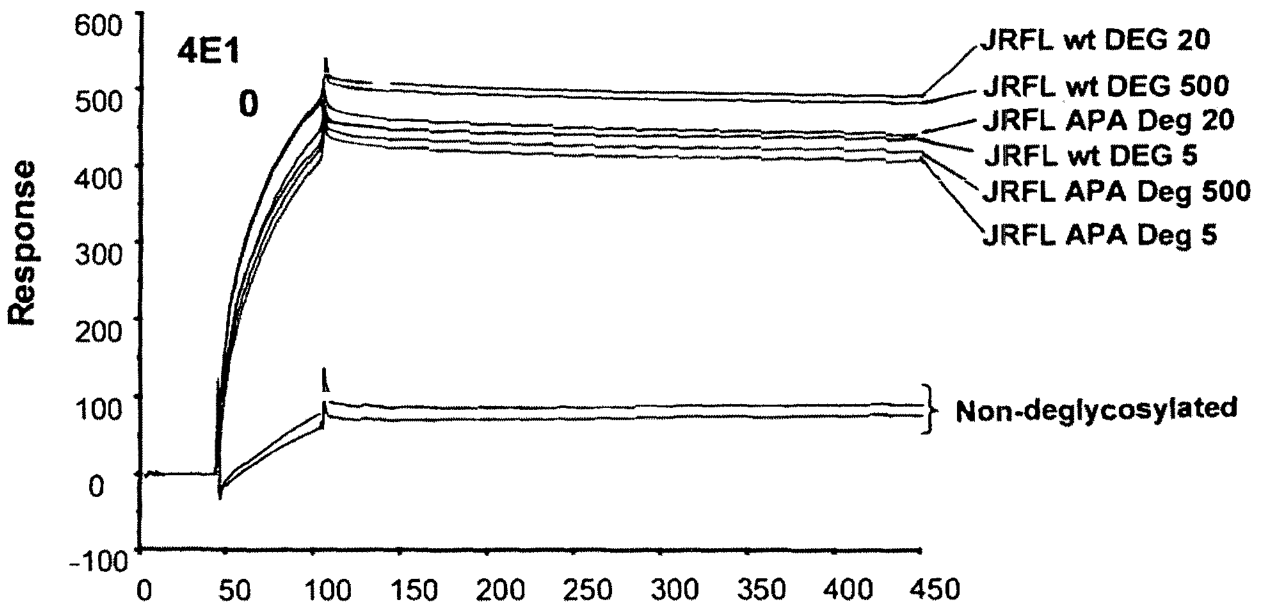
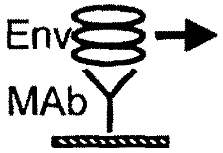
| gp140 protein | $K_{on}$ ($x10^3$ $M^{-1}s^{-1}$) | $K_{off}$ ($x10^{-3}$ $s^{-1}$) | Kd (μM) |
|---|---|---|---|
| JRFFL wt | 0.6 | 1.3 | 2.2 |
| JRFL wt DEG 5 | 7.4 | 1.0 | 0.135 |
| JRFL wt DEG 20 | 27 | 0.99 | 0.04 |
| JRFL wt DEG 500 | 21 | 1.0 | 0.05 |
| JRFL APA | 0.72 | 1.0 | 1.38 |
| JRFL APA DEG 5 | 6.8 | 1.0 | 0.14 |
| JRFL APA DEG 20 | 6.6 | 1.0 | 0.15 |
| JRFL APA DEG 500 | 5.5 | 1.0 | 0.18 |
Figure 22

**A fusion-intermediate state of HIV-1 gp41 targeted by broadly neutralizing antibodies. Frey et al., 2008; *Proc. Natl. Acad. Sci.*, 105:3739** gp41-inter

WT 4E10 binds to the gp41 inter at Kd=1nM.

Lead candidate immunogens
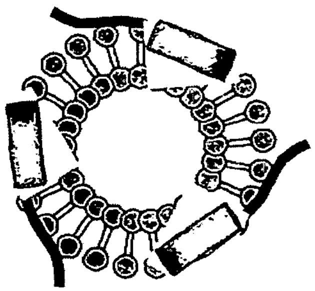
MPER656 liposome
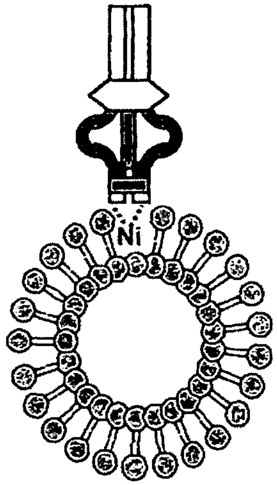
gp41-inter liposome
Figure 25

Figure 27

>1086C _140C
MRVRGIWKNWPQWLIWSILGFWIGNMEGSWVTVYYGVPVWKEAKTTLFCASDAKAYEKEVHNVWATHACVPTDPNPQEMV
LANVTENFNMWKNDMVEQMHEDIISLWDESLKPCVKLTPLCVTLNCTNVKGNESDTSEVMKNCSFKATTELKDKKHKVHA
LFYKLDVVPLNGNSSSSGEYRLINCNTSAITQACPKVSFDPIPLHYCAPAGFAILKCNNKTFNGTGPCRNVSTVQCTHGI
KPVVSTQLLLNGSLAEEEIIIRSENLTNNAKTIIVHLNESVNIVCTRPNNNTRKSIRIGPGQTFYATGDIIGNIRQAHCN
INESKWNNTLQKVGEELAKHFPSKTIKFEPSSGGDLEITTHSFNCRGEFFYCNTSDLFNGTYRNGTYNHTGRSSNGTITL
QCKIKQIINMWQEVGRAIYAPPIEGEITCNSNITGLLLLRDGGQSNETNDTETFRPGGGDMRDNWRSELYKYKVVEIKPL
GVAPTEAKERVVEREKEAVGIGAVFLGFLGAAGSTMGAASMTLTVQARQLLSGIVQQQSNLLRAIEAQQHMLQLTVWGIK
QLQARVLAIERYLKDQQLLGMWGCSGKLICTTAVPWNSSWSNKSQNEIWGNMTWMQWDREINNYTNTIYRLLEDSQNQQE
KNEKDLLALDSWKNLWNWFDISKWLWYIK_
1086C_140C.opt
ATGCGCGTGCGCGGCATCTGGAAGAACTGGCCCCAGTGGCTGATCTGGTCCATCCTGGGCTTCTGGATCGGCAACATGGA
GGGCTCCTGGGTGACCGTGTACTACGGCGTGCCCGTGTGGAAGGAGGCCAAGACCACCCTGTTCTGCGCCTCCGACGCCA
AGGCCTACGAGAAGGAGGTGCACAACGTGTGGGCCACCCACGCCTGCGTGCCCACCGACCCCAACCCCCAGGAGATGGTG
CTGGCCAACGTGACCGAGAACTTCAACATGTGGAAGAACGACATGGTGGAGCAGATGCACGAGGACATCATCTCCCTGTG
GGACGAGTCCCTGAAGCCCTGCGTGAAGCTGACCCCCCTGTGCGTGACCCTGAACTGCACCAACGTGAAGGGCAACGAGT
CCGACACCTCCGAGGTGATGAAGAACTGCTCCTTCAAGGCCACCACCGAGCTGAAGGACAAGAAGCACAAGGTGCACGCC
CTGTTCTACAAGCTGGACGTGGTGCCCCTGAACGGCAACTCCTCCTCCTCCGGCGAGTACCGCCTGATCAACTGCAACAC
CTCCGCCATCACCCAGGCCTGCCCCAAGGTGTCCTTCGACCCCATCCCCCTGCACTACTGCGCCCCCGCCGGCTTCGCCA
TCCTGAAGTGCAACAACAAGACCTTCAACGGCACCGGCCCCTGCCGCAACGTGTCCACCGTGCAGTGCACCCACGGCATC
AAGCCCGTGGTGTCCACCCAGCTGCTGCTGAACGGCTCCCTGGCCGAGGAGGAGATCATCATCCGCTCCGAGAACCTGAC
CAACAACGCCAAGACCATCATCGTGCACCTGAACGAGTCCGTGAACATCGTGTGCACCCGCCCCAACAACAACACCCGCA
AGTCCATCCGCATCGGCCCCGGCCAGACCTTCTACGCCACCGGCGACATCATCGGCAACATCCGCCAGGCCCACTGCAAC
ATCAACGAGTCCAAGTGGAACAACACCCTGCAGAAGGTGGGCGAGGAGCTGGCCAAGCACTTCCCCTCCAAGACCATCAA
GTTCGAGCCCTCCTCCGGCGGCGACCTGGAGATCACCACCCACTCCTTCAACTGCCGCGGCGAGTTCTTCTACTGCAACA
CCTCCGACCTGTTCAACGGCACCTACCGCAACGGCACCTACAACCACACCGGCCGCTCCTCCAACGGCACCATCACCCTG
CAGTGCAAGATCAAGCAGATCATCAACATGTGGCAGGAGGTGGGCCGCGCCATCTACGCCCCCCCCATCGAGGGCGAGAT
CACCTGCAACTCCAACATCACCGGCCTGCTGCTGCTGCGCGACGGCGGCCAGTCCAACGAGACCAACGACACCGAGACCT
TCCGCCCCGGCGGCGGCGACATGCGCGACAACTGGCGCTCCGAGCTGTACAAGTACAAGGTGGTGGAGATCAAGCCCCTG
GGCGTGGCCCCCACCGAGGCCAAGGAGCGCGTGGTGGAGCGCGAGAAGGAGGCCGTGGGCATCGGCGCCGTGTTCCTGGG
CTTCCTGGGCGCCGCCGGCTCCACCATGGGCGCCGCCTCCATGACCCTGACCGTGCAGGCCCGCCAGCTGCTGTCCGGCA
TCGTGCAGCAGCAGTCCAACCTGCTGCGCGCCATCGAGGCCCAGCAGCACATGCTGCAGCTGACCGTGTGGGGCATCAAG
CAGCTGCAGGCCCGCGTGCTGGCCATCGAGCGCTACCTGAAGGACCAGCAGCTGCTGGGCATGTGGGGCTGCTCCGGCAA
GCTGATCTGCACCACCGCCGTGCCCTGGAACTCCTCCTGGTCCAACAAGTCCCAGAACGAGATCTGGGGCAACATGACCT
GGATGCAGTGGGACCGCGAGATCAACAACTACACCAACACCATCTACCGCCTGCTGGAGGACTCCCAGAACCAGCAGGAG
AAGAACGAGAAGGACCTGCTGGCCCTGGACTCCTGGAAGAACCTGTGGAACTGGTTCGACATCTCCAAGTGGCTGTGGTA
CATCAAGTAGGGATCCTCTAGA_

089C 140C.pep
MRVRGMLRNCQQWWIWGILGFWMLMICSVVGNLWVTVYYGVPVWKEAKTTLFCASDARAYEREVHNVWATHACVPTDPNP
QEMVLVNVTENFNMWKNDMVDQMHEDIISLWDQSLKPCVKLTPLCVILECNNANGTTNNGSVIVVNENSTMYGEIQNCSF
KVNSEIKGKKQDVYALFNSLDIVKLYNNGTSQYRLINCNTSTLTQACPKVSFDPIPIHYCAPAGYAILKCNNKTFNGTGP
CNNVSTVQCTHGIKPVVSTQLLLNGSLAEGEIIIRSKNLTDNTKTIIVHLNESIKINCIRPNNNTRRSIRIGPGQAFYAA
NGIVGNIRQAHCNISEGEWNKTLYRVSRKLAEHFPGKEIKFKPHSGGDLEITTHSFNCRGEFFYCNTSKLFNGTYNGTYT
NNDTNSTIILPCRIKQIINMWQEVGQAMYAPPIEGIIACNSTITGLLLTRDGGDKNGSKPEIFRPGGGDMRDNWRSELYK
YKVVEIKPLGIAPTKAKERVVEKEKTIQKEAVGIGAVFLGFLGAAGSTMGAASITLTVQARQLLSGIVQQQSNLLRAIEA
QQHMLQLTVWGIKQLQARVLAMERYLQDQQLLGIWGCSGKLICTTAVPWNSSWSNKTLEYIWGNMTWMQWDREIDNYTGI
IYDLLEDSQIQQEKNEKDLLALDSWKNLWSWFSITNWLWYIK_
089C_140C.opt
ATGCGCGTGCGCGGCATGCTGCGCAACTGCCAGCAGTGGTGGATCTGGGGCATCCTGGGCTTCTGGATGCTGATGATCTG
CTCCGTGGTGGGCAACCTGTGGGTGACCGTGTACTACGGCGTGCCCGTGTGGAAGGAGGCCAAGACCACCCTGTTCTGCG
CCTCCGACGCCCGCGCCTACGAGCGCGAGGTGCACAACGTGTGGGCCACCCACGCCTGCGTGCCCACCGACCCCAACCCC
CAGGAGATGGTGCTGGTGAACGTGACCGAGAACTTCAACATGTGGAAGAACGACATGGTGGACCAGATGCACGAGGACAT
CATCTCCCTGTGGGACCAGTCCCTGAAGCCCTGCGTGAAGCTGACCCCCCTGTGCGTGATCCTGGAGTGCAACAACGCCA
ACGGCACCACCAACAACGGCTCCGTGATCGTGGTGAACGAGAACTCCACCATGTACGGCGAGATCCAGAACTGCTCCTTC
AAGGTGAACTCCGAGATCAAGGGCAAGAAGCAGGACGTGTACGCCCTGTTCAACTCCCTGGACATCGTGAAGCTGTACAA
CAACGGCACCTCCCAGTACCGCCTGATCAACTGCAACACCTCCACCCTGACCCAGGCCTGCCCCAAGGTGTCCTTCGACC
CCATCCCCATCCACTACTGCGCCCCCGCCGGCTACGCCATCCTGAAGTGCAACAACAAGACCTTCAACGGCACCGGCCCC
TGCAACAACGTGTCCACCGTGCAGTGCACCCACGGCATCAAGCCCGTGGTGTCCACCCAGCTGCTGCTGAACGGCTCCCT
GGCCGAGGGCGAGATCATCATCCGCTCCAAGAACCTGACCGACAACACCAAGACCATCATCGTGCACCTGAACGAGTCCA
TCAAGATCAACTGCATCCGCCCCAACAACAACACCCGCCGCTCCATCCGCATCGGCCCCGGCCAGGCCTTCTACGCCGCC
AACGGCATCGTGGGCAACATCCGCCAGGCCCACTGCAACATCTCCGAGGGCGAGTGGAACAAGACCCTGTACCGCGTGTC
CCGCAAGCTGGCCGAGCACTTCCCCGGCAAGGAGATCAAGTTCAAGCCCCACTCCGGCGGCGACCTGGAGATCACCACCC
ACTCCTTCAACTGCCGCGGCGAGTTCTTCTACTGCAACACCTCCAAGCTGTTCAACGGCACCTACAACGGCACCTACACC
AACAACGACACCAACTCCACCATCATCCTGCCCTGCCGCATCAAGCAGATCATCAACATGTGGCAGGAGGTGGGCCAGGC
CATGTACGCCCCCCCCATCGAGGGCATCATCGCCTGCAACTCCACCATCACCGGCCTGCTGCTGACCCGCGACGGCGGCG
ACAAGAACGGCTCCAAGCCCGAGATCTTCCGCCCCGGCGGCGGCGACATGCGCGACAACTGGCGCTCCGAGCTGTACAAG
TACAAGGTGGTGGAGATCAAGCCCCTGGGCATCGCCCCCACCAAGGCCAAGGAGCGCGTGGTGGAGAAGGAGAAGACCAT
CCAGAAGGAGGCCGTGGGCATCGGCGCCGTGTTCCTGGGCTTCCTGGGCGCCGCCGGCTCCACCATGGGCGCCGCCTCCA
TCACCCTGACCGTGCAGGCCCGCCAGCTGCTGTCCGGCATCGTGCAGCAGCAGTCCAACCTGCTGCGCGCCATCGAGGCC

Figure 27 cont'd

CAGCAGCACATGCTGCAGCTGACCGTGTGGGGCATCAAGCAGCTGCAGGCCCGCGTGCTGGCCATGGAGCGCTACCTGCA
GGACCAGCAGCTGCTGGGCATCTGGGGCTGCTCCGGCAAGCTGATCTGCACCACCGCCGTGCCCTGGAACTCCTCCTGGT
CCAACAAGACCCTGGAGTACATCTGGGGCAACATGACCTGGATGCAGTGGGACCGCGAGATCGACAACTACACCGGCATC
ATCTACGACCTGCTGGAGGACTCCCAGATCCAGCAGGAGAAGAACGAGAAGGACCTGCTGGCCCTGGACTCCTGGAAGAA
CCTGTGGTCCTGGTTCTCCATCACCAACTGGCTGTGGTACATCAAG_

>700010040_C9 140C
MRVMGIRKNYQHLWREGILLLGILMICSAADNLWVTVYYGVPVWREATTTLFCASDAKAYDTEAHNVWATHACVPTDPNP
QEVELKNVTENFNMWENNMVEQMHEDIISLWDQSLKPCVKLTPLCVTLNCTDLGNVTNTTNSNGEMMEKGEVKNCSFKIT
TDIKDRTRKEYALFYKLDVVPINDTRYRLVSCNTSVITQACPKVSFEPIPIHYCAPAGFAILKCNDKQFIGTGPCTNVST
VQCTHGIRPVVSTQLLLNGSLAEEEVVIRSVNFSDNAKTIIVQLNKSVEITCTRPNNNTRKSIPMGPGKAFYARGDITGD
IRKAYCEINGTEWHSTLKLVVEKLREQYNKTIVFNRSSGGDPEIVMYSFNCGGEFFYCNSTKLFNSTWPWNDTKGSHDTN
GTLILPCKIKQIINMWQGVGKAMYAPPIEGKIRCSSNITGLLLTRDGGYESNETDEIFRPGGGDMRDNWRSELYKYKVVK
IEPLGVAPTKAKERVVQREKEAFGLGAVFLGFLGAAGSTMGAASITLTVQARQLLSGIVQQQNNLLRAIEAQQHLLQLTV
WGIKQLQARVLAVERYLKDQQLLGIWGCSGKLICTTTVPWNTSWSNKSLEQIWDNMTWMEWEREIDNYTGYIYQLIEESQ
NQQEKNEQELLALDKWASLWNWFDITNWLWYIK
>700010040_C9 140C.Opt
ATGCGCGTGATGGGCATCCGCAAGAACTACCAGCACCTGTGGCGCGAGGGCATCCTGCTGCTGGGCATCCTGATGATCTG
CTCCGCCGCCGACAACCTGTGGGTGACCGTGTACTACGGCGTGCCCGTGTGGCGCGAGGCCACCACCACCCTGTTCTGCG
CCTCCGACGCCAAGGCCTACGACACCGAGGCCCACAACGTGTGGGCCACCCACGCCTGCGTGCCCACCGACCCCAACCCC
CAGGAGGTGGAGCTGAAGAACGTGACCGAGAACTTCAACATGTGGGAGAACAACATGGTGGAGCAGATGCACGAGGACAT
CATCTCCCTGTGGGACCAGTCCCTGAAGCCCTGCGTGAAGCTGACCCCCCTGTGCGTGACCCTGAACTGCACCGACCTGG
GCAACGTGACCAACACCACCAACTCCAACGGCGAGATGATGGAGAAGGGCGAGGTGAAGAACTGCTCCTTCAAGATCACC
ACCGACATCAAGGACCGCACCCGCAAGGAGTACGCCCTGTTCTACAAGCTGGACGTGGTGCCCATCAACGACACCCGCTA
CCGCCTGGTGTCCTGCAACACCTCCGTGATCACCCAGGCCTGCCCCAAGGTGTCCTTCGAGCCCATCCCCATCCACTACT
GCGCCCCCGCCGGCTTCGCCATCCTGAAGTGCAACGACAAGCAGTTCATCGGCACCGGCCCCTGCACCAACGTGTCCACC
GTGCAGTGCACCCACGGCATCCGCCCCGTGGTGTCCACCCAGCTGCTGCTGAACGGCTCCCTGGCCGAGGAGGAGGTGGT
GATCCGCTCCGTGAACTTCTCCGACAACGCCAAGACCATCATCGTGCAGCTGAACAAGTCCGTGGAGATCACCTGCACCC
GCCCCAACAACAACACCCGCAAGTCCATCCCCATGGGCCCCGGCAAGGCCTTCTACGCCCGCGGCGACATCACCGGCGAC
ATCCGCAAGGCCTACTGCGAGATCAACGGCACCGAGTGGCACTCCACCCTGAAGCTGGTGGTGGAGAAGCTGCGCGAGCA
GTACAACAAGACCATCGTGTTCAACCGCTCCTCCGGCGGCGACCCCGAGATCGTGATGTACTCCTTCAACTGCGGCGGCG
AGTTCTTCTACTGCAACTCCACCAAGCTGTTCAACTCCACCTGGCCCTGGAACGACACCAAGGGCTCCCACGACACCAAC
GGCACCCTGATCCTGCCCTGCAAGATCAAGCAGATCATCAACATGTGGCAGGGCGTGGGCAAGGCCATGTACGCCCCCCC
CATCGAGGGCAAGATCCGCTGCTCCTCCAACATCACCGGCCTGCTGCTGACCCGCGACGGCGGCTACGAGTCCAACGAGA
CCGACGAGATCTTCCGCCCCGGCGGCGGCGACATGCGCGACAACTGGCGCTCCGAGCTGTACAAGTACAAGGTGGTGAAG
ATCGAGCCCCTGGGCGTGGCCCCCACCAAGGCCAAGGAGCGCGTGGTGCAGCGCGAGAAGGAGGCCTTCGGCCTGGGCGC
CGTGTTCCTGGGCTTCCTGGGCGCCGCCGGCTCCACCATGGGCGCCGCCTCCATCACCCTGACCGTGCAGGCCCGCCAGC
TGCTGTCCGGCATCGTGCAGCAGCAGAACAACCTGCTGCGCGCCATCGAGGCCCAGCAGCACCTGCTGCAGCTGACCGTG
TGGGGCATCAAGCAGCTGCAGGCCCGCGTGCTGGCCGTGGAGCGCTACCTGAAGGACCAGCAGCTGCTGGGCATCTGGGG
CTGCTCCGGCAAGCTGATCTGCACCACCACCGTGCCCTGGAACACCTCCTGGTCCAACAAGTCCCTGGAGCAGATCTGGG
ACAACATGACCTGGATGGAGTGGGAGCGCGAGATCGACAACTACACCGGCTACATCTACCAGCTGATCGAGGAGTCCCAG
AACCAGCAGGAGAAGAACGAGCAGGAGCTGCTGGCCCTGGACAAGTGGGCCTCCCTGTGGAACTGGTTCGACATCACCAA
CTGGCTGTGGTACATCAAG_

>63521_TC21 gp140C
MRVKGIRKNYQHLWRWGTMLLGILMICSAAAQLWVTVYYGVPVWKEATTTLFCASDAKAYDTEVHNVWATHACVPTDPNP
QELVLANVTENFNMWNNTMVEQMHEDIISLWDQSLKPCVKLTPLCVTLNCTDVTNATNINATNINNSSGGVESGEIKNCS
FNITTSVRDKVQKEYALFYKLDIVPITNESSKYRLISCNTSVLTQACPKVSFEPIPIHYCAPAGFAILKCNNETFNGKGP
CINVSTVQCTHGIRPVVSTQLLLNGSLAEKEVIIRSDNFSDNAKNIIVQLKEYVKINCTRPNNNTRKSIHIGPGRAFYAT
GEIIGNIRQAHCNISRSKWNDTLKQIAAKLGEQFRNKTIVFNPSSGGDLEIVTHSFNCGGEFFYCNTTKLFNSTWIREGN
NGTWNGTIGLNDTAGNDTIILPCKIKQIINMWQEVGKAMYAPPIRGQIRCSSNITGLILTRDGGKDDSNGSEILEIFRPG
GGDMRDNWRSELYKYKVVRIEPLGVAPTRARERVVQKEKEAVGLGAMFLGFLGAAGSAMGAASMTLTVQARQLLSGIVQQ
QNNLLRAIEAQQHMLQLTVWGIKQLQARVLAVERYLKDQQLLGIWGCSGKLICTTDVPWDTSWSNKTLDDIWGSNMTWME
WEREIDNYTSTIYTLLEEAQYQQEKNEKELLELDKWASLWNWFDITNWLWYIR
>63251_TC21_140C.opt
ATGCGCGTGAAGGGCATCCGCAAGAACTACCAGCACCTGTGGCGCTGGGGCACCATGCTGCTGGGCATCCTGATGATCTG
CTCCGCCGCCGCCCAGCTGTGGGTGACCGTGTACTACGGCGTGCCCGTGTGGAAGGAGGCCACCACCACCCTGTTCTGCG
CCTCCGACGCCAAGGCCTACGACACCGAGGTGCACAACGTGTGGGCCACCCACGCCTGCGTGCCCACCGACCCCAACCCC
CAGGAGCTGGTGCTGGCCAACGTGACCGAGAACTTCAACATGTGGAACAACACCATGGTGGAGCAGATGCACGAGGACAT
CATCTCCCTGTGGGACCAGTCCCTGAAGCCCTGCGTGAAGCTGACCCCCCTGTGCGTGACCCTGAACTGCACCGACGTGA
CCAACGCCACCAACATCAACGCCACCAACATCAACAACTCCTCCGGCGGCGTGGAGTCCGGCGAGATCAAGAACTGCTCC
TTCAACATCACCACCTCCGTGCGCGACAAGGTGCAGAAGGAGTACGCCCTGTTCTACAAGCTGGACATCGTGCCCATCAC
CAACGAGTCCTCCAAGTACCGCCTGATCTCCTGCAACACCTCCGTGCTGACCCAGGCCTGCCCCAAGGTGTCCTTCGAGC
CCATCCCCATCCACTACTGCGCCCCCGCCGGCTTCGCCATCCTGAAGTGCAACAACGAGACCTTCAACGGCAAGGGCCCC
TGCATCAACGTGTCCACCGTGCAGTGCACCCACGGCATCCGCCCCGTGGTGTCCACCCAGCTGCTGCTGAACGGCTCCCT
GGCCGAGAAGGAGGTGATCATCCGCTCCGACAACTTCTCCGACAACGCCAAGAACATCATCGTGCAGCTGAAGGAGTACG

Figure 27 cont'd

TGAAGATCAACTGCACCCGCCCCAACAACAACACCCGCAAGTCCATCCACATCGGCCCCGGCCGCGCCTTCTACGCCACC
GGCGAGATCATCGGCAACATCCGCCAGGCCCACTGCAACATCTCCCGCTCCAAGTGGAACGACACCCTGAAGCAGATCGC
CGCCAAGCTGGGCGAGCAGTTCCGCAACAAGACCATCGTGTTCAACCCCTCCTCCGGCGGCGACCTGGAGATCGTGACCC
ACTCCTTCAACTGCGGCGGCGAGTTCTTCTACTGCAACACCACCAAGCTGTTCAACTCCACCTGGATCCGCGAGGGCAAC
AACGGCACCTGGAACGGCACCATCGGCCTGAACGACACCGCCGGCAACGACACCATCATCCTGCCCTGCAAGATCAAGCA
GATCATCAACATGTGGCAGGAGGTGGGCAAGGCCATGTACGCCCCCCCCATCCGCGGCCAGATCCGCTGCTCCTCCAACA
TCACCGGCCTGATCCTGACCCGCGACGGCGGCAAGGACGACTCCAACGGCTCCGAGATCCTGGAGATCTTCCGCCCCGGC
GGCGGCGACATGCGCGACAACTGGCGCTCCGAGCTGTACAAGTACAAGGTGGTGCGCATCGAGCCCCTGGGCGTGGCCCC
CACCCGCGCCCGCGAGCGCGTGGTGCAGAAGGAGAAGGAGGCCGTGGGCCTGGGCGCCATGTTCCTGGGCTTCCTGGGCG
CCGCCGGCTCCGCCATGGGCGCCGCCTCCATGACCCTGACCGTGCAGGCCCGCCAGCTGCTGTCCGGCATCGTGCAGCAG
CAGAACAACCTGCTGCGCGCCATCGAGGCCCAGCAGCACATGCTGCAGCTGACCGTGTGGGGCATCAAGCAGCTGCAGGC
CCGCGTGCTGGCCGTGGAGCGCTACCTGAAGGACCAGCAGCTGCTGGGCATCTGGGGCTGCTCCGGCAAGCTGATCTGCA
CCACCGACGTGCCCTGGGACACCTCCTGGTCCAACAAGACCCTGGACGACATCTGGGGCTCCAACATGACCTGGATGGAG
TGGGAGCGCGAGATCGACAACTACACCTCCACCATCTACACCCTGCTGGAGGAGGCCCAGTACCAGCAGGAGAAGAACGA
GAAGGAGCTGCTGGAGCTGGACAAGTGGGCCTCCCTGTGGAACTGGTTCGACATCACCAACTGGCTGTGGTACATCCGCT
AGGGATCC

Figure 28

>JRFL gp140CF.opt
ATGCCCATGGGGTCTCTGCAACCGCTGGCCACCTTGTACCTGCTGGGGATGCTGGTCGCTTCCGTGCTAGCTGTGGAGAA
GCTGTGGGTGACTGTATACTATGGGGTGCCTGTGTGGAAGGAGGCCACCACCACCCTGTTCTGTGCCTCTGATGCCAAGG
CCTATGACACTGAGGTCCACAATGTCTGGGCCACCCATGCCTGTGTGCCCACTGACCCCAACCCTCAGGAGGTGGTGCTG
GAGAATGTGACTGAGCACTTCAACATGTGGAAGAACAACATGGTGGAGCAGATGCAGGAGGACATCATCAGCCTGTGGGA
CCAGAGCCTGAAGCCCTGTGTGAAGCTGACCCCCCTGTGTGTGACCCTGAACTGCAAGGATGTGAACGCCACCAACACCA
CCAATGACTCTGAGGGCACTATGGAGAGGGGTGAGATCAAGAACTGCAGCTTCAACATCACCACCAGCATCAGGGATGAG
GTGCAGAAGGAGTATGCCCTGTTCTACAAGCTGGATGTGGTGCCCATTGACAACAACAACACCAGCTACAGGCTGATCAG
CTGTGACACCTCTGTGATCACCCAGGCCTGCCCCAAGATCAGCTTTGAGCCCATCCCCATCCACTACTGTGCCCCTGCTG
GCTTTGCCATCCTGAAGTGCAATGACAAGACCTTCAATGGCAAAGGCCCTTGCAAGAATGTGAGCACTGTGCAGTGCACT
CATGGCATCAGGCCTGTGGTGAGCACCCAGCTGCTGCTGAATGGCAGCCTGGCTGAGGAGGAGGTGGTGATCAGGTCTGA
CAACTTCACCAACAATGCCAAGACCATCATTGTGCAGCTGAAGGAGTCTGTGGAGATCAACTGCACCAGGCCCAACAACA
ACACCAGGAAGAGCATTCACATTGGCCCTGGCAGGGCCTTCTACACCACTGGGGAGATCATTGGGGACATCAGGCAGGCC
CACTGCAACATCAGCAGGGCCAAGTGGAATGACACCCTGAAGCAGATTGTGATCAAGCTGAGGGAGCAGTTTGAGAACAA
GACCATTGTGTTCAATCACAGCTCTGGTGGTGATCCTGAGATTGTGATGCACAGCTTCAACTGTGGTGGTGAGTTCTTCT
ACTGCAACAGCACCCAGCTGTTCAACAGCACCTGGAACAACAACACTGAGGGCAGCAACAACACTGAGGGCAACACCATC
ACCCTGCCTTGCAGGATCAAGCAGATCATCAACATGTGGCAGGAGGTGGGCAAGGCCATGTATGCTCCTCCCATCAGGGG
CCAGATCAGGTGCAGCAGCAACATCACTGGCCTGCTGCTGACCAGGGATGGTGGCATCAATGAGAATGGCACTGAGATTT
TCAGGCCTGGTGGTGGGGACATGAGGGACAACTGGAGGTCTGAGCTGTACAAGTACAAGGTGGTGAAGATTGAGCCCCTT
GGTGTGGCTCCCACCAAGGCTAAGACCCTGACTGTGCAGGCCAGGCTGCTGCTGTCTGGCATTGTGCAGCAGCAGAACAA
CCTGCTGAGGGCCATTGAGGCTCAACAGAGGATGCTCCAGCTCACTGTCTGGGGCATCAAGCAGCTCCAGGCCAGGGTGC
TGGCTGTGGAGAGGTATCTTGGGGATCAGCAGCTCCTTGGCATCTGGGGCTGCTCTGGCAAGCTGATCTGCACCACTGCT
GTGCCCTGGAATGCCAGCTGGAGCAACAAGAGCCTGGACAGGATCTGGAACAACATGACCTGGATGGAGTGGGAGAGGGA
GATTGACAACTACACCTCTGAGATTTACACCCTGATTGAGGAGAGCCAGAACCAGCAGGAGAAGAATGAGCAGGAGCTGC
TGGAGCTGGACAAGTGGGCCAGCCTGTGGAACTGGTTTGACATCACCAAGTGGCTGTGGTAG_

>JRFL gp140CF.pep
MPMGSLQPLATLYLLGMLVASVLAVEKLWVTVYYGVPVWKEATTTLFCASDAKAYDTEVHNVWATHACVPTDPNPQEVVL
ENVTEHFNMWKNNMVEQMQEDIISLWDQSLKPCVKLTPLCVTLNCKDVNATNTTNDSEGTMERGEIKNCSFNITTSIRDE
VQKEYALFYKLDVVPIDNNNTSYRLISCDTSVITQACPKISFEPIPIHYCAPAGFAILKCNDKTFNGKGPCKNVSTVQCT
HGIRPVVSTQLLLNGSLAEEEVVIRSDNFTNNAKTIIVQLKESVEINCTRPNNNTRKSIHIGPGRAFYTTGEIIGDIRQA
HCNISRAKWNDTLKQIVIKLREQFENKTIVFNHSSGGDPEIVMHSFNCGGEFFYCNSTQLFNSTWNNNTEGSNNTEGNTI
TLPCRIKQIINMWQEVGKAMYAPPIRGQIRCSSNITGLLLTRDGGINENGTEIFRPGGGDMRDNWRSELYKYKVVKIEPL
GVAPTKAKTLTVQARLLLSGIVQQQNNLLRAIEAQQRMLQLTVWGIKQLQARVLAVERYLGDQQLLGIWGCSGKLICTTA
VPWNASWSNKSLDRIWNNMTWMEWEREIDNYTSEIYTLIEESQNQQEKNEQELLELDKWASLWNWFDITKWLW*

>62400_TA5_140C.opt
ATGCGCGTGAAGGGCATCCGCAAGAACTACCAGCACCTGTGGCGCTGGGGCATCTGGCGCTGGGGCATCATGCTGCTGGG
CACCCTGATGATCTGCTCCGCCACCGAGAAGCTGTGGGTGACCGTGTACTACGGCGTGCCCGTGTGGAAGGAGGCCACCA
CCACCCTGTTCTGCGCCTCCGACGCCAAGGCCTACTCCCCCGAGAAGCACAACATCTGGGCCACCCACGCCTGCGTGCCC
ACCGACCCCAACCCCCAGGAGCTGGTGCTGGGCAACGTGACCGAGGACTTCAACATGTGGAAGAACAACATGGTGGAGCA
GATGCACGAGGACATCATCTCCCTGTGGGACCAGTCCCTGAAGCCCTGCGTGAAGCTGACCCCCCTGTGCGTGACCCTGA
ACTGCACCGACCTGAAGAACTCCGCCACCGACACCAACGGCACCTCCGGCACCAACAACCGCACCGTGGAGCAGGGCATG
GAGACCGAGATCAAGAACTGCTCCTTCAACATCACCACCGGCATCGGCAACAAGATGCAGAAGGAGTACGCCCTGTTCTA
CAAGCTGGACGTGGTGCCCATCGACTCCAACAACAACTCCGACAACACCTCCTACCGCCTGATCTCCTGCAACACCTCCG
TGGTGACCCAGGCCTGCCCCAAGACCTCCTTCGAGCCCATCCCCATCCACTACTGCGCCCCCGCCGGCTTCGCCATCCTG
AAGTGCAACAACAAGACCTTCTCCGGCAAGGGCCCCTGCAAGAACGTGTCCACCGTGCAGTGCACCCACGGCATCCGCCC
CGTGGTGTCCACCCAGCTGCTGCTGAACGGCTCCCTGGCCGAGGAGGAGATCGTGATCCGCTCCGAGAACTTCACCAACA
ACGCCAAGACCATCATCGTGCAGCTGAACGAGTCCGTGATCATCAACTGCACCCGCCCCAACAACAACACCCGCAAGGGC
ATCCACATCGGCCTGGGCCGCGCCCTGTACGCCACCGGCGACATCATCGGCGACATCCGCCAGGCCCACTGCAACCTGTC
CTCCAAGTCCTGGAACAAGACCCTGCAGCAGGTGGTGCGCAAGCTGCGCGAGCAGTTCGGCAACAAGACCATCGCCTTCA
ACCAGTCCTCCGGCGGCGACCAGGAGATCGTGAAGCACTCCTTCAACTGCGGCGGCGAGTTCTTCTACTGCGACACCACC
CAGCTGTTCAACTCCACCTGGTCCTCCAACGACACCTGGAACTCCACCGGCGTGCAGGACAACAACATCACCCTGCCCTG
CCGCATCAAGCAGATCATCAACATGTGGCAGGAGGTGGGCAAGGCCATGTACGCCCCCCCCATCCAGGGCCTGATCTCCT
GCTCCTCCAACATCACCGGCCTGCTGCTGACCCGCGACGGCGGCACCAACAACACCAACGCCACCGAGATCTTCCGCCCC
GGCGGCGGCGACATGCGCGACAACTGGCGCTCCGAGCTGTACAAGTACAAGGTGGTGAAGATCGAGCCCCTGGGCATCGC
CCCCACCAAGGCCAAGGAGCGCGTGGTGCAGCGCGAGAAGGAGGCCGTGGGCCTGGGCGCCGTGTTCATCGGCTTCCTGG
GCGCCGCCGGCTCCACCATGGGCGCCGCCTCCGTGACCCTGACCGTGCAGGCCCGCCAGCTGCTGTCCGGCATCGTGCAG
CAGCAGAACAACCTGCTGCGCGCCATCGAGGCCCAGCAGCACATGCTGCAGCTGACCGTGTGGGGCATCAAGCAGCTGCA
GGCCCGCATCCTGGCCGTGGAGCGCTACCTGAAGGACCAGCAGATCCTGGGCATCTGGGGCTGCTCCGGCAAGCTGATCT
GCCCCACCGCCGTGCCCTGGAACGCCTCCTGGTCCAACAAGTCCCTGACCGCCATCTGGAACAACATGACCTGGATGGAG
TGGGAGCGCGAGATCGACAACTACACCGGCCTGATCTACTCCCTGATCGAGGAGTCCCAGATCCAGCAGGAGCAGAACGA
GAAGGAGCTGCTGGAGCTGGACAAGTGGGCCTCCCTGTGGAACTGGTTCGACATCACCAAGTGGCTGTGGTACATCAAGT
AG_

Figure 28 cont'd

>624008_TA5_140C
MRVKGIRKNYQHLWRWGIWRWGIMLLGTLMICSATEKLWVTVYYGVPVWKEATTTLFCASDAKAYSPEKHNIWATHACVP
TDPNPQELVLGNVTEDFNMWKNNMVEQMHEDIISLWDQSLKPCVKLTPLCVTLNCTDLKNSATDTNGTSGTNNRTVEQGM
ETEIKNCSFNITTGIGNKMQKEYALFYKLDVVPIDSNNNSDNTSYRLISCNTSVVTQACPKTSFEPIPIHYCAPAGFAIL
KCNNKTFSGKGPCKNVSTVQCTHGIRPVVSTQLLLNGSLAEEEIVIRSENFTNNAKTIIVQLNESVIINCTRPNNNTRKG
IHIGLGRALYATGDIIGDIRQAHCNLSSKSWNKTLQQVVRKLREQFGNKTIAFNQSSGGDQEIVKHSFNCGGEFFYCDTT
QLFNSTWSSNDTWNSTGVQDNNITLPCRIKQIINMWQEVGKAMYAPPIQGLISCSSNITGLLLTRDGGTNNTNATEIFRP
GGGDMRDNWRSELYKYKVVKIEPLGIAPTKAKERVVQREKEAVGLGAVFIGFLGAAGSTMGAASVTLTVQARQLLSGIVQ
QQNNLLRAIEAQQHMLQLTVWGIKQLQARILAVERYLKDQQILGIWGCSGKLICPTAVPWNASWSNKSLTAIWNNMTWME
WEREIDNYTGLIYSLIEESQIQQEQNEKELLELDKWASLWNWFDITKWLWYIK*

Early B Cell Response To HIV-1: the Role of Innate B Cells

Figure 29

Early B Cell Response To HIV-1: the Role of Innate B Cells

- The need to recruit innate anti-HIV-1 activity by a vaccine
- The role of polyreactive B cells in the initial antibody response to HIV-1
- Implications for vaccine development

Figure 29 cont'd

Early B Cell Response To HIV-1: the Role of Innate B Cells

- The need to recruit innate anti-HIV-1 activity by a vaccine
- The role of polyreactive B cells in the initial antibody response to HIV-1
- Implications for vaccine development

Figure 29 cont'd

Composite Alignment of the Earliest Innate and Adaptive Immune Responses Detected After HIV-1 Transmission

Nature Reviews in Immunology, 2010

Early B Cell Response To HIV-1: the Role of Innate B Cells

- The need to recruit innate anti-HIV-1 activity by a vaccine
- The role of polyreactive B cells in the initial antibody response to HIV-1
- Implications for vaccine development

Figure 29 cont'd

Blood and Bone Marrow CD27+/CD38hi/CD20lo Plasmablasts During the First 30 Days of Acute HIV-1 Infection

HA Clone from 7 days after influenza vaccination – all 14 sequences are positive for HA

Heavy – VH3-49, DH2, JH4, IgG1, Kappa – VK1-51, JK2

Of clones studied in 8 patients with influenza vaccination or Influenza infection, 94% of antibodies in clones reacted with influenza antigens

Plasma Cell Antibody Repertoire
in Pt. 684-6, ~20 days after HIV
transmission
217 VH+VL total pairs; PCs=19.7%
-52 antibodies in this clone
-heavily mutated Heavy – VH3-7, DH1-26, JH5, IgG3
Kappa – VK1-39 JK4

Of clones studied in 5 patients with acute HIV infection, only 37% of antibodies in clones reacted with HIV antigens

Two Possibilities of Clonal Origin

- HIV gp41 triggers a germline BCR-bearing naïve B cell to expand

- HIV gp41 triggers a preexisting antibody clone in which the germline doesn't react with gp41 but an intermediate clone antibody acquires gp41 reactivity and then expands.

Figure 29 cont'd

Is There Evidence of Antigen Drive In This Clone By gp41?

Produced Additional Inferred Intermediate Clone Antibodies: ELISA, Luminex, SPR, Autoreactive IF

All Inferred and actual isolated clone MAbs were expressed in mg quantities and assayed at a wide concentration range

Acquisition of gp41 reactivity in 6846 Clone 52 Germline and Inferred Intermediate Antibodies

Circles = inferred intermediate antibodies
Boxes = actual isolated clone antibodies

What is the polyreactive status of clone antibodies?

Reactivity with HEP-2 epithelial cells

Reactivity with Lipids

Figure 29 cont'd

Polyreactivity of 6846 Clone 52 Germline and Inferred Intermediate gp41 Antibodies

Polyreactivity of 6846 Clone 52 Germline and Inferred Intermediate gp41 Antibodies

Natural Antibodies

- Antibodies produced by “innate” B cells (B1, marginal zone B cells) that are low affinity, polyreactive Abs that bind to pathogens and hold them at bay (i.e. “opsonins” that coat pneumococci) until high affinity monospecific antibodies can be made.

- Natural antibodies make up large component of serum immunoglobulin

Figure 29 cont'd

Early B Cell Response To HIV-1: the Role of Innate B Cells

- The need to recruit innate anti-HIV-1 activity by a vaccine
- The role of polyreactive B cells in the initial antibody response to HIV-1
- Implications for vaccine development

Figure 29 cont'd

If HIV is initially stimulating polyreactive antibodies, why are the broadly reactive, polyreactive antibodies not made?

- Do germline BCR of broad neutralizing antibodies react with Env?

Figure 29 cont'd

Does the germline of broadly neutralizing antibodies bind HIV Env?

- X5 original mAb- yes, germline- yes
- 2F5 original mAb- yes, germline- no
- 2G12 original mAb- yes, germline- no
- 1b12 original mAb- yes, germline- no Xiao X, Dimitrov D et al BBRC
2009

Figure 29 cont'd

Implications For Vaccine Development

- Need Ab clones from those pts that develop BNAbs followed from AHI through development of BNAb breadth to identify inferred and real intermediate precursors of BNAbs.

- ?Design immunogens based on the germline and first intermediate reactivity to non-HIV antigens Antigen for Germline BCRs + Env

Figure 29 cont'd

If HIV is initially stimulating polyreactive antibodies, why are the broadly reactive, polyreactive antibodies not made?

- Hypothesis: Broad Nabs with sufficient self-reactivity are prevented from developing or are modified in periphery by immunologic tolerance mechanisms.

Figure 29 cont'd

The 2F5 and 4E10 $V_H^{+/+}$ knock-in phenotypes are consistent with central deletion of immature B cells bearing 2F5 chimeric HCs and additional mechanisms controlling 2F5 HC autoreactivity in residual peripheral B cells

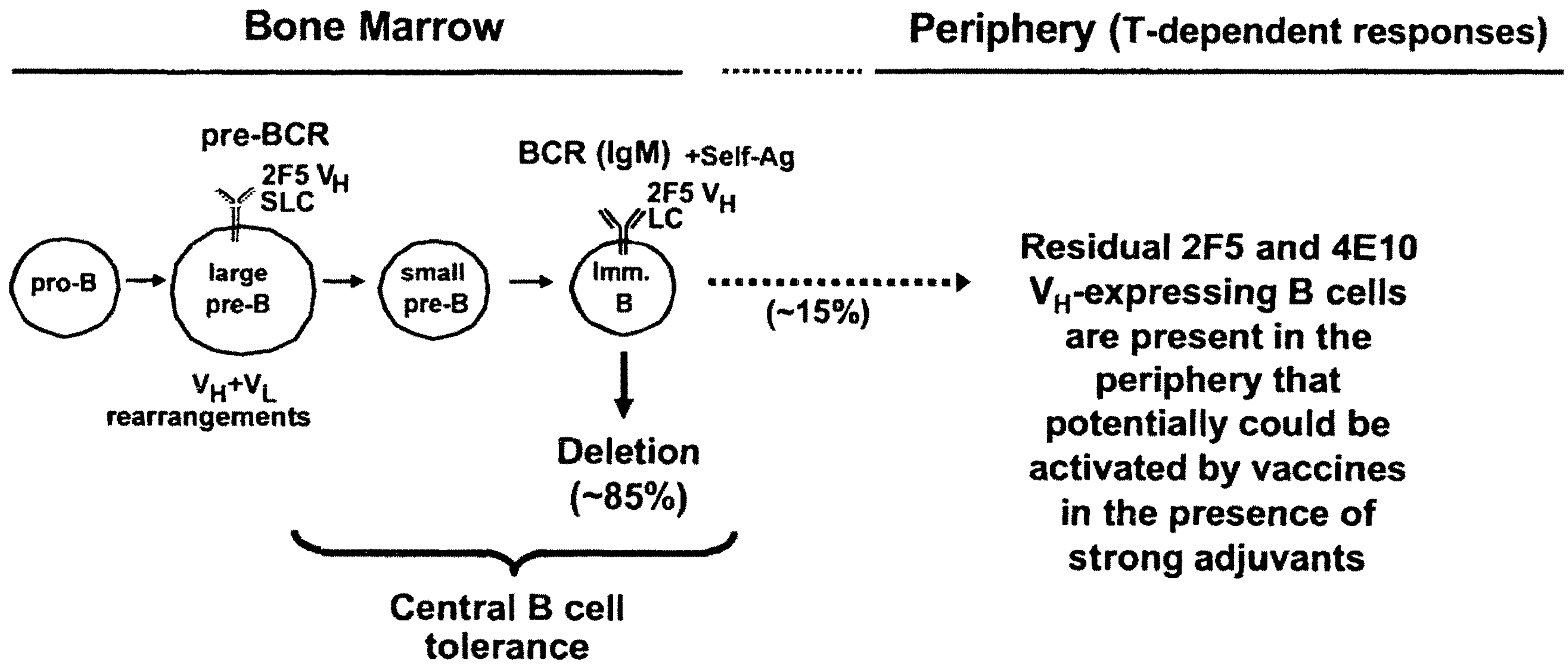

Verkoczy, L et al. Autoreactivity in an HIV-1 broadly reactive neutralizing antibody Variable region heavy chain induces immunological tolerance *PNAS* 107·181, 2010

Figure 29 cont'd

Two Roadblocks For Induction of Broad Neutralizing Antibodies

Early B Cell Response To HIV-1: the Role of Innate B Cells

- The need to recruit innate anti-HIV-1 activity by a vaccine
- The role of polyreactive B cells in the initial antibody response to HIV-1
- Implications for vaccine development

Figure 29 cont'd

The 2F5 and 4E10 BNAb React with Self-Antigens that are Phylogenetically Conserved

2F5 4E10

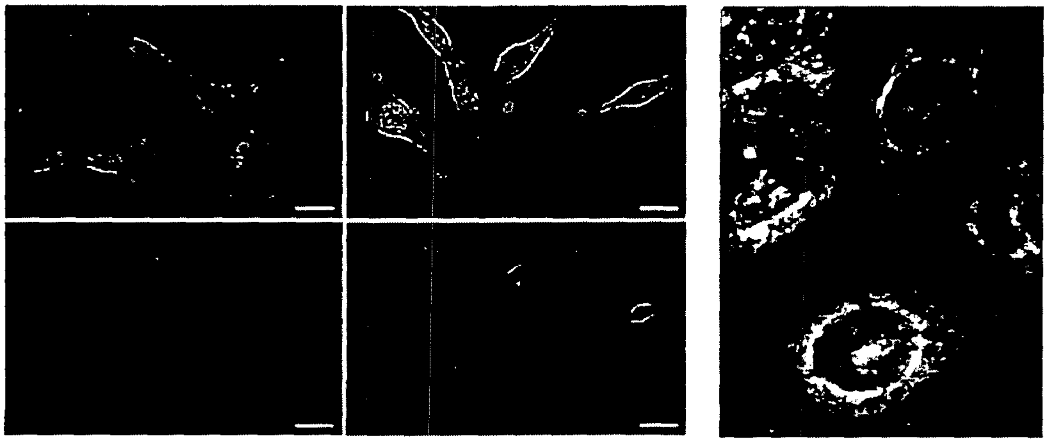

To understand how self tolerance may influence protective humoral responses to HIV-1, it is crucial to determine which self-antigens are mimicked by HIV-1 epitopes and where/when these self-antigens are exposed to T- and B lymphocytes.

This figure demonstrates that monoclonal human antibodies specific for epitopes of the HIV-1 gp41 MPER also react with self-antigens present in acetone fixed mouse 3T3 cells.

Figure 30

2F5 Specifically Binds to 43 kDa, 50 kDa, 79 kDa, and 350 kDa 3T3 (Mouse) Cellular Proteins 4%-20% gradient gel; blocking 1% FG, 2% BSA; scan intensity 2

This western blot demonstrates at least four discrete molecules can be immunoprecipitated from mouse 3T3 cells by biotinylated 2F5 antibody. The dominant species precipitated has an apparent molecular mass of approximately 50 – 54 kDa.

Conserved Self-Antigens that Carry the 2F5 Nominal Epitope

| | | |
|---|---|---|
| *2F5 MPER core epitope* | ...ELDKWA... | |
| Human | 90 ... 100 | |
| kynureninase α | ...YLEEELDKWAKIAAY... | 51 kDa |
| kynureninase β | ...YLEEELDKWAKIAAY... | |
| Mouse | | |
| kynureninase | ...YLEEELDKWAK**MG**AY... | |

the ability of 2F5 to bind a linear epitope with high affinity will be useful in identifying candidate self-antigens and speed protein identification by mass spectroscopy

A conserved mammalian protein, kynureninase (KYNU) carries the core 2F5 epitope and has a molecular mass of 51 kDa.

Figure 32

The Kynureninase H3 Domain is Highly Conserved

The 2F5 Epitope is Present in Diverse Mammals

| | |
|---|---|
| *Homo sapiens* | SLGLQPKMVKTYLEE ELDKWA KIAA |
| *Pan troglodytes* | SLGLQPKMVKTYLEE ELDKWA KIAA |
| *Mus musculus* | SLGLQPKMV**R**TYLEE ELDKWA K**M**GA |
| *Ailuropoda melanoleuca* | SLGLQPKMVKTYLEE ELDKWA K**M**GA |
| *Bos taurus* | SLGLQPKMVKTYLEE ELDKWA K**M**GA |
| *Oryctolagus cuniculus* | SLGLQPKMVKTYLEE ELDKWA K**M**GA |
| *Equus caballus* | SLGLQPKMVKTYLEE ELDKWA K**M**GG |
| *Monodelphis domestica* | SLGLQP**RN**VK**K**YLEE EL**E**KWA K**M**GG |
| *Ornithorhynchus anatinus* | SLGLQPK**K**VK**A**YLEE ELDKWA K**M**GA |
| *Gallus gallus* | SLGLQPK**K**VK**T**YL**D**E ELDKWA **RT**GV |
| *Danio rerio* | SLGLQPK**NT**KKY**ID**E EL**E**KWA KTGV |

The 2F5 core epitope is present in the KYNU of many vertebrate species.

Figure 33

Structure of Human Kynureninase (PDB 2HZP) and Location of ELDKWA Motif

"front" and "rear" images of human KYNU (180° rotation) identify the location of the conserved H3 domain and the ELDKWA motif specific ELDKWA residues are color-coded

The core 2F5 epitope is present in the conserved H3 domain of KYNU.

Structure of Human Kynureninase (PDB 2HZP) and Location of ELDKWA Motif
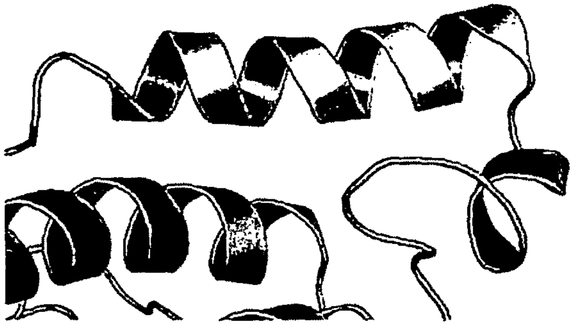
Ribbon Diagram
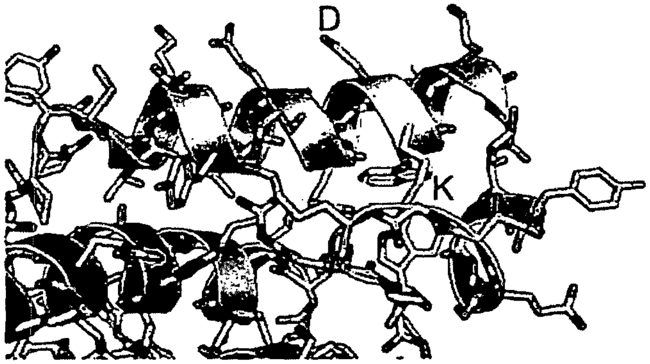
Ribbons and Sticks
Human KYNU (PDB 2HZP) shows its ELDKWA region in a well-ordered alpha helix. The DKW motif is not surface-exposed.
Illustration of the DKW residues (ELDKWA) in human KYNU.
Figure 35

Structure of Human Kynureninase (PDB 2HZP) and Location of ELDKWA Motif

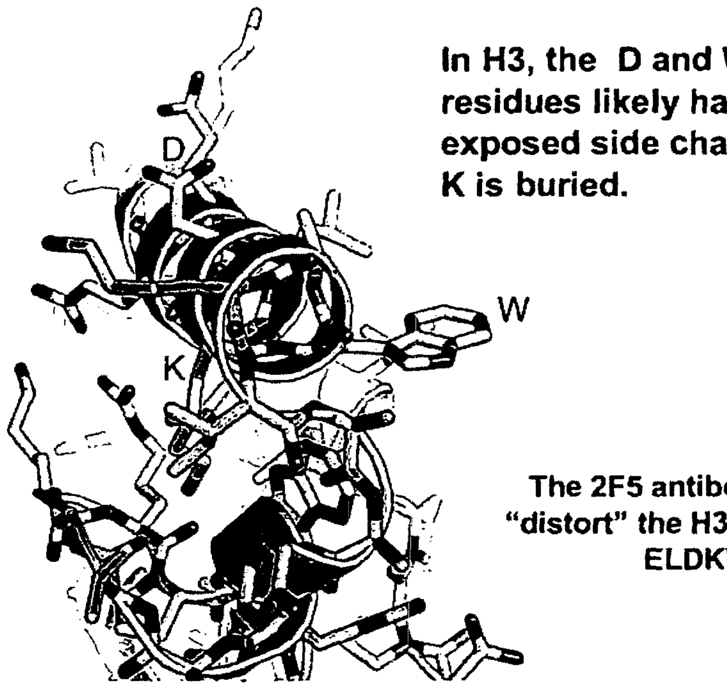

In H3, the D and W residues likely have exposed side chains, but K is buried.

The 2F5 antibody may necessarily "distort" the H3 helix to bind the core ELDKWA epitope.

This view is along the helical axis of the human KYNU H3 domain with C-terminal residues nearest the viewer and N-terminal structure receding into the background.

Binding of the 2F5 antibody to human KYNU may require a distortion of the He domain, potentially resulting in a slowed $K_{on}$.

Figure 36

Structure of Human Kynureninase (PDB 2HZP) and Location of ELDKWA Motif

The low B factors and well-ordered alpha helical fold of domain H3 could be a consequence of multimerization.

Indeed, under physiological conditions KYNU is thought to be a homodimer.

The ELDKWA motif may be available to the 2F5 antibody in KYNU monomers but is unlikely to be accessible when KYNU forms dimers.

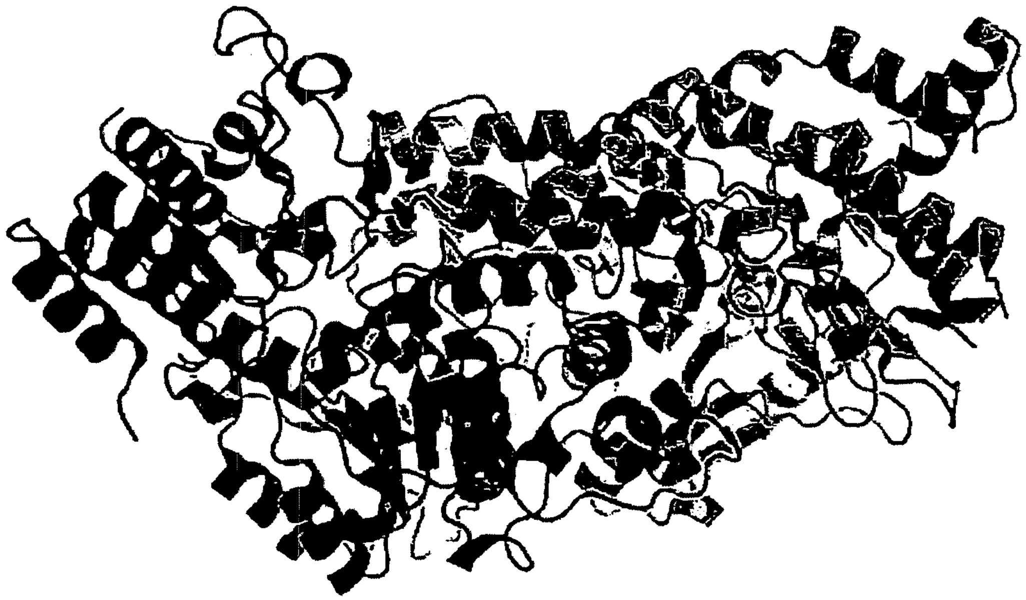

KYNU dimers likely obscure the potential 2F5 binding site.

Figure 37 rhKynureninase Monomers but not Dimers are Recognized by the 2F5 (and 4E10?) Antibodies
(non-reducing conditions)

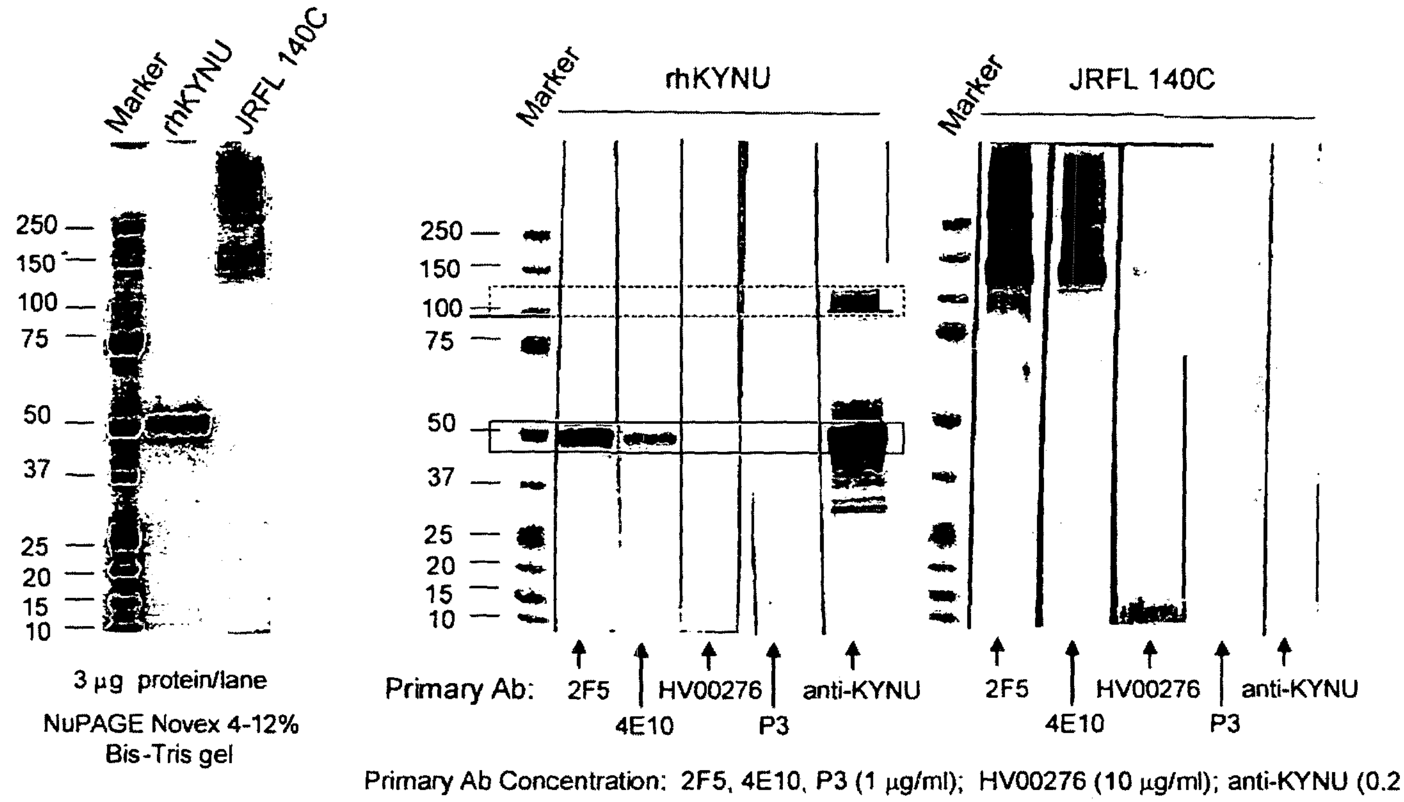

Primary Ab Concentration: 2F5, 4E10, P3 (1 µg/ml); HV00276 (10 µg/ml); anti-KYNU (0.2 µg/ml).

Secondary Ab: AP-goat anti-hIgG (1:$10^4$), AP-goat anti-moIgG (Sigma, 1:$5x10^3$), AP-rabbit anti-goIgG (Sigma, 1:$3x10^4$); all Sigma.

1 µg protein/lane

NuPAGE Novex 4-12% Bis-Tris gel

Figure 38

The 2F5 and possibly 4E10 antibodies bind to recombinant human KYNU in western blots.

Figure 39

Kynureninase is Recognized by 2F5-Family Antibodies
(reducing conditions)

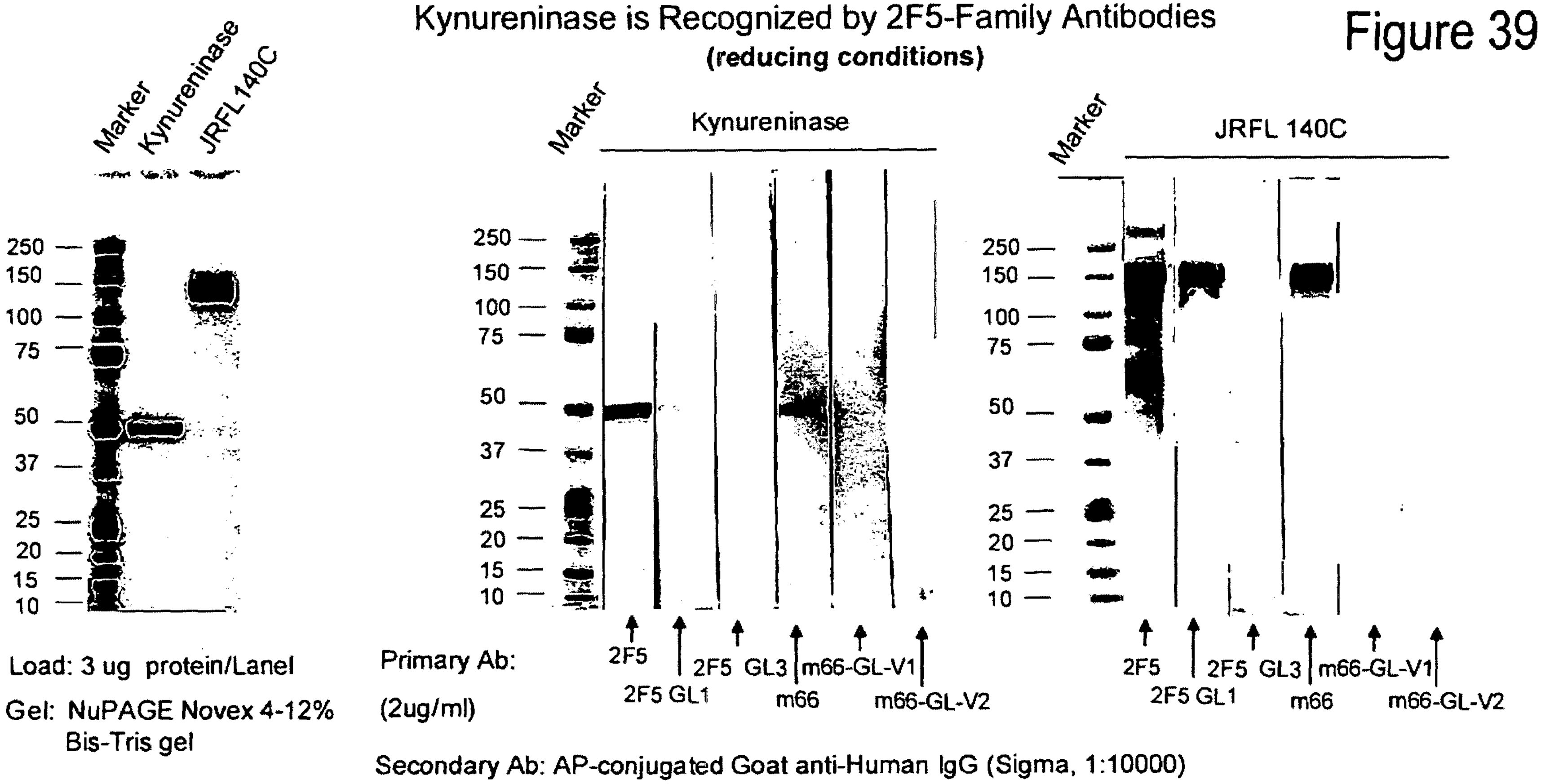

Secondary Ab: AP-conjugated Goat anti-Human IgG (Sigma, 1:10000)

Antigen: 1 ug protein/Lanel

Gel: NuPAGE Novex 4-12% Bis-Tris gel

Note: Original mAb concentration:

1). 2F5: 1.23 mg/ml 2). 2F5 GL1: 0.81 mg/ml 3). 2F5 GL3: 0.75 mg/ml
4). m66 (HV00739): 0.89 mg/ml 5). m66-GL-V1(HV00740): 0.06 mg/ml 6). m66-GL-V2 (HV00785): 0.16 mg/ml

Putative germline 2F5 antibodies also react with rhKYNU. This is an important point in that it demonstrates that KYNU could be the original ligand of B cells that eventually produced the mutated, high affinity 2F5 antibody.

Demonstration that the 2F5 antibody avidly reacts with rhKYNU in a standard ELISA.

Demonstration that the 2F5 antibody avidly reacts with a peptide (DP178-Q16L) containing the 2F5 epitope whereas anti-KYNU antibody does not.

2F5 binding to rhKYNU and DP178-Q16L is comparable in a standard ELISA.

Antibody binding in these ELISA plates is antigen specific.

13H11, a non-neutralizing mouse HIV-1 MPER monoclonal antibody that recognizes an epitope proximal to the 2F5 determinant does not bind rhKYNU.

13H11 Reacts with DP178-Q16L but not MPER-656

*human KYNU H3 sequence* YLEEELDKWAKIAAY

DP178-Q16L

YTSLIHSLIEESQNQLQEKNEQELLELDKWASLWNF

MPER-656

EQELLELDKWASLWNWFNITNWLWYIK

Mapping of residues that distinguish the binding sites of 2F5 and 13H11 monoclonal antibodies to the HIV-1 gp41 MPER.

Competitive inhibition of 2F5 binding to rhKYNU by recombinant HIV-1 gp140 env (JRFL), DP178-Q16L, and an irrelevant peptide antigen, R4A.

JRFL recombinant HIV-1 gp140 comparably inhibits the binding of 2F5 to JRFL (homologous inhibition) and to rhKYNU (heterologous inhibition). The similarity of the inhibition curves indicates that a single, common epitope is responsible for 2F5 binding to both JRFL and rhKYNU.

Figure 48

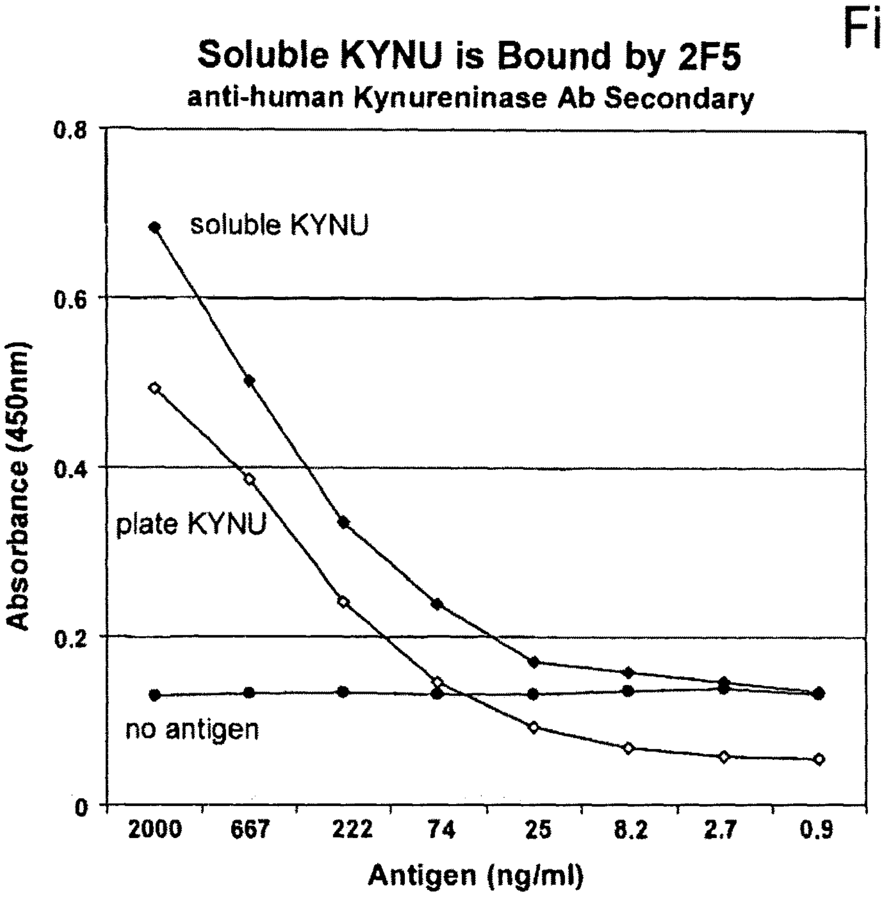

2F5 monoclonal antibody binds both plate-bound and soluble rhKYNU comparably.

Figure 49

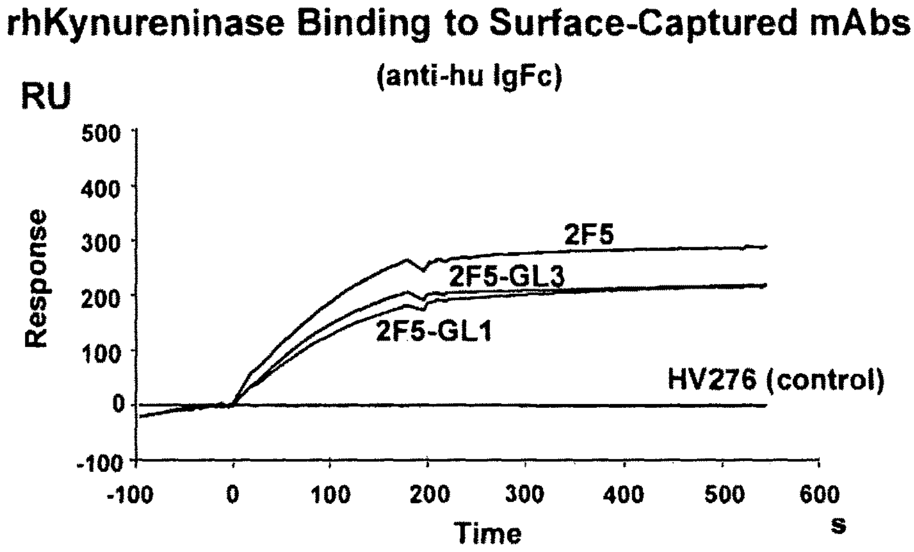

Surface plasmon resonance studies demonstrate that both 2F5 and its unmutated precursors are capable of binding avidly to rhKYNU. The slower Kon is consistent with the 2F5 antibodies distorting the native KYNU structure in order to achieve maximal interaction. Koff rates are very slow indicating that the bound KYNU interacts stably with all 2F5 types.

Figure 50A

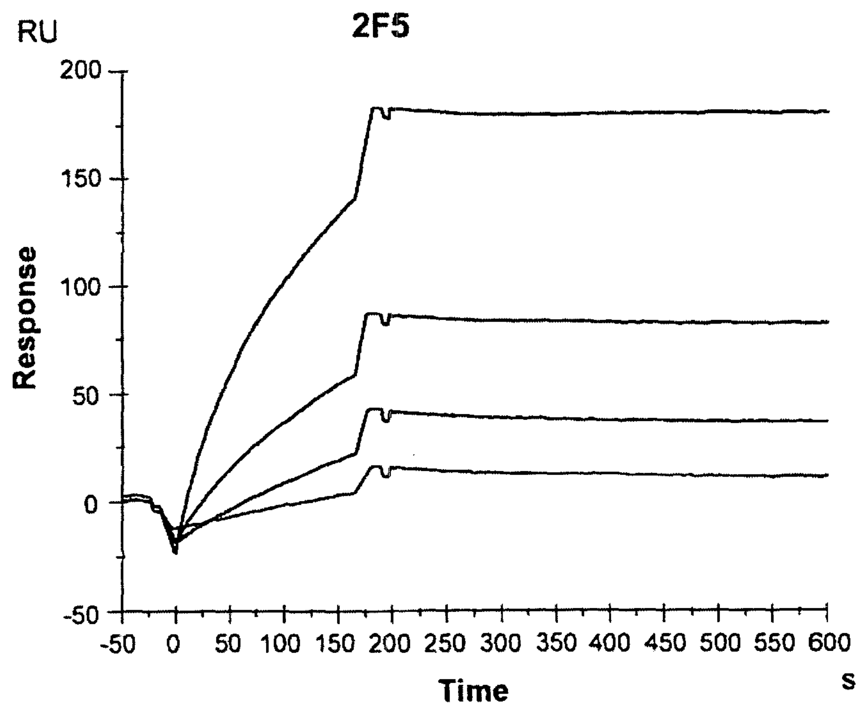

Binding of 2F5 mAb and 2F5 RUA antibodies to Kynureninase. SPR binding analysis shows that the 2F5 mAb and its RUA (2F5-GL1 and 2F5-GL3) bind to Kynureninase. Each of the antibodies was captured on a human anti-Fc immobilized sensor surface and soluble Kynureninase was injected at concentrations 50, 30, 20, and 10ug/mL. Overlay of the binding curves show specific binding of Kynureninase to each antibody. Non-specific binding was measured using a control mAb ( Synagis, anti-RSV) which showed no binding to Kynureninase.

Figure 50B

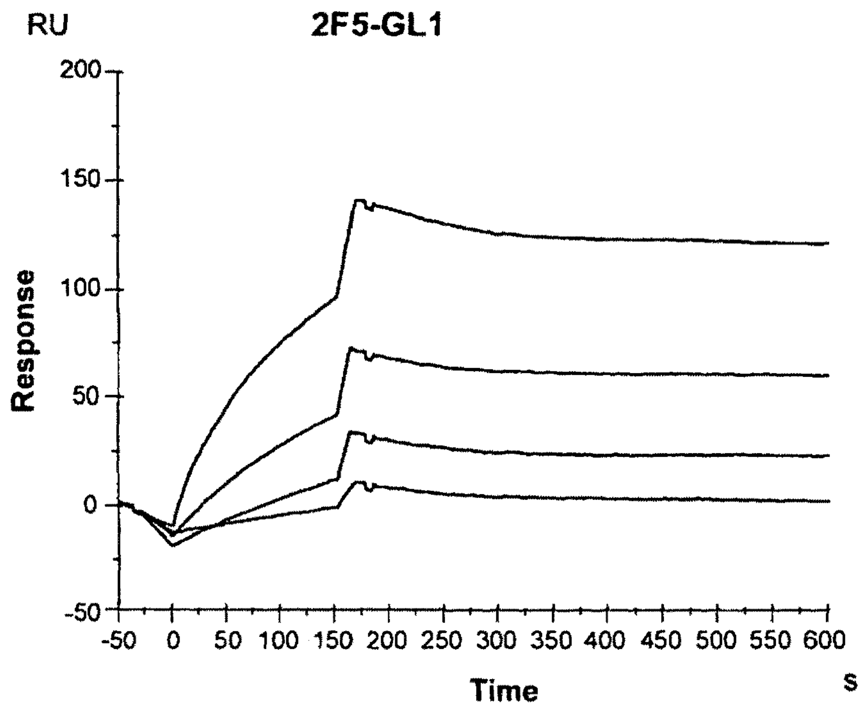

Figure 50C

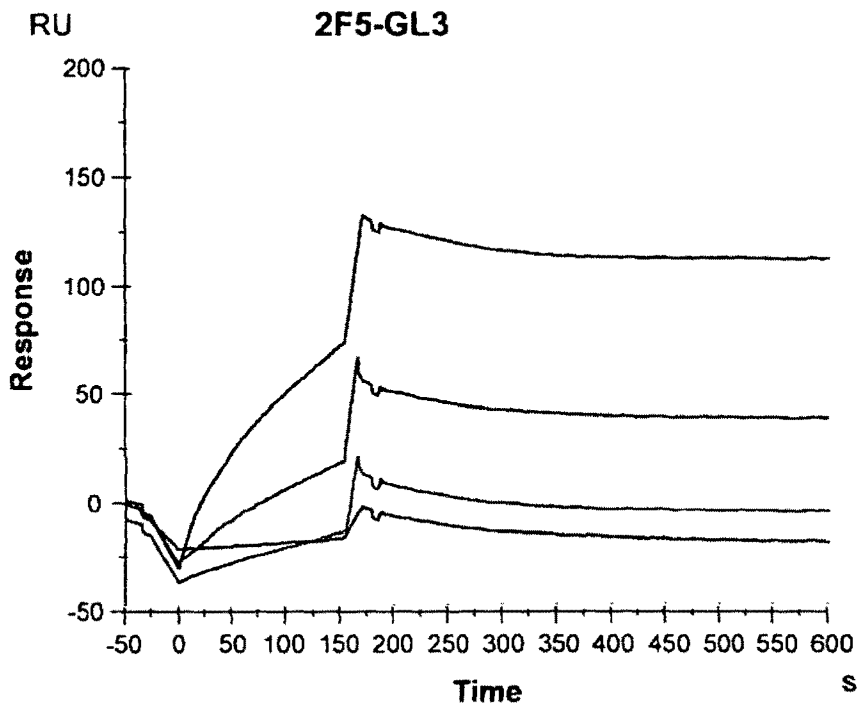

Binding of 2F5 mAb and 2F5 RUA antibodies to Kynureninase. SPR binding analysis shows that the 2F5 mAb and its RUA (2F5-GL1 and 2F5-GL3) bind to Kynureninase. Each of the antibodies was captured on a human anti-Fc immobilized sensor surface and soluble Kynureninase was injected at concentrations 50, 30, 20, and 10ug/mL. Overlay of the binding curves show specific binding of Kynureninase to each antibody. Non-specific binding was measured using a control mAb ( Synagis, anti-RSV) which showed no binding to Kynureninase.

Inhibition of 2F5 binding to 3T3 cells by recombinant HIV-1 gp140 (JRFL), and the DP178 and R4A peptides.

Figure 52A

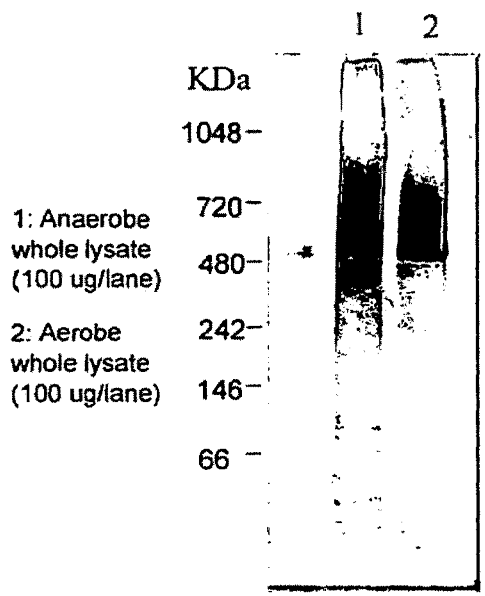

Figure 52B

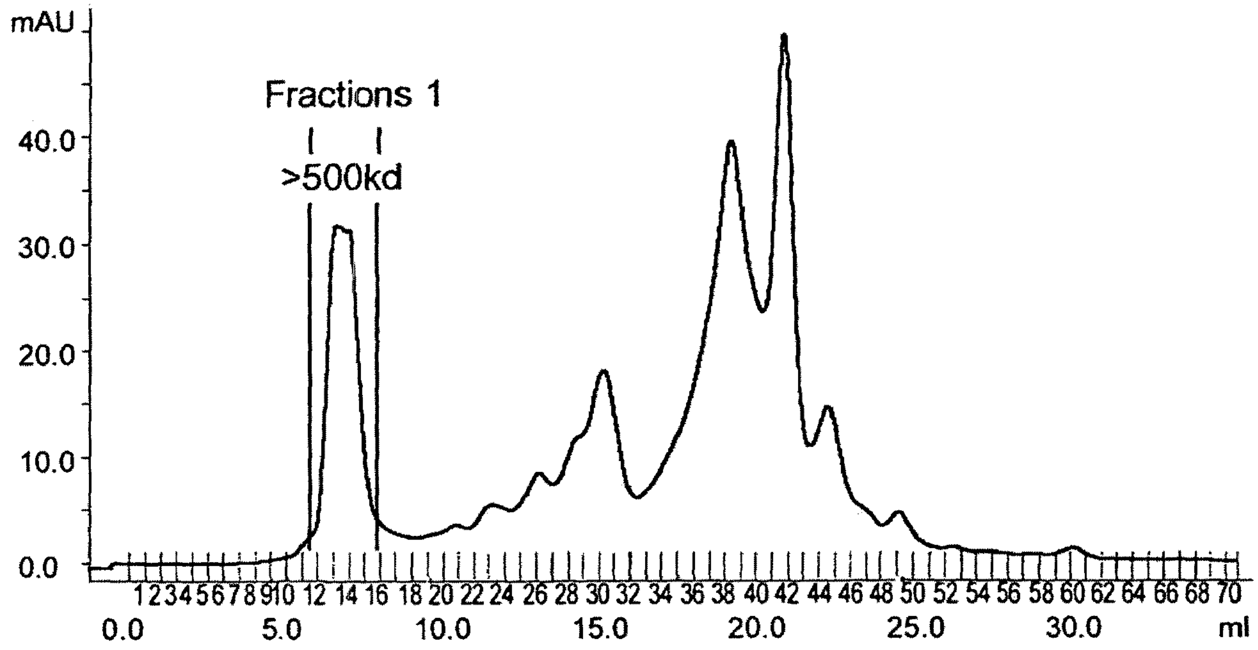

Enrichment and identification of protein band in intestinal bacterial lysate reactive to mAb HV00276. (A) Western blot analysis following Native PAGE gel run showing that mAb HV00276 binds to a ~520 kDa protein band in anaerobe and aerobe intestinal bacterial lysate. (B) Protein fractions from bacterial lysate with molecular wt ~500kDa were collected following size exclusion chromatography (SEC). (C) SEC fractions show enrichment of 520 kDa protein by coomassie blue (1) and silver staining (2) and western blotting (3, arrow) with mAb HV00276. (D) Isoelectric zoom fractionation show migration of mAb reactive protein to gel compartment A4 with pH6.2 -7 The 520 kDa band from the enriched fractions was subjected to LC-MS analysis for protein identification. RNA Polymerase β, β' and α subunits were identified by LC-MS (see MS data in next Figure).

Figure 52C

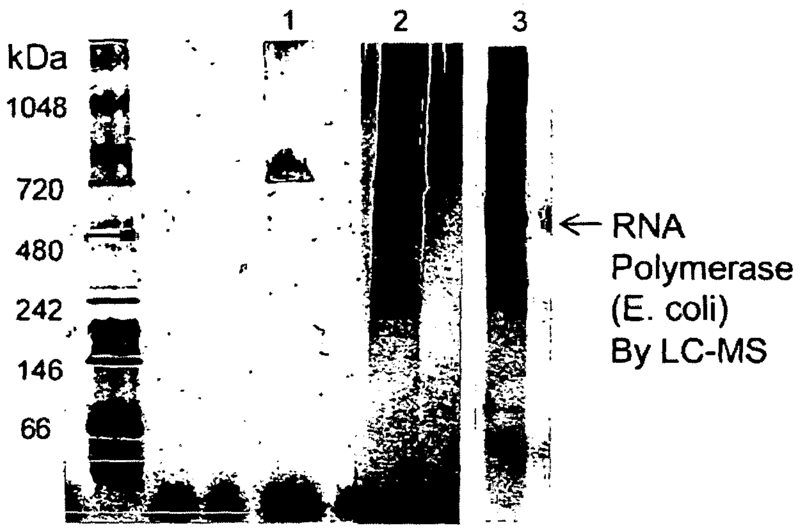

Figure 52D

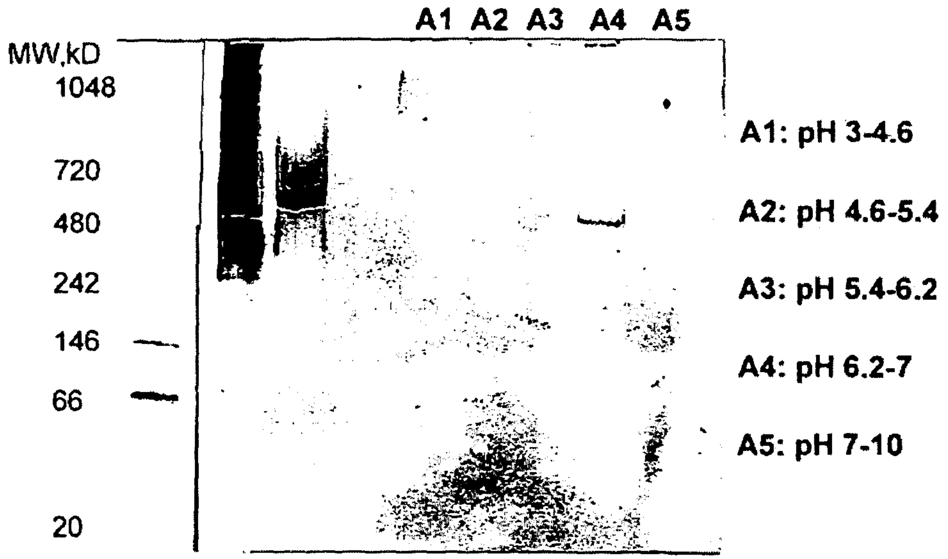

Enrichment and identification of protein band in intestinal bacterial lysate reactive to mAb HV00276. (A) Western blot analysis following Native PAGE gel run showing that mAb HV00276 binds to a ~520 kDa protein band in anaerobe and aerobe intestinal bacterial lysate. (B) Protein fractions from bacterial lysate with molecular wt ~500kDa were collected following size exclusion chromatography (SEC). (C) SEC fractions show enrichment of 520 kDa protein by coomassie blue (1) and silver staining (2) and western blotting (3, arrow) with mAb HV00276. (D) Isoelectric zoom fractionation show migration of mAb reactive protein to gel compartment A4 with pH6.2 -7 The 520 kDa band from the enriched fractions was subjected to LC-MS analysis for protein identification. RNA Polymerase β, β' and α subunits were identified by LC-MS (see MS data in next Figure).

RNA Pol beta subunit:

Figure 53A

RPOB_ECO24 (100%), 150,635.9 Da
DNA-directed RNA polymerase subunit beta OS=Escherichia coli O139:H28 (strain E24377A / ETEC) GN=rpoB PE=3 SV=1
22 unique peptides, 22 unique spectra, 24 total spectra, 232/1342 amino acids (17% coverage)

| | | | | |
|---|---|---|---|---|
| MVYSYTEKKR | IRKDFGKRPQ | VLDVPYLLSI | QLDSFQKFIE | QDPEGQYGLE |
| AAFRSVFPIQ | SYSGNSELQY | VSYRLGEPVF | DVQECQIRGV | TYSAPLRVKL |
| RLVIYEREAP | EGTVKDIKEQ | EVYMGEIPLM | TDNGTFVING | TERVIVSQLH |
| RSPGVFFDSD | KGKTHSSGKV | LYNARIIPYR | GSWLDFEFDP | KDNLFVRIDR |
| RRKLPATIIL | RALNYTTEQI | LDLFFEKVIF | EIRDNKLQME | LVPERLRGET |
| ASFDIEANGK | VYVEKGRRIT | ARHIRQLEKD | DVKLIEVPVE | YIAGKVVAKD |
| YIDESTGELI | CAANMELSLD | LLAKLSQSGH | KRIETLFTND | LDHGPYISET |
| LRVDPTNDRL | SALVEIYRMM | RPGEPPTREA | AESLFENLFF | SEDRYDLSAV |
| GRMKFNRSLL | REEIEGSGIL | SKDDIIDVMK | KLIDIRNGKG | EVDDIDHLGN |
| RRIRSVGEMA | ENQFRVGLVR | VERAVKERLS | LGDLDTLMPQ | DMINAKPISA |
| AVKEFFGSSQ | LSQFMDQNNP | LSEITHKRRI | SALGPGGLTR | ERAGFEVRDV |
| HPTHYGRVCP | IETPEGPNIG | LINSLSVYAQ | TNEYGFLETP | YRKVTDGVVT |
| DEIHYLSAIE | EGNYVIAQAN | SNLDEEGHFV | EDLVTCRSKG | ESSLFSRDQV |
| DYMDVSTQQV | VSVGASLIPF | LEHDDANRAL | MGANMQRQAV | PTLRADKPLV |
| GTGMERAVAV | DSGVTAVAKR | GGVVQYVDAS | RIVIKVNEDE | MYPGEAGIDI |
| YNLTKYTRSN | QNTCINQMPC | VSLGEPVERG | DVLADGPSTD | LGELALGQNM |
| RVAFMPWNGY | NFEDSILVSE | RVVQEDRFTT | IHIQELACVS | RDTKLGPEEI |
| TADIPNVGEA | ALSKLDESGI | VYIGAEVTGG | DILVGKVTPK | GETQLTPEEK |
| LLRAIFGEKA | SDVKDSSLRV | PNGVSGTVID | VQVFTRDGVE | KDKRALEIEE |
| MQLKQAKKDL | SEELQILEAG | LFSRIRAVLV | AGGVEAEKLD | KLPRDRWLEL |
| GLTDEEKQNQ | LEQLAEQYDE | LKHEFEKKLE | AKRRKITQGD | DLAPGVLKIV |
| KVYLAVKRRI | QPGDKMAGRH | GNKGVISKIN | PIEDMPYDEN | GTPVDIVLNP |
| LGVPSRMNIG | QILETHLGMA | AKGIGDKINA | MLKQQQEVAK | LREFIQRAYD |
| LGADVRQKVD | LSTFSDEEVM | RLAENLRKGM | PIATPVFDGA | KEAEIKELLK |
| LGDLPTSGQI | RLYDGRTGEQ | FERPVTVGYM | YMLKLNHLVD | DKMHARSTGS |
| YSLVTQQPLG | GKAQFGGQRF | GEMEVWALEA | YGAAYTLQEM | LTVKSDDVNG |
| RTKMYKNIVD | GNHQMEPGMP | ESFNVLLKEI | RSLGINIELE | DE |

LC-MS identification of RNA Polymerase β subunit peptides. 24 total spectra – 22 unique spectra resulting in 22 unique peptides were identified

Figure 53B

RNA Pol beta' subunit:

RPOC_ECO24 (100%), 155,164.1 Da

DNA-directed RNA polymerase subunit beta' OS=Escherichia coli O139:H28 (strain E24377A / ETEC) GN=rpoC PE=3 SV=1

19 unique peptides, 19 unique spectra, 22 total spectra, 196/1407 amino acids (14% coverage)

MKDLLKFLKA QTKTEEFDAI KIALASPDMI RSWSFGEVKK PETINYRTFK
PERDGLFCAR IFGPVKDYEC LCGKYKRLKH RGVICEKCGV EVTQTKVRRE
RMGHIELASP TAHIWFLKSL PSRIGLLLDM PLRDIERVLY FESYVVIEGG
MTNLERQQIL TEEQYLDALE EFGDEFDAKM GAEAIQALLK SMDLEQECEQ
LREELNETNS ETKRKKLTKR IKLLEAFVQS GNKPEWMILT VLPVLPPDLR
PLVPLDGGRF ATSDLNDLYR RVINRNNRLK RLLDLAAPDI IVRNEKRMLQ
EAVDALLDNG RRGRAITGSN KRPLKSLADM IKGKQGRFRQ NLLGKRVDYS
GRSVITVGPY LRLHQCGLPK KMALELFKPF IYGKLELRGL ATTIKAAKKM
VEREEAVVWD ILDEVIREHP VLLNRAPTLH RLGIQAFEPV LIEGKAIQLH
PLVCAAYNAD FDGDQMAVHV PLTLEAQLEA RALMMSTNNI LSPANGEPII
VPSQDVVLGL YYMTRDCVNA KGEGMVLTGP KEAERLYRSG LASLHARVKV
RITEYEKDAN GELVAKTSLK DTTVGRAILW MIVPKGLPYS IVNQALGKKA
ISKMLNTCYR ILGLKPTVIF ADQIMYTGFA YAARSGASVG IDDMVIPEKK
HEIISEAEAE VAEIQEQFQS GLVTAGERYN KVIDIWAAAN DRVSKAMMDN
LQTETVINRD GQEEKQVSFN SIYMMADSGA RGSAAQIRQL AGMRGLMAKP
DGSIIETPIT ANFREGLNVL QYFISTHGAR KGLADTALKT ANSGYLTRRL
VDVAQDLVVT EDDCGTHEGI MMTPVIEGGD VKEPLRDRVL GRVTAEDVLK
PGTADILVPR NTLLHEQWCD LLEENSVDAV KVRSVVSCDT DFGVCAHCYG
RDLARGHIIN KGEAIGVIAA QSIGEPGTQL TMRTFHIGGA ASRAAAESSI
QVKNKGSIKL SNVKSVVNSS GKLVITSRNT ELKLIDEFGR TKESYKVPYG
AVLAKGDGEQ VAGGETVANW DPHTMPVITE VSGFVRFTDM IDGQTITRQT
DELTGLSSLV VLDSAERTAG GKDLRPALKI VDAQGNDVLI PGTDMPAQYF
LPGKAIVQLE DGVQISSGDT LARIPQESGG TKDITGGLPR VADLFEARRP
KEPAILAEIS GIVSFGKETK GKRRLVITPV DGSDPYEEMI PKWRQLNVFE
GERVERGDVI SDGPEAPHDI LRLRGVHAVT RYIVNEVQDV YRLQGVKIND
KHIEVIVRQM LRKATIVNAG SSDFLEGEQV EYSRVKIANR ELEANGKVGA
TYSRDLLGIT KASLATESFI SAASFQETTR VLTEAAVAGK RDELRGLKEN
VIVGRLIPAG TGYAYHQDRM RRRAAGEAPA APQVTAEDAS ASLAELLNAG
LGGSDNE

LC-MS identification of RNA Polymerase β 'subunit peptides. 19 unique spectra resulting in 22 unique peptides were identified.

LC-MS Identification of RNA Polymerase alpha subunit:

Figure 53C

RPOA_CITK8 (100%), 36,512.1 Da
DNA-directed RNA polymerase subunit alpha OS=Citrobacter koseri (strain ATCC BAA-895 / CDC 4225-83 / SGSC4696) GN=rpoA PE=3 SV=4 unique peptides, 4 unique spectra, 4 total spectra, 34/329 amino acids (10% coverage)

MQGSVTEFLK PRLVDIEQVS STHAKVTLEP LERGFGHTLG NALRRILLSS
MPGCAVTEVE IDGVLHEYST KEGVQEDILE ILLNLKGLAV RVQGKDEVIL
TLNKSGIGPV TAADITHDGD VEIVKPQHVI CHLTDENASI SMRIKVQRGR
GYVPASTRIH SEEDERPIGR LLVDACYSPV ERIAYNVEAA RVEQRTDLDK
LVIEMETNGT IDPEEAIRRA ATILAEQLEA FVDLRDVRQP EVKEEKPEFD
PILLRPVDDL ELTVRSANCL KAEAIHYIGD LVQRTEVELL KTPNLGKKSL
TEIKDVLASR GLSLGMRLEN WPPASIADE

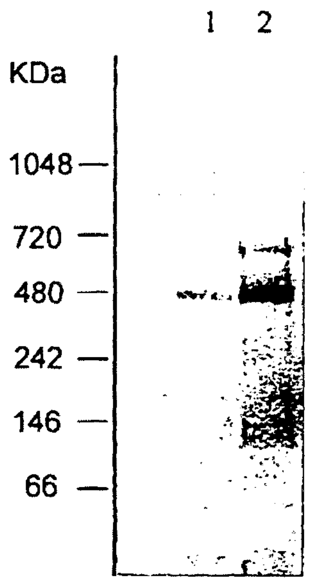

Gel: NativePAGE Novex 4-16% Bis-Tris gel

1: E coli RNA Polymerase Coreenzyme (5 ug/lane )
2: E coli RNA Polymerase Holloenzyme (5 ug/lane )

Primary Ab: HV00276 (10 ug/ml)

Mab HV00276 binds to RNA Polymerase Core protein. *E.coli* RNA Polymerase Core protein and Holoenzyme (Core protein+ σ subunit) (Epicentre Biotechnologies, Madison, WI) were run on a NativePAGE gel, and reactivity of mAb HV00276 detected by western blotting. Reactivity to both Core and Holoenzyme was detected and thus, suggesting that mAb HV00276 binds to RNA Polymerase Core protein.

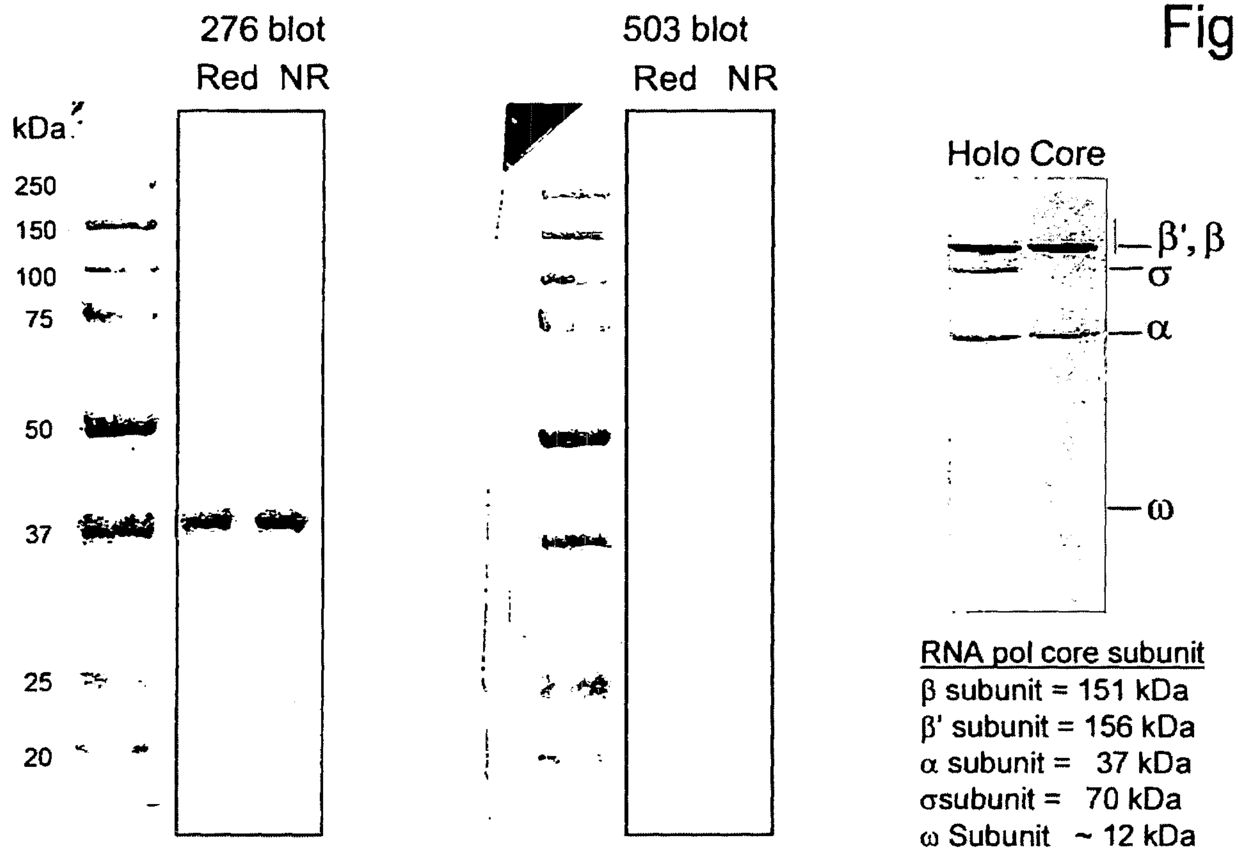

Mab HV00276 binds to the α subunit of RNA Polymerase Core protein. *E.coli* RNA Polymerase Core protein (Epicentre Biotechnologies, Madison, WI) was run on a denaturing SDS-PAGE gel under both reducing (Red) and non-reducing (NR) conditions (Left panel) . On denaturing SDS-PAGE, the individual subunits (β, β', α and ω ) of the Core protein can be resolved and visualized following Coomassie Blue staining (Right panel). Western blot analysis of the transferred gel show that 276 mAb binds only to the 37 kDa α-subunit of the RNA Polymerase Core Protein. No reactivity of HV00503 mAb, which was negative for intestinal bacterial lysate proteins, was observed with any of the Core protein subunits.

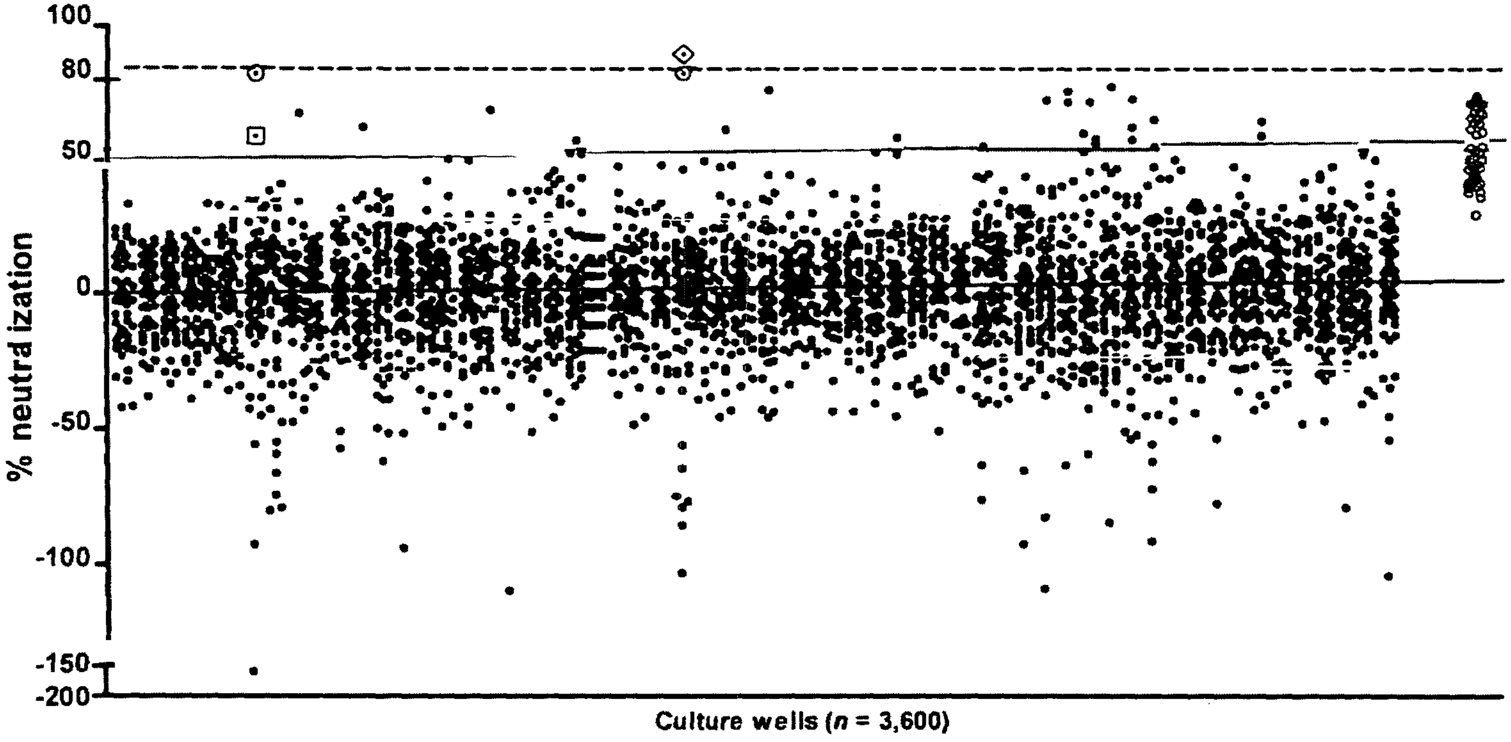

Figure 56

Neutralization screening of primary memory B cell cultures. Memory B cells from peripheral blood of CHAVI01 chronically-HIV-1 infected volunteer 707-01-021-9 were EBV-transformed and stimulated for 14 days in presence of CD40 ligand, oCpGs and CHK-2 inhibitor at a density of 8 cells/well. At the end of stimulation supernatants were tested for neutralizing activity against the reporter tier 2 clade C CAP45 virus. Solid dots represent the percentage of neutralization of each of the 3,600 cultures. Monoclonal antibodies CH01-CH05 were isolated from the cultures represented with open dotted symbols. Positive controls (HIV Ig) are shown as open circles on the far right.

Figure 57A

```
                    10        20        30        40        50        60        70
            ....|....|....|....|....|....|....|....|....|....|....|....|....|....|
0219HRUA    GAGGTGCAGCTGGTGGAGTCTGGGGGAGGTGTGGTACGGCCTGGGGGGTCCCTGAGACTCTCCTGTGCAG
CH01H       .....T...................C.AA...T........G........................AA..
CH02H       .....T.....................A.......G.....G........................AG..
CH03H       ...................................G.....G............................
CH04H       .....K........................C.CA.......G........................AA..
CH05H       .....K........................C.CA.......G........................AA..

                    80        90       100       110       120       130       140
            ....|....|....|....|....|....|....|....|....|....|....|....|....|....|
0219HRUA    CCTCTGGATTCACCTTTGATGATTATGGCATGAGCTGGGTCCGCCAAGCTCCAGGGAAGGGGCTGGAGTG
CH01H       .G..C.......T......AA...T...TT.T..T...........G..................TC...
CH02H       .G..C.......T......GA.C......C...CT.............T.........A.....AC.T..
CH03H       .G..C.......TT.....GA.C..C...T...CT.............T.........A......C.T..
CH04H       G...C..T....T......GA...T....T.CG...............G.....................
CH05H       G...C..T....T......GA...T....T.CG...............G.....................

                   150       160       170       180       190       200       210
            ....|....|....|....|....|....|....|....|....|....|....|....|....|....|
0219HRUA    GGTCTCTGGTATTAATTGGAATGGTGGTAGCACAGGTTATGCAGACTCTGTGAAGGGCCGATTCACCATC
CH01H       ....G.....C.................GA....C..............................GA..G
CH02H       ......C..G..G...............GA...GC..................G.........T.G...G
CH03H       ......C.....G...............GA...GC..................G...........G...G
CH04H       ...G.....C.C.............A...GA.T..C......G........................A...
CH05H       ...G.....C.C.............A...GA.T..C......G........................A...

                   220       230       240       250       260       270       280
            ....|....|....|....|....|....|....|....|....|....|....|....|....|....|
0219HRUA    TCCAGAGACAACGCCAAGAACTCCCTGTATCTGCAAATGAACAGTCTGAGAGCCGAGGACACGGCCTTRT
CH01H       ............T...G...T.TTG.....T..G.C...G.T.AAG..G...T...C...........C.
CH02H       ............AG...C...AT.GCA..............T.A........TG................
CH03H       ............AG...T..TAT.GCA..............A.A........T...C.............
CH04H       ............AG...C..T.T.G.C..C.....................C..............A...
CH05H       ............AG...C..T.T.G.C..C.....................C..............A...

                   290       300       310       320       330       340       350
            ....|....|....|....|....|....|....|....|....|....|....|....|....|....|
0219HRUA    ATTACTGTGCGAGAGGGACCGATTACACTATTGACGACCAGGGGATCCKTTATCAAGGTTCGGGGACCTT
CH01H       ......................................GC........A...C.................
CH02H       .......C....................G..A...........A.GAT..........A...........
CH03H       ............................G..A...........A..TT.....A................
CH04H       ....T................................T..............................T..
CH05H       ....T................................T..............................T..

                   360       370       380       390       400
            ....|....|....|....|....|....|....|....|....|....|..
0219HRUA    CTGGTACTTCGATCTCTGGGGCCGTGGCACCCTGGTCACTGTCTCCTCAGNN
CH01H       ......................................G......T......
CH02H       .............T.T..............A..............T......
CH03H       .............................................T......
CH04H       .............G..........C..............G............
CH05H       .............G..........C..............G............
```

Figure 57B

```
                     10        20        30        40        50        60        70
            ....|....|....|....|....|....|....|....|....|....|....|....|....|....|
0219LRUA    GAAATTGTGTTGACGCAGTCTCCAGGCACCCTGTCTTTGTCTCCAGGGGAAAGAGCCACCCTCTCCTGCA
CH01L_      ..............A.......................................................
CH02L_      .........................C..........G.......G.....G...................
CH03L_      .........................C..................G.........................
CH04L       ..............R..........A...............C........G..............A....

                     80        90       100       110       120       130       140
            ....|....|....|....|....|....|....|....|....|....|....|....|....|....|
0219LRUA    GGGCCAGTCAGAGTGTTAGCAGCAGCTACTTAGCCTGGTACCAGCAGAAACCTGGCCAGGCTCCCAGGCT
CH01L_      ..........C.A...CCA.CC..AA..T..C.................G.........T.....C.A..
CH02L_      ............A...CCA.CC...A..T..C........T..A..A....G.......T..........
CH03L_      ................CCA.CC..AA..T..C...........................T..........
CH04L       .................CA......A.....T..............T............C.......A..

                    150       160       170       180       190       200       210
            ....|....|....|....|....|....|....|....|....|....|....|....|....|....|
0219LRUA    CCTCATCTATGGTGCATCCAGCAGGGCCACTGGCATCCCAGACAGGTTCAGTGGCAGTGGGTCTGGGACA
CH01L_      ..............GG....C.......G.......T....G..A......C.................C
CH02L_      .......C..A...G.....C.......G........G.................G..........A.TG
CH03L_      ..........A...G.....CT......G........G.................G..........A.T.
CH04L       ..............GG....C..................TA.T..A.......C.G.C............

                    220       230       240       250       260       270       280
            ....|....|....|....|....|....|....|....|....|....|....|....|....|....|
0219LRUA    GACTTCACTCTCACCATCAGCAGACTGGAGCCTGAAGATTTTGCAGTGTATTACTGTCAGCAGTATGGTA
CH01L_      ....................TC..G....C.................T.....................G
CH02L_      C..................C....G......................C....T......A..A..C...G
CH03L_      C..................C....G...........................T......A..A..C...G
CH04L       C.G............G...A..........G.............G..A.....................C

                    290       300       310       320
            ....|....|....|....|....|....|....|....|..
0219LRUA    GCTCCCCGTACACGTTCGGCCAAGGGACCAAGGTGGAAATCA
CH01L_      ..........................................
CH02L_      .T..T..C..............G.......G.......C...
CH03L_      .T.....C..............G...............C...
CH04L       .....................................G....
```

Figure 57C

```
               10        20        30        40        50        60        70
       ....|....|....|....|....|....|....|....|....|....|....|....|....|....|
CH05L  ..C..CCA.W....C.........TC.T........GCA...GTG..A..C....T....A..A.T...C

               80        90       100       110       120       130       140
       ....|....|....|....|....|....|....|....|....|....|....|....|....|....|
CH05L  ....A......G.CA....A.ATGAT.TAGGCTGG.ATC.G...A..CC.GG.AAAGCCCA.AAGCTC..

              150       160       170       180       190       200       210
       ....|....|....|....|....|....|....|....|....|....|....|....|....|....|
CH05L  .A..TATGC..CAT.TAGTTTACAAAGTGGG.T.CCAT..CGGTTCAG.G.CA.TG.GTCTGGCACAGAT

              220       230       240       250       260       270       280
       ....|....|....|....|....|....|....|....|....|....|....|....|....|....|
CH05L  TT.ACTCTCAC..T..G....CTG.A.CCTGAA..TTT.GCAA.TTAT..C.GTCTA..AG.T..CA..T

              290       300       310       320
       ....|....|....|....|....|....|....|....|....
CH05L  A.C.GTATACTTTTGG.CAGGGACC.A.CT..A.ATC.AGCGA
```

V-heavy and V-light chain alignments of monoclonal antibodies CH01-CH05. Alignment of the sequences of the CH01-CH05 V-heavy chains (a), CH01-CH04 (b) and CH05 (c) V-light chains. The putative reverted unmutated ancestor sequence was used as template for both the V-heavy and the CH01-CH04 V-light alignments. Since CH05 has an unrelated Vκ 1~6 chain, it is shown separately.

Phylogenetic tree of the V-heavy chains of the CH01-CH05 monoclonal antibodies.

Figure 59

```
                    10        20        30        40        50        60        70
            ....|....|....|....|....|....|....|....|....|....|....|....|....|....|
0219-RUA1   GAGGTGCAGCTGGTGGAGTCTGGGGGAGGTGTGGTACGGCCTGGGGGGTCCCTGAGACTCTCCTGTGCAG
0219-RUA2   ......................................................................
CH01-RUA1   ......................................................................
CH02-RUA1   ......................................................................
CH02-RUA2   ......................................................................
CH03-RUA1   ......................................................................
CH03-RUA2   ......................................................................
CH03-RUA3   ......................................................................
CH03-RUA4   ......................................................................
CH04-RUA1   .....t................................................................
CH04-RUA2   ......................................................................

                    80        90       100       110       120       130       140
            ....|....|....|....|....|....|....|....|....|....|....|....|....|....|
0219-RUA1   CCTCTGGATTCACCTTTGATGATTATGGCATGAGCTGGGTCCGCCAAGCTCCAGGGAAGGGGCTGGAGTG
0219-RUA2   ......................................................................
CH01-RUA1   ......................................................................
CH02-RUA1   ......................................................................
CH02-RUA2   ......................................................................
CH03-RUA1   ......................................................................
CH03-RUA2   ......................................................................
CH03-RUA3   ......................................................................
CH03-RUA4   ......................................................................
CH04-RUA1   ......................................................................
CH04-RUA2   ......................................................................

                   150       160       170       180       190       200       210
            ....|....|....|....|....|....|....|....|....|....|....|....|....|....|
0219-RUA1   GGTCTCTGGTATTAATTGGAATGGTGGTAGCACAGGTTATGCAGACTCTGTGAAGGGCCGATTCACCATC
0219-RUA2   ......................................................................
CH01-RUA1   ......................................................................
CH02-RUA1   ......................................................................
CH02-RUA2   ......................................................................
CH03-RUA1   ......................................................................
CH03-RUA2   ......................................................................
CH03-RUA3   ......................................................................
CH03-RUA4   ......................................................................
CH04-RUA1   ......................................................................
CH04-RUA2   ......................................................................

                   220       230       240       250       260       270       280
            ....|....|....|....|....|....|....|....|....|....|....|....|....|....|
0219-RUA1   TCCAGAGACAACGCCAAGAACTCCCTGTATCTGCAAATGAACAGTCTGAGAGCCGAGGACACGGCCTTRT
0219-RUA2   ......................................................................
CH01-RUA1   ......................................................................
CH02-RUA1   ......................................................................
CH02-RUA2   ......................................................................
CH03-RUA1   ......................................................................
CH03-RUA2   ......................................................................
CH03-RUA3   ......................................................................
CH03-RUA4   ......................................................................
CH04-RUA1   ......................................................................
CH04-RUA2   ......................................................................

                   290       300       310       320       330       340       350
            ....|....|....|....|....|....|....|....|....|....|....|....|....|....|
0219-RUA1   ATTACTGTGCGAGAGGGACCGATTACACTATTGACGACCAGGGGATCCTTTATCAAGGTTCGGGGACCTT
0219-RUA2   ................................................G.....................
CH01-RUA1   ..C...................................GC........A...CT.T.............A
CH02-RUA1   ..C.........................G..A...........A.GATA...CT.T.............A
CH02-RUA2   ..C.........................G..A...........A.GATA...CT.T.............A
CH03-RUA1   ..C.........................G..A...........A..TTA...CT.T.............A
CH03-RUA2   ..C.........................G..A...........A..TTA...CT.T.............A
CH03-RUA3   ..C.........................G..A...........A..TTA...CT.T.............A
```

Figure 59 cont'd

```
                    360       370       380       390       400       410       420
            ....|....|....|....|....|....|....|....|....|....|....|....|....|....|
0219-RUA1   CTGGTACTTCGATCTCTGGGGCCGTGGCACCCTGGTCACTGTCTCCTCAG~~~GAAATTGTGTTGACGCA
0219-RUA2   ..................................................~~~.................
CH01-RUA1   ..................................................~~~~................
CH02-RUA1   ..................................................~~~~................
CH02-RUA2   ..................................................~~~~................
CH03-RUA1   ..................................................~~~~................
CH03-RUA2   ..................................................~~~~................
CH03-RUA3   ..................................................~~~~................
CH03-RUA4   ..................................................~~~~................
CH04-RUA1   ..................................................~~~.................
CH04-RUA2   ..................................................~~~.................

                    430       440       450       460       470       480       490
            ....|....|....|....|....|....|....|....|....|....|....|....|....|....|
0219-RUA1   GTCTCCAGGCACCCTGTCTTTGTCTCCAGGGGAAAGAGCCACCCTCTCCTGCAGGGCCAGTCAGAGTGTT
0219-RUA2   ......................................................................
CH01-RUA1   ......................................................................
CH02-RUA1   ........C.............................................................
CH02-RUA2   ........C.............................................................
CH03-RUA1   ......................................................................
CH03-RUA2   ......................................................................
CH03-RUA3   ........C.............................................................
CH03-RUA4   ........C.............................................................
CH04-RUA1   ......................................................................
CH04-RUA2   ......................................................................

                    500       510       520       530       540       550       560
            ....|....|....|....|....|....|....|....|....|....|....|....|....|....|
0219-RUA1   AGCAGCAGCTACTTAGCCTGGTACCAGCAGAAACCTGGCCAGGCTCCCAGGCTCCTCATCTATGGTGCAT
0219-RUA2   ......................................................................
CH01-RUA1   ......................................................................
CH02-RUA1   ................................................................A.....
CH02-RUA2   ................................................................A.....
CH03-RUA1   ......................................................................
CH03-RUA2   ......................................................................
CH03-RUA3   ................................................................A.....
CH03-RUA4   ................................................................A.....
CH04-RUA1   ......................................................................
CH04-RUA2   ......................................................................

                    570       580       590       600       610       620       630
            ....|....|....|....|....|....|....|....|....|....|....|....|....|....|
0219-RUA1   CCAGCAGGGCCACTGGCATCCCAGACAGGTTCAGTGGCAGTGGGTCTGGGACAGACTTCACTCTCACCAT
0219-RUA2   ......................................................................
CH01-RUA1   ......................................................................
CH02-RUA1   ......................................................................
CH02-RUA2   ......................................................................
CH03-RUA1   ......................................................................
CH03-RUA2   ......................................................................
CH03-RUA3   ......................................................................
CH03-RUA4   ......................................................................
CH04-RUA1   ......................................................................
CH04-RUA2   ......................................................................

                    640       650       660       670       680       690       700
            ....|....|....|....|....|....|....|....|....|....|....|....|....|....|
0219-RUA1   CAGCAGACTGGAGCCTGAAGATTTTGCAGTGTATTACTGTCAGCAGTATGGTAGCTCCCCGTACACGTTC
0219-RUA2   ......................................................................
CH01-RUA1   ....................................................G.T.....C.........
CH02-RUA1   ..............................C..............A..C...G.T..T..C.....T..T
```

```
CH02-RUA2  ..............................C..............A..C...G.T.....C.........
CH03-RUA1  ....................................................G.T.....C.....T..T
CH03-RUA2  ....................................................G.T.....C.........
CH03-RUA3  ..............................C..............A..C...G.T..T..C.....T..T
CH03-RUA4  ..............................C..............A..C...G.T.....C.........
CH04-RUA1  ......................................................................
CH04-RUA2  ......................................................................

                    710       720
           ....|....|....|....|....|
0219-RUA1  GGCCAAGGGACCAAGGTGGAAATCA
0219-RUA2  .........................
CH01-RUA1  .........................
CH02-RUA1  .....G.........C....G....
CH02-RUA2  .........................
CH03-RUA1  .....G.........C....G....
CH03-RUA2  .........................
CH03-RUA3  .....G.........C....G....
CH03-RUA4  .........................
CH04-RUA1  .........................
CH04-RUA2  .........................
```

Alignment of the inferred putative reverted unmutated ancestor antibodies. The alignment of all the putative reverted unmutated ancestor antibodies inferred by applying the V-heavy chains are separated from the V-light chains by "~~~"

Figure 59 cont'd

Binding of Reverted Unmutated Ancestors of CH01, CH02, CH03 Quarternary Broad Neutralizing Antibodies to A244 gp120

Potential Relevance of gD Immunogenicity

HSV-1 KYALVDASLKMADPNRFRGKDLPVLDQLTDPP

HSV-2 KYALVDPSLKMADPNRFRGKNLPVLDQLTDPP

1. Motif for gp120 binding to a4b7 is LDV and LDI

HSV gD LPV and LDQ

*This raises the question whether antibodies to gD can block binding of HIV gp120 to a4b7.*

2. LDQ of HSV-gD is a receptor binding site for host cellular receptor heparan sulfate.

*This raises the question whether antibodies to gD can block binding HIV Env to heparan sulfate.*

3. The LDQ is also the receptor binding site for the second HSV receptor HVEM. The anti-HSV antibody response to LDQ could be protective against HSV.

*Therefore an anti-gD response could be protective for HIV by reducing active infection.*

Figure 66

HEP-2 binding

Effect of kifunensine treatment on the ability of CH01 to mediate neutralization – Superimposition of the sequence of CH01 (here called 1-27-G2) with the PG16 Fab Alignment 1

Dfire score = 0.466

PG16 Fab structure 1-27-G2 sequence threaded onto PG16 Fab structure

Superposition of PG16 Fab structure (red) and 1-27-G2 model (green)

TABLE 4

The preferential neutralization of tier 2 viruses over tier 1 viruses is important in that previous work demonstrated that broad neutralization of easy-to-neutralize tier 1 isolates does not translate into breadth against more difficult-to-neutralize tier 2 isolates and, therefore, those kinds of antibodies could be of limited help in preventing or controlling HIV-1 infection.

| Virus | Clade | Tier | Fie-big |
|---|---|---|---|
| MN.3 | B | 1A | 7 |
| SF162.LS | B | 1A | 7 |
| MW965.26 | C | 1A | 7 |
| TH023.6 | AE | 1A | 7 |
| Bal.26 | B | 1B | 7 |
| Bx08.16 | B | 1B | 7 |
| Np03.13 | AE | 1B | 7 |
| CN244.ecl | AE | 2 | 7 |
| 6535.3 | B | 2 | 5 |
| QH0692.42 | B | 2 | 5 |
| PVO.4 | B | 2 | 3 |
| RHPA4259.7 | B | 2 | 4 |
| SC422661.8 | B | 2 | 4 |
| TRO.11 | B | 2 | 3 |
| AC10.0.29 | B | 2 | 3 |
| THRO4156.18 | B | 2 | 2 |
| REJO4541.67 | B | 2 | 2 |
| TRJO4551.58 | B | 2 | 2 |
| WITO4160.33 | B | 2 | 2 |
| CAAN5342.A2 | B | 2 | 5 |
| WEAU_d15_410_5017 | B (T/F) | 2 | 2 |
| 1006_11_C3_1601 | B (T/F) | 2 | 3 |
| 1054_07_TC4_1499 | B (T/F) | 2 | 2 |
| 1056_10_TA11_1826 | B (T/F) | 2 | 2 |

*FIG. 70*

TABLE 4-1 (CONTINUED)

| MoAbs from 0219 | | | | | Other bNabs | | | | | |
|---|---|---|---|---|---|---|---|---|---|---|
| Clonal family | | | | | Quaternary | | CD4bs | CHO | MPER | |
| CH01 | CH02 | CH03 | CH04 | CH05 | PG9 | PG16 | IgG1b12 | 2G12 | 2F5 | 4E10 |
| >50 | >90 | >48 | >50 | >50 | | | | >25 | | 0.1 |
| >50 | >90 | >48 | >50 | >50 | | | 0.3 | 0.7 | 0.9 | 1.6 |
| >50 | >90 | >48 | >50 | >50 | | | 0.2 | >25 | >25 | |
| >50 | >50 | >31 | >50 | >50 | | | | | | |
| 4.7 | >90 | >48 | >50 | >50 | | | 0.2 | 0.9 | 0.8 | 0.7 |
| 0.6 | 9.56 | 6.81 | >50 | >50 | | | 4.2 | 5.4 | 2.6 | 2.4 |
| >50 | >50 | >31 | >50 | >50 | | | | | | |
| | | | | | | | | | | |
| 0.6 | >90 | 8.56 | >50 | >50 | | | 17.5 | 2 | 1.9 | 0.2 |
| >50 | >90 | >48 | >50 | >50 | | | 0.3 | 2.8 | ? | 1.4 |
| 30.6 | >90 | 11.34 | 8.04 | 9.7 | 10.56 | 15.3 | >50 | 1.2 | >50 | 6.5 |
| 13.5 | >90 | ? | 0.21 | 0.3 | 22.5 | ? | 0.1 | >50 | 12 | 6.9 |
| >50 | >70 | >28 | >50 | >50 | 10.55 | ? | 0.2 | 2.1 | ? | 10.9 |
| >50 | >70 | >28 | >50 | >50 | 43.2 | 1.9 | >50 | 1.2 | >50 | 6.5 |
| 0.7 | >70 | 2.4 | 9.46 | 1.4 | 0.12 | | 1.9 | >50 | 1.3 | 0.3 |
| 4.5 | >70 | 15.5 | >50 | >50 | 24.5 | 6.8 | 0.5 | >50 | >50 | 0.3 |
| 0.2 | 0.7 | 0.6 | >50 | >50 | | | 0.7 | >50 | 10.6 | 0.7 |
| >50 | >70 | >28 | >50 | >50 | 0.5 | 1.0 | >50 | >50 | >50 | 4.5 |
| | | | | | | | 3.1 | 1.1 | 0.5 | 0.3 |
| >50 | >70 | >28 | >50 | >50 | 4.6 | 1.8 | >50 | >50 | 3.6 | 2.7 |
| >50 | >70 | >28 | >50 | >50 | 4.1 | 0.4 | 1.1 | 0.2 | 0.9 | 1 |
| >50 | >70 | >28 | >50 | >50 | 0.37 | >50 | 3.9 | 2.6 | 7.5 | 6.1 |
| >50 | >50 | >28 | >50 | >50 | >50 | >50 | 11.1 | >25 | >25 | 1.1 |
| >50 | >50 | >28 | >50 | 5.53 | 6.3 | 0.32 | 2 | 22.9 | 0.4 | 0.6 |

*FIG. 70 CON'T*

TABLE 4-2 (CONTINUED)

| | | | |
|---|---|---|---|
| 1012_11_TC21_3257 | B (T/F) | 2 | 3 |
| 6240_08_TA5_4622 | B (T/F) | 2 | 2 |
| 6244_13_B5_4576 | B (T/F) | 2 | 2 |
| 62357_14_D3_4589 | B (T/F) | 2 | 2 |
| SC05_8C11_2344 | B (T/F) | 2 | 2 |
| Du156.12 | C | 2 | 3 |
| Du422.1 | C | 2 | 5 |
| ZM197M.PB7 | C | 2 | 5 |
| CAP45.2.00.G3 | C | 2 | 6 |
| Du172.17 | C | 2 | 6 |
| ZM214M.PL15 | C | 2 | 5 |
| ZM233M.PB6 | C | 2 | 5 |
| ZM249M.PL1 | C | 2 | 2 |
| ZM53M.PB12 | C | 2 | 5 |
| ZM109F.PB4 | C | 2 | 5 |
| ZM135M.PL10a | C | 2 | 5 |
| CAP210.2.00.E8 | C | 2 | 4 |
| Ce1086_B2 | C (T/F) | 2 | 1 |
| Ce0393_C3 | C (T/F) | 2 | 4 |
| Ce1176_A3 | C (T/F) | 2 | 1 |
| Ce1172_H1 | C (T/F) | 2 | 1 |
| Ce2010_F5 | C (T/F) | 2 | 4 |
| Ce0682_E4 | C (T/F) | 2 | 1 |
| Ce2060_G9 | C (T/F) | 2 | 1 |

*FIG. 70 CON'T*

TABLE 4-3 (CONTINUED)

| | | | | | | | | | | |
|---|---|---|---|---|---|---|---|---|---|---|
| 5.8 | >50 | 5.19 | 5.51 | 8.12 | (?) | | >25 | >25 | 2.4 | 3.5 |
| >50 | >50 | >28 | >50 | >50 | 1.7 | >50 | >25 | 0.6 | 12.8 | 8.3 |
| >50 | >50 | >28 | >50 | >50 | >50 | >50 | >25 | >25 | >25 | 0.5 |
| >50 | >50 | >28 | >50 | >50 | >50 | >50 | >25 | >25 | 3.7 | 1.9 |
| 9.3 | 18.3 | 5.76 | 3.74 | 3.52 | 0.89 | | 3.1 | 18.7 | 3.7 | 6.4 |
| 0.5 | >90 | 0.3 | 0.29 | (?) | | | 0.8 | >50 | >50 | 0.2 |
| >50 | >90 | >50 | >50 | 20.1 | 0.81 | 0.26 | 0.2 | >50 | >50 | 0.(?) |
| >50 | >90 | >28 | 31.95 | 35.3 | 0.90 | 1.5 | 19.9 | >50 | 12.3 | 0.5 |
| | | | | | | | 0.7 | >50 | >50 | 2.6 |
| 22.4 | 25.64 | 7.18 | 7.09 | 8.62 | 0.61 | | 1 | >50 | >50 | 0.3 |
| >50 | >50 | >28 | >50 | >50 | >50 | >50 | 3 | >50 | >50 | 4 |
| | | | | | | | >50 | >50 | >50 | 1.2 |
| >50 | 2.25 | 0.(?) | 0.49 | 0.82 | 0.17 | 0.13 | 3.2 | >50 | >50 | 2.1 |
| >50 | >50 | >28 | >50 | >50 | | | 25.9 | >50 | >50 | 7 |
| >50 | >50 | >28 | >50 | >50 | 0.26 | 7.0 | >50 | >50 | >50 | 0.6 |
| >50 | >50 | >28 | >50 | >50 | 20.6 | >50 | >50 | >50 | >50 | 0.6 |
| 1.1 | >50 | 12.62 | 2.23 | 3.(?) | 0.27 | | 20.4 | >50 | >50 | 1.2 |
| >50 | >50 | >28 | >50 | >50 | >50 | >50 | 14.8 | >25 | >25 | 0.3 |
| 2.2 | 1.7 | 1.16 | 1.04 | 0.92 | | | >25 | >25 | >25 | 2.4 |
| | 0.13 | | | | | | >25 | >25 | >25 | 4.6 |
| >50 | >50 | >28 | >50 | >50 | >50 | >50 | 10.4 | >25 | 17.2 | >25 |
| >50 | >50 | >28 | >50 | >50 | 0.20 | | 1.6 | >25 | >25 | 2.4 |
| >50 | >50 | >31 | >50 | >50 | | | >25 | >25 | >25 | 2.4 |

*FIG. 70 CON'T*

TABLE 4-4 (CONTINUED)

| | | | |
|---|---|---|---|
| Ce703010054_2A2 | C (T/F) | 2 | 5 |
| BF1266.431a | C (T/F) | 2 | 1 |
| 246F CIG | C (T/F) | 2 | 2 |
| 249M B10 | C (T/F) | 2 | 4 |
| ZM247v1(Rev-) | C (T/F) | 2 | 2 |
| 7030102001E5(Rev-) | C (T/F) | 2 | 1 |
| 1394C9G1(Rev-) | C (T/F) | 2 | 1 |
| Ce704809221_11B3 | C (T/F) | 2 | 1 |
| Q23.17 | A | 2 | 6 |
| Q259.d2.17 | A | 2 | 5 |
| Q769.d22 | A | 2 | 5 |
| Q842.d12 | A | 2 | 5 |
| Q461.e2 | AD | 2 | 5 |
| 191955_A11 | A (T/F) | 2 | 4 |
| 191084 B7-19 | A (T/F) | 2 | 4 |
| 9004SS_A3_4 | A (T/F) | 2 | 4 |
| 21020_13 | A | 2 | 6 |
| R18553_E1 | A | 2 | 5 |
| 851891.4.15 | A | 2 | 1 |
| T257-31 | CRF02_AG | 2 | 5 |
| 928-28 | CRF02_AG | 2 | 5 |
| 263-8 | CRF02_AG | 2 | 7 |
| T250-4 | CRF02_AG | 2 | 7 |
| T251-18 | CRF02_AG | 2 | 7 |

*FIG. 70 CON'T*

TABLE 4-5 (CONTINUED)

| | | | | | | | | | | |
|---|---|---|---|---|---|---|---|---|---|---|
| >50 | >50 | >31 | >50 | >50 | | | >25 | >25 | >25 | 18.9 |
| 1.5 | 0.97 | 0.39 | 1.28 | | | | >25 | >25 | >25 | 6.4 |
| >50 | >50 | >31 | >50 | >50 | >50 | >50 | 22.7 | 13.6 | >25 | 7.9 |
| >50 | >50 | >31 | >50 | >50 | | | 23.6 | >25 | >25 | 20 |
| >50 | >50 | >31 | >50 | >50 | 0.? | | >25 | >25 | >25 | 0.93 |
| >50 | >50 | >31 | >50 | >50 | >50 | >50 | >25 | 2.1 | >25 | 23.5 |
| 0.5 | 0.57 | 0.21 | 0.27 | 0.18 | | | 19 | >25 | >25 | 2.26 |
| 0.7 | 0.29 | 0.21 | 0.44 | 0.27 | | | >25 | >25 | >25 | 4.4 |
| | | | | | | | >50 | >50 | 2.9 | 1.3 |
| >50 | >90 | >28 | >50 | >50 | | | >50 | >50 | 7.1 | 8.5 |
| >50 | >90 | >28 | >50 | >50 | | | >50 | >50 | 0.5 | 0.4 |
| 1.3 | 38.8 | 6.1 | 0.18 | 7.3 | | | >50 | >50 | 5.2 | 2 |
| >50 | >50 | >31 | >50 | >50 | 1.5 | 1.8 | >50 | >50 | 4.1 | 2 |
| | 0.19 | | | | | | 22.7 | 21.2 | 0.5 | 0.3 |
| 0.6 | 4.15 | 0.22 | 0.58 | 0.38 | | | >25 | >25 | 14.8 | 19.3 |
| 1.2 | 14.42 | 0.54 | 1.71 | 1.38 | | | >25 | >25 | 0.8 | 2.3 |
| >50 | >50 | >31 | >50 | >50 | | | 19.8 | >25 | 4 | 1.7 |
| 0.5 | 0.12 | | | | | | >25 | >25 | 2.5 | 1.5 |
| 0.1 | 3.55 | 0.4 | 0.27 | 0.33 | | | >25 | >25 | >25 | >25 |
| 2.4 | 4.65 | 0.49 | ?.05 | | | | >50 | >50 | 1 | 1.2 |
| 4.5 | 8.25 | 2.29 | 4.91 | 3.24 | 0.10 | | >50 | >50 | 1 | 0.5 |
| >50 | >50 | >31 | >50 | >50 | 0.29 | 0.35 | >50 | 15 | >50 | 1.4 |
| | | | | | | | >50 | 12.8 | 2.4 | 3.1 |
| 26.7 | 12.64 | >31 | 15.59 | 14.64 | >50 | 1.7 | >50 | 9.3 | 13 | 2.6 |

*FIG. 70 CON'T*

TABLE 4-6 (CONTINUED)

| | | | |
|---|---|---|---|
| T278-50 | CRF02_AG | 2 | 7 |
| T255-34 | CRF02_AG | 2 | 7 |
| 211-9 | CRF02_AG | 2 | 7 |
| 235-47 | CRF02_AG | 2 | 7 |
| 620345.c01 | CRF01_AE | 2 | 1 |
| 703357.c02 | CRF01_AE | 2 | 1 |
| C1080.c03 | CRF01_AE | 2 | 7 |
| R2184.c04 | CRF01_AE | 2 | 7 |
| R1166.c01 | CRF01_AE | 2 | 7 |
| R3265.c06 | CRF01_AE | 2 | 7 |
| C2101.c01 | CRF01_AE | 2 | 7 |
| C3347.c11 | CRF01_AE | 2 | 7 |
| C4118.c09 | CRF01_AE | 2 | 7 |
| X1193_cl | G | 2 | 7 |
| P0402_c2_11 | G | 2 | 7 |
| X1254_c3 | G | 2 | 7 |
| X2088_c9 | G | 2 | 7 |
| X2131_C1_B5 | G | 2 | |
| P1981_C5_3 | G | 2 | |
| X1632_S2_B10 | G | 2 | 7 |
| 3016.v5.c45 | D | 2 | 1 |
| A07412M1.vrc12 | D | 2 | |
| 231965.c01 | D | 2 | 1 |
| 231966.c02 | D | 2 | 1 |

>50(?) 50(?)-10 0.1 -0.02 <0.02 n/a (?) indicates text missing or illegible when filed

*FIG. 70 CON'T*

TABLE 4-7 (CONTINUED)

| | | | | | | | | | | |
|---|---|---|---|---|---|---|---|---|---|---|
| 1.8 | 5.2 | 1.17 | 0.95 | 0.99 | 0.39 | 0.28 | 3.6 | >50 | 2.8 | 1.3 |
| >50 | >50 | >31 | >50 | >50 | | | >50 | >50 | >50 | 0.? |
| 2.6 | 1.65 | 0.85 | 1.35 | 1.46 | | | >50 | 38.3 | 4.7 | 5.9 |
| 2.1 | >50 | 0.88 | 2.47 | 2.55 | 0.23 | | >50 | 0.7 | >50 | |
| >50 | >50 | >31 | >50 | >50 | 1.3 | >50 | >25 | >25 | 0.2 | 0.3 |
| >50 | >50 | >31 | >50 | >50 | 1.2 | 0.? | >25 | >25 | 2.6 | 2 |
| | 0.13 | | | | | | >25 | >25 | 0.7 | 1.4 |
| >50 | >50 | >31 | >50 | >50 | 0.26 | 0.57 | >25 | >25 | 3.2 | 2.9 |
| >50 | >50 | >31 | >50 | >50 | 0.74 | 0.28 | >25 | >25 | 1.2 | 0.7 |
| 1.9 | 0.79 | 0.34 | 0.59 | 0.55 | 0.16 | | >25 | >25 | >25 | >25 |
| 1.2 | 2.88 | 0.46 | 1.13 | 1.11 | | | >25 | >25 | ? | 2 |
| 8.9 | 4.12 | 2.71 | 2.84 | 4.61 | | | >25 | >25 | 0.4 | 0.1 |
| 0.5 | 0.29 | 0.2 | 0.35 | 0.51 | | | >25 | >25 | 5 | 2.7 |
| >50 | >50 | >31 | 44.92 | 41.4 | 0.11 | | >50 | >50 | 5.5 | 3.6 |
| >50 | >50 | >31 | >50 | >50 | 0.? | | >50 | >50 | 14.1 | 5.3 |
| >50 | >50 | >31 | >50 | >50 | | | >50 | >50 | 19.7 | 19.4 |
| >50 | >50 | >31 | 43.16 | >50 | >50 | >50 | >50 | >50 | >50 | >50 |
| 0.6 | 0.6 | 0.5 | 0.8 | 0.66 | | | >50 | >50 | 9.1 | 2.8 |
| >50 | >50 | >31 | >50 | >50 | 0.26 | 0.38 | >50 | >50 | >50 | 0.7 |
| >50 | >50 | >31 | >50 | >50 | 0.11 | | >50 | >50 | 5.5 | 6.1 |
| >50 | >50 | >31 | >50 | >50 | 2.6 | >50 | 2.4 | >50 | 0.9 | 2.3 |
| >50 | >50 | >31 | >50 | >50 | 0.70 | 0.34 | 9.9 | >25 | 1.4 | 1.4 |
| >50 | >50 | >31 | >50 | >50 | 1.3 | 1.4 | 0.9 | >25 | 8.5 | 22.8 |
| >50 | >50 | >31 | >50 | >50 | | | 5.4 | >25 | 0.24 | 0.6 |

*FIG. 70 CON'T*

TABLE 5

| Neutralization profile of the inferred putative reverted unmutated ancestors | | | |
|---|---|---|---|
| Virus | Clade | Tier | Fiebig |
| MN.3 | B | 1A | 7 |
| SF162.LS | B | 1A | 7 |
| MW965.26 | C | 1A | 7 |
| TH023.6 | AE | 1A | 7 |
| NP03.13 | AE | 1B | 7 |
| CM244.ec1 | AE | 2 | 7 |
| 6535.3 | B | 2 | 5 |
| AC10.0.29 | B | 2 | 3 |
| REJO451.67 | B | 2 | 2 |
| WITO4160.33 | B | 2 | 2 |
| 1012_11_TC21_3257 | B | 2 | 3 |
| SC05_8C11_2344 | B | 2 | 2 |
| Du156.12 | C | 2 | 3 |
| CAP45.2.00.G3 | C | 2 | 6 |
| Du172.17 | C | 2 | 6 |
| ZM233M.PB6 | C | 2 | 5 |
| ZM249M.PL1 | C | 2 | 2 |
| CAP210.2.00.E8 | C | 2 | 4 |
| Ce0393_C3 | C | 2 | 4 |
| Ce1176_A3 | C | 2 | 1 |
| Q23.17 | A | 2 | 6 |
| Q842.d12 | A | 2 | 5 |
| 191955_A11 | A | 2 | 4 |
| 851891.4.15 | A | 2 | 1 |

>50(?) 50(?)-10 10-1 1-0.1 0.1-0.02# <0.02#

(?) indicates text missing or illegible when filed

TABLE 5 (CONTINUED)

| CH01-RUA1 | CH02-RUA1 | CH03-RUA1 | CH02-RUA2 | CH03-RUA3 | CH03-RUA4 |
|---|---|---|---|---|---|
| >50 | >50 | >50 | >50 | >50 | >50 |
| >50 | >50 | >50 | >50 | >50 | >50 |
| >50 | >50 | >50 | >50 | >50 | >50 |
| >50 | >50 | >50 | >50 | >50 | >50 |
| >50 | >50 | >50 | >50 | >50 | >50 |
| >50 | >50 | 4.45 | >50 | 18.82 | 5.26 |
| >50 | >50 | >50 | >50 | >50 | >50 |
| >50 | >50 | >50 | >50 | >50 | >50 |
| >50 | >50 | >50 | >50 | >50 | >50 |
| 0.4 | 0.47 | 0.11 | | 0.3 | 0.24 |
| >50 | >50 | >50 | >50 | >50 | >50 |
| >50 | >50 | >50 | >50 | >50 | >50 |
| >50 | >50 | >50 | >50 | >50 | >50 |
| >50 | >50 | >50 | >50 | >50 | >50 |
| >50 | >50 | >50 | >50 | >50 | >50 |
| 4.59 | >50 | 1.26 | >50 | 3.09 | 2.38 |
| >50 | >50 | >50 | >50 | >50 | >50 |
| >50 | >50 | >50 | >50 | >50 | >50 |
| >50 | >50 | >50 | >50 | >50 | >50 |
| >50 | >50 | >50 | >50 | >50 | >50 |
|  | 29.54 |  | 10.38 |  |  |
| >50 | >50 | >50 | >50 | >50 | >50 |
| >50 | >50 | >50 | >50 | >50 | >50 |
| >50 | >50 | >50 | >50 | 49.57 | 48.96 |

FIG. 71 CON'T

Table 6 - CH01-CH05 ELISA binding to monomeric gp120/gp140 envelope proteins

| Source | Clade | Env | Env Name | CH01 | CH02 | CH03 | CH04 | CH05 | CH01-RUA1 | CH03-RUA1 | CH02-RUA1 | CH02-RUA2 | synagis |
|---|---|---|---|---|---|---|---|---|---|---|---|---|---|
| Chronic | A | gp140 00M SA 4076 | | NB | NB | NB | NB | NB | NB | NB | NB | NB | NB |
| Chronic | A | gp140 VRC A | | NB | NB | NB | NB | NB | NB | NB | NB | NB | NB |
| Chronic | Anc | gp140 US-1* | | NB | NB | NB | NB | NB | NB | NB | NB | NB | NB |
| Chronic | B | gp140 VRC B | | NB | NB | NB | NB | NB | NB | NB | NB | NB | NB |
| Chronic | B | gp140 JRFL | | NB | NB | NB | NB | NB | NB | NB | NB | NB | NB |
| Chronic | Clade | gp140 97CNGX2F 140 CF | | NB | NB | NB | NB | NB | NB | NB | NB | NB | NB |
| Chronic | Clade | gp140 DU 123 | | NB | NB | NB | NB | NB | NB | NB | NB | NB | NB |
| Chronic | Clade | gp140 CN54 | | NB | NB | NB | NB | NB | NB | NB | NB | NB | NB |
| Chronic | G | gp140 HV 14000 (DRCBL) | | NB | NB | NB | NB | NB | NB | NB | NB | NB | NB |
| Chronic | B | gp120 W61D | | NB | NB | NB | NB | NB | NB | NB | NB | NB | NB |
| Chronic | B | gp120 MN | | NB | NB | NB | NB | NB | NB | NB | NB | NB | NB |
| Chronic | B | gp120 VBD2** | | NB | NB | NB | NB | NB | NB | NB | NB | NB | NB |
| Chronic | E | gp120 A244gD+ | | 7.8 | 150 | 34.5 | 23.1 | 28.7 | >666.7 | >666.7 | NB | NB | NB |
| Chronic | Clade | gp120 ZM651 | | NB | NB | NB | NB | NB | NB | NB | NB | NB | NB |
| Chronic | AE | gp120 CM 243 | | 12.7 | >666.7 | 97.3 | >666.7 | >666.7 | NB | NB | NB | NB | NB |
| Consensus | A1.CON | gp140 A1.con.env03 140 CF | | NB | NB | NB | NB | NB | NB | NB | NB | NB | NB |
| Consensus | AE.CON | gp140 HV 13700 (Aecon.env03 140 CF) | | NB | NB | NB | NB | NB | NB | NB | NB | NB | NB |
| Consensus | B.CON | gp140 B.con.env03 140 CF | | NB | NB | NB | NB | NB | NB | NB | NB | NB | NB |
| Consensus | C.CON | gp140 C.con.env03 140 CF | | NB | NB | NB | NB | NB | NB | NB | NB | NB | NB |
| Consensus | M | gp140 Con 6 140 CF | | NB | NB | NB | NB | NB | NB | NB | NB | NB | NB |
| Consensus | M | gp140 Con S 140 CFI | | NB | NB | NB | NB | NB | NB | NB | NB | NB | NB |
| T/F | A | gp140 HV 13341 (0219) | | NB | NB | NB | NB | NB | NB | NB | NB | NB | |
| T/F | B | gp140 FIKEgp140C | | NB | NB | NB | NB | NB | NB | NB | NB | NB | NB |
| T/F | B | gp140 HV00043 (63521 TC21 140C) | | NB | NB | NB | NB | NB | NB | NB | NB | NB | NB |
| T/F | B | gp140 HV00044 (6240 TZ5 140C) | | NB | NB | NB | NB | NB | NB | NB | NB | NB | NB |
| T/F | B | gp140 HV00045 (6235714 D3 140C) | | NB | NB | NB | NB | NB | NB | NB | NB | NB | NB |
| T/F | B | gp140 HV00046 (902114 B2 140C) | | 63.2 | 240 | NB | NB | NB | NB | NB | NB | NB | NB |
| T/F | B | gp140 HV00049 (700010040 C9 140C) | | NB | NB | NB | NB | NB | NB | NB | NB | NB | NB |
| T/F | B | gp140 MOJO gp140C | | NB | NB | NB | NB | NB | NB | NB | NB | NB | NB |
| T/F | C | gp140 HV00047 (089C 140C.) | | NB | NB | NB | NB | NB | NB | NB | NB | NB | NB |
| T/F | C | gp140 HV00048 (1086C a40C) | | NB | NB | NB | NB | NB | NB | NB | NB | NB | NB |
| T/F | B | gp120 FIKE gp120 | | NB | NB | NB | NB | NB | NB | NB | NB | NB | NB |

FIG. 72

SEQUENCE LISTING

```
<160> NUMBER OF SEQ ID NOS: 96

<210> SEQ ID NO 1
<211> LENGTH: 32
<212> TYPE: PRT
<213> ORGANISM: Human immunodeficiency virus

<400> SEQUENCE: 1

Gln Gln Glu Lys Asn Glu Gln Glu Leu Leu Glu Leu Asp Lys Trp Ala
1               5                   10                  15

Ser Leu Trp Asn Trp Phe Asp Ile Thr Asn Trp Leu Trp Tyr Ile Lys
            20                  25                  30


<210> SEQ ID NO 2
<211> LENGTH: 6
<212> TYPE: PRT
<213> ORGANISM: Homo sapiens

<400> SEQUENCE: 2

Glu Leu Asp Lys Trp Ala
1               5


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Leu Glu Lys Trp Ala
1               5


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

tcgtcgtttt tcggtcgttt t                                              21


<210> SEQ ID NO 5
<211> LENGTH: 43
<212> TYPE: PRT
<213> ORGANISM: Human immunodeficiency virus

<400> SEQUENCE: 5

Arg Val Leu Ala Val Glu Arg Tyr Leu Arg Asp Gln Gln Leu Leu Gly
1               5                   10                  15

Ile Trp Gly Cys Ser Gly Lys Leu Ile Cys Thr Thr Ala Val Pro Trp
            20                  25                  30
```

```
Asn Ala Ser Trp Ser Asn Lys Ser Leu Asn Lys
        35                  40


<210> SEQ ID NO 6
<211> LENGTH: 20
<212> TYPE: PRT
<213> ORGANISM: Human immunodeficiency virus

<400> SEQUENCE: 6

Gln Gln Glu Lys Asn Glu Gln Glu Leu Leu Glu Leu Asp Lys Trp Ala
1               5                   10                  15

Ser Leu Trp Asn
            20


<210> SEQ ID NO 7
<211> LENGTH: 27
<212> TYPE: PRT
<213> ORGANISM: Herpes simplex virus

<400> SEQUENCE: 7

Lys Tyr Ala Leu Val Asp Ala Ser Leu Lys Met Ala Asp Pro Asn Arg
1               5                   10                  15

Phe Arg Gly Lys Asp Leu Pro Val Leu Asp Gln
            20                  25


<210> SEQ ID NO 8
<211> LENGTH: 26
<212> TYPE: PRT
<213> ORGANISM: Homo sapiens

<400> SEQUENCE: 8

Ala Arg Gly Thr Asp Tyr Thr Ile Asp Asp Ala Gly Ile His Tyr Gln
1               5                   10                  15

Gly Ser Gly Thr Phe Trp Tyr Phe Asp Leu
            20                  25


<210> SEQ ID NO 9
<211> LENGTH: 30
<212> TYPE: PRT
<213> ORGANISM: Human immunodeficiency virus

<400> SEQUENCE: 9

Glu Asn Lys Thr Ile Val Phe Asn His Ser Ser Gly Gly Asp Pro Glu
1               5                   10                  15

Ile Val Met His Ser Phe Asn Cys Gly Gly Glu Phe Phe Tyr
            20                  25                  30


<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Asn Lys Thr Ile Val Phe Asn His Ser Ser Gly Gly Ala Pro Ala
1               5                   10                  15

Ile Val Met His Ser Phe Asn Cys Gly Gly Glu Phe Phe Tyr
            20                  25                  30


<210> SEQ ID NO 11
```

-continued

<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 11

His His His His His His
1 5

<210> SEQ ID NO 12
<211> LENGTH: 669
<212> TYPE: PRT
<213> ORGANISM: Human immunodeficiency virus

<400> SEQUENCE: 12

Met Arg Val Arg Gly Ile Trp Lys Asn Trp Pro Gln Trp Leu Ile Trp
1 5 10 15

Ser Ile Leu Gly Phe Trp Ile Gly Asn Met Glu Gly Ser Trp Val Thr
20 25 30

Val Tyr Tyr Gly Val Pro Val Trp Lys Glu Ala Lys Thr Thr Leu Phe
35 40 45

Cys Ala Ser Asp Ala Lys Ala Tyr Glu Lys Glu Val His Asn Val Trp
50 55 60

Ala Thr His Ala Cys Val Pro Thr Asp Pro Asn Pro Gln Glu Met Val
65 70 75 80

Leu Ala Asn Val Thr Glu Asn Phe Asn Met Trp Lys Asn Asp Met Val
85 90 95

Glu Gln Met His Glu Asp Ile Ile Ser Leu Trp Asp Glu Ser Leu Lys
100 105 110

Pro Cys Val Lys Leu Thr Pro Leu Cys Val Thr Leu Asn Cys Thr Asn
115 120 125

Val Lys Gly Asn Glu Ser Asp Thr Ser Glu Val Met Lys Asn Cys Ser
130 135 140

Phe Lys Ala Thr Thr Glu Leu Lys Asp Lys Lys His Lys Val His Ala
145 150 155 160

Leu Phe Tyr Lys Leu Asp Val Val Pro Leu Asn Gly Asn Ser Ser Ser
165 170 175

Ser Gly Glu Tyr Arg Leu Ile Asn Cys Asn Thr Ser Ala Ile Thr Gln
180 185 190

Ala Cys Pro Lys Val Ser Phe Asp Pro Ile Pro Leu His Tyr Cys Ala
195 200 205

Pro Ala Gly Phe Ala Ile Leu Lys Cys Asn Asn Lys Thr Phe Asn Gly
210 215 220

Thr Gly Pro Cys Arg Asn Val Ser Thr Val Gln Cys Thr His Gly Ile
225 230 235 240

Lys Pro Val Val Ser Thr Gln Leu Leu Leu Asn Gly Ser Leu Ala Glu
245 250 255

Glu Glu Ile Ile Ile Arg Ser Glu Asn Leu Thr Asn Asn Ala Lys Thr
260 265 270

Ile Ile Val His Leu Asn Glu Ser Val Asn Ile Val Cys Thr Arg Pro
275 280 285

Asn Asn Asn Thr Arg Lys Ser Ile Arg Ile Gly Pro Gly Gln Thr Phe
290 295 300

Tyr Ala Thr Gly Asp Ile Ile Gly Asn Ile Arg Gln Ala His Cys Asn
305 310 315 320

```
Ile Asn Glu Ser Lys Trp Asn Asn Thr Leu Gln Lys Val Gly Glu Glu
                325                 330                 335

Leu Ala Lys His Phe Pro Ser Lys Thr Ile Lys Phe Glu Pro Ser Ser
            340                 345                 350

Gly Gly Asp Leu Glu Ile Thr Thr His Ser Phe Asn Cys Arg Gly Glu
        355                 360                 365

Phe Phe Tyr Cys Asn Thr Ser Asp Leu Phe Asn Gly Thr Tyr Arg Asn
    370                 375                 380

Gly Thr Tyr Asn His Thr Gly Arg Ser Ser Asn Gly Thr Ile Thr Leu
385                 390                 395                 400

Gln Cys Lys Ile Lys Gln Ile Ile Asn Met Trp Gln Glu Val Gly Arg
                405                 410                 415

Ala Ile Tyr Ala Pro Pro Ile Glu Gly Glu Ile Thr Cys Asn Ser Asn
            420                 425                 430

Ile Thr Gly Leu Leu Leu Leu Arg Asp Gly Gly Gln Ser Asn Glu Thr
        435                 440                 445

Asn Asp Thr Glu Thr Phe Arg Pro Gly Gly Gly Asp Met Arg Asp Asn
    450                 455                 460

Trp Arg Ser Glu Leu Tyr Lys Tyr Lys Val Val Glu Ile Lys Pro Leu
465                 470                 475                 480

Gly Val Ala Pro Thr Glu Ala Lys Glu Arg Val Val Glu Arg Glu Lys
                485                 490                 495

Glu Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
        515                 520                 525

Gln Leu Leu Ser Gly Ile Val Gln Gln Gln Ser Asn Leu Leu Arg Ala
    530                 535                 540

Ile Glu Ala Gln Gln His Met Leu Gln Leu Thr Val Trp Gly Ile Lys
545                 550                 555                 560

Gln Leu Gln Ala Arg Val Leu Ala Ile Glu Arg Tyr Leu Lys Asp Gln
                565                 570                 575

Gln Leu Leu Gly Met Trp Gly Cys Ser Gly Lys Leu Ile Cys Thr Thr
            580                 585                 590

Ala Val Pro Trp Asn Ser Ser Trp Ser Asn Lys Ser Gln Asn Glu Ile
        595                 600                 605

Trp Gly Asn Met Thr Trp Met Gln Trp Asp Arg Glu Ile Asn Asn Tyr
    610                 615                 620

Thr Asn Thr Ile Tyr Arg Leu Leu Glu Asp Ser Gln Asn Gln Gln Glu
625                 630                 635                 640

Lys Asn Glu Lys Asp Leu Leu Ala Leu Asp Ser Trp Lys Asn Leu Trp
                645                 650                 655

Asn Trp Phe Asp Ile Ser Lys Trp Leu Trp Tyr Ile Lys
            660                 665
```

<210> SEQ ID NO 13
<211> LENGTH: 2022
<212> TYPE: DNA
<213> ORGANISM: Human immunodeficiency virus

<400> SEQUENCE: 13

```
atgcgcgtgc gcggcatctg gaagaactgg ccccagtggc tgatctggtc catcctgggc      60

ttctggatcg gcaacatgga gggctcctgg gtgaccgtgt actacggcgt gcccgtgtgg     120
```

-continued aaggaggcca agaccaccct gttctgcgcc tccgacgcca aggcctacga gaaggaggtg 180
cacaacgtgt gggccaccca cgcctgcgtg cccaccgacc ccaaccccca ggagatggtg 240
ctggccaacg tgaccgagaa cttcaacatg tggaagaacg acatggtgga gcagatgcac 300
gaggacatca tctccctgtg ggacgagtcc ctgaagccct gcgtgaagct gacccccctg 360
tgcgtgaccc tgaactgcac caacgtgaag ggcaacgagt ccgacacctc cgaggtgatg 420
aagaactgct ccttcaaggc caccaccgag ctgaaggaca agaagcacaa ggtgcacgcc 480
ctgttctaca agctggacgt ggtgcccctg aacggcaact cctcctcctc cggcgagtac 540
cgcctgatca actgcaacac ctccgccatc acccaggcct gccccaaggt gtccttcgac 600
cccatccccc tgcactactg cgcccccgcc ggcttcgcca tcctgaagtg caacaacaag 660
accttcaacg gcaccggccc ctgccgcaac gtgtccaccg tgcagtgcac ccacggcatc 720
aagcccgtgg tgtccaccca gctgctgctg aacggctccc tggccgagga ggagatcatc 780
atccgctccg agaacctgac caacaacgcc aagaccatca tcgtgcacct gaacgagtcc 840
gtgaacatcg tgtgcacccg ccccaacaac aacacccgca agtccatccg catcggcccc 900
ggccagacct tctacgccac cggcgacatc atcggcaaca tccgccaggc ccactgcaac 960
atcaacgagt ccaagtggaa caacaccctg cagaaggtgg gcgaggagct ggccaagcac 1020
ttcccctcca agaccatcaa gttcgagccc tcctccggcg gcgacctgga gatcaccacc 1080
cactccttca actgccgcgg cgagttcttc tactgcaaca cctccgacct gttcaacggc 1140
acctaccgca acggcaccta caaccacacc ggccgctcct ccaacggcac catcaccctg 1200
cagtgcaaga tcaagcagat catcaacatg tggcaggagg tgggccgcgc catctacgcc 1260
ccccccatcg agggcgagat cacctgcaac tccaacatca ccggcctgct gctgctgcgc 1320
gacggcggcc agtccaacga gaccaacgac accgagacct tccgccccgg cggcggcgac 1380
atgcgcgaca actggcgctc cgagctgtac aagtacaagg tggtggagat caagcccctg 1440
ggcgtggccc ccaccgaggc caaggagcgc gtggtggagc gcgagaagga ggccgtgggc 1500
atcggcgccg tgttcctggg cttcctgggc gccgccggct ccaccatggg cgccgcctcc 1560
atgaccctga ccgtgcaggc ccgccagctg ctgtccggca tcgtgcagca gcagtccaac 1620
ctgctgcgcg ccatcgaggc ccagcagcac atgctgcagc tgaccgtgtg gggcatcaag 1680
cagctgcagg cccgcgtgct ggccatcgag cgctacctga aggaccagca gctgctgggc 1740
atgtggggct gctccggcaa gctgatctgc accaccgccg tgccctggaa ctcctcctgg 1800
tccaacaagt cccagaacga gatctggggc aacatgacct ggatgcagtg ggaccgcgag 1860
atcaacaact acaccaacac catctaccgc ctgctggagg actcccagaa ccagcaggag 1920
aagaacgaga aggacctgct ggccctggac tcctggaaga acctgtggaa ctggttcgac 1980
atctccaagt ggctgtggta catcaagtag ggatcctcta ga 2022

<210> SEQ ID NO 14
<211> LENGTH: 682
<212> TYPE: PRT
<213> ORGANISM: Human immunodeficiency virus

<400> SEQUENCE: 14

Met Arg Val Arg Gly Met Leu Arg Asn Cys Gln Gln Trp Trp Ile Trp
1 5 10 15

Gly Ile Leu Gly Phe Trp Met Leu Met Ile Cys Ser Val Val Gly Asn
20 25 30

Leu Trp Val Thr Val Tyr Tyr Gly Val Pro Val Trp Lys Glu Ala Lys

-continued

```
        35                  40                  45

Thr Thr Leu Phe Cys Ala Ser Asp Ala Arg Ala Tyr Glu Arg Glu Val
    50                  55                  60

His Asn Val Trp Ala Thr His Ala Cys Val Pro Thr Asp Pro Asn Pro
65                  70                  75                  80

Gln Glu Met Val Leu Val Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Ile Leu
        115                 120                 125

Glu Cys Asn Asn Ala Asn Gly Thr Thr Asn Asn Gly Ser Val Ile Val
    130                 135                 140

Val Asn Glu Asn Ser Thr Met Tyr Gly Glu Ile Gln Asn Cys Ser Phe
145                 150                 155                 160

Lys Val Asn Ser Glu Ile Lys Gly Lys Lys Gln Asp Val Tyr Ala Leu
                165                 170                 175

Phe Asn Ser Leu Asp Ile Val Lys Leu Tyr Asn Asn Gly Thr Ser Gln
            180                 185                 190

Tyr Arg Leu Ile Asn Cys Asn Thr Ser Thr Leu Thr Gln Ala Cys Pro
        195                 200                 205

Lys Val Ser Phe Asp Pro Ile Pro Ile His Tyr Cys Ala Pro Ala Gly
    210                 215                 220

Tyr Ala Ile Leu Lys Cys Asn Asn Lys Thr Phe Asn Gly Thr Gly Pro
225                 230                 235                 240

Cys Asn Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Ile
            260                 265                 270

Ile Ile Arg Ser Lys Asn Leu Thr Asp Asn Thr Lys Thr Ile Ile Val
        275                 280                 285

His Leu Asn Glu Ser Ile Lys Ile Asn Cys Ile Arg Pro Asn Asn Asn
    290                 295                 300

Thr Arg Arg Ser Ile Arg Ile Gly Pro Gly Gln Ala Phe Tyr Ala Ala
305                 310                 315                 320

Asn Gly Ile Val Gly Asn Ile Arg Gln Ala His Cys Asn Ile Ser Glu
                325                 330                 335

Gly Glu Trp Asn Lys Thr Leu Tyr Arg Val Ser Arg Lys Leu Ala Glu
            340                 345                 350

His Phe Pro Gly Lys Glu Ile Lys Phe Lys Pro His Ser Gly Gly Asp
        355                 360                 365

Leu Glu Ile Thr Thr His Ser Phe Asn Cys Arg Gly Glu Phe Phe Tyr
    370                 375                 380

Cys Asn Thr Ser Lys Leu Phe Asn Gly Thr Tyr Asn Gly Thr Tyr Thr
385                 390                 395                 400

Asn Asn Asp Thr Asn Ser Thr Ile Ile Leu Pro Cys Arg Ile Lys Gln
                405                 410                 415

Ile Ile Asn Met Trp Gln Glu Val Gly Gln Ala Met Tyr Ala Pro Pro
            420                 425                 430

Ile Glu Gly Ile Ile Ala Cys Asn Ser Thr Ile Thr Gly Leu Leu Leu
        435                 440                 445

Thr Arg Asp Gly Gly Asp Lys Asn Gly Ser Lys Pro Glu Ile Phe Arg
    450                 455                 460
```

-continued

```
Pro Gly Gly Gly Asp Met Arg Asp Asn Trp Arg Ser Glu Leu Tyr Lys
465                 470                 475                 480

Tyr Lys Val Val Glu Ile Lys Pro Leu Gly Ile Ala Pro Thr Lys Ala
                485                 490                 495

Lys Glu Arg Val Val Glu Lys Glu Lys Thr Ile Gln Lys Glu Ala Val
            500                 505                 510

Gly Ile Gly Ala Val Phe Leu Gly Phe Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Ala Arg Val Leu Ala Met Glu Arg Tyr Leu Gln Asp Gln Gln Leu Leu
            580                 585                 590

Gly Ile Trp Gly Cys Ser Gly Lys Leu Ile Cys Thr Thr Ala Val Pro
        595                 600                 605

Trp Asn Ser Ser Trp Ser Asn Lys Thr Leu Glu Tyr Ile Trp Gly Asn
    610                 615                 620

Met Thr Trp Met Gln Trp Asp Arg Glu Ile Asp Asn Tyr Thr Gly Ile
625                 630                 635                 640

Ile Tyr Asp Leu Leu Glu Asp Ser Gln Ile Gln Gln Glu Lys Asn Glu
                645                 650                 655

Lys Asp Leu Leu Ala Leu Asp Ser Trp Lys Asn Leu Trp Ser Trp Phe
            660                 665                 670

Ser Ile Thr Asn Trp Leu Trp Tyr Ile Lys
        675                 680


<210> SEQ ID NO 15
<211> LENGTH: 2046
<212> TYPE: DNA
<213> ORGANISM: Human immunodeficiency virus

<400> SEQUENCE: 15

atgcgcgtgc gcggcatgct gcgcaactgc cagcagtggt ggatctgggg catcctgggc      60

ttctggatgc tgatgatctg ctccgtggtg ggcaacctgt gggtgaccgt gtactacggc     120

gtgcccgtgt ggaaggaggc caagaccacc ctgttctgcg cctccgacgc ccgcgcctac     180

gagcgcgagg tgcacaacgt gtgggccacc cacgcctgcg tgcccaccga ccccaacccc     240

caggagatgg tgctggtgaa cgtgaccgag aacttcaaca tgtggaagaa cgacatggtg     300

gaccagatgc acgaggacat catctccctg tgggaccagt ccctgaagcc ctgcgtgaag     360

ctgacccccc tgtgcgtgat cctggagtgc aacaacgcca acggcaccac caacaacggc     420

tccgtgatcg tggtgaacga gaactccacc atgtacggcg agatccagaa ctgctccttc     480

aaggtgaact ccgagatcaa gggcaagaag caggacgtgt acgccctgtt caactccctg     540

gacatcgtga agctgtacaa caacggcacc tcccagtacc gcctgatcaa ctgcaacacc     600

tccaccctga cccaggcctg ccccaaggtg tccttcgacc ccatccccat ccactactgc     660

gcccccgccg gctacgccat cctgaagtgc aacaacaaga ccttcaacgg caccggcccc     720

tgcaacaacg tgtccaccgt gcagtgcacc cacggcatca agcccgtggt gtccacccag     780

ctgctgctga acggctccct ggccgagggc gagatcatca tccgctccaa gaacctgacc     840
```

-continued

```
gacaacacca agaccatcat cgtgcacctg aacgagtcca tcaagatcaa ctgcatccgc    900
cccaacaaca acacccgccg ctccatccgc atcggccccg gccaggcctt ctacgccgcc    960
aacggcatcg tgggcaacat ccgccaggcc cactgcaaca tctccgaggg cgagtggaac   1020
aagaccctgt accgcgtgtc ccgcaagctg gccgagcact tccccggcaa ggagatcaag   1080
ttcaagcccc actccggcgg cgacctggag atcaccaccc actccttcaa ctgccgcggc   1140
gagttcttct actgcaacac ctccaagctg ttcaacggca cctacaacgg cacctacacc   1200
aacaacgaca ccaactccac catcatcctg ccctgccgca tcaagcagat catcaacatg   1260
tggcaggagg tgggccaggc catgtacgcc ccccccatcg agggcatcat cgcctgcaac   1320
tccaccatca ccggcctgct gctgacccgc gacggcggcg acaagaacgg ctccaagccc   1380
gagatcttcc gccccggcgg cggcgacatg cgcgacaact ggcgctccga gctgtacaag   1440
tacaaggtgg tggagatcaa gcccctgggc atcgccccca ccaaggccaa ggagcgcgtg   1500
gtggagaagg agaagaccat ccagaaggag gccgtgggca tcggcgccgt gttcctgggc   1560
ttcctgggcg ccgccggctc caccatgggc gccgcctcca tcaccctgac cgtgcaggcc   1620
cgccagctgc tgtccggcat cgtgcagcag cagtccaacc tgctgcgcgc catcgaggcc   1680
cagcagcaca tgctgcagct gaccgtgtgg ggcatcaagc agctgcaggc ccgcgtgctg   1740
gccatggagc gctacctgca ggaccagcag ctgctgggca tctggggctg ctccggcaag   1800
ctgatctgca ccaccgccgt gccctggaac tcctcctggt ccaacaagac cctggagtac   1860
atctggggca acatgacctg gatgcagtgg gaccgcgaga tcgacaacta caccggcatc   1920
atctacgacc tgctggagga ctcccagatc cagcaggaga agaacgagaa ggacctgctg   1980
gccctggact cctggaagaa cctgtggtcc tggttctcca tcaccaactg gctgtggtac   2040
atcaag                                                              2046
```

<210> SEQ ID NO 16
<211> LENGTH: 673
<212> TYPE: PRT
<213> ORGANISM: Human immunodeficiency virus

<400> SEQUENCE: 16

```
Met Arg Val Met Gly Ile Arg Lys Asn Tyr Gln His Leu Trp Arg Glu
1               5                   10                  15

Gly Ile Leu Leu Leu Gly Ile Leu Met Ile Cys Ser Ala Ala Asp Asn
            20                  25                  30

Leu Trp Val Thr Val Tyr Tyr Gly Val Pro Val Trp Arg Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Glu
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Gly Asn Val Thr Asn Thr Thr Asn Ser Asn Gly
    130                 135                 140

Glu Met Met Glu Lys Gly Glu Val Lys Asn Cys Ser Phe Lys Ile Thr
145                 150                 155                 160
```

-continued

```
Thr Asp Ile Lys Asp Arg Thr Arg Lys Glu Tyr Ala Leu Phe Tyr Lys
                165                 170                 175

Leu Asp Val Val Pro Ile Asn Asp Thr Arg Tyr Arg Leu Val Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Lys Cys
    210                 215                 220

Asn Asp Lys Gln Phe Ile Gly Thr Gly Pro Cys Thr Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Glu Val Val Ile Arg Ser Val Asn
            260                 265                 270

Phe Ser Asp Asn Ala Lys Thr Ile Ile Val Gln Leu Asn Lys Ser Val
        275                 280                 285

Glu Ile Thr Cys Thr Arg Pro Asn Asn Asn Thr Arg Lys Ser Ile Pro
    290                 295                 300

Met Gly Pro Gly Lys Ala Phe Tyr Ala Arg Gly Asp Ile Thr Gly Asp
305                 310                 315                 320

Ile Arg Lys Ala Tyr Cys Glu Ile Asn Gly Thr Glu Trp His Ser Thr
                325                 330                 335

Leu Lys Leu Val Val Glu Lys Leu Arg Glu Gln Tyr Asn Lys Thr Ile
            340                 345                 350

Val Phe Asn Arg Ser Ser Gly Gly Asp Pro Glu Ile Val Met Tyr Ser
        355                 360                 365

Phe Asn Cys Gly Gly Glu Phe Phe Tyr Cys Asn Ser Thr Lys Leu Phe
    370                 375                 380

Asn Ser Thr Trp Pro Trp Asn Asp Thr Lys Gly Ser His Asp Thr Asn
385                 390                 395                 400

Gly Thr Leu Ile Leu Pro Cys Lys Ile Lys Gln Ile Ile Asn Met Trp
                405                 410                 415

Gln Gly Val Gly Lys Ala Met Tyr Ala Pro Pro Ile Glu Gly Lys Ile
            420                 425                 430

Arg Cys Ser Ser Asn Ile Thr Gly Leu Leu Leu Thr Arg Asp Gly Gly
        435                 440                 445

Tyr Glu Ser Asn Glu Thr Asp Glu Ile Phe Arg Pro Gly Gly Gly Asp
    450                 455                 460

Met Arg Asp Asn Trp Arg Ser Glu Leu Tyr Lys Tyr Lys Val Val Lys
465                 470                 475                 480

Ile Glu Pro Leu Gly Val Ala Pro Thr Lys Ala Lys Glu Arg Val Val
                485                 490                 495

Gln Arg Glu Lys Glu Ala Phe Gly Leu Gly Ala Val Phe Leu Gly Phe
            500                 505                 510

Leu Gly Ala Ala Gly Ser Thr Met Gly Ala Ala Ser Ile Thr Leu Thr
        515                 520                 525

Val Gln Ala Arg Gln Leu Leu Ser Gly Ile Val Gln Gln Gln Asn Asn
    530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575
```

```
Leu Lys Asp Gln Gln Leu Leu Gly Ile Trp Gly Cys Ser Gly Lys Leu
            580                 585                 590

Ile Cys Thr Thr Thr Val Pro Trp Asn Thr Ser Trp Ser Asn Lys Ser
        595                 600                 605

Leu Glu Gln Ile Trp Asp Asn Met Thr Trp Met Glu Trp Glu Arg Glu
    610                 615                 620

Ile Asp Asn Tyr Thr Gly Tyr Ile Tyr Gln Leu Ile Glu Glu Ser Gln
625                 630                 635                 640

Asn Gln Gln Glu Lys Asn Glu Gln Glu Leu Leu Ala Leu Asp Lys Trp
                645                 650                 655

Ala Ser Leu Trp Asn Trp Phe Asp Ile Thr Asn Trp Leu Trp Tyr Ile
            660                 665                 670

Lys


<210> SEQ ID NO 17
<211> LENGTH: 2019
<212> TYPE: DNA
<213> ORGANISM: Human immunodeficiency virus

<400> SEQUENCE: 17

atgcgcgtga tgggcatccg caagaactac cagcacctgt ggcgcgaggg catcctgctg     60

ctgggcatcc tgatgatctg ctccgccgcc gacaacctgt gggtgaccgt gtactacggc    120

gtgcccgtgt ggcgcgaggc caccaccacc ctgttctgcg cctccgacgc caaggcctac    180

gacaccgagg cccacaacgt gtgggccacc cacgcctgcg tgcccaccga ccccaacccc    240

caggaggtgg agctgaagaa cgtgaccgag aacttcaaca tgtgggagaa caacatggtg    300

gagcagatgc acgaggacat catctccctg tgggaccagt ccctgaagcc ctgcgtgaag    360

ctgacccccc tgtgcgtgac cctgaactgc accgacctgg gcaacgtgac caacaccacc    420

aactccaacg gcgagatgat ggagaagggc gaggtgaaga actgctcctt caagatcacc    480

accgacatca aggaccgcac ccgcaaggag tacgccctgt tctacaagct ggacgtggtg    540

cccatcaacg acacccgcta ccgcctggtg tcctgcaaca cctccgtgat cacccaggcc    600

tgccccaagg tgtccttcga gcccatcccc atccactact gcgcccccgc cggcttcgcc    660

atcctgaagt gcaacgacaa gcagttcatc ggcaccggcc cctgcaccaa cgtgtccacc    720

gtgcagtgca cccacggcat ccgccccgtg gtgtccaccc agctgctgct gaacggctcc    780

ctggccgagg aggaggtggt gatccgctcc gtgaacttct ccgacaacgc caagaccatc    840

atcgtgcagc tgaacaagtc cgtggagatc acctgcaccc gccccaacaa caacacccgc    900

aagtccatcc ccatgggccc cggcaaggcc ttctacgccc gcggcgacat caccggcgac    960

atccgcaagg cctactgcga gatcaacggc accgagtggc actccaccct gaagctggtg   1020

gtggagaagc tgcgcgagca gtacaacaag accatcgtgt tcaaccgctc ctccggcggc   1080

gaccccgaga tcgtgatgta ctccttcaac tgcggcggcg agttcttcta ctgcaactcc   1140

accaagctgt tcaactccac ctggccctgg aacgacacca agggctccca cgacaccaac   1200

ggcaccctga tcctgccctg caagatcaag cagatcatca acatgtggca gggcgtgggc   1260

aaggccatgt acgccccccc catcgagggc aagatccgct gctcctccaa catcaccggc   1320

ctgctgctga cccgcgacgg cggctacgag tccaacgaga ccgacgagat cttccgcccc   1380

ggcggcggcg acatgcgcga caactggcgc tccgagctgt acaagtacaa ggtggtgaag   1440

atcgagcccc tgggcgtggc ccccaccaag gccaaggagc gcgtggtgca gcgcgagaag   1500

gaggccttcg gcctgggcgc cgtgttcctg ggcttcctgg gcgccgccgg ctccaccatg   1560
```

```
ggcgccgcct ccatcaccct gaccgtgcag gcccgccagc tgctgtccgg catcgtgcag   1620

cagcagaaca acctgctgcg cgccatcgag gcccagcagc acctgctgca gctgaccgtg   1680

tggggcatca agcagctgca ggcccgcgtg ctggccgtgg agcgctacct gaaggaccag   1740

cagctgctgg gcatctgggg ctgctccggc aagctgatct gcaccaccac cgtgccctgg   1800

aacacctcct ggtccaacaa gtccctggag cagatctggg acaacatgac ctggatggag   1860

tgggagcgcg agatcgacaa ctacaccggc tacatctacc agctgatcga ggagtcccag   1920

aaccagcagg agaagaacga gcaggagctg ctggccctgg acaagtgggc ctccctgtgg   1980

aactggttcg acatcaccaa ctggctgtgg tacatcaag                          2019
```

```
<210> SEQ ID NO 18
<211> LENGTH: 693
<212> TYPE: PRT
<213> ORGANISM: Human immunodeficiency virus

<400> SEQUENCE: 18

Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Ala Ala Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Leu Val Leu Ala Asn Val Thr Glu Asn Phe Asn Met Trp Asn
                85                  90                  95

Asn Thr Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Thr Asn Ala Thr Asn Ile Asn Ala Thr Asn Ile
    130                 135                 140

Asn Asn Ser Ser Gly Gly Val Glu Ser Gly Glu Ile Lys Asn Cys Ser
145                 150                 155                 160

Phe Asn Ile Thr Thr Ser Val Arg Asp Lys Val Gln Lys Glu Tyr Ala
                165                 170                 175

Leu Phe Tyr Lys Leu Asp Ile Val Pro Ile Thr Asn Glu Ser Ser Lys
            180                 185                 190

Tyr Arg Leu Ile Ser Cys Asn Thr Ser Val Leu Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Asn Asn Glu Thr Phe Asn Gly Lys Gly Pro
225                 230                 235                 240

Cys Ile Asn Val Ser Thr Val Gln Cys Thr His Gly Ile Arg Pro Val
                245                 250                 255

Val Ser Thr Gln Leu Leu Leu Asn Gly Ser Leu Ala Glu Lys Glu Val
            260                 265                 270

Ile Ile Arg Ser Asp Asn Phe Ser Asp Asn Ala Lys Asn Ile Ile Val
        275                 280                 285
```

-continued

```
Gln Leu Lys Glu Tyr Val Lys Ile Asn Cys Thr Arg Pro Asn Asn Asn
    290                 295                 300

Thr Arg Lys Ser Ile His Ile Gly Pro Gly Arg Ala Phe Tyr Ala Thr
305                 310                 315                 320

Gly Glu Ile Ile Gly Asn Ile Arg Gln Ala His Cys Asn Ile Ser Arg
                325                 330                 335

Ser Lys Trp Asn Asp Thr Leu Lys Gln Ile Ala Ala Lys Leu Gly Glu
            340                 345                 350

Gln Phe Arg Asn Lys Thr Ile Val Phe Asn Pro Ser Ser Gly Gly Asp
        355                 360                 365

Leu Glu Ile Val Thr His Ser Phe Asn Cys Gly Gly Glu Phe Phe Tyr
    370                 375                 380

Cys Asn Thr Thr Lys Leu Phe Asn Ser Thr Trp Ile Arg Glu Gly Asn
385                 390                 395                 400

Asn Gly Thr Trp Asn Gly Thr Ile Gly Leu Asn Asp Thr Ala Gly Asn
                405                 410                 415

Asp Thr Ile Ile Leu Pro Cys Lys Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Ile Leu Thr Arg Asp Gly Gly
    450                 455                 460

Lys Asp Asp Ser Asn Gly Ser Glu Ile Leu Glu Ile Phe Arg Pro Gly
465                 470                 475                 480

Gly Gly Asp Met Arg Asp Asn Trp Arg Ser Glu Leu Tyr Lys Tyr Lys
                485                 490                 495

Val Val Arg Ile Glu Pro Leu Gly Val Ala Pro Thr Arg Ala Arg Glu
            500                 505                 510

Arg Val Val Gln Lys Glu Lys Glu Ala Val Gly Leu Gly Ala Met Phe
        515                 520                 525

Leu Gly Phe Leu Gly Ala Ala Gly Ser Ala Met Gly Ala Ala Ser Met
    530                 535                 540

Thr Leu Thr Val Gln Ala Arg Gln Leu Leu Ser Gly Ile Val Gln Gln
545                 550                 555                 560

Gln Asn Asn Leu Leu Arg Ala Ile Glu Ala Gln Gln His Met Leu Gln
                565                 570                 575

Leu Thr Val Trp Gly Ile Lys Gln Leu Gln Ala Arg Val Leu Ala Val
            580                 585                 590

Glu Arg Tyr Leu Lys Asp Gln Gln Leu Leu Gly Ile Trp Gly Cys Ser
        595                 600                 605

Gly Lys Leu Ile Cys Thr Thr Asp Val Pro Trp Asp Thr Ser Trp Ser
    610                 615                 620

Asn Lys Thr Leu Asp Asp Ile Trp Gly Ser Asn Met Thr Trp Met Glu
625                 630                 635                 640

Trp Glu Arg Glu Ile Asp Asn Tyr Thr Ser Thr Ile Tyr Thr Leu Leu
                645                 650                 655

Glu Glu Ala Gln Tyr Gln Gln Glu Lys Asn Glu Lys Glu Leu Leu Glu
            660                 665                 670

Leu Asp Lys Trp Ala Ser Leu Trp Asn Trp Phe Asp Ile Thr Asn Trp
        675                 680                 685

Leu Trp Tyr Ile Arg
    690
```

-continued

<210> SEQ ID NO 19
<211> LENGTH: 2088
<212> TYPE: DNA
<213> ORGANISM: Human immunodeficiency virus

<400> SEQUENCE: 19

```
atgcgcgtga agggcatccg caagaactac cagcacctgt ggcgctgggg caccatgctg     60
ctgggcatcc tgatgatctg ctccgccgcc gcccagctgt gggtgaccgt gtactacggc    120
gtgcccgtgt ggaaggaggc caccaccacc ctgttctgcg cctccgacgc caaggcctac    180
gacaccgagg tgcacaacgt gtgggccacc cacgcctgcg tgcccaccga ccccaacccc    240
caggagctgg tgctggccaa cgtgaccgag aacttcaaca tgtggaacaa caccatggtg    300
gagcagatgc acgaggacat catctccctg tgggaccagt ccctgaagcc ctgcgtgaag    360
ctgacccccc tgtgcgtgac cctgaactgc accgacgtga ccaacgccac caacatcaac    420
gccaccaaca tcaacaactc ctccggcggc gtggagtccg gcgagatcaa gaactgctcc    480
ttcaacatca ccacctccgt gcgcgacaag gtgcagaagg agtacgccct gttctacaag    540
ctggacatcg tgcccatcac caacgagtcc tccaagtacc gcctgatctc ctgcaacacc    600
tccgtgctga cccaggcctg ccccaaggtg tccttcgagc ccatccccat ccactactgc    660
gcccccgccg gcttcgccat cctgaagtgc aacaacgaga ccttcaacgg caagggcccc    720
tgcatcaacg tgtccaccgt gcagtgcacc cacggcatcc gccccgtggt gtccacccag    780
ctgctgctga acggctccct ggccgagaag gaggtgatca tccgctccga caacttctcc    840
gacaacgcca agaacatcat cgtgcagctg aaggagtacg tgaagatcaa ctgcacccgc    900
cccaacaaca acacccgcaa gtccatccac atcggccccg gccgcgcctt ctacgccacc    960
ggcgagatca tcggcaacat ccgccaggcc cactgcaaca tctcccgctc caagtggaac   1020
gacaccctga agcagatcgc cgccaagctg ggcgagcagt tccgcaacaa gaccatcgtg   1080
ttcaacccct cctccggcgg cgacctggag atcgtgaccc actccttcaa ctgcggcggc   1140
gagttcttct actgcaacac caccaagctg ttcaactcca cctggatccg cgagggcaac   1200
aacggcacct ggaacggcac catcggcctg aacgacaccg ccggcaacga caccatcatc   1260
ctgccctgca agatcaagca gatcatcaac atgtggcagg aggtgggcaa ggccatgtac   1320
gcccccccca tccgcggcca gatccgctgc tcctccaaca tcaccggcct gatcctgacc   1380
cgcgacggcg gcaaggacga ctccaacggc tccgagatcc tggagatctt ccgccccggc   1440
ggcggcgaca tgcgcgacaa ctggcgctcc gagctgtaca agtacaaggt ggtgcgcatc   1500
gagcccctgg gcgtggcccc cacccgcgcc cgcgagcgcg tggtgcagaa ggagaaggag   1560
gccgtgggcc tgggcgccat gttcctgggc ttcctgggcg ccgccggctc cgccatgggc   1620
gccgcctcca tgaccctgac cgtgcaggcc cgccagctgc tgtccggcat cgtgcagcag   1680
cagaacaacc tgctgcgcgc catcgaggcc cagcagcaca tgctgcagct gaccgtgtgg   1740
ggcatcaagc agctgcaggc ccgcgtgctg gccgtggagc gctacctgaa ggaccagcag   1800
ctgctgggca tctggggctg ctccggcaag ctgatctgca ccaccgacgt gccctgggac   1860
acctcctggt ccaacaagac cctggacgac atctggggct ccaacatgac ctggatggag   1920
tgggagcgcg agatcgacaa ctacacctcc accatctaca ccctgctgga ggaggcccag   1980
taccagcagg agaagaacga gaaggagctg ctggagctgg acaagtgggc ctccctgtgg   2040
aactggttcg acatcaccaa ctggctgtgg tacatccgct agggatcc                2088
```

<210> SEQ ID NO 20

-continued

<211> LENGTH: 1902
<212> TYPE: DNA
<213> ORGANISM: Human immunodeficiency virus

<400> SEQUENCE: 20
atgcccatgg ggtctctgca accgctggcc accttgtacc tgctggggat gctggtcgct 60
tccgtgctag ctgtggagaa gctgtgggtg actgtatact atggggtgcc tgtgtggaag 120
gaggccacca ccaccctgtt ctgtgcctct gatgccaagg cctatgacac tgaggtccac 180
aatgtctggg ccacccatgc ctgtgtgccc actgacccca accctcagga ggtggtgctg 240
gagaatgtga ctgagcactt caacatgtgg aagaacaaca tggtggagca gatgcaggag 300
gacatcatca gcctgtggga ccagagcctg aagccctgtg tgaagctgac ccccctgtgt 360
gtgaccctga actgcaagga tgtgaacgcc accaacacca ccaatgactc tgagggcact 420
atggagaggg gtgagatcaa gaactgcagc ttcaacatca ccaccagcat cagggatgag 480
gtgcagaagg agtatgccct gttctacaag ctggatgtgg tgcccattga caacaacaac 540
accagctaca ggctgatcag ctgtgacacc tctgtgatca cccaggcctg ccccaagatc 600
agctttgagc ccatccccat ccactactgt gccccctgctg gctttgccat cctgaagtgc 660
aatgacaaga ccttcaatgg caaaggccct tgcaagaatg tgagcactgt gcagtgcact 720
catggcatca ggcctgtggt gagcacccag ctgctgctga atggcagcct ggctgaggag 780
gaggtggtga tcaggtctga caacttcacc aacaatgcca agaccatcat tgtgcagctg 840
aaggagtctg tggagatcaa ctgcaccagg cccaacaaca acaccaggaa gagcattcac 900
attggccctg gcagggcctt ctacaccact ggggagatca ttggggacat caggcaggcc 960
cactgcaaca tcagcagggc caagtggaat gacaccctga agcagattgt gatcaagctg 1020
agggagcagt ttgagaacaa gaccattgtg ttcaatcaca gctctggtgg tgatcctgag 1080
attgtgatgc acagcttcaa ctgtggtggt gagttcttct actgcaacag cacccagctg 1140
ttcaacagca cctggaacaa caacactgag ggcagcaaca acactgaggg caacaccatc 1200
accctgcctt gcaggatcaa gcagatcatc aacatgtggc aggaggtggg caaggccatg 1260
tatgctcctc ccatcagggg ccagatcagg tgcagcagca acatcactgg cctgctgctg 1320
accagggatg gtggcatcaa tgagaatggc actgagattt tcaggcctgg tggtggggac 1380
atgagggaca actggaggtc tgagctgtac aagtacaagg tggtgaagat tgagcccctt 1440
ggtgtggctc ccaccaaggc taagaccctg actgtgcagg ccaggctgct gctgtctggc 1500
attgtgcagc agcagaacaa cctgctgagg gccattgagg ctcaacagag gatgctccag 1560
ctcactgtct ggggcatcaa gcagctccag gccagggtgc tggctgtgga gaggtatctt 1620
ggggatcagc agctccttgg catctggggc tgctctggca agctgatctg caccactgct 1680
gtgccctgga atgccagctg gagcaacaag agcctggaca ggatctggaa caacatgacc 1740
tggatggagt gggagaggga gattgacaac tacacctctg agatttacac cctgattgag 1800
gagagccaga accagcagga gaagaatgag caggagctgc tggagctgga caagtgggcc 1860
agcctgtgga actggtttga catcaccaag tggctgtggt ag 1902

<210> SEQ ID NO 21
<211> LENGTH: 633
<212> TYPE: PRT
<213> ORGANISM: Human immunodeficiency virus

<400> SEQUENCE: 21

Met Pro Met Gly Ser Leu Gln Pro Leu Ala Thr Leu Tyr Leu Leu Gly

-continued

```
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Glu
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430
```

-continued

```
Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Thr Leu Thr Val Gln Ala Arg Leu
                485                 490                 495

Leu Leu Ser Gly Ile Val Gln Gln Gln Asn Asn Leu Leu Arg Ala Ile
            500                 505                 510

Glu Ala Gln Gln Arg Met Leu Gln Leu Thr Val Trp Gly Ile Lys Gln
        515                 520                 525

Leu Gln Ala Arg Val Leu Ala Val Glu Arg Tyr Leu Gly Asp Gln Gln
    530                 535                 540

Leu Leu Gly Ile Trp Gly Cys Ser Gly Lys Leu Ile Cys Thr Thr Ala
545                 550                 555                 560

Val Pro Trp Asn Ala Ser Trp Ser Asn Lys Ser Leu Asp Arg Ile Trp
                565                 570                 575

Asn Asn Met Thr Trp Met Glu Trp Glu Arg Glu Ile Asp Asn Tyr Thr
            580                 585                 590

Ser Glu Ile Tyr Thr Leu Ile Glu Glu Ser Gln Asn Gln Gln Glu Lys
        595                 600                 605

Asn Glu Gln Glu Leu Leu Glu Leu Asp Lys Trp Ala Ser Leu Trp Asn
    610                 615                 620

Trp Phe Asp Ile Thr Lys Trp Leu Trp
625                 630
```

<210> SEQ ID NO 22
<211> LENGTH: 2082
<212> TYPE: DNA
<213> ORGANISM: Human immunodeficiency virus

<400> SEQUENCE: 22

```
atgcgcgtga agggcatccg caagaactac cagcacctgt ggcgctgggg catctggcgc      60

tggggcatca tgctgctggg caccctgatg atctgctccg ccaccgagaa gctgtgggtg     120

accgtgtact acggcgtgcc cgtgtggaag gaggccacca ccaccctgtt ctgcgcctcc     180

gacgccaagg cctactcccc cgagaagcac aacatctggg ccacccacgc ctgcgtgccc     240

accgacccca acccccagga gctggtgctg ggcaacgtga ccgaggactt caacatgtgg     300

aagaacaaca tggtggagca gatgcacgag gacatcatct ccctgtggga ccagtccctg     360

aagccctgcg tgaagctgac ccccctgtgc gtgaccctga actgcaccga cctgaagaac     420

tccgccaccg acaccaacgg cacctccggc accaacaacc gcaccgtgga gcagggcatg     480

gagaccgaga tcaagaactg ctccttcaac atcaccaccg gcatcggcaa caagatgcag     540

aaggagtacg ccctgttcta caagctggac gtggtgccca tcgactccaa caacaactcc     600

gacaacacct cctaccgcct gatctcctgc aacacctccg tggtgaccca ggcctgcccc     660

aagacctcct tcgagcccat ccccatccac tactgcgccc ccgccggctt cgccatcctg     720

aagtgcaaca acaagacctt ctccggcaag ggcccctgca agaacgtgtc caccgtgcag     780

tgcacccacg gcatccgccc cgtggtgtcc acccagctgc tgctgaacgg ctccctggcc     840

gaggaggaga tcgtgatccg ctccgagaac ttcaccaaca acgccaagac catcatcgtg     900

cagctgaacg agtccgtgat catcaactgc acccgcccca acaacaacac ccgcaagggc     960
```

-continued

```
atccacatcg gcctgggccg cgccctgtac gccaccggcg acatcatcgg cgacatccgc   1020

caggcccact gcaacctgtc ctccaagtcc tggaacaaga ccctgcagca ggtggtgcgc   1080

aagctgcgcg agcagttcgg caacaagacc atcgccttca accagtcctc cggcggcgac   1140

caggagatcg tgaagcactc cttcaactgc ggcggcgagt tcttctactg cgacaccacc   1200

cagctgttca actccacctg gtcctccaac gacacctgga actccaccgg cgtgcaggac   1260

aacaacatca ccctgccctg ccgcatcaag cagatcatca acatgtggca ggaggtgggc   1320

aaggccatgt acgccccccc catccagggc ctgatctcct gctcctccaa catcaccggc   1380

ctgctgctga cccgcgacgg cggcaccaac aacaccaacg ccaccgagat cttccgcccc   1440

ggcggcggcg acatgcgcga caactggcgc tccgagctgt acaagtacaa ggtggtgaag   1500

atcgagcccc tgggcatcgc ccccaccaag gccaaggagc gcgtggtgca gcgcgagaag   1560

gaggccgtgg gcctgggcgc cgtgttcatc ggcttcctgg gcgccgccgg ctccaccatg   1620

ggcgccgcct ccgtgaccct gaccgtgcag gcccgccagc tgctgtccgg catcgtgcag   1680

cagcagaaca acctgctgcg cgccatcgag gcccagcagc acatgctgca gctgaccgtg   1740

tggggcatca agcagctgca ggcccgcatc ctggccgtgg agcgctacct gaaggaccag   1800

cagatcctgg gcatctgggg ctgctccggc aagctgatct gccccaccgc cgtgccctgg   1860

aacgcctcct ggtccaacaa gtccctgacc gccatctgga acaacatgac ctggatggag   1920

tgggagcgcg agatcgacaa ctacaccggc ctgatctact ccctgatcga ggagtcccag   1980

atccagcagg agcagaacga gaaggagctg ctggagctgg acaagtgggc ctccctgtgg   2040

aactggttcg acatcaccaa gtggctgtgg tacatcaagt ag                      2082
```

```
<210> SEQ ID NO 23
<211> LENGTH: 693
<212> TYPE: PRT
<213> ORGANISM: Human immunodeficiency virus

<400> SEQUENCE: 23

Met Arg Val Lys Gly Ile Arg Lys Asn Tyr Gln His Leu Trp Arg Trp
1               5                   10                  15

Gly Ile Trp Arg Trp Gly Ile Met Leu Leu Gly Thr Leu Met Ile Cys
            20                  25                  30

Ser Ala Thr Glu Lys Leu Trp Val Thr Val Tyr Tyr Gly Val Pro Val
        35                  40                  45

Trp Lys Glu Ala Thr Thr Thr Leu Phe Cys Ala Ser Asp Ala Lys Ala
    50                  55                  60

Tyr Ser Pro Glu Lys His Asn Ile Trp Ala Thr His Ala Cys Val Pro
65                  70                  75                  80

Thr Asp Pro Asn Pro Gln Glu Leu Val Leu Gly Asn Val Thr Glu Asp
                85                  90                  95

Phe Asn Met Trp Lys Asn Asn Met Val Glu Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu Asn Cys Thr Asp Leu Lys Asn Ser Ala Thr Asp
    130                 135                 140

Thr Asn Gly Thr Ser Gly Thr Asn Asn Arg Thr Val Glu Gln Gly Met
145                 150                 155                 160

Glu Thr Glu Ile Lys Asn Cys Ser Phe Asn Ile Thr Thr Gly Ile Gly
                165                 170                 175
```

```
Asn Lys Met Gln Lys Glu Tyr Ala Leu Phe Tyr Lys Leu Asp Val Val
            180                 185                 190

Pro Ile Asp Ser Asn Asn Asn Ser Asp Asn Thr Ser Tyr Arg Leu Ile
        195                 200                 205

Ser Cys Asn Thr Ser Val Val Thr Gln Ala Cys Pro Lys Thr Ser Phe
    210                 215                 220

Glu Pro Ile Pro Ile His Tyr Cys Ala Pro Ala Gly Phe Ala Ile Leu
225                 230                 235                 240

Lys Cys Asn Asn Lys Thr Phe Ser Gly Lys Gly Pro Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Glu Ile Val Ile Arg Ser
        275                 280                 285

Glu Asn Phe Thr Asn Asn Ala Lys Thr Ile Ile Val Gln Leu Asn Glu
    290                 295                 300

Ser Val Ile Ile Asn Cys Thr Arg Pro Asn Asn Asn Thr Arg Lys Gly
305                 310                 315                 320

Ile His Ile Gly Leu Gly Arg Ala Leu Tyr Ala Thr Gly Asp Ile Ile
                325                 330                 335

Gly Asp Ile Arg Gln Ala His Cys Asn Leu Ser Ser Lys Ser Trp Asn
            340                 345                 350

Lys Thr Leu Gln Gln Val Val Arg Lys Leu Arg Glu Gln Phe Gly Asn
        355                 360                 365

Lys Thr Ile Ala Phe Asn Gln Ser Ser Gly Gly Asp Gln Glu Ile Val
    370                 375                 380

Lys His Ser Phe Asn Cys Gly Gly Glu Phe Phe Tyr Cys Asp Thr Thr
385                 390                 395                 400

Gln Leu Phe Asn Ser Thr Trp Ser Ser Asn Asp Thr Trp Asn Ser Thr
                405                 410                 415

Gly Val Gln Asp Asn Asn Ile Thr Leu Pro Cys Arg Ile Lys Gln Ile
            420                 425                 430

Ile Asn Met Trp Gln Glu Val Gly Lys Ala Met Tyr Ala Pro Pro Ile
        435                 440                 445

Gln Gly Leu Ile Ser Cys Ser Ser Asn Ile Thr Gly Leu Leu Leu Thr
    450                 455                 460

Arg Asp Gly Gly Thr Asn Asn Thr Asn Ala Thr Glu Ile Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Ile Ala Pro Thr Lys Ala Lys
            500                 505                 510

Glu Arg Val Val Gln Arg Glu Lys Glu Ala Val Gly Leu Gly Ala Val
        515                 520                 525

Phe Ile Gly Phe Leu Gly Ala Ala Gly Ser Thr Met Gly Ala Ala Ser
    530                 535                 540

Val Thr Leu Thr Val Gln Ala Arg Gln Leu Leu Ser Gly Ile Val Gln
545                 550                 555                 560

Gln Gln Asn Asn Leu Leu Arg Ala Ile Glu Ala Gln Gln His Met Leu
                565                 570                 575

Gln Leu Thr Val Trp Gly Ile Lys Gln Leu Gln Ala Arg Ile Leu Ala
            580                 585                 590
```

```
Val Glu Arg Tyr Leu Lys Asp Gln Gln Ile Leu Gly Ile Trp Gly Cys
        595                 600                 605

Ser Gly Lys Leu Ile Cys Pro Thr Ala Val Pro Trp Asn Ala Ser Trp
    610                 615                 620

Ser Asn Lys Ser Leu Thr Ala Ile Trp Asn Asn Met Thr Trp Met Glu
625                 630                 635                 640

Trp Glu Arg Glu Ile Asp Asn Tyr Thr Gly Leu Ile Tyr Ser Leu Ile
                645                 650                 655

Glu Glu Ser Gln Ile Gln Gln Glu Gln Asn Glu Lys Glu Leu Leu Glu
            660                 665                 670

Leu Asp Lys Trp Ala Ser Leu Trp Asn Trp Phe Asp Ile Thr Lys Trp
        675                 680                 685

Leu Trp Tyr Ile Lys
    690


<210> SEQ ID NO 24
<211> LENGTH: 15
<212> TYPE: PRT
<213> ORGANISM: Homo sapiens

<400> SEQUENCE: 24

Tyr Leu Glu Glu Glu Leu Asp Lys Trp Ala Lys Ile Ala Ala Tyr
1               5                   10                  15


<210> SEQ ID NO 25
<211> LENGTH: 15
<212> TYPE: PRT
<213> ORGANISM: Mus musculus

<400> SEQUENCE: 25

Tyr Leu Glu Glu Glu Leu Asp Lys Trp Ala Lys Met Gly Ala Tyr
1               5                   10                  15


<210> SEQ ID NO 26
<211> LENGTH: 25
<212> TYPE: PRT
<213> ORGANISM: Homo sapiens

<400> SEQUENCE: 26

Ser Leu Gly Leu Gln Pro Lys Met Val Lys Thr Tyr Leu Glu Glu Glu
1               5                   10                  15

Leu Asp Lys Trp Ala Lys Ile Ala Ala
            20                  25


<210> SEQ ID NO 27
<211> LENGTH: 25
<212> TYPE: PRT
<213> ORGANISM: Pan troglodytes

<400> SEQUENCE: 27

Ser Leu Gly Leu Gln Pro Lys Met Val Lys Thr Tyr Leu Glu Glu Glu
1               5                   10                  15

Leu Asp Lys Trp Ala Lys Ile Ala Ala
            20                  25


<210> SEQ ID NO 28
<211> LENGTH: 25
<212> TYPE: PRT
<213> ORGANISM: Mus musculus

<400> SEQUENCE: 28
```

```
Ser Leu Gly Leu Gln Pro Lys Met Val Arg Thr Tyr Leu Glu Glu Glu
1               5                   10                  15

Leu Asp Lys Trp Ala Lys Met Gly Ala
            20                  25


<210> SEQ ID NO 29
<211> LENGTH: 25
<212> TYPE: PRT
<213> ORGANISM: Ailuropoda melanoleuca

<400> SEQUENCE: 29

Ser Leu Gly Leu Gln Pro Lys Met Val Lys Thr Tyr Leu Glu Glu Glu
1               5                   10                  15

Leu Asp Lys Trp Ala Lys Met Gly Ala
            20                  25


<210> SEQ ID NO 30
<211> LENGTH: 25
<212> TYPE: PRT
<213> ORGANISM: Bos taurus

<400> SEQUENCE: 30

Ser Leu Gly Leu Gln Pro Lys Met Val Lys Thr Tyr Leu Glu Glu Glu
1               5                   10                  15

Leu Asp Lys Trp Ala Lys Met Gly Ala
            20                  25


<210> SEQ ID NO 31
<211> LENGTH: 25
<212> TYPE: PRT
<213> ORGANISM: Oryctolagus cuniculus

<400> SEQUENCE: 31

Ser Leu Gly Leu Gln Pro Lys Met Val Lys Thr Tyr Leu Glu Glu Glu
1               5                   10                  15

Leu Asp Lys Trp Ala Lys Met Gly Ala
            20                  25


<210> SEQ ID NO 32
<211> LENGTH: 25
<212> TYPE: PRT
<213> ORGANISM: Equus caballus

<400> SEQUENCE: 32

Ser Leu Gly Leu Gln Pro Lys Met Val Lys Thr Tyr Leu Glu Glu Glu
1               5                   10                  15

Leu Asp Lys Trp Ala Lys Met Gly Gly
            20                  25


<210> SEQ ID NO 33
<211> LENGTH: 25
<212> TYPE: PRT
<213> ORGANISM: Monodelphis domestica

<400> SEQUENCE: 33

Ser Leu Gly Leu Gln Pro Arg Asn Val Lys Lys Tyr Leu Glu Glu Glu
1               5                   10                  15

Leu Glu Lys Trp Ala Lys Met Gly Gly
            20                  25


<210> SEQ ID NO 34
<211> LENGTH: 25
```

```
<212> TYPE: PRT
<213> ORGANISM: Ornithorhynchus anatinus

<400> SEQUENCE: 34

Ser Leu Gly Leu Gln Pro Lys Lys Val Lys Ala Tyr Leu Glu Glu Glu
1               5                   10                  15

Leu Asp Lys Trp Ala Lys Met Gly Ala
            20                  25


<210> SEQ ID NO 35
<211> LENGTH: 25
<212> TYPE: PRT
<213> ORGANISM: Gallus gallus

<400> SEQUENCE: 35

Ser Leu Gly Leu Gln Pro Lys Lys Val Lys Ala Tyr Leu Asp Glu Glu
1               5                   10                  15

Leu Asp Lys Trp Ala Arg Thr Gly Val
            20                  25


<210> SEQ ID NO 36
<211> LENGTH: 25
<212> TYPE: PRT
<213> ORGANISM: Danio rerio

<400> SEQUENCE: 36

Ser Leu Gly Leu Gln Pro Lys Asn Thr Lys Lys Tyr Ile Asp Glu Glu
1               5                   10                  15

Leu Glu Lys Trp Ala Lys Thr Gly Val
            20                  25


<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Tyr Thr Ser Leu Ile His Ser Leu Ile Glu Glu Ser Gln Asn Gln Leu
1               5                   10                  15

Gln Glu Lys Asn Glu Gln Glu Leu Leu Glu Leu Asp Lys Trp Ala Ser
            20                  25                  30

Leu Trp Asn Phe
        35


<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Gln Glu Leu Leu Glu Leu Asp Lys Trp Ala Ser Leu Trp Asn Trp
1               5                   10                  15

Phe Asn Ile Thr Asn Trp Leu Trp Tyr Ile Lys
            20                  25


<210> SEQ ID NO 39
<211> LENGTH: 1332
```

-continued

```
<212> TYPE: PRT
<213> ORGANISM: Escherichia coli

<400> SEQUENCE: 39

Met Val Tyr Ser Tyr Thr Glu Lys Lys Arg Ile Arg Lys Asp Phe Gly
1               5                   10                  15

Lys Arg Pro Gln Val Leu Asp Val Pro Tyr Leu Leu Ser Ile Gln Leu
            20                  25                  30

Asp Ser Phe Gln Lys Phe Ile Glu Gln Asp Pro Glu Gly Gln Tyr Gly
        35                  40                  45

Leu Glu Ala Ala Phe Arg Ser Val Phe Pro Ile Gln Ser Tyr Ser Gly
    50                  55                  60

Asn Ser Glu Leu Gln Tyr Val Ser Tyr Arg Leu Gly Glu Pro Val Phe
65                  70                  75                  80

Asp Val Gln Glu Cys Gln Ile Arg Gly Val Thr Tyr Ser Ala Pro Leu
                85                  90                  95

Arg Val Lys Leu Arg Leu Val Ile Tyr Glu Arg Glu Ala Pro Glu Gly
            100                 105                 110

Thr Val Lys Asp Ile Lys Glu Gln Glu Val Tyr Met Gly Glu Ile Leu
        115                 120                 125

Met Thr Asp Asn Gly Thr Phe Val Ile Asn Gly Thr Glu Arg Val Ile
    130                 135                 140

Val Ser Gln Leu His Arg Ser Pro Gly Val Phe Phe Asp Ser Asp Lys
145                 150                 155                 160

Gly Lys Thr His Ser Ser Gly Lys Val Leu Tyr Asn Ala Arg Ile Ile
                165                 170                 175

Pro Tyr Arg Gly Ser Trp Leu Asp Phe Glu Phe Asp Pro Lys Asp Asn
            180                 185                 190

Leu Phe Val Arg Ile Asp Arg Arg Arg Lys Leu Pro Ala Thr Ile Ile
        195                 200                 205

Leu Arg Ala Leu Asn Tyr Thr Thr Glu Gln Ile Leu Asp Leu Phe Phe
    210                 215                 220

Glu Lys Val Ile Phe Glu Ile Arg Asp Asn Lys Leu Gln Met Glu Leu
225                 230                 235                 240

Val Pro Glu Arg Leu Arg Gly Glu Thr Ala Ser Phe Asp Ile Ala Asn
                245                 250                 255

Gly Lys Val Tyr Val Glu Lys Gly Arg Arg Ile Thr Ala Arg His Ile
            260                 265                 270

Arg Gln Leu Glu Lys Asp Asp Val Lys Leu Ile Glu Val Pro Val Glu
        275                 280                 285

Tyr Ile Ala Gly Lys Val Val Ala Lys Asp Tyr Ile Asp Glu Ser Thr
    290                 295                 300

Gly Glu Leu Ile Cys Ala Ala Asn Met Glu Leu Ser Leu Asp Leu Leu
305                 310                 315                 320

Ala Lys Leu Ser Gln Ser Gly His Lys Arg Ile Glu Thr Leu Phe Thr
                325                 330                 335

Asn Asp Leu Asp His Gly Pro Tyr Ile Ser Glu Thr Leu Arg Val Asp
            340                 345                 350

Pro Thr Asn Asp Arg Leu Ser Ala Leu Val Glu Ile Tyr Arg Met Met
        355                 360                 365

Arg Pro Gly Glu Pro Pro Thr Arg Glu Ala Ala Glu Ser Phe Glu Asn
    370                 375                 380

Leu Phe Phe Ser Glu Asp Arg Tyr Asp Leu Ser Ala Val Gly Arg Met
385                 390                 395                 400
```

-continued

```
Lys Phe Asn Arg Ser Leu Leu Arg Glu Glu Ile Glu Gly Ser Gly Ile
                405                 410                 415

Leu Ser Lys Asp Asp Ile Ile Asp Val Met Lys Lys Leu Ile Asp Ile
            420                 425                 430

Arg Asn Gly Lys Gly Glu Val Asp Asp Ile Asp His Leu Gly Asn Arg
        435                 440                 445

Arg Ile Arg Ser Val Gly Glu Met Ala Glu Asn Gln Phe Arg Val Gly
    450                 455                 460

Leu Val Arg Val Glu Arg Ala Val Lys Glu Arg Leu Ser Leu Gly Asp
465                 470                 475                 480

Leu Asp Thr Leu Met Pro Gln Asp Met Ile Asn Ala Lys Pro Ile Ser
                485                 490                 495

Ala Ala Val Lys Glu Phe Phe Gly Ser Ser Gln Leu Gln Phe Met Asp
            500                 505                 510

Gln Asn Asn Pro Leu Ser Glu Ile Thr His Lys Arg Arg Ile Ser Ala
        515                 520                 525

Leu Gly Pro Gly Gly Leu Thr Arg Glu Arg Ala Gly Phe Glu Val Arg
    530                 535                 540

Asp Val His Pro Thr His Tyr Gly Arg Val Cys Pro Ile Glu Thr Pro
545                 550                 555                 560

Glu Gly Pro Asn Ile Gly Leu Ile Asn Ser Leu Ser Val Tyr Ala Gln
                565                 570                 575

Thr Asn Glu Tyr Gly Phe Leu Glu Thr Pro Tyr Arg Lys Val Thr Asp
            580                 585                 590

Gly Val Val Thr Asp Glu Ile His Tyr Leu Ser Ala Ile Glu Glu Gly
        595                 600                 605

Asn Tyr Val Ile Ala Gln Ala Asn Ser Asn Leu Asp Glu Glu Gly His
    610                 615                 620

Phe Val Glu Asp Leu Val Thr Cys Arg Ser Lys Glu Ser Ser Leu Phe
625                 630                 635                 640

Ser Arg Asp Gln Val Asp Tyr Met Asp Val Ser Thr Gln Gln Val Val
                645                 650                 655

Ser Val Gly Ala Ser Leu Ile Pro Phe Leu Glu His Asp Asp Ala Asn
            660                 665                 670

Arg Ala Leu Met Gly Ala Asn Met Gln Arg Gln Ala Val Pro Thr Leu
        675                 680                 685

Arg Ala Asp Lys Pro Leu Val Gly Thr Gly Met Glu Arg Ala Val Ala
    690                 695                 700

Val Asp Ser Gly Val Thr Ala Val Ala Lys Arg Gly Gly Val Val Gln
705                 710                 715                 720

Tyr Val Asp Ala Ser Arg Ile Val Ile Lys Val Asn Glu Asp Glu Met
                725                 730                 735

Tyr Pro Gly Glu Ala Gly Ile Asp Ile Tyr Asn Leu Thr Lys Tyr Thr
            740                 745                 750

Arg Ser Asn Gln Asn Thr Cys Ile Asn Gln Pro Cys Val Ser Leu Gly
        755                 760                 765

Glu Pro Val Glu Arg Gly Asp Val Leu Ala Asp Gly Pro Ser Thr Asp
    770                 775                 780

Leu Gly Glu Leu Ala Leu Gly Gln Asn Met Arg Val Ala Phe Met Pro
785                 790                 795                 800

Trp Asn Gly Tyr Asn Phe Glu Asp Ser Ile Leu Val Ser Glu Arg Val
                805                 810                 815
```

-continued

```
Val Gln Glu Asp Arg Phe Thr Thr Ile His Ile Gln Glu Leu Ala Cys
            820                 825                 830

Val Ser Arg Asp Thr Lys Leu Gly Pro Glu Glu Ile Thr Ala Asp Ile
        835                 840                 845

Pro Asn Val Gly Glu Ala Ala Leu Ser Lys Leu Asp Glu Ser Gly Ile
    850                 855                 860

Val Tyr Ile Gly Ala Glu Val Thr Gly Gly Asp Ile Leu Val Gly Lys
865                 870                 875                 880

Val Thr Pro Lys Gly Glu Thr Gln Leu Pro Glu Glu Lys Leu Leu Arg
                885                 890                 895

Ala Ile Phe Gly Glu Lys Ala Ser Asp Val Lys Asp Ser Ser Leu Arg
            900                 905                 910

Val Pro Asn Gly Val Ser Gly Thr Val Ile Asp Val Gln Val Phe Thr
        915                 920                 925

Arg Asp Gly Val Glu Lys Asp Lys Arg Ala Leu Glu Ile Glu Glu Met
    930                 935                 940

Gln Leu Lys Gln Ala Lys Lys Asp Leu Ser Glu Glu Leu Gln Ile Leu
945                 950                 955                 960

Glu Ala Gly Leu Phe Ser Arg Ile Arg Ala Val Leu Val Ala Gly Gly
                965                 970                 975

Val Glu Ala Glu Lys Leu Asp Lys Leu Pro Arg Asp Arg Trp Leu Glu
            980                 985                 990

Leu Gly Leu Thr Asp Glu Glu Lys  Gln Asn Gln Leu Glu  Gln Leu Ala
        995                 1000                1005

Glu Gln  Tyr Asp Glu Leu Lys  His Phe Glu Lys Lys  Leu Glu Ala
    1010                1015                1020

Lys Arg  Arg Lys Ile Thr Gln  Gly Asp Asp Leu Ala  Pro Gly Val
    1025                1030                1035

Leu Lys  Ile Val Lys Val Tyr  Leu Ala Val Lys Arg  Arg Ile Gln
    1040                1045                1050

Pro Gly  Asp Lys Met Ala Gly  Arg His Gly Asn Lys  Gly Val Ile
    1055                1060                1065

Ser Lys  Ile Asn Pro Ile Glu  Asp Met Pro Tyr Asp  Glu Asn Gly
    1070                1075                1080

Thr Pro  Val Asp Ile Val Leu  Asn Pro Leu Gly Val  Pro Ser Arg
    1085                1090                1095

Met Asn  Ile Gly Gln Ile Leu  Glu Thr His Leu Gly  Met Ala Ala
    1100                1105                1110

Lys Gly  Ile Gly Asp Lys Ile  Asn Ala Met Leu Lys  Gln Gln Gln
    1115                1120                1125

Glu Val  Ala Lys Leu Arg Glu  Phe Ile Gln Arg Ala  Tyr Asp Leu
    1130                1135                1140

Ala Asp  Val Arg Gln Lys Val  Asp Leu Ser Thr Phe  Ser Asp Glu
    1145                1150                1155

Glu Val  Met Arg Leu Ala Glu  Asn Leu Arg Lys Gly  Met Pro Ile
    1160                1165                1170

Ala Thr  Pro Val Phe Asp Gly  Ala Lys Glu Ala Glu  Ile Lys Glu
    1175                1180                1185

Leu Leu  Lys Leu Gly Asp Leu  Pro Thr Ser Gly Gln  Ile Arg Leu
    1190                1195                1200

Tyr Asp  Gly Arg Thr Gly Glu  Gln Phe Glu Arg Pro  Val Thr Val
    1205                1210                1215

Gly Tyr  Met Tyr Met Leu Lys  Leu Asn His Leu Val  Asp Asp Lys
```

-continued

```
    1220                1225                1230

Met His  Ala Arg Ser Thr Gly  Ser Tyr Ser Leu Val  Thr Gln Gln
    1235                1240                1245

Pro Leu  Gly Gly Lys Ala Gln  Phe Gly Gly Gln Arg  Phe Gly Glu
    1250                1255                1260

Met Glu  Val Trp Ala Leu Glu  Tyr Gly Ala Ala Tyr  Thr Leu Gln
    1265                1270                1275

Glu Met  Leu Thr Val Lys Ser  Asp Asp Val Asn Gly  Arg Thr Lys
    1280                1285                1290

Met Tyr  Lys Asn Ile Val Asp  Gly Asn His Gln Met  Glu Pro Gly
    1295                1300                1305

Met Pro  Glu Ser Phe Asn Val  Leu Leu Lys Glu Ile  Arg Ser Leu
    1310                1315                1320

Gly Ile  Asn Ile Glu Leu Glu  Asp Glu
    1325                1330


<210> SEQ ID NO 40
<211> LENGTH: 1407
<212> TYPE: PRT
<213> ORGANISM: Escherichia coli

<400> SEQUENCE: 40

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
            100                 105                 110

His Ile Trp Phe Leu Lys Ser Leu Pro Ser Arg Ile Gly Leu Leu Leu
        115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
            180                 185                 190

Asp Leu Glu Gln Glu Cys Glu Gln Leu Arg Glu Glu Leu Asn Glu Thr
        195                 200                 205

Asn Ser Glu Thr Lys Arg Lys Lys Leu Thr Lys Arg Ile Lys Leu Leu
    210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255
```

-continued

Gly Gly Arg Phe Ala Thr Ser Asp Leu Asn Asp Leu Tyr Arg Arg Val
260 265 270

Ile Asn Arg Asn Asn Arg Leu Lys Arg Leu Leu Asp Leu Ala Ala Pro
275 280 285

Asp Ile Ile Val Arg Asn Glu Lys Arg Met Leu Gln Glu Ala Val Asp
290 295 300

Ala Leu Leu Asp Asn Gly Arg Arg Gly Arg Ala Ile Thr Gly Ser Asn
305 310 315 320

Lys Arg Pro Leu Lys Ser Leu Ala Asp Met Ile Lys Gly Lys Gln Gly
325 330 335

Arg Phe Arg Gln Asn Leu Leu Gly Lys Arg Val Asp Tyr Ser Gly Arg
340 345 350

Ser Val Ile Thr Val Gly Pro Tyr Leu Arg Leu His Gln Cys Gly Leu
355 360 365

Pro Lys Lys Met Ala Leu Glu Leu Phe Lys Pro Phe Ile Tyr Gly Lys
370 375 380

Leu Glu Leu Arg Gly Leu Ala Thr Thr Ile Lys Ala Ala Lys Lys Met
385 390 395 400

Val Glu Arg Glu Glu Ala Val Val Trp Asp Ile Leu Asp Glu Val Ile
405 410 415

Arg Glu His Pro Val Leu Leu Asn Arg Ala Pro Thr Leu His Arg Leu
420 425 430

Gly Ile Gln Ala Phe Glu Pro Val Leu Ile Glu Gly Lys Ala Ile Gln
435 440 445

Leu His Pro Leu Val Cys Ala Ala Tyr Asn Ala Asp Phe Asp Gly Asp
450 455 460

Gln Met Ala Val His Val Pro Leu Thr Leu Glu Ala Gln Leu Glu Ala
465 470 475 480

Arg Ala Leu Met Met Ser Thr Asn Asn Ile Leu Ser Pro Ala Asn Gly
485 490 495

Glu Pro Ile Ile Val Pro Ser Gln Asp Val Val Leu Gly Leu Tyr Tyr
500 505 510

Met Thr Arg Asp Cys Val Asn Ala Lys Gly Glu Gly Met Val Leu Thr
515 520 525

Gly Pro Lys Glu Ala Glu Arg Leu Tyr Arg Ser Gly Leu Ala Ser Leu
530 535 540

His Ala Arg Val Lys Val Arg Ile Thr Glu Tyr Glu Lys Asp Ala Asn
545 550 555 560

Gly Glu Leu Val Ala Lys Thr Ser Leu Lys Asp Thr Thr Val Gly Arg
565 570 575

Ala Ile Leu Trp Met Ile Val Pro Lys Gly Leu Pro Tyr Ser Ile Val
580 585 590

Asn Gln Ala Leu Gly Lys Lys Ala Ile Ser Lys Met Leu Asn Thr Cys
595 600 605

Tyr Arg Ile Leu Gly Leu Lys Pro Thr Val Ile Phe Ala Asp Gln Ile
610 615 620

Met Tyr Thr Gly Phe Ala Tyr Ala Ala Arg Ser Gly Ala Ser Val Gly
625 630 635 640

Ile Asp Asp Met Val Ile Pro Glu Lys Lys His Glu Ile Ile Ser Glu
645 650 655

Ala Glu Ala Glu Val Ala Glu Ile Gln Glu Gln Phe Gln Ser Gly Leu
660 665 670

Val Thr Ala Gly Glu Arg Tyr Asn Lys Val Ile Asp Ile Trp Ala Ala

-continued

```
        675                 680                 685

Ala Asn Asp Arg Val Ser Lys Ala Met Met Asp Asn Leu Gln Thr Glu
    690                 695                 700

Thr Val Ile Asn Arg Asp Gly Gln Glu Glu Lys Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Asp Cys Gly Thr
                805                 810                 815

His Glu Gly Ile Met Met Thr Pro Val Ile Glu Gly Gly Asp Val Lys
            820                 825                 830

Glu Pro Leu Arg Asp Arg Val Leu Gly Arg Val Thr Ala Glu Asp Val
        835                 840                 845

Leu Lys Pro Gly Thr Ala Asp Ile Leu Val Pro Arg Asn Thr Leu Leu
    850                 855                 860

His Glu Gln Trp Cys Asp Leu Leu Glu Glu Asn Ser Val Asp Ala Val
865                 870                 875                 880

Lys Val Arg Ser Val Val Ser Cys Asp Thr Asp Phe Gly Val Cys Ala
                885                 890                 895

His Cys Tyr Gly Arg Asp Leu Ala Arg Gly His Ile Ile Asn Lys Gly
            900                 905                 910

Glu Ala Ile Gly Val Ile Ala Ala Gln Ser Ile Gly Glu Pro Gly Thr
        915                 920                 925

Gln Leu Thr Met Arg Thr Phe His Ile Gly Gly Ala Ala Ser Arg Ala
    930                 935                 940

Ala Ala Glu Ser Ser Ile Gln Val Lys Asn Lys Gly Ser Ile Lys Leu
945                 950                 955                 960

Ser Asn Val Lys Ser Val Val Asn Ser Ser Gly Lys Leu Val Ile Thr
                965                 970                 975

Ser Arg Asn Thr Glu Leu Lys Leu Ile Asp Glu Phe Gly Arg Thr Lys
            980                 985                 990

Glu Ser Tyr Lys Val Pro Tyr Gly  Ala Val Leu Ala Lys  Gly Asp Gly
        995                 1000                1005

Glu Gln  Val Ala Gly Gly Glu  Thr Val Ala Asn Trp  Asp Pro His
    1010                1015                1020

Thr Met  Pro Val Ile Thr Glu  Val Ser Gly Phe Val  Arg Phe Thr
    1025                1030                1035

Asp Met  Ile Asp Gly Gln Thr  Ile Thr Arg Gln Thr  Asp Glu Leu
    1040                1045                1050

Thr Gly  Leu Ser Ser Leu Val  Val Leu Asp Ser Ala  Glu Arg Thr
    1055                1060                1065

Ala Gly  Gly Lys Asp Leu Arg  Pro Ala Leu Lys Ile  Val Asp Ala
    1070                1075                1080

Gln Gly  Asn Asp Val Leu Ile  Pro Gly Thr Asp Met  Pro Ala Gln
    1085                1090                1095
```

```
Tyr Phe  Leu Pro Gly Lys Ala  Ile Val Gln Leu Glu  Asp Gly Val
    1100                 1105                 1110

Gln Ile  Ser Ser Gly Asp Thr  Leu Ala Arg Ile Pro  Gln Glu Ser
    1115                 1120                 1125

Gly Gly  Thr Lys Asp Ile Thr  Gly Gly Leu Pro Arg  Val Ala Asp
    1130                 1135                 1140

Leu Phe  Glu Ala Arg Arg Pro  Lys Glu Pro Ala Ile  Leu Ala Glu
    1145                 1150                 1155

Ile Ser  Gly Ile Val Ser Phe  Gly Lys Glu Thr Lys  Gly Lys Arg
    1160                 1165                 1170

Arg Leu  Val Ile Thr Pro Val  Asp Gly Ser Asp Pro  Tyr Glu Glu
    1175                 1180                 1185

Met Ile  Pro Lys Trp Arg Gln  Leu Asn Val Phe Glu  Gly Glu Arg
    1190                 1195                 1200

Val Glu  Arg Gly Asp Val Ile  Ser Asp Gly Pro Glu  Ala Pro His
    1205                 1210                 1215

Asp Ile  Leu Arg Leu Arg Gly  Val His Ala Val Thr  Arg Tyr Ile
    1220                 1225                 1230

Val Asn  Glu Val Gln Asp Val  Tyr Arg Leu Gln Gly  Val Lys Ile
    1235                 1240                 1245

Asn Asp  Lys His Ile Glu Val  Ile Val Arg Gln Met  Leu Arg Lys
    1250                 1255                 1260

Ala Thr  Ile Val Asn Ala Gly  Ser Ser Asp Phe Leu  Glu Gly Glu
    1265                 1270                 1275

Gln Val  Glu Tyr Ser Arg Val  Lys Ile Ala Asn Arg  Glu Leu Glu
    1280                 1285                 1290

Ala Asn  Gly Lys Val Gly Ala  Thr Tyr Ser Arg Asp  Leu Leu Gly
    1295                 1300                 1305

Ile Thr  Lys Ala Ser Leu Ala  Thr Glu Ser Phe Ile  Ser Ala Ala
    1310                 1315                 1320

Ser Phe  Gln Glu Thr Thr Arg  Val Leu Thr Glu Ala  Ala Val Ala
    1325                 1330                 1335

Gly Lys  Arg Asp Glu Leu Arg  Gly Leu Lys Glu Asn  Val Ile Val
    1340                 1345                 1350

Gly Arg  Leu Ile Pro Ala Gly  Thr Gly Tyr Ala Tyr  His Gln Asp
    1355                 1360                 1365

Arg Met  Arg Arg Arg Ala Ala  Gly Glu Ala Pro Ala  Ala Pro Gln
    1370                 1375                 1380

Val Thr  Ala Glu Asp Ala Ser  Ala Ser Leu Ala Glu  Leu Leu Asn
    1385                 1390                 1395

Ala Gly  Leu Gly Gly Ser Asp  Asn Glu
    1400                 1405

<210> SEQ ID NO 41
<211> LENGTH: 327
<212> TYPE: PRT
<213> ORGANISM: Citrobacter koseri

<400> SEQUENCE: 41

Met Gln Gly Ser Val Thr Glu Phe Leu Lys Pro Arg Leu Val Asp Ile
1               5                   10                  15

Glu Gln Val Ser Ser Thr His Ala Lys Val Thr Leu Glu Pro Leu Glu
            20                  25                  30

Arg Gly Phe Gly His Thr Leu Gly Asn Ala Leu Arg Arg Ile Leu Leu
```

```
        35                  40                  45

Ser Ser Met Pro Gly Cys Ala Val Thr Glu Val Glu Ile Asp Gly Val
    50                  55                  60

Leu His Glu Tyr Ser Thr Lys Glu Gly Val Gln Glu Asp Ile Leu Glu
65                  70                  75                  80

Ile Leu Leu Asn Leu Lys Gly Leu Ala Val Arg Val Gln Gly Lys Asp
                85                  90                  95

Glu Val Ile Leu Thr Leu Asn Lys Ser Gly Ile Gly Pro Val Thr Ala
            100                 105                 110

Ala Asp Ile Thr His Asp Gly Asp Val Glu Ile Val Lys Pro Gln Val
        115                 120                 125

Ile Cys His Leu Thr Asp Glu Asn Ala Ser Ile Ser Met Arg Ile Lys
    130                 135                 140

Val Gln Arg Gly Arg Gly Tyr Val Pro Ala Ser Thr Arg Ile His Ser
145                 150                 155                 160

Glu Glu Asp Glu Arg Pro Ile Gly Arg Leu Leu Val Asp Ala Cys Tyr
                165                 170                 175

Ser Pro Val Glu Arg Ile Ala Tyr Asn Val Glu Ala Ala Arg Val Glu
            180                 185                 190

Gln Arg Thr Asp Leu Asp Lys Leu Val Ile Glu Met Glu Thr Asn Gly
        195                 200                 205

Thr Ile Asp Pro Glu Glu Ala Ile Arg Arg Ala Ala Thr Ile Leu Ala
    210                 215                 220

Glu Gln Leu Glu Ala Phe Val Asp Leu Arg Asp Val Arg Gln Pro Glu
225                 230                 235                 240

Val Lys Glu Glu Lys Pro Glu Phe Asp Pro Ile Leu Leu Arg Val Asp
                245                 250                 255

Asp Leu Glu Leu Thr Val Arg Ser Ala Asn Cys Leu Lys Ala Glu Ala
            260                 265                 270

Ile His Tyr Ile Gly Asp Leu Val Gln Arg Thr Glu Val Glu Leu Leu
        275                 280                 285

Lys Thr Pro Asn Leu Gly Lys Lys Ser Leu Thr Glu Ile Lys Asp Val
    290                 295                 300

Leu Ala Ser Arg Gly Leu Ser Leu Gly Met Arg Leu Glu Asn Trp Pro
305                 310                 315                 320

Pro Ala Ser Ile Ala Asp Glu
                325
```

<210> SEQ ID NO 42
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 42

```
gaggtgcagc tggtggagtc tgggggaggt gtggtacggc ctggggggtc cctgagactc     60

tcctgtgcag cctctggatt cacctttgat gattatggca tgagctgggt ccgccaagct    120

ccagggaagg ggctggagtg ggtctctggt attaattgga atggtggtag cacaggttat    180

gcagactctg tgaagggccg attcaccatc tccagagaca acgccaagaa ctccctgtat    240

ctgcaaatga acagtctgag agccgaggac acggccttrt attactgtgc gagagggacc    300

gattacacta ttgacgacca ggggatcckt tatcaaggtt cggggacctt ctggtacttc    360
```

gatctctggg gccgtggcac cctggtcact gtctcctcag nn 402

<210> SEQ ID NO 43
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 43
gaggttcagc tggtggagtc tggggcaaat gttgtacggc cggggggggtc cctgagactc 60 tcctgtaaag cgtccggatt catctttgaa aattttggtt ttagttgggt ccgccaggct 120
ccagggaagg ggcttcagtg ggtcgctggt cttaattgga atggtggtga cacacgttat 180
gcagactctg tgaagggccg attcagaatg tccagagaca actccaggaa ttttgtgtat 240
ttggacatgg ataaagtggg agtcgacgac acggccttct attactgtgc gagagggacc 300
gattacacta ttgacgacgc ggggatccat taccaaggtt cggggacctt ctggtacttc 360
gatctctggg gccgtggcac cctggtcagt gtctcttcag nn 402

<210> SEQ ID NO 44
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 44
gaggttcagc tggtggagtc tgggggaagt gtggtgcggc cggggggggtc cctgagactc 60 tcctgtagag cgtccggatt catctttgag aactatggcc tgacttgggt ccgccaagtt 120
ccagggaaag ggctacattg ggtctccggg atgaattgga atggtggtga cacgcgttat 180
gcagactctg tgaggggccg atttagcatg tccagagaca acagcaacaa catcgcatat 240
ctgcaaatga ataatctgag agtggaggac acggccttrt attactgcgc gagagggacc 300
gattacacga tagacgacca gggaagatkt tatcaaggat cggggacctt ctggtacttc 360
gatttttggg gccgtggcac actggtcact gtctcttcag nn 402

<210> SEQ ID NO 45
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 45
gaggtgcagc tggtggagtc tgggggaggt gtggtgcggc cggggggggtc cctgagactc 60 tcctgtgcag cgtccggatt catttttgag aactacggct tgacttgggt ccgccaagtt 120
ccagggaaag ggctgcattg ggtctccggt atgaattgga atggtggtga cacgcgttat 180
gcagactctg tgaggggccg attcagcatg tccagagaca acagcaataa tatcgcatat 240
ctgcaaatga aaaatctgag agtcgacgac acggccttrt attactgtgc gagagggacc 300
gattacacga tagacgacca gggaatttkt tataaaggtt cggggacctt ctggtacttc 360
gatctctggg gccgtggcac cctggtcact gtctcttcag nn 402

<210> SEQ ID NO 46
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 46
gaggtkcagc tggtggagtc tgggggaggt ctcatacggc cggggggtc cctgagactc 60 tcctgtaaag gctccggttt catctttgag aattttggct tcggctgggt ccgccaaggt 120
ccagggaagg ggctggagtg ggtgtctggc actaattgga atggaggtga ctcacgttat 180
ggagactctg tgaagggccg attcacaatc tccagagaca acagcaacaa tttcgtctac 240
ctgcaaatga acagtctgag acccgaggac acggccatrt attattgtgc gagagggacc 300
gattacacta ttgacgatca ggggatcckt tatcaaggtt cggggacttt ctggtacttc 360
gatgtctggg gccgcggcac cctggtcacg gtctcctcag nn 402

<210> SEQ ID NO 47
<211> LENGTH: 402
<212> TYPE: DNA
<213> ORGANISM: Homo sapiens
<220> FEATURE:
<221> NAME/KEY: modified_base
<222> LOCATION: (401)..(402)
<223> OTHER INFORMATION: a, c, t, g, unknown or other

<400> SEQUENCE: 47
gaggtkcagc tggtggagtc tgggggaggt ctcatacggc cggggggtc cctgagactc 60 tcctgtaaag gctccggttt catctttgag aattttggct tcggctgggt ccgccaaggt 120
ccagggaagg ggctggagtg ggtgtctggc actaattgga atggaggtga ctcacgttat 180
ggagactctg tgaagggccg attcacaatc tccagagaca acagcaacaa tttcgtctac 240
ctgcaaatga acagtctgag acccgaggac acggccatrt attattgtgc gagagggacc 300
gattacacta ttgacgatca ggggatcckt tatcaaggtt cggggacttt ctggtacttc 360
gatgtctggg gccgcggcac cctggtcacg gtctcctcag nn 402

<210> SEQ ID NO 48
<211> LENGTH: 322
<212> TYPE: DNA
<213> ORGANISM: Homo sapiens

<400> SEQUENCE: 48
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctccccgta cacgttcggc 300
caagggacca aggtggaaat ca 322

<210> SEQ ID NO 49
<211> LENGTH: 322
<212> TYPE: DNA
<213> ORGANISM: Homo sapiens

<400> SEQUENCE: 49
gaaattgtgt tgacacagtc tccaggcacc ctgtctttgt ctccagggga aagagccacc 60
ctctcctgca gggccagtca caatgtccac cccaaatatt tcgcctggta ccagcagaag 120
cctggccagt ctccccgact cctcatctat ggtgggtcca ccagggccgc tggcattcca 180
ggcaagttca gcggcagtgg gtctgggacc gacttcactc tcaccatcag tcgagtggac 240
cctgaagatt ttgcagttta ttactgtcag cagtatggtg gctccccgta cacgttcggc 300
caagggacca aggtggaaat ca 322

<210> SEQ ID NO 50
<211> LENGTH: 322
<212> TYPE: DNA
<213> ORGANISM: Homo sapiens

<400> SEQUENCE: 50
gaaattgtgt tgacgcagtc tccagccacc ctgtctgtgt ctccggggga gagagccacc 60
ctctcctgca gggccagtca gaatgtccac cccagatatt tcgcctggta tcaacaaaaa 120
cgtggccagt ctcccaggct cctcatccat agtggatcca ccagggccgc tggcatcgca 180
gacaggttca gtggcggtgg gtctggaatg cacttcactc tcaccatcac cagagtggag 240
cctgaagatt ttgcagtcta tttctgtcaa caatacggtg gttctcccta cacgttcggc 300
caggggacca gggtggaact ca 322

<210> SEQ ID NO 51
<211> LENGTH: 322
<212> TYPE: DNA
<213> ORGANISM: Homo sapiens

<400> SEQUENCE: 51
gaaattgtgt tgacgcagtc tccagccacc ctgtctttgt ctccggggga aagagccacc 60
ctctcctgca gggccagtca gagtgtccac cccaaatatt tcgcctggta ccagcagaaa 120
cctggccagt ctcccaggct cctcatctat agtggatcca ctagggccgc tggcatcgca 180
gacaggttca gtggcggtgg gtctggaata cacttcactc tcaccatcac cagagtggag 240
cctgaagatt ttgcagtgta tttctgtcaa caatacggtg gttcccccta cacgttcggc 300
caggggacca aggtggaact ca 322

<210> SEQ ID NO 52
<211> LENGTH: 322
<212> TYPE: DNA
<213> ORGANISM: Homo sapiens

<400> SEQUENCE: 52
gaaattgtgt tgacrcagtc tccagacacc ctgtctttgt ccccagggga gagagccacc 60
ctctcatgca gggccagtca gagtgttcac agcagatact ttgcctggta ccagcataaa 120
cctggccagc ctcccagact cctcatctat ggtgggtcca ccagggccac tggcatccct 180
aatagattca gtgccggcgg gtctgggaca cagttcactc tcaccgtcaa cagactggag 240
gctgaagatt ttgcggtata ttactgtcag cagtatggtc gctccccgta cacgttcggc 300
caagggacca aggtggagat ca 322

<210> SEQ ID NO 53
<211> LENGTH: 324
<212> TYPE: DNA

<213> ORGANISM: Homo sapiens

<400> SEQUENCE: 53
gacatccagw tgacccagtc tccatcctcc ctgtctgcat ctgtgggaga cagagtcacc 60
atcacttgcc gggcaagtca gggcattaga aatgatttag gctggtatca gcagaagcca 120
ggtaaagccc ataagctcct catctatgct gcatctagtt tacaaagtgg ggtcccatca 180
cggttcagcg gcagtgggtc tggcacagat ttcactctca ccatcagcag cctgcagcct 240
gaagattttg caacttatta ctgtctacaa gattacagtt acccgtatac ttttggccag 300
gggaccaacc tggagatcaa gcga 324

<210> SEQ ID NO 54
<211> LENGTH: 400
<212> TYPE: DNA
<213> ORGANISM: Homo sapiens

<400> SEQUENCE: 54
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt attactgtgc gagagggacc 300
gattacacta ttgacgacca ggggatcctt tatcaaggtt cggggacctt ctggtacttc 360
gatctctggg gccgtggcac cctggtcact gtctcctcag 400

<210> SEQ ID NO 55
<211> LENGTH: 322
<212> TYPE: DNA
<213> ORGANISM: Homo sapiens

<400> SEQUENCE: 55
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctccccgta cacgttcggc 300
caagggacca aggtggaaat ca 322

<210> SEQ ID NO 56
<211> LENGTH: 400
<212> TYPE: DNA
<213> ORGANISM: Homo sapiens

<400> SEQUENCE: 56
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt attactgtgc gagagggacc 300
gattacacta ttgacgacca ggggatccgt tatcaaggtt cggggacctt ctggtacttc 360
gatctctggg gccgtggcac cctggtcact gtctcctcag 400

<210> SEQ ID NO 57
<211> LENGTH: 322
<212> TYPE: DNA
<213> ORGANISM: Homo sapiens

<400> SEQUENCE: 57
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctccccgta cacgttcggc 300
caagggacca aggtggaaat ca 322

<210> SEQ ID NO 58
<211> LENGTH: 400
<212> TYPE: DNA
<213> ORGANISM: Homo sapiens

<400> SEQUENCE: 58
gaggtgcagc tggtggagtc tgggggaggt gtggtacggc ctgggggggtc cctgagactc 60 tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt atcactgtgc gagagggacc 300
gattacacta ttgacgacgc ggggatccat tactatggtt cggggaccta ctggtacttc 360
gatctctggg gccgtggcac cctggtcact gtctcctcag 400

<210> SEQ ID NO 59
<211> LENGTH: 321
<212> TYPE: DNA
<213> ORGANISM: Homo sapiens

<400> SEQUENCE: 59
aaattgtgtt gacgcagtct ccaggcaccc tgtctttgtc tccaggggaa agagccaccc 60
tctcctgcag ggccagtcag agtgttagca gcagctactt agcctggtac cagcagaaac 120
ctggccaggc tcccaggctc ctcatctatg gtgcatccag cagggccact ggcatcccag 180
acaggttcag tggcagtggg tctgggacag acttcactct caccatcagc agactggagc 240
ctgaagattt tgcagtgtat tactgtcagc agtatggtgg ttccccctac acgttcggcc 300
aagggaccaa ggtggaaatc a 321

<210> SEQ ID NO 60
<211> LENGTH: 400
<212> TYPE: DNA
<213> ORGANISM: Homo sapiens

<400> SEQUENCE: 60
gaggtgcagc tggtggagtc tgggggaggt gtggtacggc ctgggggggtc cctgagactc 60 tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240

-continued

```
ctgcaaatga acagtctgag agccgaggac acggccttrt atcactgtgc gagagggacc    300

gattacacga tagacgacca gggaagatat tactatggtt cggggaccta ctggtacttc    360

gatctctggg gccgtggcac cctggtcact gtctcctcag                          400
```

<210> SEQ ID NO 61
<211> LENGTH: 321
<212> TYPE: DNA
<213> ORGANISM: Homo sapiens

<400> SEQUENCE: 61

```
aaattgtgtt gacgcagtct ccagccaccc tgtctttgtc tccaggggaa agagccaccc     60

tctcctgcag ggccagtcag agtgttagca gcagctactt agcctggtac cagcagaaac    120

ctggccaggc tcccaggctc ctcatctatg atgcatccag cagggccact ggcatcccag    180

acaggttcag tggcagtggg tctgggacag acttcactct caccatcagc agactggagc    240

ctgaagattt tgcagtctat tactgtcagc aatacggtgg ttctccctac acttttggcc    300

gagggaccaa cgtgggaatc a                                              321
```

<210> SEQ ID NO 62
<211> LENGTH: 400
<212> TYPE: DNA
<213> ORGANISM: Homo sapiens

<400> SEQUENCE: 62

```
gaggtgcagc tggtggagtc tgggggaggt gtggtacggc ctgggggtc cctgagactc     60

tcctgtgcag cctctggatt cacctttgat gattatggca tgagctgggt ccgccaagct    120

ccagggaagg ggctggagtg ggtctctggt attaattgga atggtggtag cacaggttat    180

gcagactctg tgaagggccg attcaccatc tccagagaca acgccaagaa ctccctgtat    240

ctgcaaatga acagtctgag agccgaggac acggccttrt atcactgtgc gagagggacc    300

gattacacga tagacgacca gggaagatat tactatggtt cggggaccta ctggtacttc    360

gatctctggg gccgtggcac cctggtcact gtctcctcag                          400
```

<210> SEQ ID NO 63
<211> LENGTH: 321
<212> TYPE: DNA
<213> ORGANISM: Homo sapiens

<400> SEQUENCE: 63

```
aaattgtgtt gacgcagtct ccagccaccc tgtctttgtc tccaggggaa agagccaccc     60

tctcctgcag ggccagtcag agtgttagca gcagctactt agcctggtac cagcagaaac    120

ctggccaggc tcccaggctc ctcatctatg atgcatccag cagggccact ggcatcccag    180

acaggttcag tggcagtggg tctgggacag acttcactct caccatcagc agactggagc    240

ctgaagattt tgcagtctat tactgtcagc aatacggtgg ttccccctac acgttcggcc    300

aagggaccaa ggtggaaatc a                                              321
```

<210> SEQ ID NO 64
<211> LENGTH: 400
<212> TYPE: DNA
<213> ORGANISM: Homo sapiens

<400> SEQUENCE: 64

```
gaggtgcagc tggtggagtc tgggggaggt gtggtacggc ctgggggtc cctgagactc     60

tcctgtgcag cctctggatt cacctttgat gattatggca tgagctgggt ccgccaagct    120
```

```
ccagggaagg ggctggagtg ggtctctggt attaattgga atggtggtag cacaggttat    180

gcagactctg tgaagggccg attcaccatc tccagagaca acgccaagaa ctccctgtat    240

ctgcaaatga acagtctgag agccgaggac acggccttrt atcactgtgc gagagggacc    300

gattacacga tagacgacca gggaatttat tactatggtt cggggaccta ctggtacttc    360

gatctctggg gccgtggcac cctggtcact gtctcctcag                          400
```

<210> SEQ ID NO 65
<211> LENGTH: 321
<212> TYPE: DNA
<213> ORGANISM: Homo sapiens

<400> SEQUENCE: 65

```
aaattgtgtt gacgcagtct ccaggcaccc tgtctttgtc tccaggggaa agagccaccc     60

tctcctgcag ggccagtcag agtgttagca gcagctactt agcctggtac cagcagaaac    120

ctggccaggc tcccaggctc ctcatctatg gtgcatccag cagggccact ggcatcccag    180

acaggttcag tggcagtggg tctgggacag acttcactct caccatcagc agactggagc    240

ctgaagattt tgcagtgtat tactgtcagc agtatggtgg ttccccctac acttttggcc    300

gagggaccaa cgtgggaatc a                                              321
```

<210> SEQ ID NO 66
<211> LENGTH: 400
<212> TYPE: DNA
<213> ORGANISM: Homo sapiens

<400> SEQUENCE: 66

```
gaggtgcagc tggtggagtc tgggggaggt gtggtacggc ctggggggtc cctgagactc     60

tcctgtgcag cctctggatt cacctttgat gattatggca tgagctgggt ccgccaagct    120

ccagggaagg ggctggagtg ggtctctggt attaattgga atggtggtag cacaggttat    180

gcagactctg tgaagggccg attcaccatc tccagagaca acgccaagaa ctccctgtat    240

ctgcaaatga acagtctgag agccgaggac acggccttrt atcactgtgc gagagggacc    300

gattacacga tagacgacca gggaatttat tactatggtt cggggaccta ctggtacttc    360

gatctctggg gccgtggcac cctggtcact gtctcctcag                          400
```

<210> SEQ ID NO 67
<211> LENGTH: 321
<212> TYPE: DNA
<213> ORGANISM: Homo sapiens

<400> SEQUENCE: 67

```
aaattgtgtt gacgcagtct ccaggcaccc tgtctttgtc tccaggggaa agagccaccc     60

tctcctgcag ggccagtcag agtgttagca gcagctactt agcctggtac cagcagaaac    120

ctggccaggc tcccaggctc ctcatctatg gtgcatccag cagggccact ggcatcccag    180

acaggttcag tggcagtggg tctgggacag acttcactct caccatcagc agactggagc    240

ctgaagattt tgcagtgtat tactgtcagc agtatggtgg ttccccctac acgttcggcc    300

aagggaccaa ggtggaaatc a                                              321
```

<210> SEQ ID NO 68
<211> LENGTH: 400
<212> TYPE: DNA
<213> ORGANISM: Homo sapiens

<400> SEQUENCE: 68
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt atcactgtgc gagagggacc 300
gattacacga tagacgacca gggaatttat tactatggtt cggggaccta ctggtacttc 360
gatctctggg gccgtggcac cctggtcact gtctcctcag 400

<210> SEQ ID NO 69
<211> LENGTH: 321
<212> TYPE: DNA
<213> ORGANISM: Homo sapiens

<400> SEQUENCE: 69
aaattgtgtt gacgcagtct ccagccaccc tgtctttgtc tccaggggaa agagccaccc 60
tctcctgcag ggccagtcag agtgttagca gcagctactt agcctggtac cagcagaaac 120
ctggccaggc tcccaggctc ctcatctatg atgcatccag cagggccact ggcatcccag 180
acaggttcag tggcagtggg tctgggacag acttcactct caccatcagc agactggagc 240
ctgaagattt tgcagtctat tactgtcagc aatacggtgg ttctccctac acttttggcc 300
gagggaccaa cgtgggaatc a 321

<210> SEQ ID NO 70
<211> LENGTH: 280
<212> TYPE: DNA
<213> ORGANISM: Homo sapiens

<400> SEQUENCE: 70
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt 280

<210> SEQ ID NO 71
<211> LENGTH: 50
<212> TYPE: DNA
<213> ORGANISM: Homo sapiens

<400> SEQUENCE: 71
ctggtacttc gatctctggg gccgtggcac cctggtcact gtctcctcag 50

<210> SEQ ID NO 72
<211> LENGTH: 321
<212> TYPE: DNA
<213> ORGANISM: Homo sapiens

<400> SEQUENCE: 72
aaattgtgtt gacgcagtct ccagccaccc tgtctttgtc tccaggggaa agagccaccc 60
tctcctgcag ggccagtcag agtgttagca gcagctactt agcctggtac cagcagaaac 120
ctggccaggc tcccaggctc ctcatctatg atgcatccag cagggccact ggcatcccag 180
acaggttcag tggcagtggg tctgggacag acttcactct caccatcagc agactggagc 240
ctgaagattt tgcagtctat tactgtcagc aatacggtgg ttccccctac acgttcggcc 300
aagggaccaa ggtggaaatc a 321

<210> SEQ ID NO 73
<211> LENGTH: 280
<212> TYPE: DNA
<213> ORGANISM: Homo sapiens

<400> SEQUENCE: 73
gaggttcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt 280

<210> SEQ ID NO 74
<211> LENGTH: 50
<212> TYPE: DNA
<213> ORGANISM: Homo sapiens

<400> SEQUENCE: 74
ctggtacttc gatctctggg gccgtggcac cctggtcact gtctcctcag 50

<210> SEQ ID NO 75
<211> LENGTH: 322
<212> TYPE: DNA
<213> ORGANISM: Homo sapiens

<400> SEQUENCE: 75
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctccccgta cacgttcggc 300
caagggacca aggtggaaat ca 322

<210> SEQ ID NO 76
<211> LENGTH: 280
<212> TYPE: DNA
<213> ORGANISM: Homo sapiens

<400> SEQUENCE: 76
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttrt 280

<210> SEQ ID NO 77
<211> LENGTH: 50
<212> TYPE: DNA
<213> ORGANISM: Homo sapiens

<400> SEQUENCE: 77
ctggtacttc gatctctggg gccgtggcac cctggtcact gtctcctcag 50

<210> SEQ ID NO 78
<211> LENGTH: 322
<212> TYPE: DNA
<213> ORGANISM: Homo sapiens

<400> SEQUENCE: 78
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctccccgta cacgttcggc 300
caagggacca aggtggaaat ca 322

<210> SEQ ID NO 79
<211> LENGTH: 32
<212> TYPE: PRT
<213> ORGANISM: Herpes simplex virus

<400> SEQUENCE: 79

Lys Tyr Ala Leu Val Asp Ala Ser Leu Lys Met Ala Asp Pro Asn Arg
1 5 10 15

Phe Arg Gly Lys Asp Leu Pro Val Leu Asp Gln Leu Thr Asp Pro Pro
20 25 30

<210> SEQ ID NO 80
<211> LENGTH: 32
<212> TYPE: PRT
<213> ORGANISM: Herpes simplex virus

<400> SEQUENCE: 80

Lys Tyr Ala Leu Val Asp Pro Ser Leu Lys Met Ala Asp Pro Asn Arg
1 5 10 15

Phe Arg Gly Lys Asn Leu Pro Val Leu Asp Gln Leu Thr Asp Pro Pro
20 25 30

<210> SEQ ID NO 81
<211> LENGTH: 9
<212> TYPE: PRT
<213> ORGANISM: Homo sapiens

<400> SEQUENCE: 81

Arg Gly Thr Asp Tyr Thr Ile Asp Asp
1 5

<210> SEQ ID NO 82
<211> LENGTH: 6
<212> TYPE: PRT
<213> ORGANISM: Homo sapiens

<400> SEQUENCE: 82

Thr Asp Tyr Thr Ile Asp
1 5

<210> SEQ ID NO 83
<211> LENGTH: 11
<212> TYPE: PRT
<213> ORGANISM: Homo sapiens

<400> SEQUENCE: 83

Asp Tyr Arg Asn Gly Tyr Asn Tyr Tyr Asp Phe
1 5 10

<210> SEQ ID NO 84
<211> LENGTH: 9
<212> TYPE: PRT
<213> ORGANISM: Homo sapiens

<400> SEQUENCE: 84

Ala Phe Ile Lys Tyr Asp Gly Ser Glu
1 5

<210> SEQ ID NO 85
<211> LENGTH: 9
<212> TYPE: PRT
<213> ORGANISM: Homo sapiens

<400> SEQUENCE: 85

Tyr Tyr Asp Phe Tyr Asp Gly Tyr Tyr
1 5

<210> SEQ ID NO 86
<211> LENGTH: 9
<212> TYPE: PRT
<213> ORGANISM: Homo sapiens

<400> SEQUENCE: 86

Glu Asp Gly Asp Tyr Leu Ser Asp Pro
1 5

<210> SEQ ID NO 87
<211> LENGTH: 10
<212> TYPE: PRT
<213> ORGANISM: Homo sapiens

<400> SEQUENCE: 87

Asp Gly Asp Tyr Leu Ser Asp Pro Phe Tyr
1 5 10

<210> SEQ ID NO 88
<211> LENGTH: 17
<212> TYPE: PRT
<213> ORGANISM: Homo sapiens

<400> SEQUENCE: 88

Asp Gly Asp Tyr Leu Ser Asp Pro Phe Tyr Tyr Asn His Gly Met Asp
1 5 10 15

Val

<210> SEQ ID NO 89
<211> LENGTH: 12
<212> TYPE: PRT
<213> ORGANISM: Homo sapiens

<400> SEQUENCE: 89

Pro Tyr Pro Asn Asp Tyr Asn Asp Tyr Ala Pro Glu
1 5 10

<210> SEQ ID NO 90
<211> LENGTH: 10
<212> TYPE: PRT
<213> ORGANISM: Homo sapiens

<400> SEQUENCE: 90

Asn Asp Tyr Asn Asp Tyr Ala Pro Glu Glu
1 5 10

<210> SEQ ID NO 91
<211> LENGTH: 8
<212> TYPE: PRT
<213> ORGANISM: Homo sapiens

<400> SEQUENCE: 91

Asn Asp Tyr Asn Asp Tyr Ala Pro
1 5

<210> SEQ ID NO 92
<211> LENGTH: 9
<212> TYPE: PRT
<213> ORGANISM: Homo sapiens

<400> SEQUENCE: 92

Asp Tyr Asn Asp Tyr Ala Pro Glu Glu
1 5

<210> SEQ ID NO 93
<211> LENGTH: 7
<212> TYPE: PRT
<213> ORGANISM: Homo sapiens

<400> SEQUENCE: 93

Asp Tyr Ala Pro Glu Glu Gly
1 5

<210> SEQ ID NO 94
<211> LENGTH: 9
<212> TYPE: PRT
<213> ORGANISM: Homo sapiens

<400> SEQUENCE: 94

Ala Ala Gly Asp Tyr Ala Asp Tyr Asp
1 5

<210> SEQ ID NO 95
<211> LENGTH: 9
<212> TYPE: PRT
<213> ORGANISM: Homo sapiens

<400> SEQUENCE: 95

Asp Tyr Ala Asp Tyr Asp Gly Gly Tyr
1 5

<210> SEQ ID NO 96
<211> LENGTH: 9
<212> TYPE: PRT
<213> ORGANISM: Homo sapiens

<400> SEQUENCE: 96

Tyr Asp Gly Gly Tyr Tyr Tyr Asp Met
1 5

METHOD OF INDUCING THE PRODUCTION OF PROTECTIVE ANTI-HIV-1 ANTIBODIES

This application is a continuation of U.S. application Ser. No. 13/581,157, filed Aug. 24, 2012, which is the U.S. national phase of International Application No. PCT/US2011/000352, filed Feb. 25, 2011, which designated the U.S. and claims priority to U.S. Provisional Appln. Nos. 61/282,526, filed Feb. 25, 2010, 61/344,457, filed Jul. 27, 2010, 61/344,580, filed Aug. 25, 2010, and 61/344,622, filed Sep. 1, 2010, the entire contents of each of which are incorporated herein by reference.

This invention was made with government support under Grant Nos. AI067854, AI 24335 and AI 81579 awarded by the National Institutes of Health. The government has certain rights in the invention.

TECHNICAL FIELD

The present invention relates, in general, to an immunogen for HIV-1 vaccination and, in particular, to a method of inducing the production of protective anti-HIV-1 antibodies by targeting B cell germline and clone intermediates using a combination of non-HIV-1 and HIV-1 immunogens. The invention also relates to compositions suitable for use in such a method.

BACKGROUND

The first antibody response to transmitted/founder HIV-1 envelope is non-neutralizing, targets Env gp41 and occurs at a mean of 13 days after appearance of plasma viremia (Tomaras et al, J. Virology 82:12449-63 (2008)). While the initial T cell response to HIV-1 that occurs at the same time as the initial antibody response drives mutations within T cell epitopes of HIV-1, the initial gp41 antibody response to HIV-1 does not. Rather, it is the autologous neutralizing antibody response, which is delayed until approximately three months after transmission, that is the first neutralizing antibody response associated with antibody escape mutants (McMichael et al, Nature Rev. Immunol. 10:11-23 (2010)).

The four epitopes on HIV-1 envelope to which rare broadly reactive neutralizing antibodies bind are the CD4 binding site (CD4BS) (mab (monoclonal antibody) IgG1b12) (Zwick et al, J. Virol. 77(10):5863-5876 (2003)), the membrane proximal external region (MPER) epitopes defined by human mabs 2F5 and 4E10 (Armbruster et al, J. Antimicrob. Chemother. 54:915-920 (2004), Stiegler and Katinger, J. Antimicrob. Chemother. 51:757-759 (2003), Zwick et al, Journal of Virology 79:1252-1261 (2005), Purtscher et al, AIDS 10:587 (1996)), and the mannan glycan epitope defined by human mab 2G12 (Scanlan et al, Adv. Exper. Med. Biol. 535:205-218 (2003)). These four rare human mabs are all unusual: two are IgG3 (2F5 and 4E10), one has a unique Ig dimer structure (2G12), one has a very hydrophobic CDR3 (2F5) (Ofek et al, J. Virol. 198:10724 (2004)), and, in all four, the CDR3 is unusually long (Burton et al, Nature Immunol. 5(3):233-236 (2004), Kunert et al, AIDS Res. Hum. Retroviruses 20(7):755-762 (2004), Zwick et al, J. Virol. 78(6):3155-3161 (2004), Cardoso et al, Immunity 22:163-172 (2005)). Of these, 2F5- and 4E10-like human mabs are quite rare. Acute HIV-1 patients do not make antibodies against the MPER or 2G12 epitopes, MPER can be defined as amino acids 652 to 683 of HIV envelope (Cardoso et al, Immunity 22:163-173 (2005) (e.g., QQEKNEQELLELDKWASLWNWFDITNWLWYIK) (SEQ ID NO: 1). CD4 binding site (BS) antibodies are commonly made early in HIV-1 infection, but these antibodies generally do not have the broad spectrum of neutralization shown by mab IgG1b12 (Burton et al, Nat. Immunol. 5(3):233-236 (2004)).

To understand the pathogenesis of the ineffective initial antibody response to HIV-1 envelope (Env), PCR has been performed for amplification of immunoglobulin variable region of heavy- and light-chain ($V_H$ and $V_L$) genes from single blood or bone marrow plasma cells from 5 acutely infected subjects from 17-30 days after HIV-1 transmission. The specificities of the plasma cell response induced by HIV-1 infection have been determined. Using PCR amplification of $V_H$ and $V_L$ genes of single human plasma cells induced by transmitted HIV-1, the initial plasma cell/plasmablast response to HIV-1 has been studied. It has been found that the first antibody response to HIV-1 is induced to HIV-1 Env gp41, and that gp41 induces an antibody response in pre-existing memory B cell clones, resulting in low-affinity, polyreactive anti-Env antibodies that cross-react with a number of host and bacterial molecules, particularly, of human gut bacterial flora.

The present invention results, at least in part, from studies designed to identify the source of both the initial anti-HIV-1 Env gp41 antibodies and the rare broadly neutralizing antibodies. The invention further results from the identification of a cellular protein expressed in most warm blooded vertebrates that is structurally similar to the 2F5, and possibly 4E10, epitopes of the HIV-1 gp41 MPER.

The invention provides an HIV-1 vaccine designed to target a naïve B cell pool that can be driven to give rise to broadly neutralizing antibodies to HIV-1.

SUMMARY OF THE INVENTION

In general, the present invention relates to an immunogen for HIV vaccination. More specifically, the invention relates to a method of inducing the production of protective anti-HIV-1 antibodies by targeting B cell germline and clone intermediates using a combination of non-HIV-1 and HIV-1 immunogens. The invention also relates to compositions suitable for use in such a method.

Objects and advantages of the present invention will be clear from the description that follows.

BRIEF DESCRIPTION OF THE DRAWINGS

FIG. 10A. Coomassie blue image. FIG. 10B. Western blot image.

FIG. 13A. Binding to HIV 89.6 gp120. FIG. 13B. Binding to lipids (PC:cardiolipin).

FIG. 16 A. Vaccines must be designed to stimulate B cell precursors by inclusion of either host (such as lipids) and/or foreign (such as gut flora) antigens to which the polyreactive naïve B cell receptors (BCRs) bind (left-most arrow), and antigens (preferred Env constructs) to target intermediate clones of B cells that arise that cross-react with Env. The Env lead candidates for this component of the vaccine is the Malawi 1086 clade C gp140 oligomer that has induced in guinea pigs considerable breadth in neutralizing antibodies mixed with the clade B JRFL gp140 Env that selectively expresses the MPER neutralizing epitopes (middle arrow) and/or the transmitted founder Envs 6240, 040 and 63521 (see FIGS. 16B, 16C and 16D) that preferentially express epitopes bound by broadly neutralizing monoclonal antibodies. Finally, to overcome peripheral deletion and/or anergy of B cells that are driven to make polyreactive neutralizing antibodies, the vaccine contains potent TLR agonists or other adjuvants to drive activation of polyreactive B cells by germline and intermediate clone-targeted vaccines (right-most arrow). FIG. 16E. SDS-PAGE images of apoferritin. FIG. 16F. Western blot images of apoferritin vs HV00274, HV00276. Acute HIV infection gp41 inferred intermediate antibodies 276 from clone 684-6B and 274 from clone 684-6A both bind to the 19 Kd apoferritin subunit. Both mabs also bind to the 60 Kd protein in the native marker.

FIGS. 19A and 19B. FIG. 19A. Immunogenicity of Group M Consensus HIV-1 Env, CON-S and Subtype C Acute HIV-1 Env, 1086C, Subtype B chronic HIV-1 Env, JRFL. FIG. 19 B. Methods. FIG. 19 B discloses SEQ ID NOS 9-10, respectively, in order of appearance.

FIG. 22. Antigenicity of JRFL gp140 Env in SPR.

FIG. 23 discloses “His6” as SEQ ID NO: 11.

FIG. 24A. Design of membrane anchored gp41-inter. FIG. 24B. 2F5 and 4E10 mAbs bind to membrane conjugated gp-41-inter with nM Kd and almost irreversible off-rates. FIG. 24A discloses “His6” as SEQ ID NO: 11.

FIG. 25. Lead candidate immunogens.

FIG. 27. Amino acid sequences for HIV-1 transmitted founder Envs 1086.C, 089.C, 040_C9, and 63521, and codon optimized encoding sequences. FIG. 27 discloses SEQ ID NOS 12-19, respectively, in order of appearance.

FIG. 28. Clade B JRFL and 6240 gp140 Env sequence and encoding sequence. FIG. 28 discloses SEQ ID NOS 20-23, respectively, in order of appearance.

FIG. 30. 2F5 and 4E10 broadly neutralizing antibodies react with self antigens that are phylogenetically conserved FIG. 31. 2F5 specifically binds to 43 kDa, 500 kDa, 70 kDa and 350 kDa 3T3 (mouse) cellular proteins on western blot FIG. 32. Conserved self-antigens that carry the 2F5 nominal epitope. FIG. 32 discloses SEQ ID NOS 2, 24 and 24-25, respectively, in order of appearance.

FIG. 33. The H3 domain of kynuereninase (KYNU) is highly conserved. FIG. 33 discloses SEQ ID NOS 26-36, respectively, in order of appearance.

FIG. 35. Illustration of the DKW residues (ELDKWA) (SEQ ID NO: 2) in human KYNU.

FIG. 36. Binding of the 2F5 antibody to human KYNU may require distortion of the H3 domain. FIG. 36 discloses “ELDKWA” as SEQ ID NO: 2.

FIG. 37. KYNU dimers likely obscure the potential 2F5 binding site. FIG. 37 discloses “ELDKWA” as SEQ ID NO: 2.

FIG. 38. 2F5 and possibly 4E10 antibodies bind to recombinant human KYNU in western blots.

FIG. 39. KYNU is recognized by 2F5-family antibodies.

FIG. 45 discloses SEQ ID NOS 24 and 37-38, respectively, in order of appearance.

FIG. 48. Soluble KYNU is bound by 2F5.

FIG. 49. rhKYNU binding to surface-captured mAbs.

FIGS. 50A-50C. Binding of 2F5 mAb and 2F5 RUA (reverted unmutated ancestor) antibodies to KYNU, (FIG. 50A) 2F5, (FIG. 50B) 2F5-GL1, (FIG. 50C) 2F5-GL3.

FIGS. 52A-52D. Enrichment and identification of protein band in intestinal bacterial lysate reactive with mAb HV00276. (FIG. 52A) Western blot analysis following Native PAGE gel run. (FIG. 52B) Protein fractions from bacterial lysate with molecular wt ~500 kDa collected following size exclusion chromatography (SEC). (FIG. 52C) SEC fractions show enrichment of 520 kDa protein by Coomassie Blue (1) and silver staining (2) and western blotting (3, arrow). (FIG. 52D) Isoelectric zoom fractionation.

FIGS. 53A-53C. Liquid chromatography-mass spectrometry (LC-MS) identification of RNA polymerase. (FIG. 53A) LC-MS identification of RNA polymerase β subunit (SEQ ID NO: 39). (FIG. 53B) LC-MS identification of RNA polymerase β' subunit (SEQ ID NO: 40). (FIG. 53C) LC-MS identification of RNA polymerase a subunit (SEQ ID NO: 41).

FIG. 54. Mab HV00276 binds to RNA polymerase core protein.

FIG. 55. Mab HV00276 binds to the α subunit of RNA polymerase core protein.

FIG. 56. Neutralization screening of primary memory B cell cultures. Memory B cells from peripheral blood of CHAVI08 chronically-HIV-1 infected volunteer 707-01-021-9 were EBV-transformed and stimulated for 14 days in presence of CD40 ligand, oCpGs and CHK-2 inhibitor at a density of 8 cells/well. At the end of stimulation supernatants were tested for neutralizing activity against the reporter tier 2 clade C CAP45 virus. Solid dots represent the percentage of neutralization of each of the 3,600 cultures. Monoclonal antibodies CH01_CH05 were isolated from the cultures represented with open dotted symbols. Positive controls (HIV 1 g) are shown as open circles on the far right.

FIGS. 57A-57C. V-heavy and V-light chain alignments of monoclonal antibodies CH01-CH05. Alignment of the sequences of the CH01-CH05 V-heavy chains (SEQ ID NOS 42-47, respectively, in order of appearance) (FIG. 57A), CH01-CH04 (SEQ ID NOS 48-52, respectively, in order of appearance) (FIG. 57B) and CH05 (SEQ ID NO: 53) (FIG. 57C) V-light chains. The putative reverted unmutated ancestor sequence was used as template for both the V-heavy and the CH01-CH04 V-light alignments. Since CH05 has an unrelated Vκ1~6 chain, it is shown separately.

FIG. 59. Alignment of the inferred putative reverted unmutated ancestor antibodies. The alignment of all the putative reverted unmutated ancestor antibodies inferred by applying the V-heavy chains are separated from the V-light chains by "~~~." FIG. 59 discloses SEQ ID NOS 54-78, respectively, in order of appearance.

FIG. 66. Potential relevance of gD immunogenicity. FIG. 66 discloses SEQ ID NOS 79-80, respectively, in order of appearance.

FIG. 72. CH01-CH05 ELISA binding to monomeric gp120/gp140 envelope proteins.

DETAILED DESCRIPTION OF THE INVENTION

Figure 15:
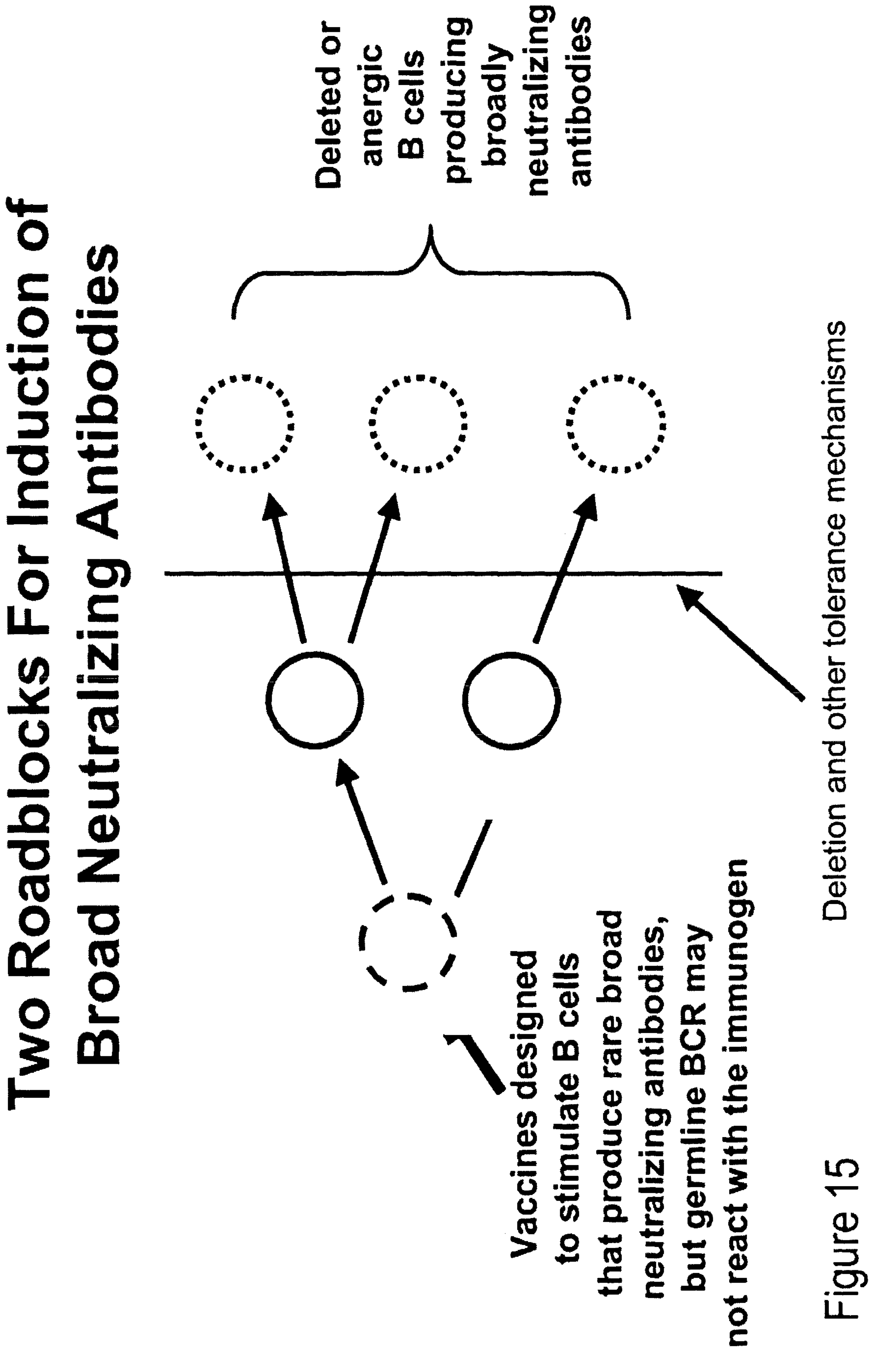
FIG. 15. Two roadblocks for induction of broad neutralizing antibodies. The first roadblock is that vaccines currently designed to stimulate B cells that produce rare broad neutralizing antibodies do not react with the germline B cell receptors of the naïve B cells that are required to respond to the immunogen. While the initial B cell response to HIV-1 Env is made early on after infection, there is a cross reactivity of gp41 with host or pre-existing foreign molecules such that the B cell antibody clones that make the initial gp41 antibody response are derived from pre-existing polyreactive natural B cell clones whose germlines also do not react with gp41 and whose reactivity to gp41 is acquired later in clonal antibody development as cross-reactivity with gp41 is acquired through host or foreign antigen-driven clonal expansion. Once gp41 reactivity is acquired, gp41 then drives the clonal expansion. The second roadblock to vaccine development comes from work showing that both of these antibodies require the long hydrophobic CDR3s with lipid reactivity to neutralize (Alam et al, Proc. Natl. Acad. Sci. USA 106:20234-9 (2009)) and that the 2F5 and 4E10 $V_H$s are sufficiently autoreactive to promote deletion in knock-in mice (Verkoczy et al, Proc. Natl. Acad. Sci. USA 107:181-186 (2010)).
Figure 16A:
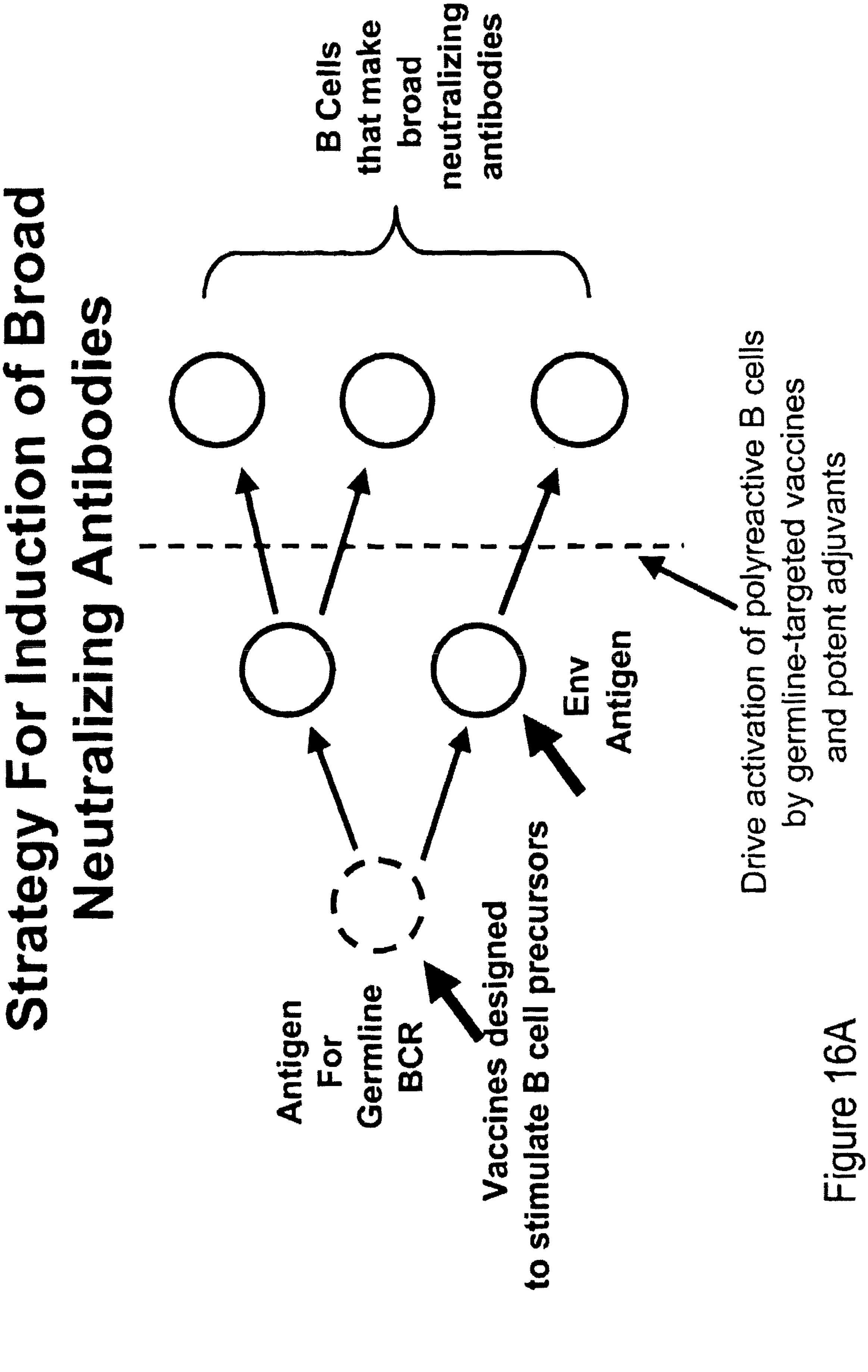
FIGS. 16A-16F. Strategy for induction of broad neutralizing antibodies.
Figure 16B:
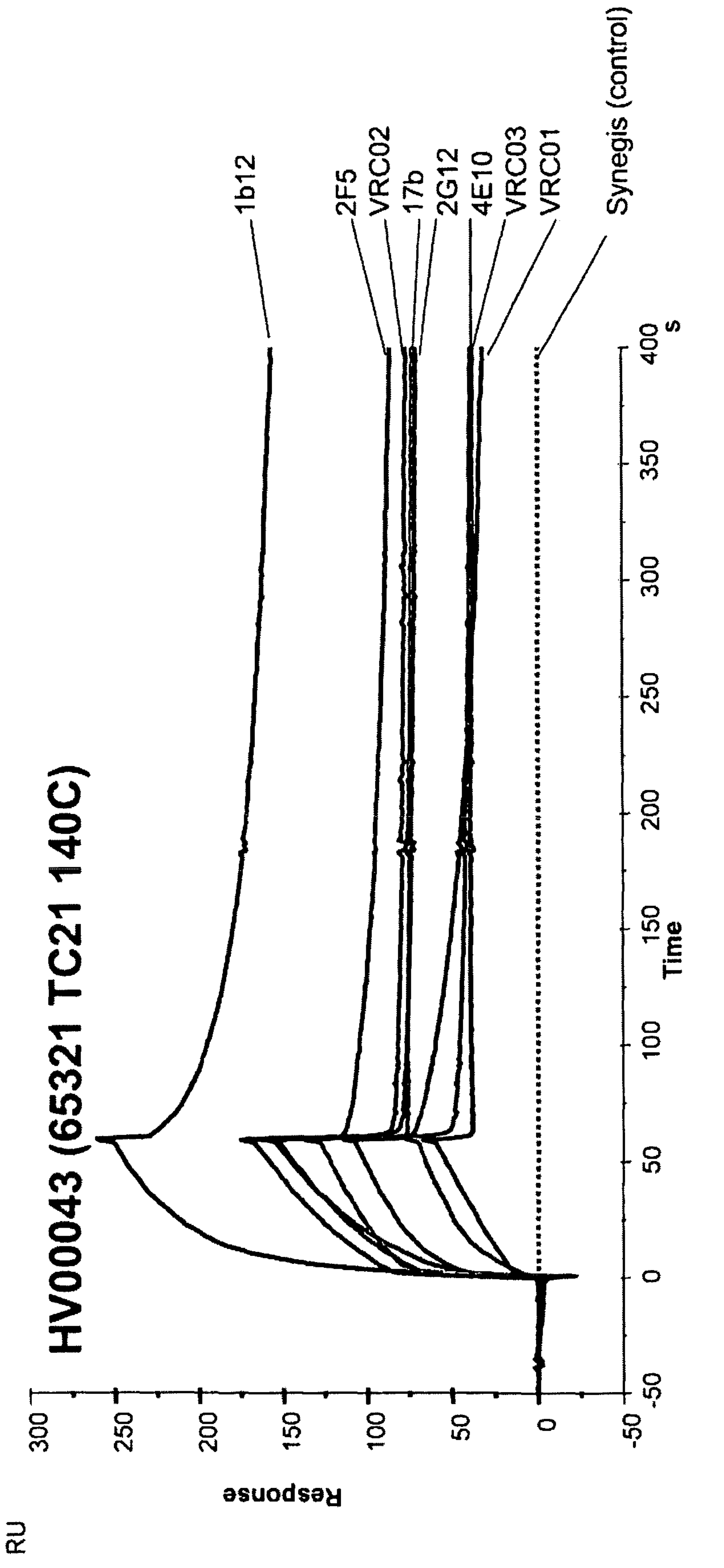
Figure 16C:
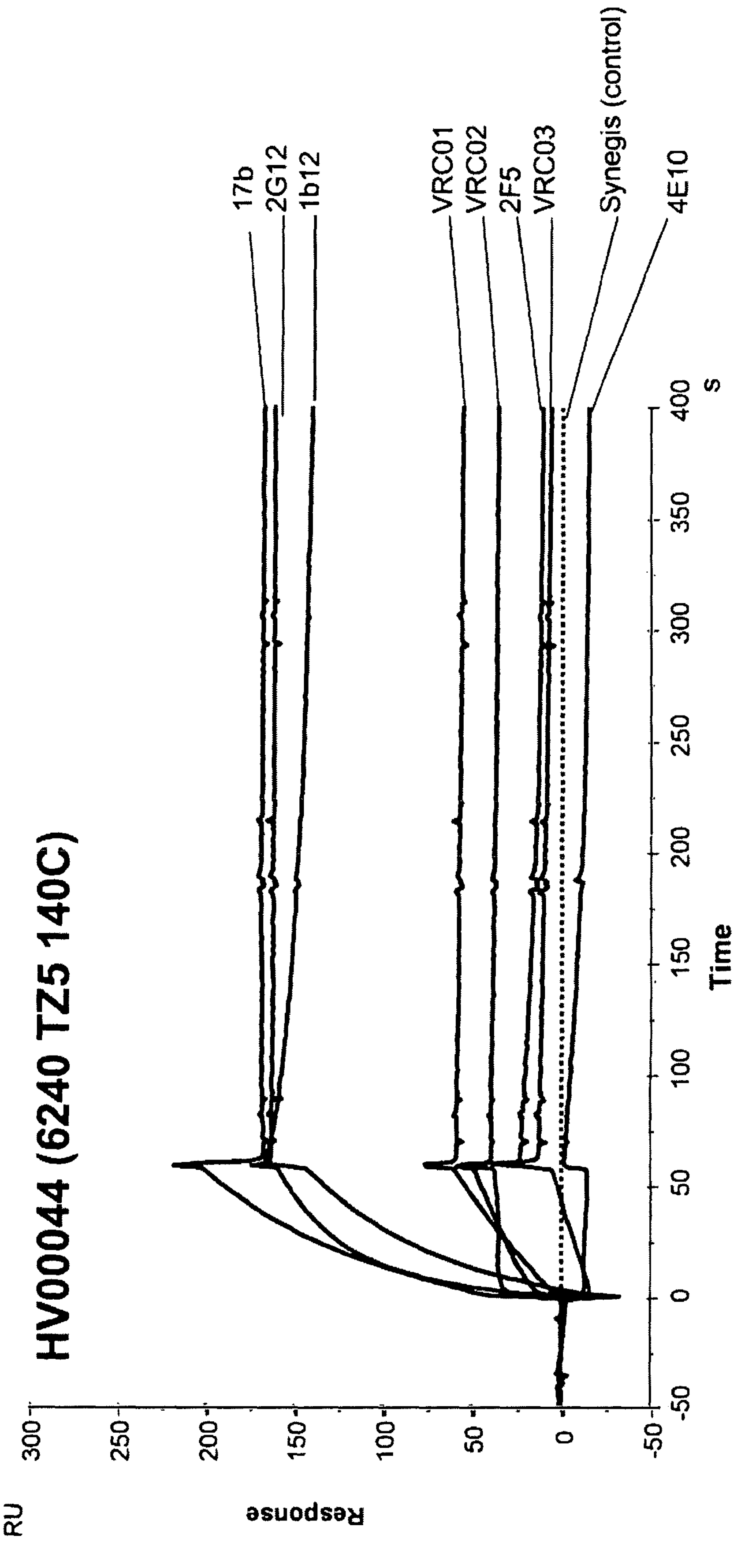
Figure 16D:
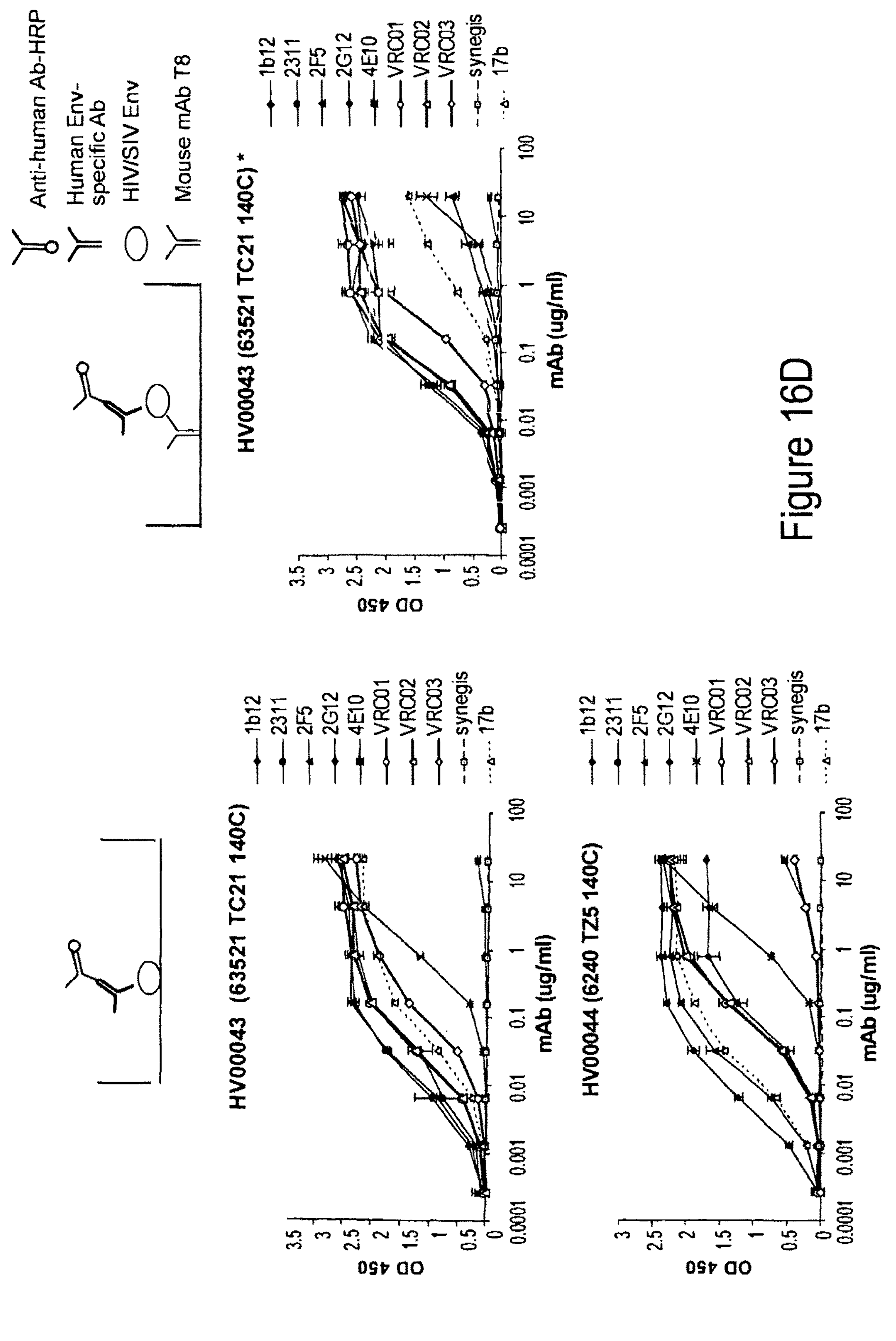
Figure 16E:
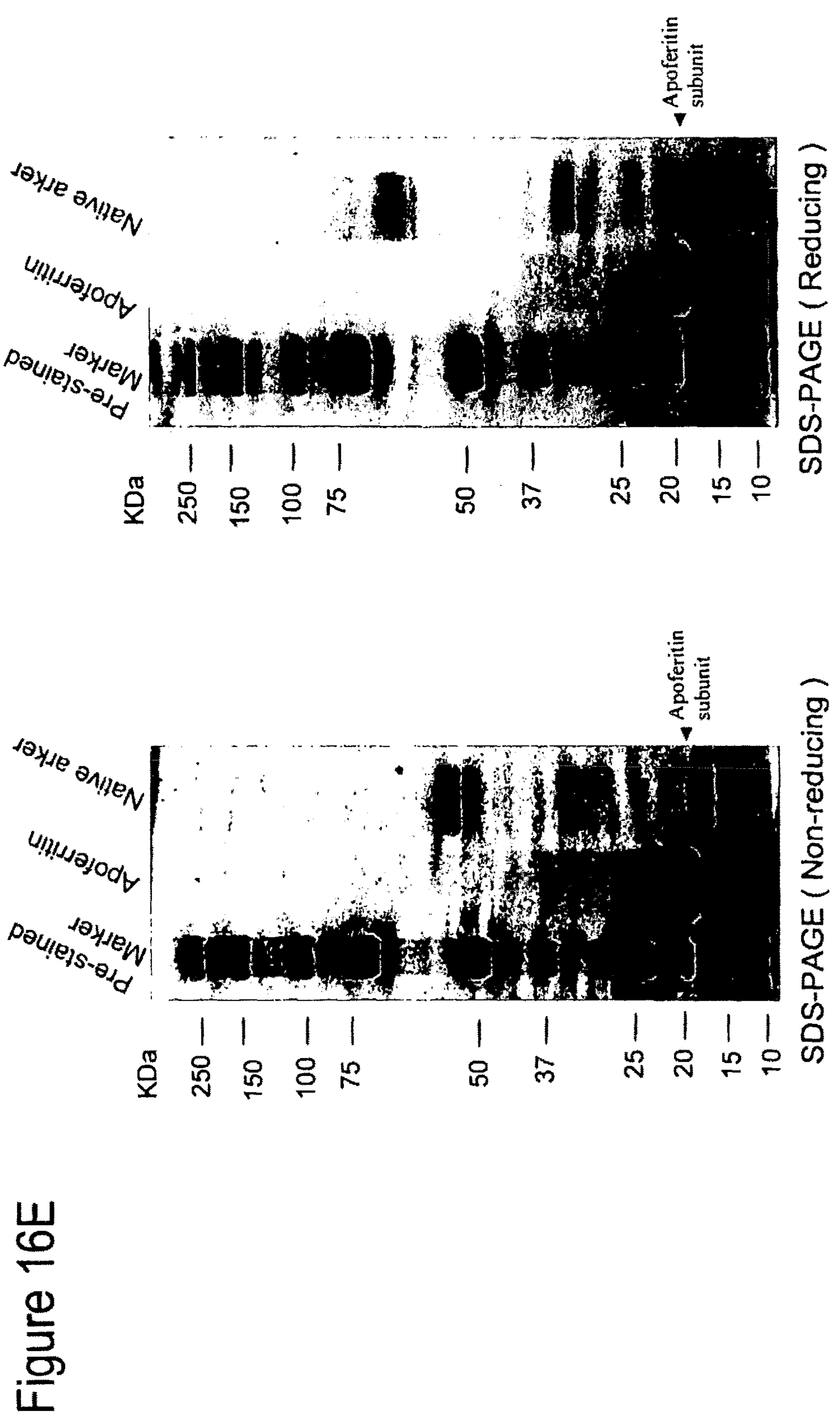
Figure 16F:
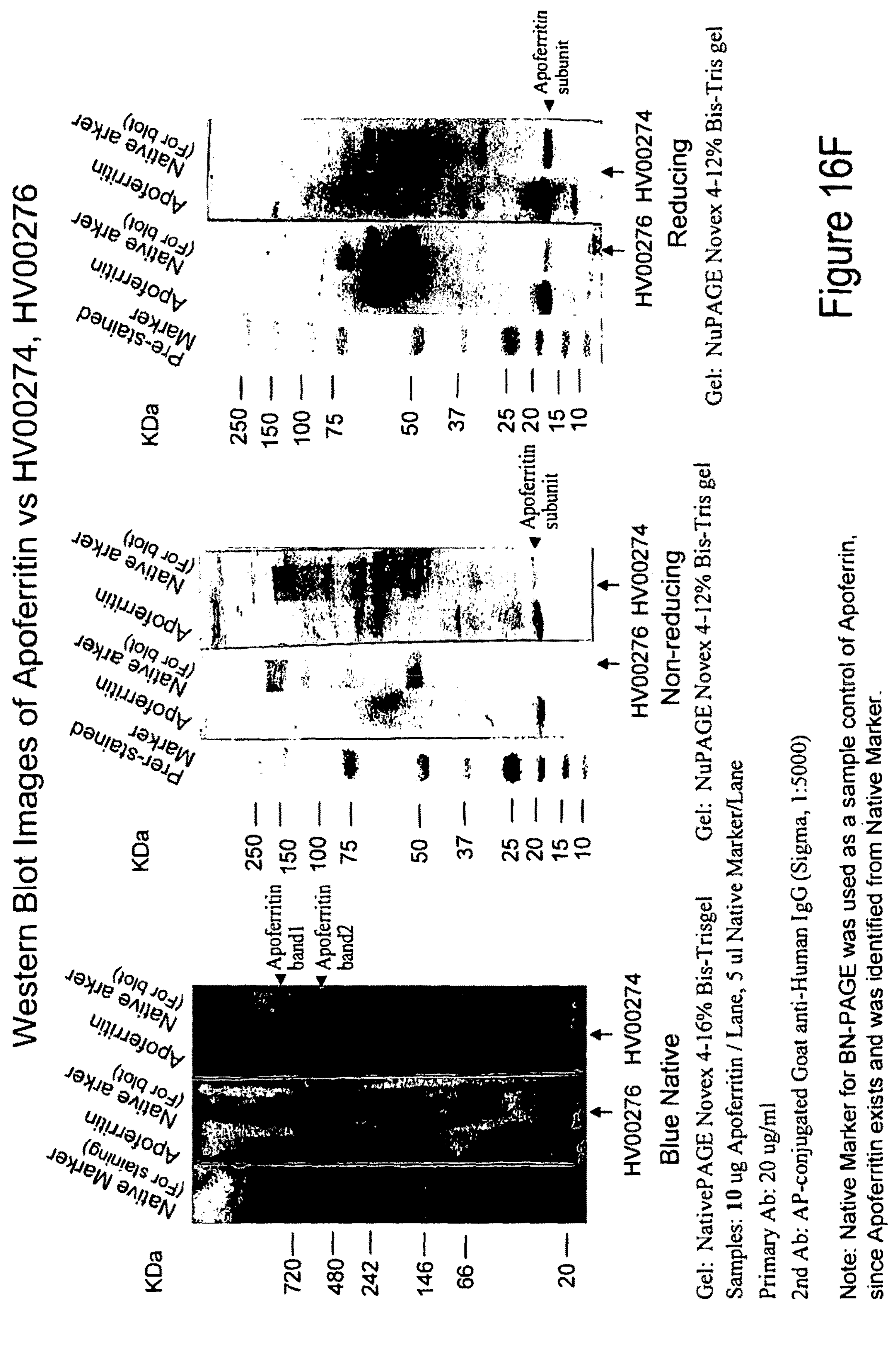
Figure 17:
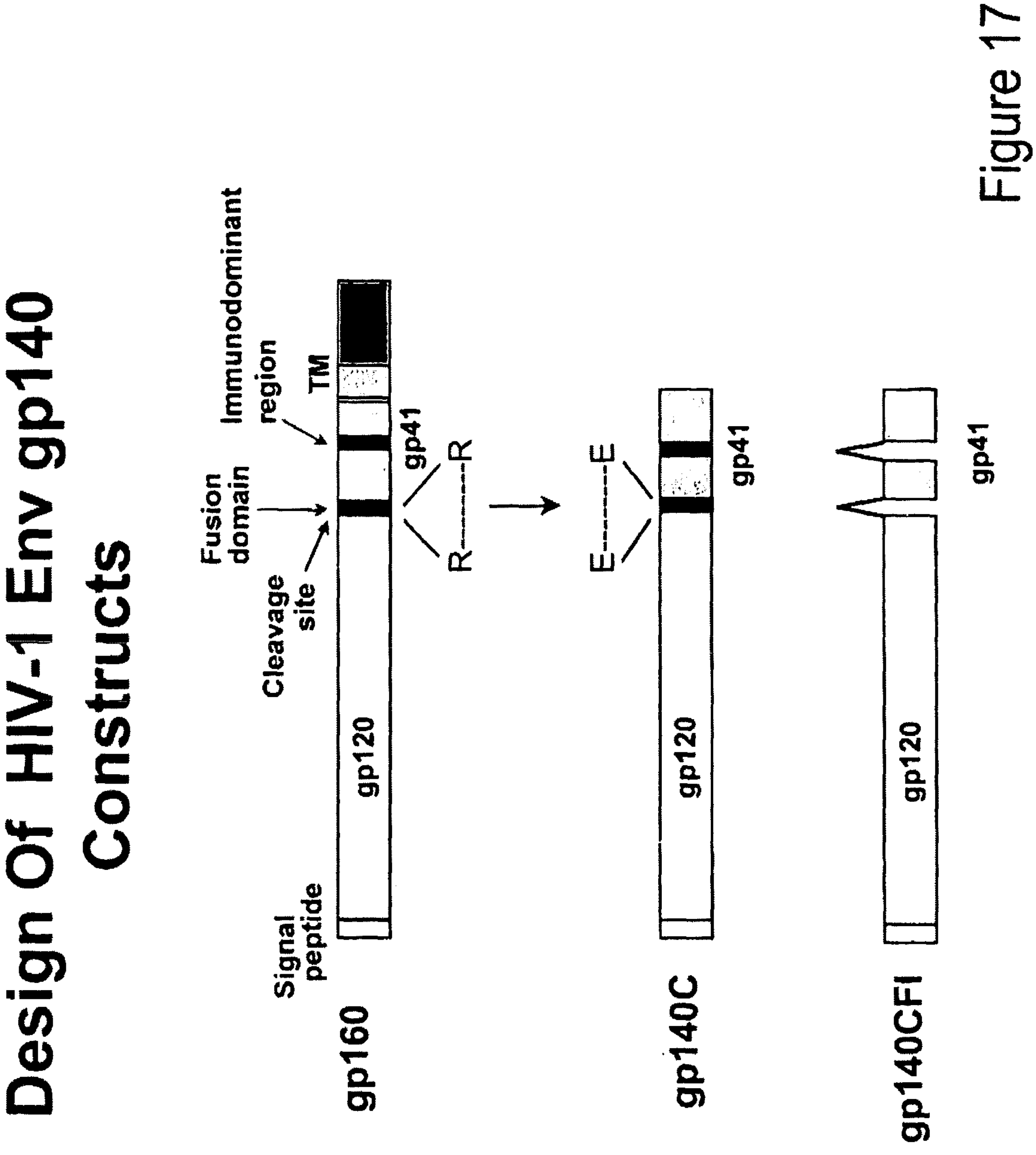
FIG. 17. Design of HIV-1 Env gp140 constructs.
Figure 18:
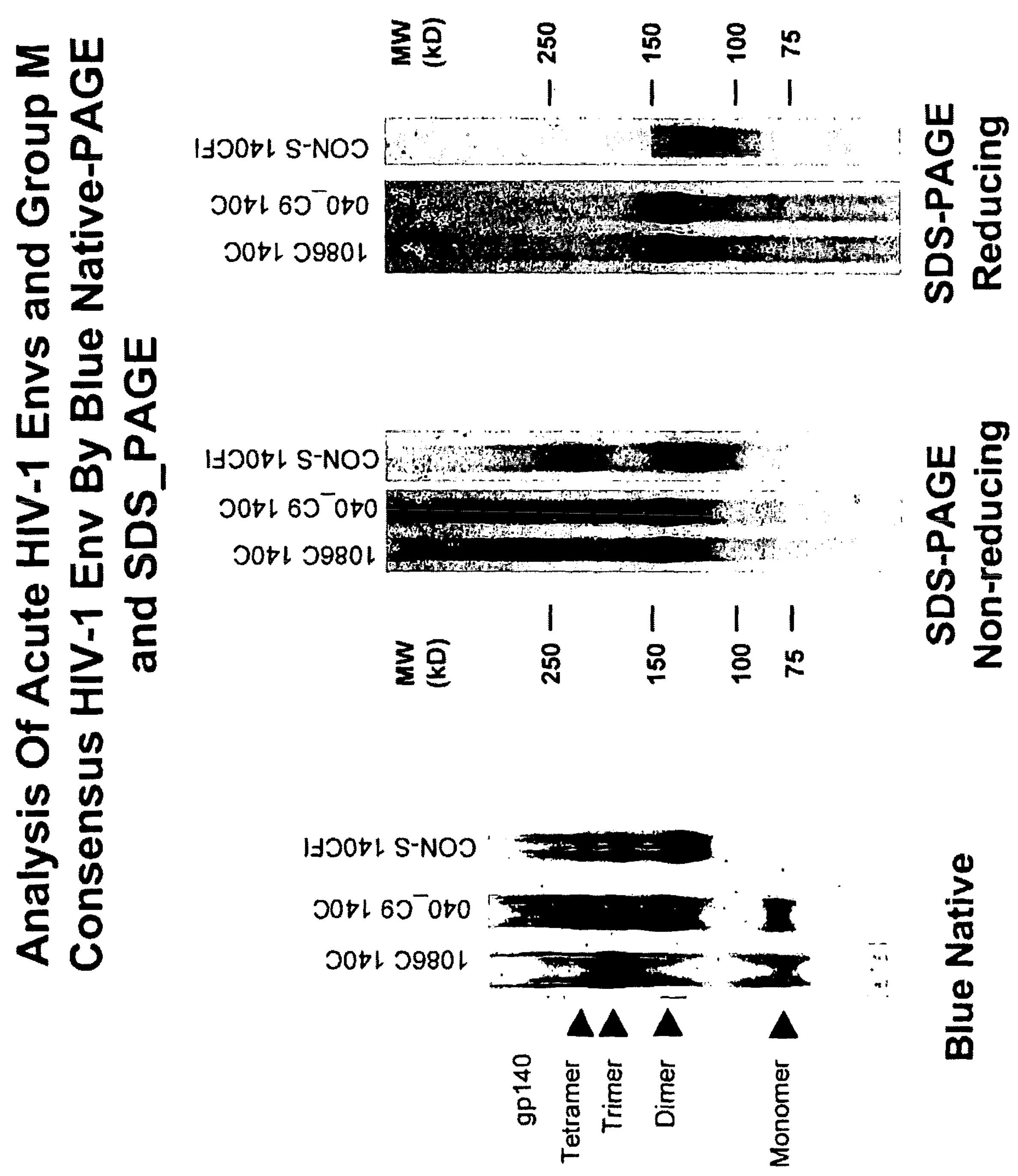
FIG. 18. Analysis of acute HIV-1 Envs and Group M consensus HIV-1 Env by Blue Native-PAGE and SDS-PAGE.

The present invention relates to a method of inducing the production in a subject (e.g., a human subject) of broadly neutralizing antibodies against HIV-1. The method comprises administering to the subject a non-HIV-1 antigen that binds to a germline B cell receptor, the non-HIV-1 antigen being administered in an amount and under conditions such that intermediate clones of B cells are produced that secrete antibodies that cross-react with HIV-1 Env. The method further comprises administering to the subject an HIV-1 antigen in an amount and under conditions such that naïve B cells or their B cell intermediate clones are produced that secrete the broadly neutralizing anti-HIV-1 antibodies. It is likely that, for some epitopes on gp120, there will be rare naïve B cells capable of binding to those epitopes while, for other epitopes, naïve B cells that can give rise to broadly neutralizing antibodies will not bind Env and will need to be stimulated by additional non-Env epitopes. Roadblocks to inducing broadly neutralizing antibodies are described in FIG. 15 and the present strategy for overcoming those roadblocks is described in FIG. 16A.

Non-HIV-1 antigens suitable for use in the invention include host and/or foreign antigens. Non-HIV-1 antigens include, for example, lipids, such as cardiolipin, phosphatidylserine, phosphatidylethanolamine, phosphatidylcholine, phosphotidylinositol, sphingomyelin, and derivatives thereof, e.g., 1-palmitoyl-2-oleoyl-sn-glycero-3-[phospho-L-serine](POPS), 1-palmitoyl-2-oleoyl-phosphatidylethanolamine (POPE), and dioleoyl phosphatidylethanolamine (DOPE), or fragments thereof. Use of hexagonal II phases of phospholipids can be advantageous and phospholipids that readily form hexagonally packed cylinders of the hexagonal II tubular phase (e.g., under physiological conditions) are preferred, as are phospholipids that can be stabilized in the hexagonal II phase. (See Rauch et al, Proc. Natl. Acad. Sci. USA 87:4112-4114 (1990); Aguilar et al et al, J. Biol. Chem. 274: 25193-25196 (1999)). Other suitable non-HIV-1 antigens include, for example, phycoerythrin (PE), C-phycocyanin (C-PC), or other phycobiliprotein, apoferritin, and anerobic or aerobic gut flora or component(s) thereof (for example, the 520 Kd antigen (or the RNA polymerase holoenzyme or the RNA polymerase core protein, or subunit thereof, such as the ac subunit of RNA polymerase core protein or portion thereof comprising the epitope to which mAb HV00276 binds), or the 60 Kd or 50 Kd antigen). The data presented in Example 2 indicates that mAb HV00276 binds to the α subunit of *E. coli* RNA polymerase core protein. The sequence homology is high between the α subunit of *E. coli* RNA polymerase core protein and a homologs from other bacteria (e.g., *B. subtilis, S. dysenteriaea, S. enterica, M. tuberculosis, H. pylori* and *H. influenza*) and eukaryotes (e.g., human and mouse proteins related to *S. cerevisiae* Rpb3 and Rpb11) (Zhang and Darst, Science 281:262-266 (1998)). Accordingly, the invention includes the use of the 520 Kd antigen (or subunit thereof, such as the α subunit of RNA polymerase core protein or portion thereof comprising the epitope to which mAb HV00276 binds) from eukaryotes and from bacteria in addition to *E. coli*. (See, for example, *E. coli* RNA polymerase α subunit: NP_289856 (gi/15803822); *S. dysenteriaea*: YP_404940(gi:82778591); *H. influenzae*: NP_438962 (gi:16272744); Rpb3: Swiss-Prot: P37382.2; Rpb3 (*Homo sapiens*): NP_116558.1(gi:14702171).)

Kynureninase (KYNU) is a member of the family of pyridoxal 5'-phosphate (PLP)-dependent enzymes known as the aspartate aminotransferase superfamily. Eukaryotic constitutive kynureninases preferentially catalyze the hydrolytic cleavage of 3-hydroxy-1-kynurenine to produce 3-hydroxyanthranilate and 1-alanine. The cloning, expression, purification, characterization and crystallization of *Homo sapiens* KYNU has been reported (Lima et al, Biochemistry 46(10): 2735-2744 (2007). As described in Example 3 below, KYNU carries the core 2F5 epitope in its conserved H3 domain.

Based on the data provided in Example 3, it is anticipated that this endogenous ligand is responsible for tolerizing B and T lymphocytes and thereby inhibiting the production of effective immune responses against HIV-1 in humans administered HIV-1 gp41 MPER epitope peptides. The invention provides, in one embodiment, methods of effecting immunization against HIV-1 comprising administering cross-reactive antigens that break this tolerance specifically, that is, without affecting tolerization against other, irrelevant self antigens. Suitable antigens include, for example, the recombinant KYNU molecule expressed in CHO or 293T cells with the ELDKWA (SEQ ID NO: 2) sequence or a mutant gp41 or KYNU sequence with the ELEKWA (SEQ ID NO: 3) sequence (ELEKWA (SEQ ID NO: 3) is not present in human proteins and thus is not expected to be tolerizing). Other immunogens that can be used include transmitted/founder or wildtype chronic envelope gp140s or gp160s or MPER peptides in liposomes with either the ELEKWA (SEQ ID NO: 3) or the ELDKWA (SEQ ID NO: 2) sequence.

Immunogens with the ELDKWA sequence are, advantageously, administered with strong adjuvants, such as squalene based monophosphoryl lipid A, oligonucleotides (oCpGs) and R848 (TRL-7/8 agonist).

HIV-1 antigens suitable for use in the invention include membrane-proximal external region (MPER) antigens (Armbruster et al, J. Antimicrob. Chemother. 54:915-920 (2004), Stiegler and Katinger, J. Antimicrob. Chemother. 512:757-759 (2003), Zwick et al, Journal of Virology 79:1252-1261 (2005), Purtscher et al, AIDS 10:587 (1996)) and variants thereof, for example, variants that confer higher neutralization sensitivity to MPER Mabs 2F5 and 4E10 or to other broadly neutralizing Envs, such as the MPER mutant Env peptide lipid complex containing a L669S mutation in the MPER (Shen et al, J. Virology 83:3617-25 (2009)). Preferred immunogens include those shown in FIGS. 25 and 26, as well as FIGS. 16B, 16C, FIG. 17, FIG. 18 and FIG. 20. In another preferred embodiment, the variant is a MPER epitope peptide with an L669S mutation that confers higher neutralization sensitivity to MPER mAbs 2F5 and 4E10 (Shen et al, J. Virology 83: 3617-25 (2009)).

Figure 19B:
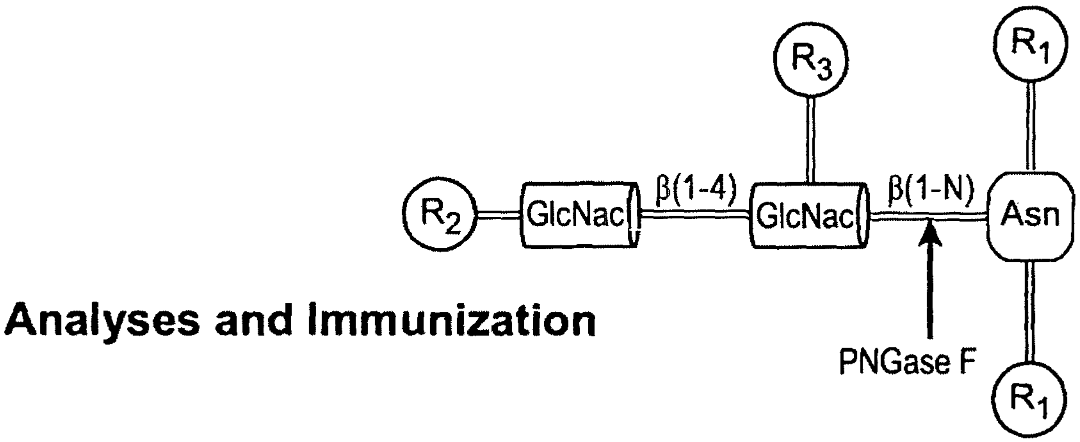
Figure 20:
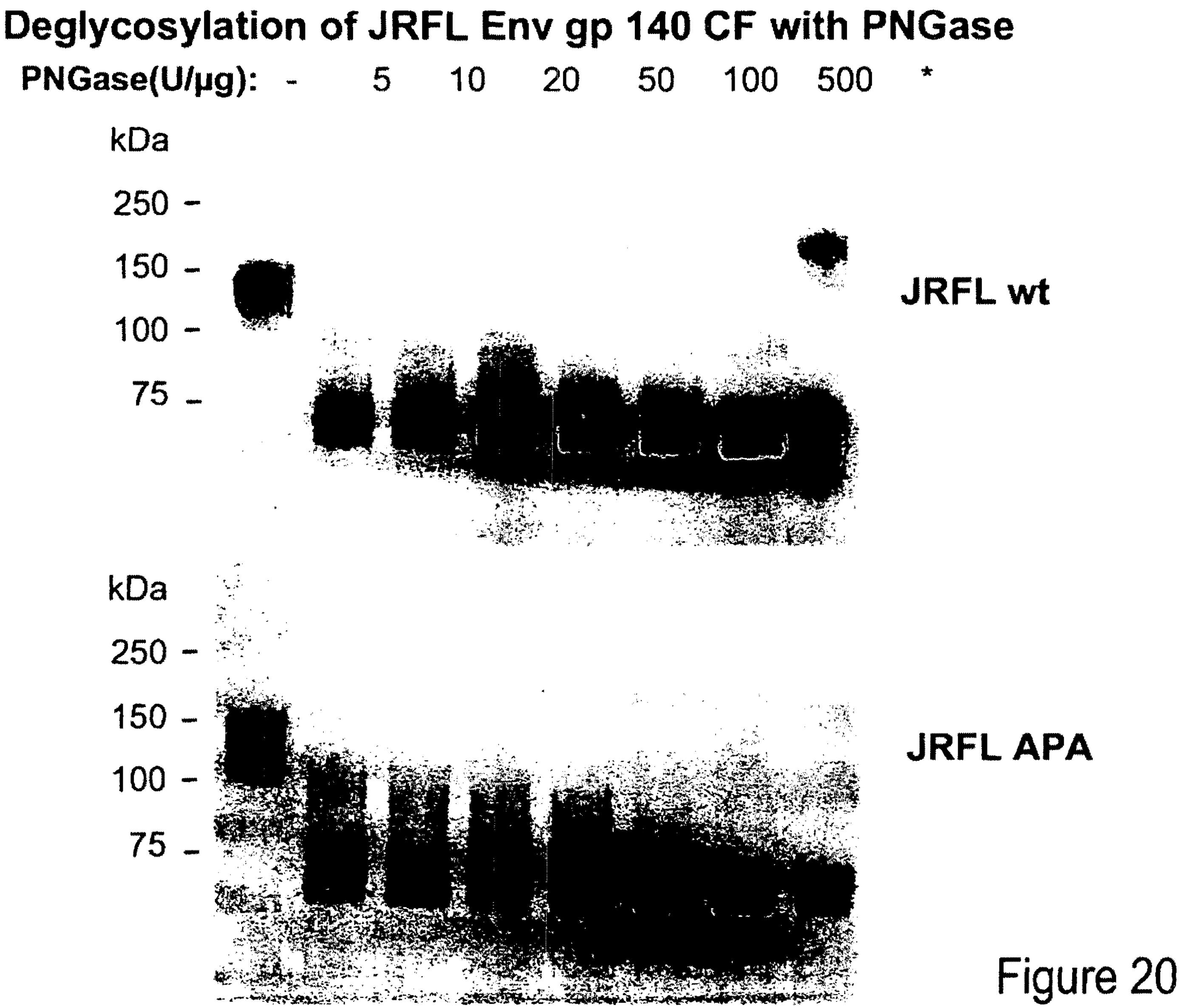
FIG. 20. Deglycosylation of JRFL Env gp 140 CF with PNGase.
Figure 21A:
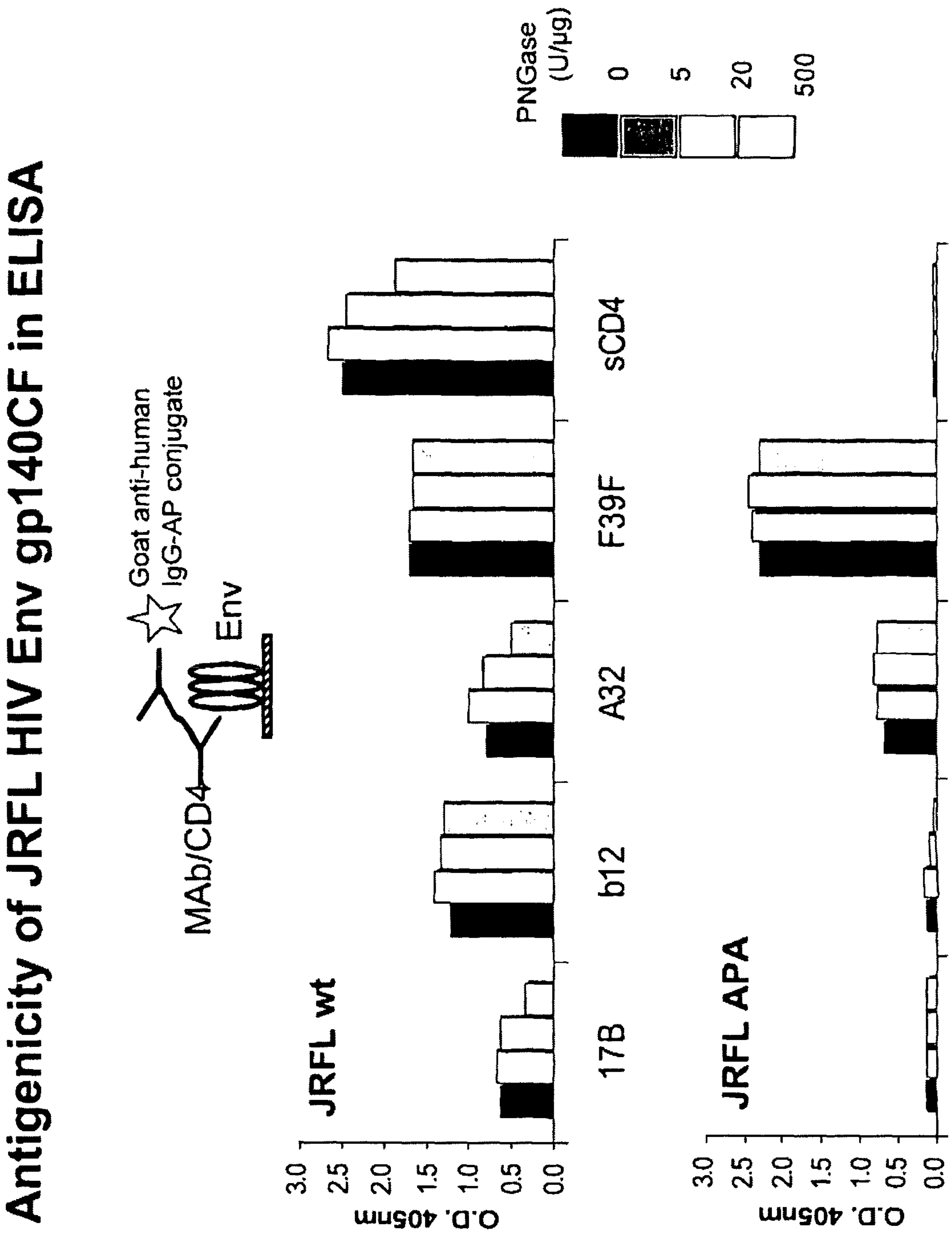
FIGS. 21A and 21B. Antigenicity of JRFL HIV Env gp140CF in ELISA.
Figure 21B:
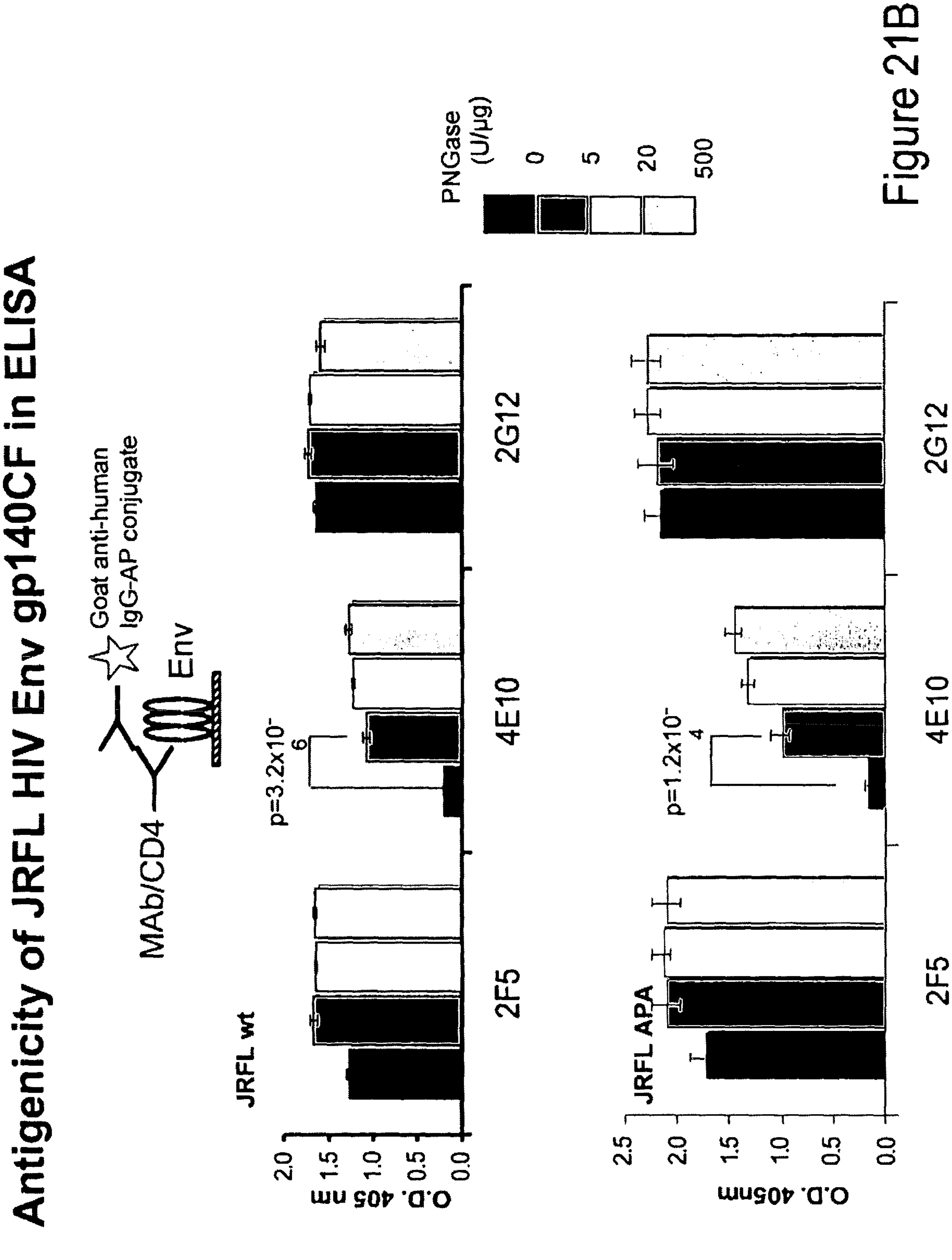

HIV-1 antigens suitable for use in the invention also include transmitted founder HIV-1 Envs, or fragments thereof. These fragments can be representative of portions of the CD4 binding site of gp120 (Chen et al, Science 362 (5956):1123-7 (2009)), MPER sequences, portions of gp120 incorporating the V2, V3 regions of gp120 (Walker et al, Science 326(5950):285-9 (2009) Epub 2009 Sep. 3), etc (e.g., see the sequences for 1086, 089, 6240, 040_C9 and 63521 set forth in FIGS. 27 and 28). Preferred Env antigens include the Malawi 1086 clade C, 6321 and the US clade B 040_C9 gp140 oligomers (FIGS. 17 and 18) (Keele et al, Proc. Natl. Acad. Sci. USA 105:7552-7 (2008)) produced as previously described (Liao et al, Virology 30:268-282 (2006)), which have induced in guinea pigs considerable breadth in neutralizing antibodies (FIG. 19A), mixed with the clade B JRFL gp140 Env, or fragment thereof, that selectively expresses the MPER neutralizing epitopes (see FIG. 28). The JRFL gp140 Env oligomer (FIGS. 19B, 20, 21A and 21B) constitutively binds the 2F5 mAb. The JRFL oligomer deglycosylated using 500 U of PNgase endoglycosidase (New England BioLabs, Ipswich, Mass.) has enhanced binding of 2F5 and new binding of the 4E10 mAb (exposure of the 4E10 epitope on gp41) (FIGS. 21A and 21B). The enhanced binding of 4E10 to deglycosylated JRFL is also shown in surface plasmon reasonance (SPR) analysis in FIG. 22.

The method of the invention can be effected by administering to the subject a prime immunization comprising a non-HIV-1 immunogen followed by one or more boosts of an HIV-1 Env antigen. As pointed out above, suitable non-HIV-1 immunogens include lipids (e.g., cardiolipin, phosphotidylserine, or other anionic lipid), components of anaerobic or aerobic gut flora bacteria, phycobiliproteins (e.g., PE) and KYNU or fragment thereof. As also pointed out above, suitable HIV-1 Env antigens include transmitted founder Env 1086.C from Malawi, 089.C from Malawi, 040_C9 from the U.S. and 63521 from a Clade B acute HIV-1 infected U.S. patient. Both the primes and the boosts suitable for use in the present method can comprise both non-HIV-1 and HIV-1 immunogens. Prime/boost regimes can be readily optimized by one skilled in the art. DNA sequences encoding proteinaceous components of such regimens can be administered under conditions such that the proteinaceous component is produced in vivo.

As described in Example 5 below, 5 clonally related B cells have been isolated from a single patient that produce broadly neutralizing antibodies (CH01 through CH05). Possible reverted unmutated ancestors of the clonally-related antibodies have been inferred and expressed as real antibodies. The phylogenetic tree of these antibodies has been reconstructed. Both the natural and inferred ancestor antibodies have been characterized for their ability to bind a panel of HIV envelope proteins and to neutralize a panel of HIV isolates. It is important to note that the reverted unmutated ancestors (RUAs) bind to A244gD+ envelope. Therefore, such envelope, or other envelopes described to be neutralized by the RUAs, can be used as the "prime" in a preferred vaccine strategy of the invention. In accordance with this strategy, the "boost" can be effected, for example, using envelopes that are bound by the mature antibodies described herein. A further "boost" can be effected, for example, with 6420 or 63521 (or other protein, peptide or polypeptide that binds).

When a DNA prime or boost is used, suitable formulations include a DNA prime and a recombinant adenovirus boost and a DNA prime and a recombinant mycobacteria boost, where the DNA or the vectors encode, for example, either HIV-1 envelope or a proteinaceous non-HIV1-1 antigen, such as a gut flora or KYNU component. Other combinations of these vectors can be used as primes or boosts, either with or without HIV-1 antigen and/or non-HIV-1 antigen.

In accordance with the invention, the non-HIV-1 antigen can be present in a liposome with the HIV-1 Env antigen and one or more adjuvants. Alternatively, the non-HIV-1 antigen can be conjugated, for example, using a hetero-bifunctional agent such as DSSP, to the HIV-1 Env antigen and formulated with one or more adjuvants.

Figure 23:
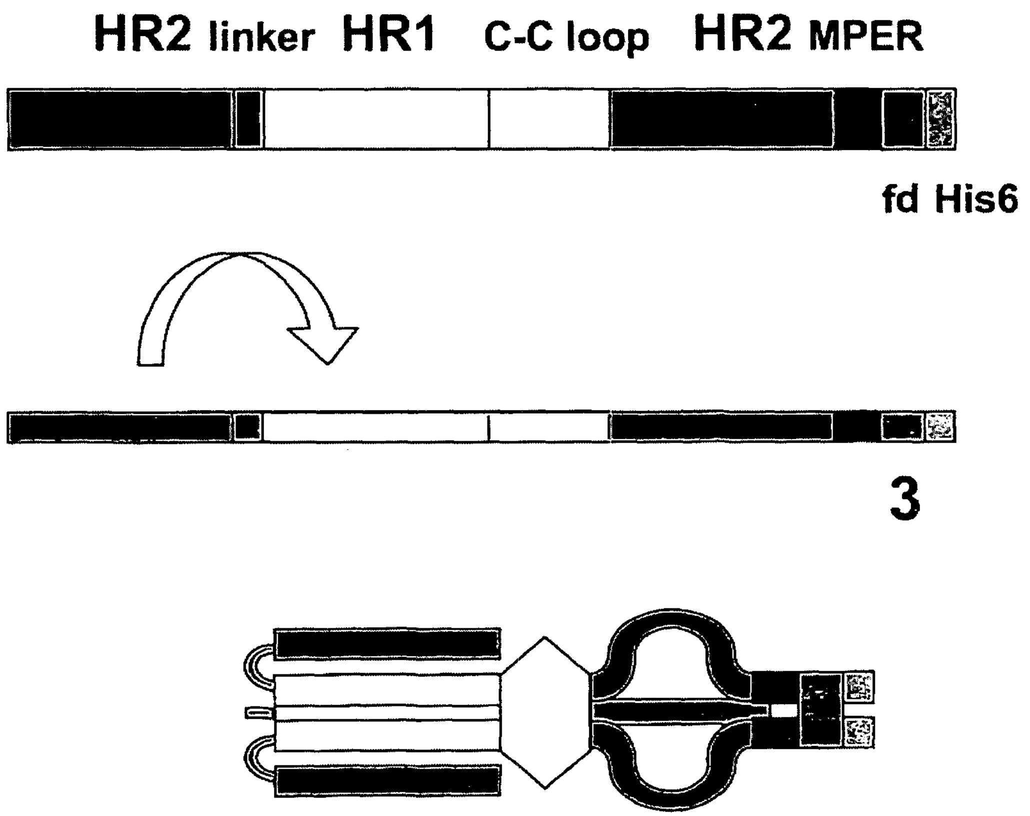
FIG. 23. Fusion-intermediate state of HIV-1 gp41 targeted by broadly neutralizing antibodies.
Figure 24A:
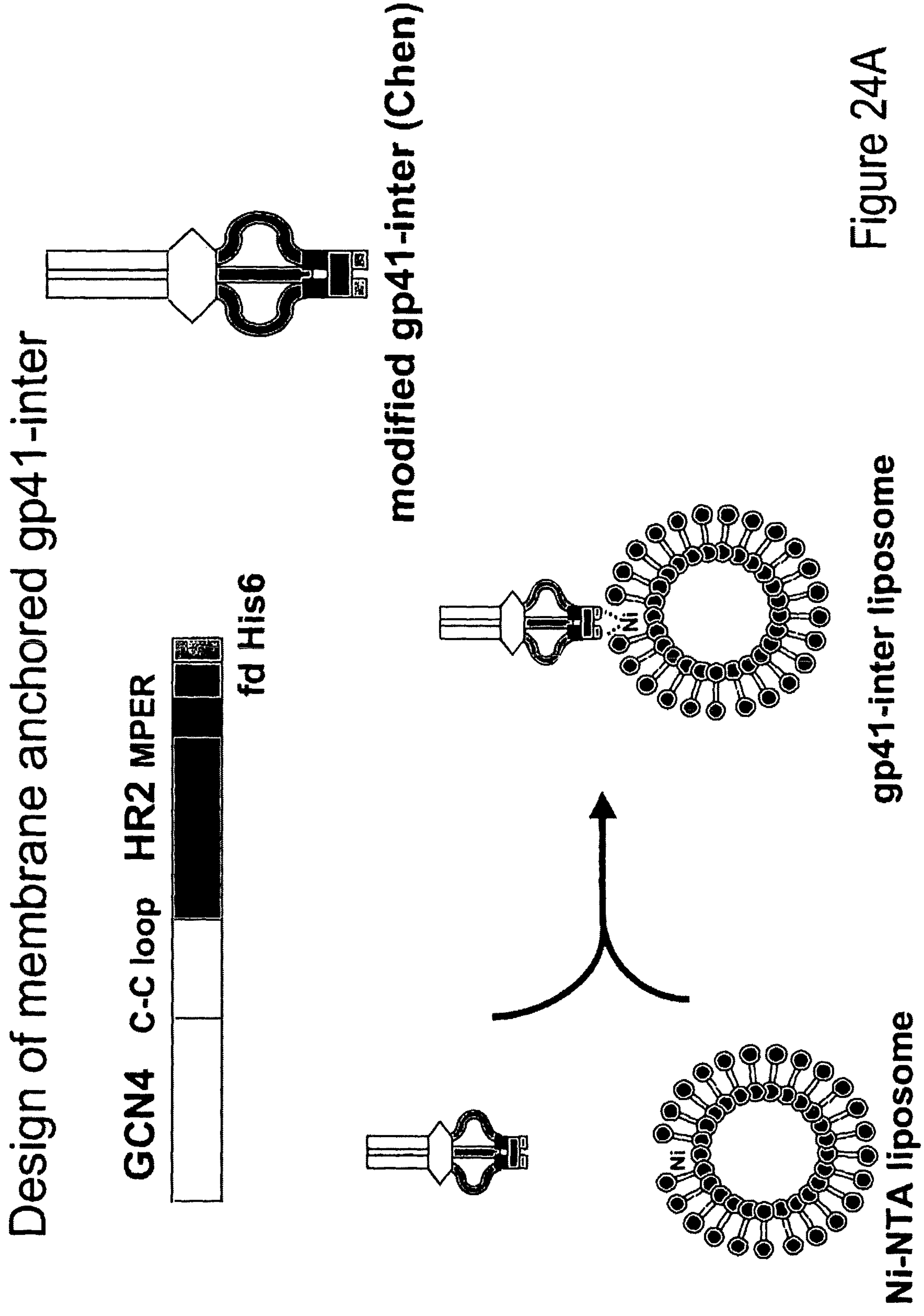
FIGS. 24A and 24B.
Figure 24B:
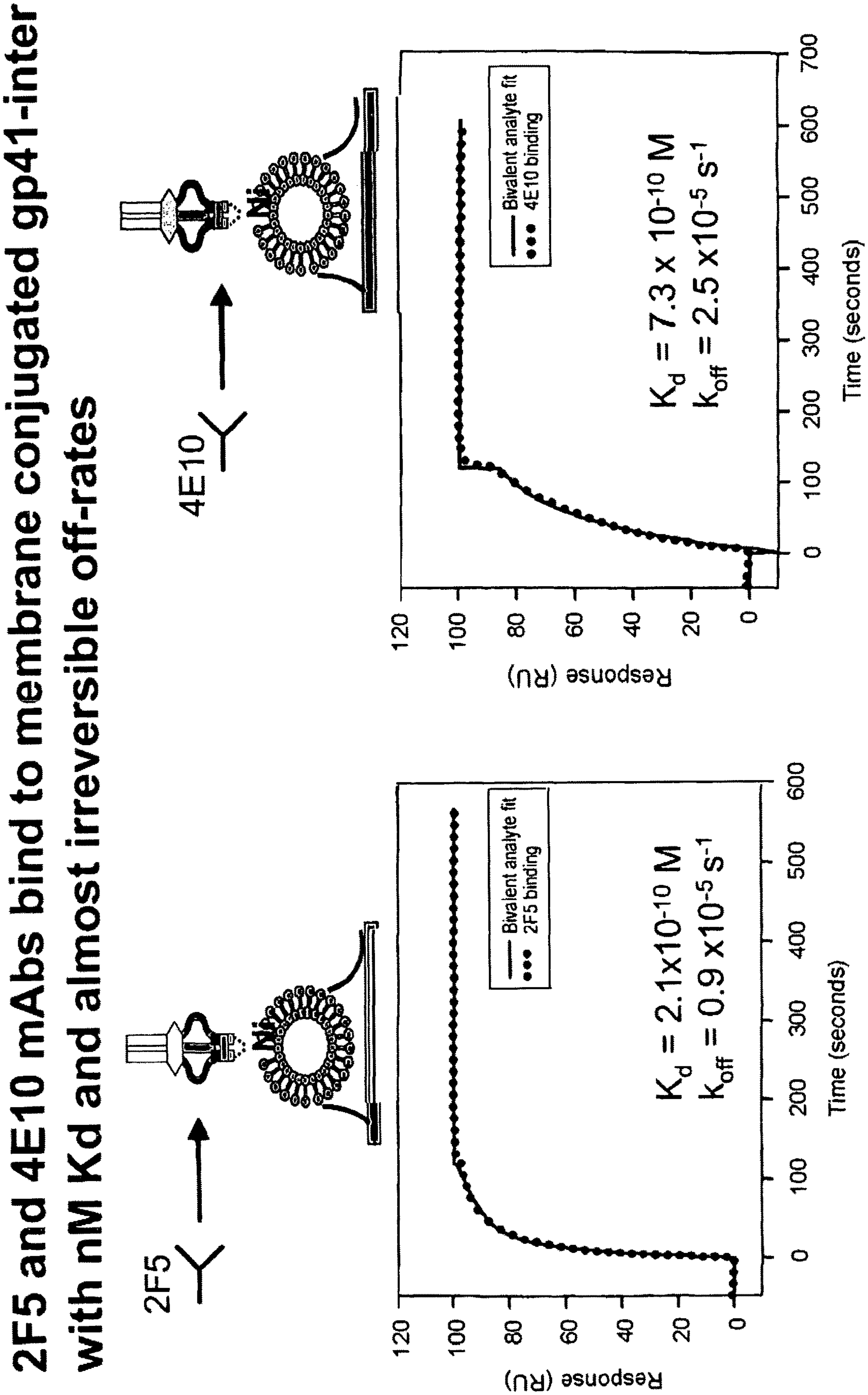
Figure 26:
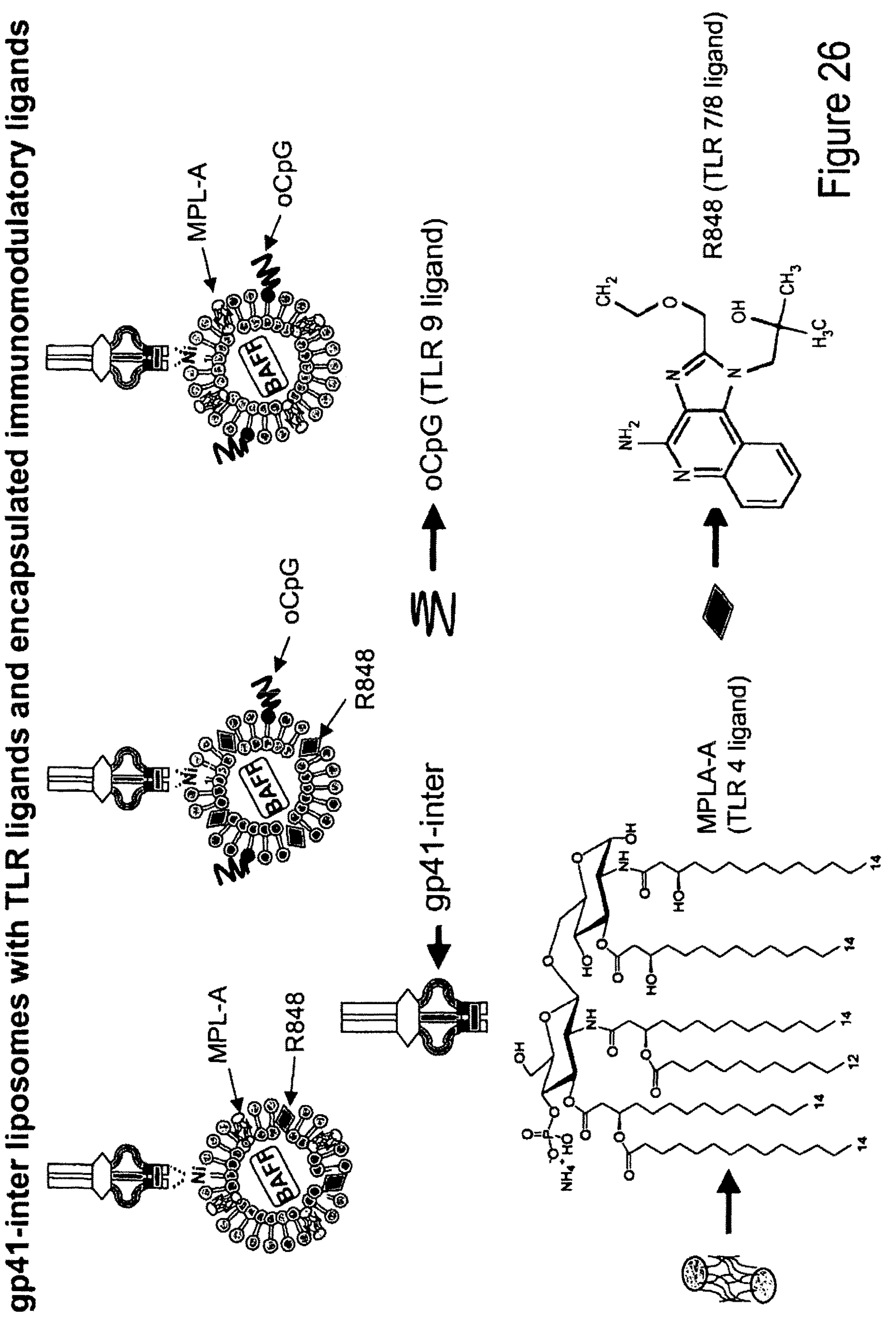
FIG. 26. Gp41-inter liposomes with TLR ligands and encapsulated immunomodulatory ligands.
Figure 29:
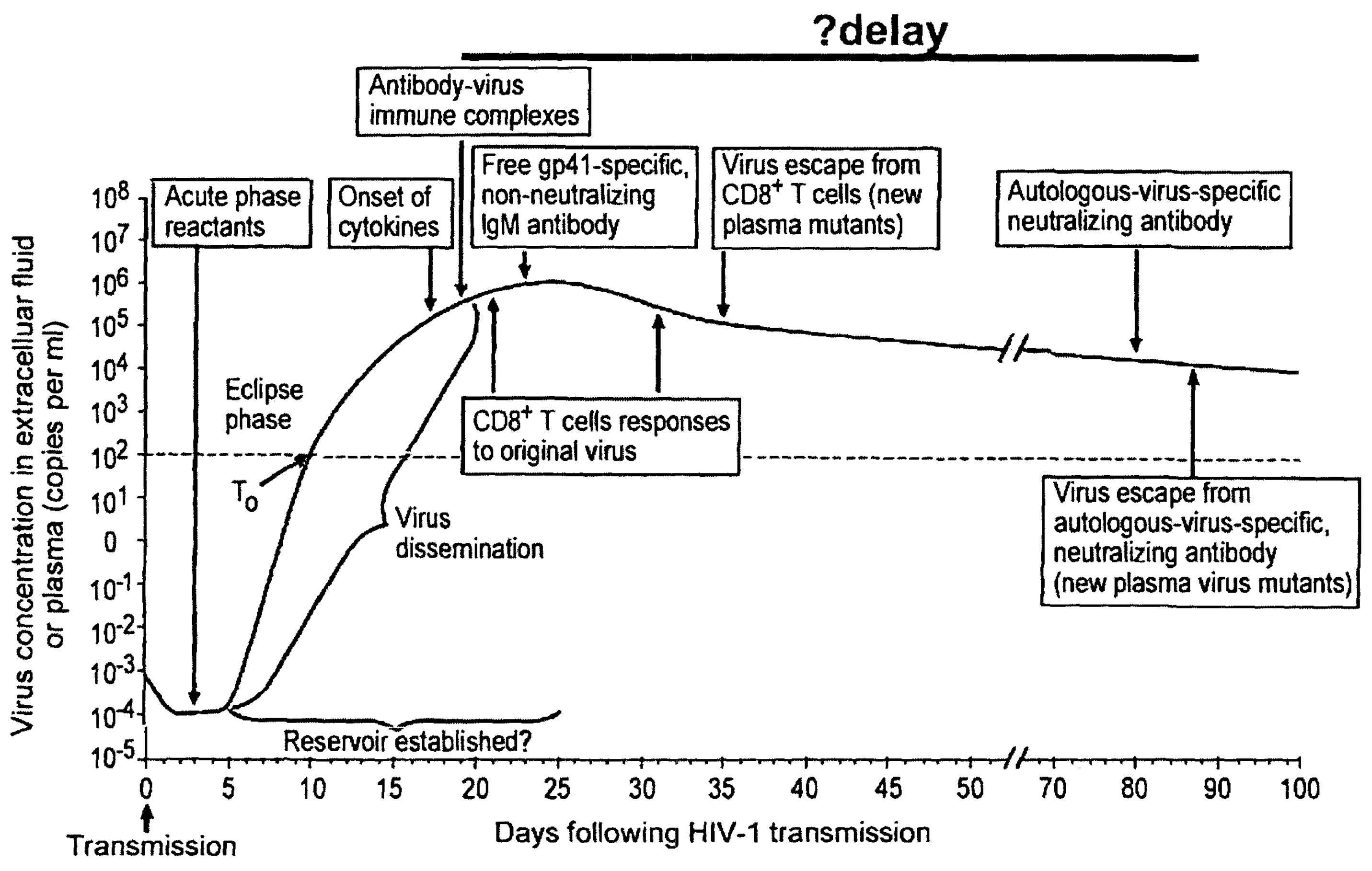
FIG. 29. Early B cell response to HIV-1: the role of innate B cells.
Figure 29:
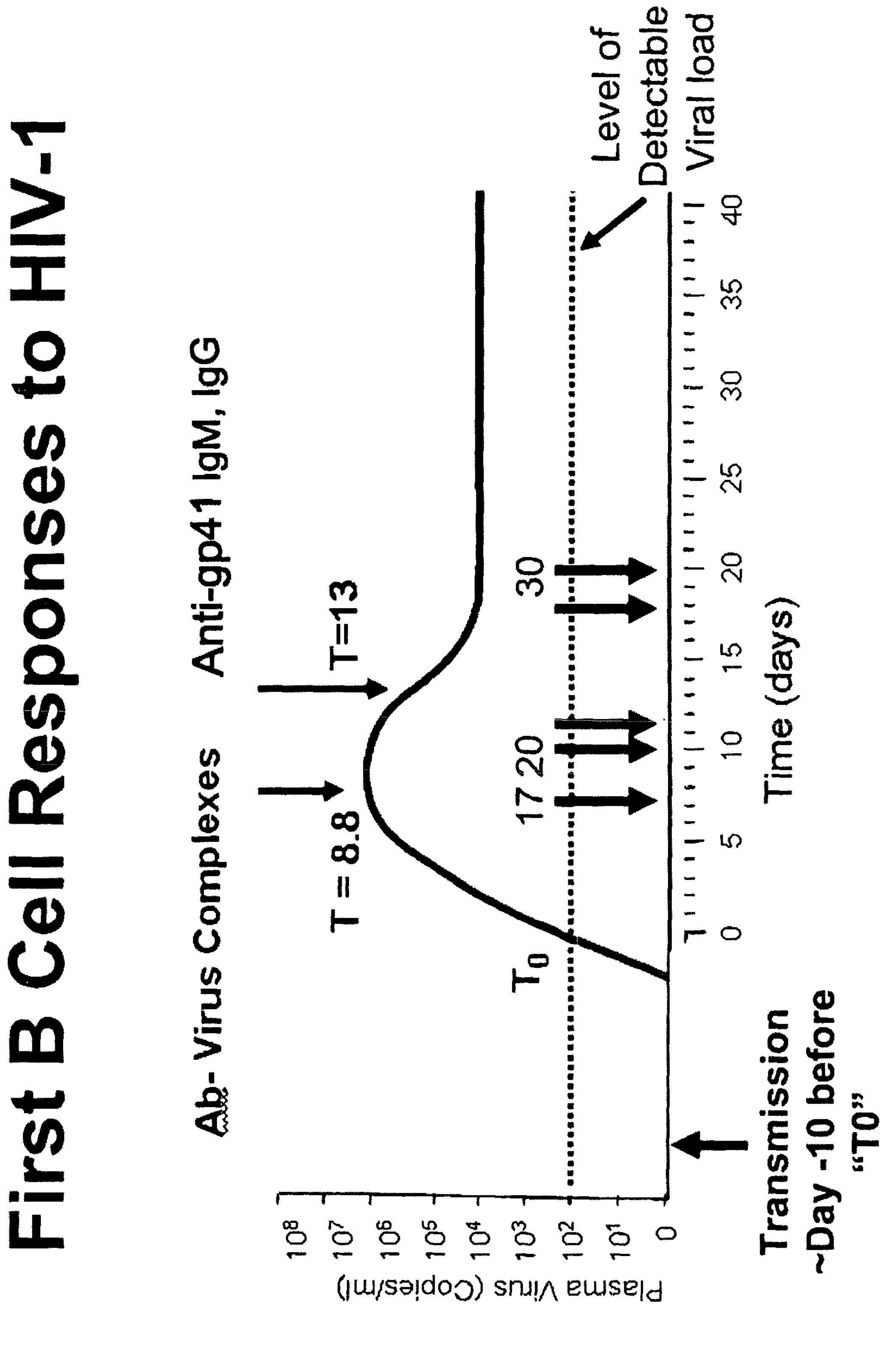
Figure 29:
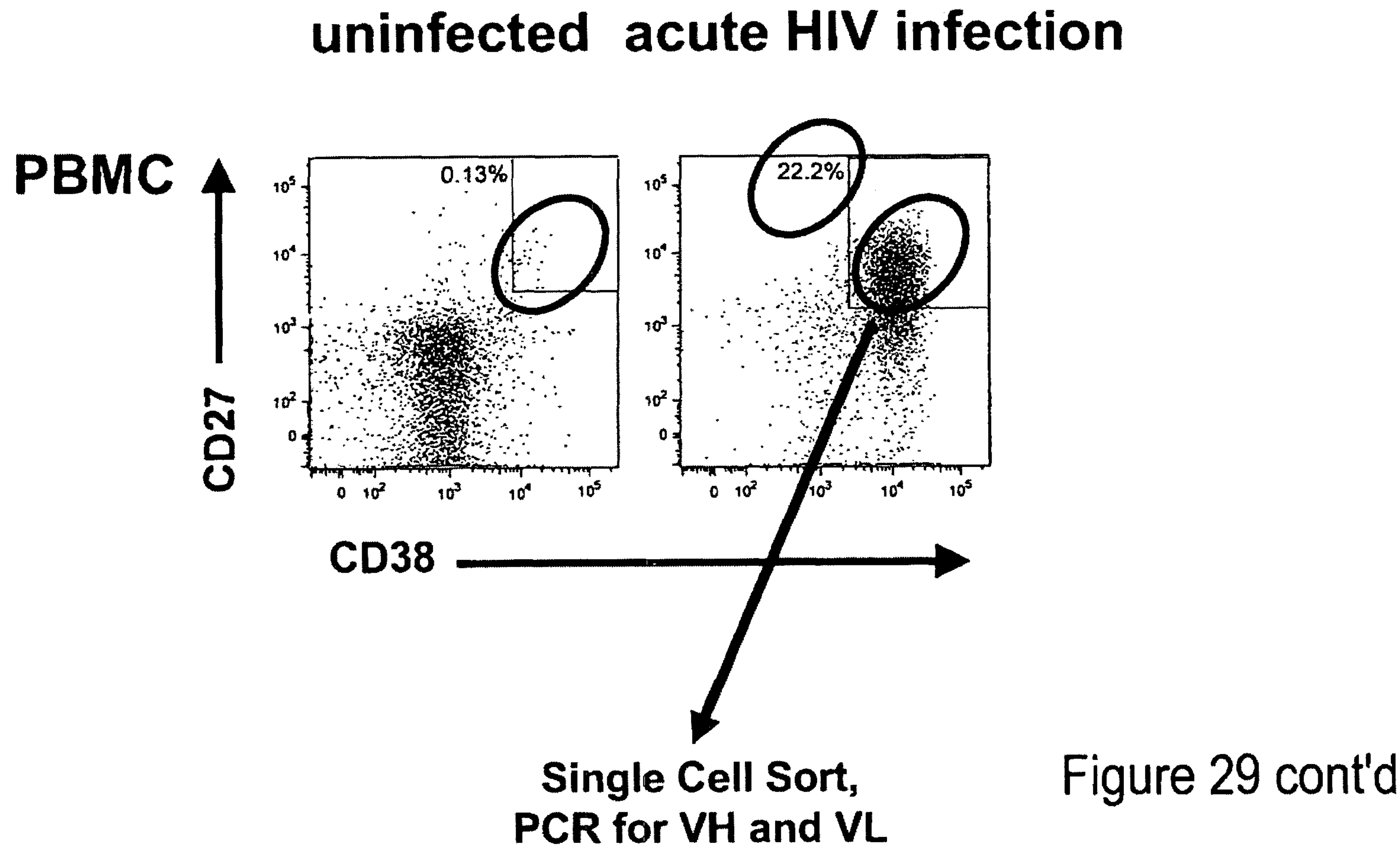
Figure 29:
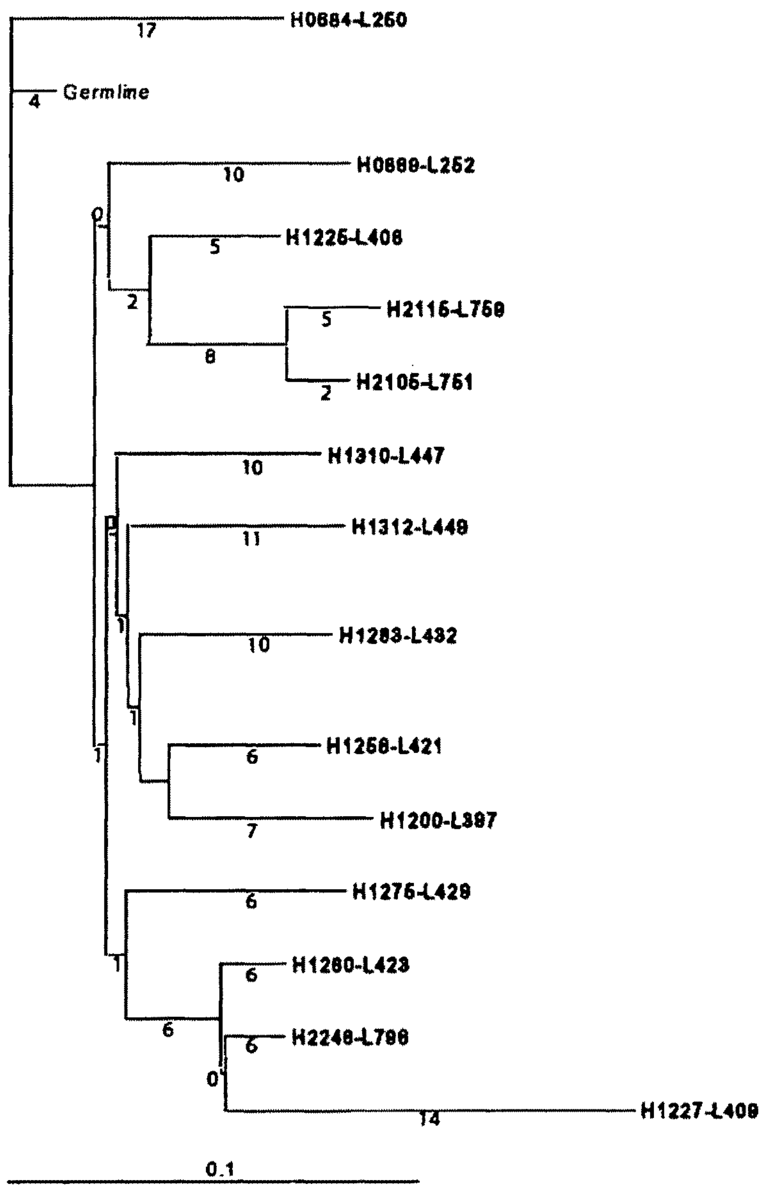
Figure 29:
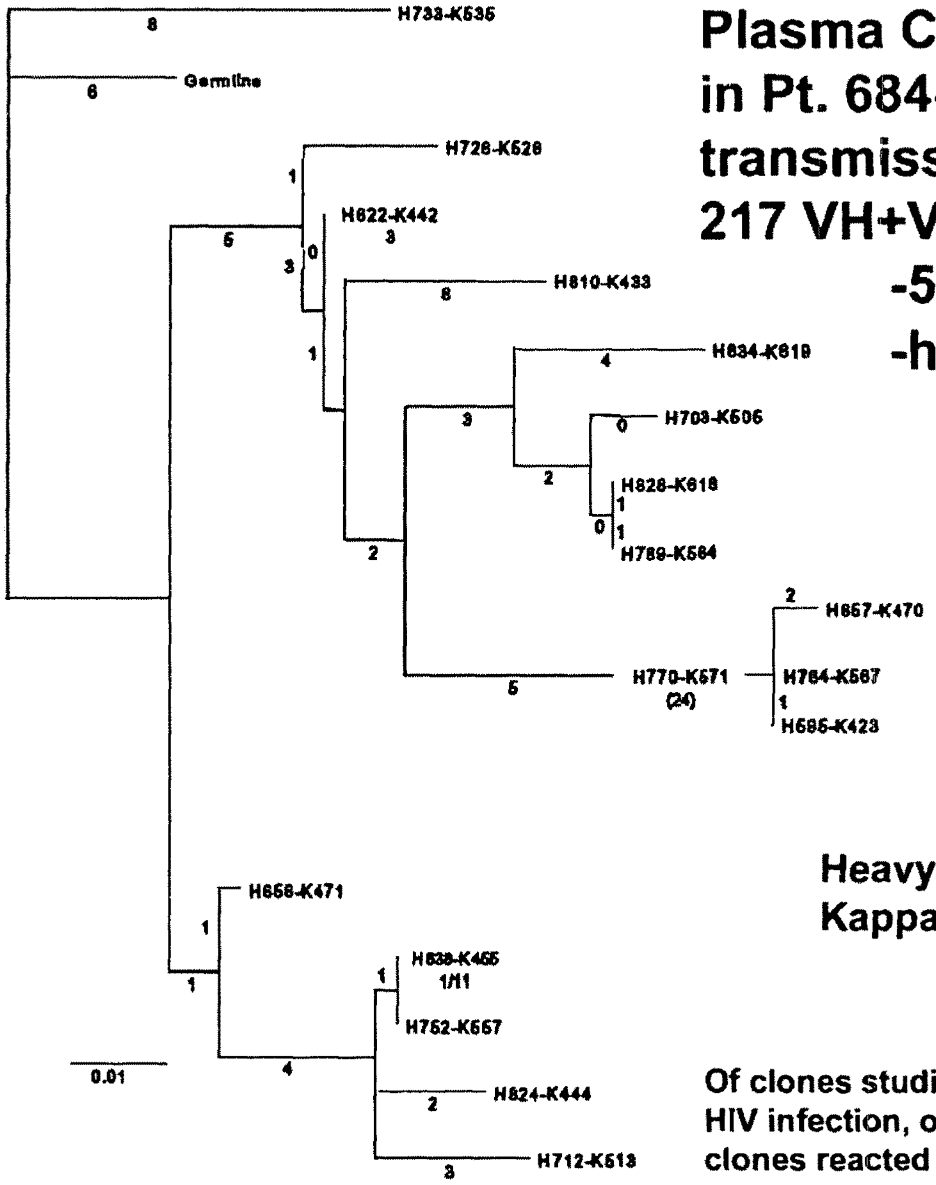
Figure 29:
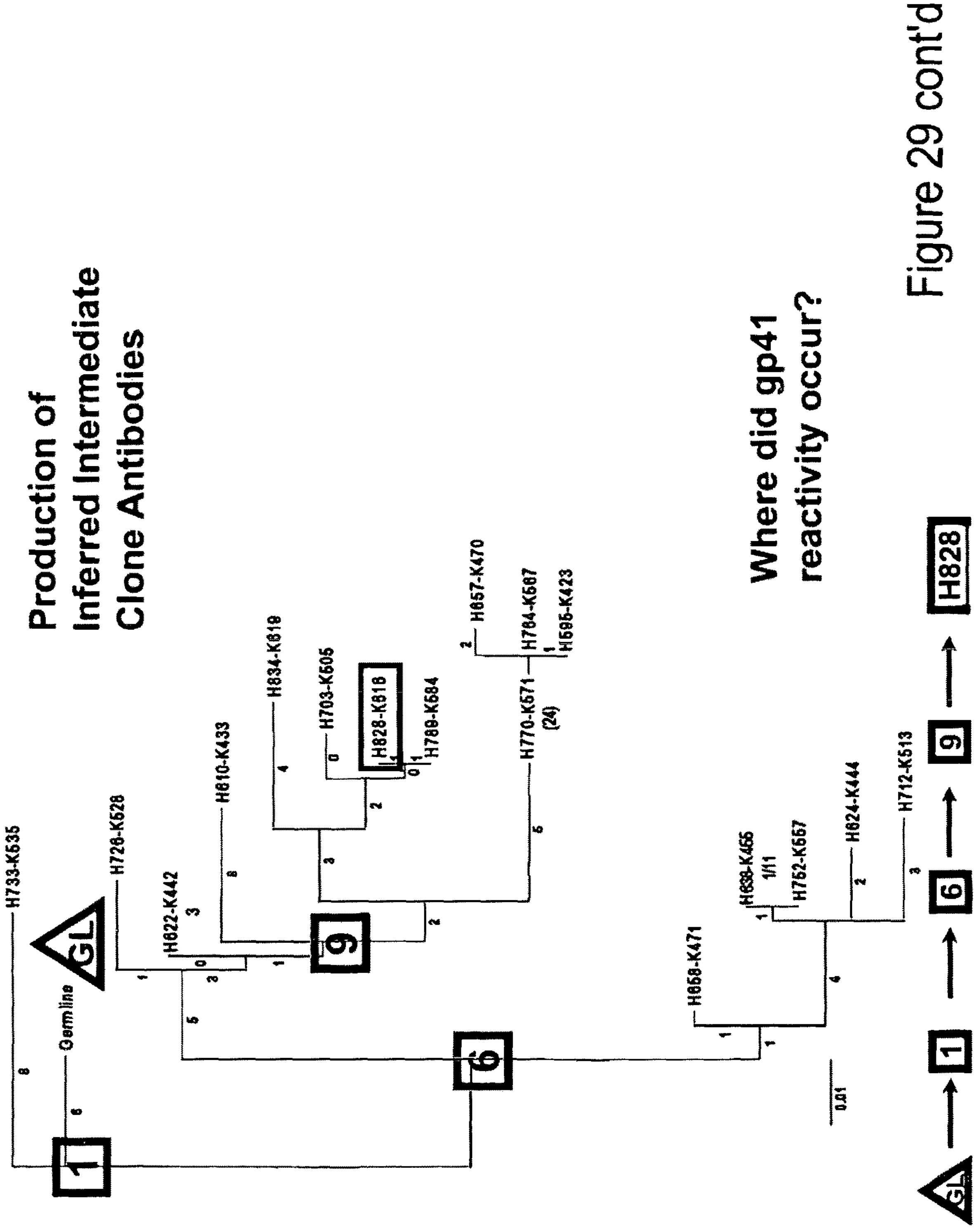
Figure 29:
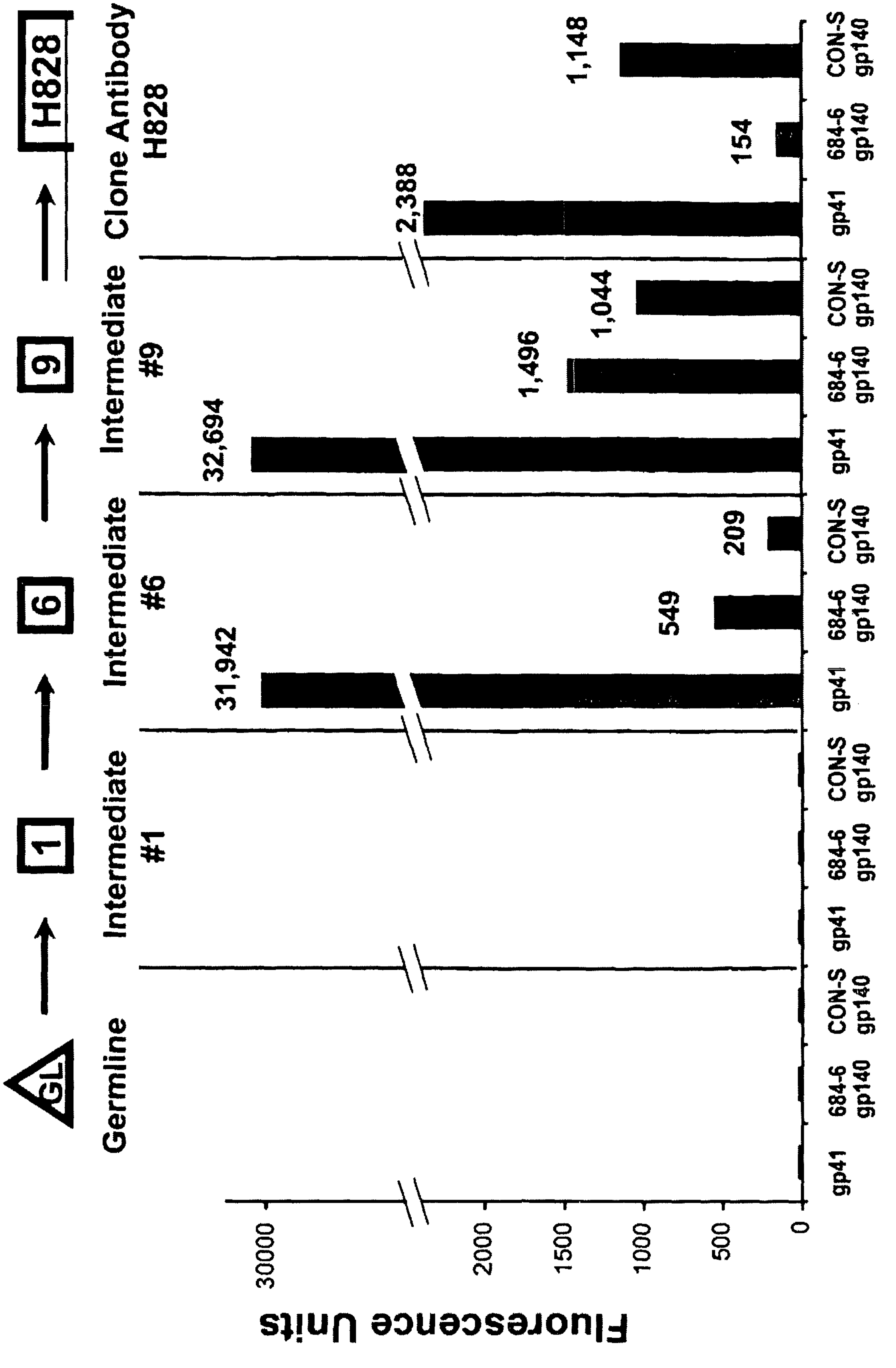
Figure 29:
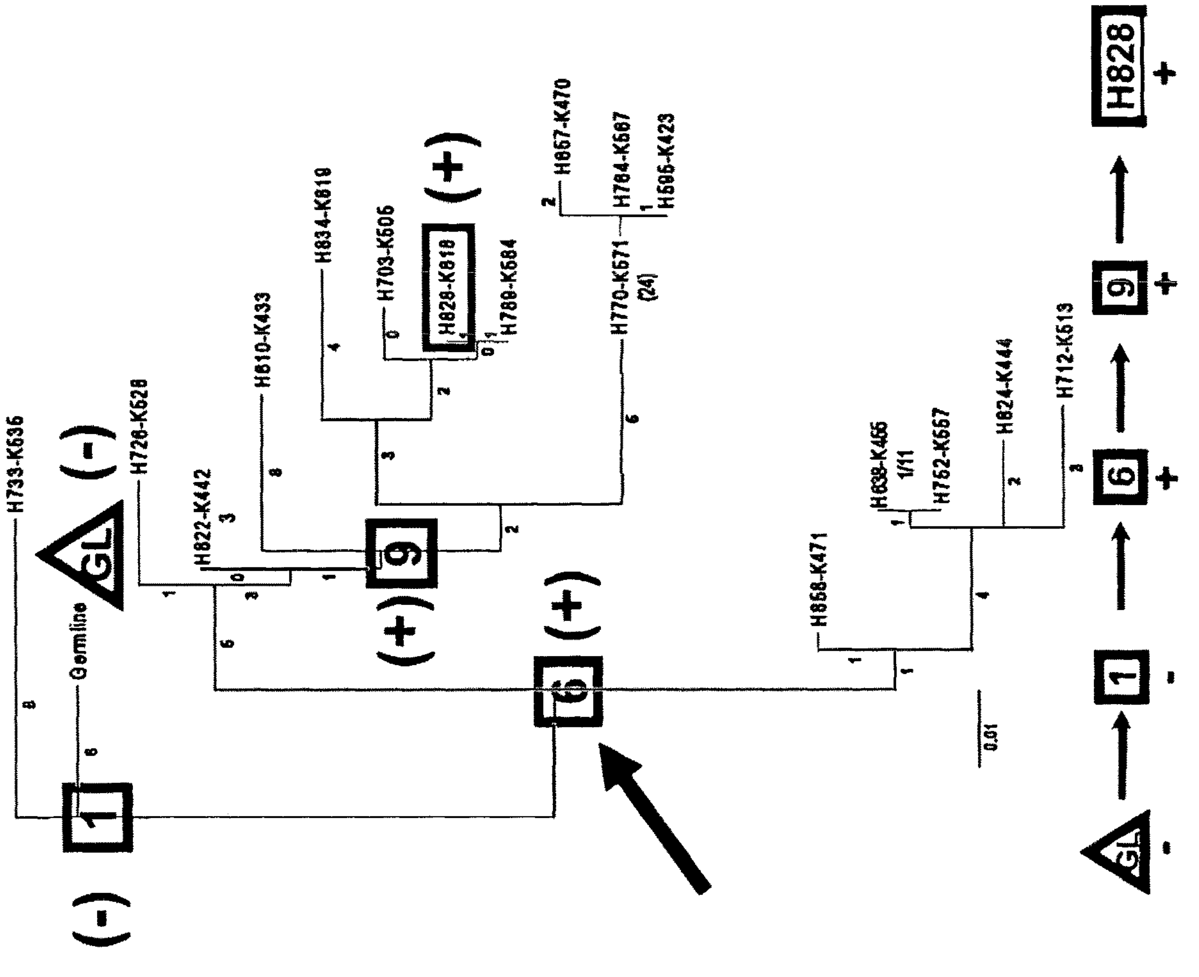
Figure 29:
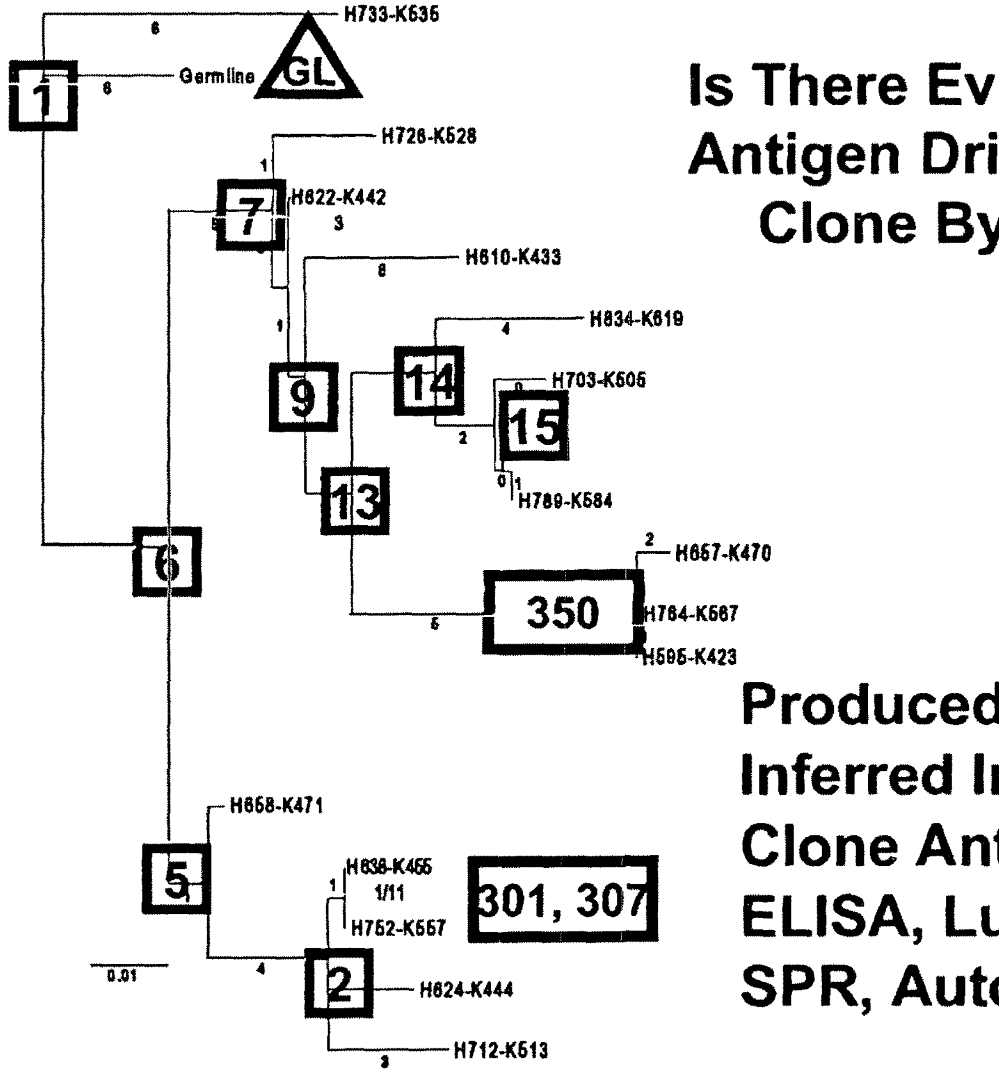
Figure 29:
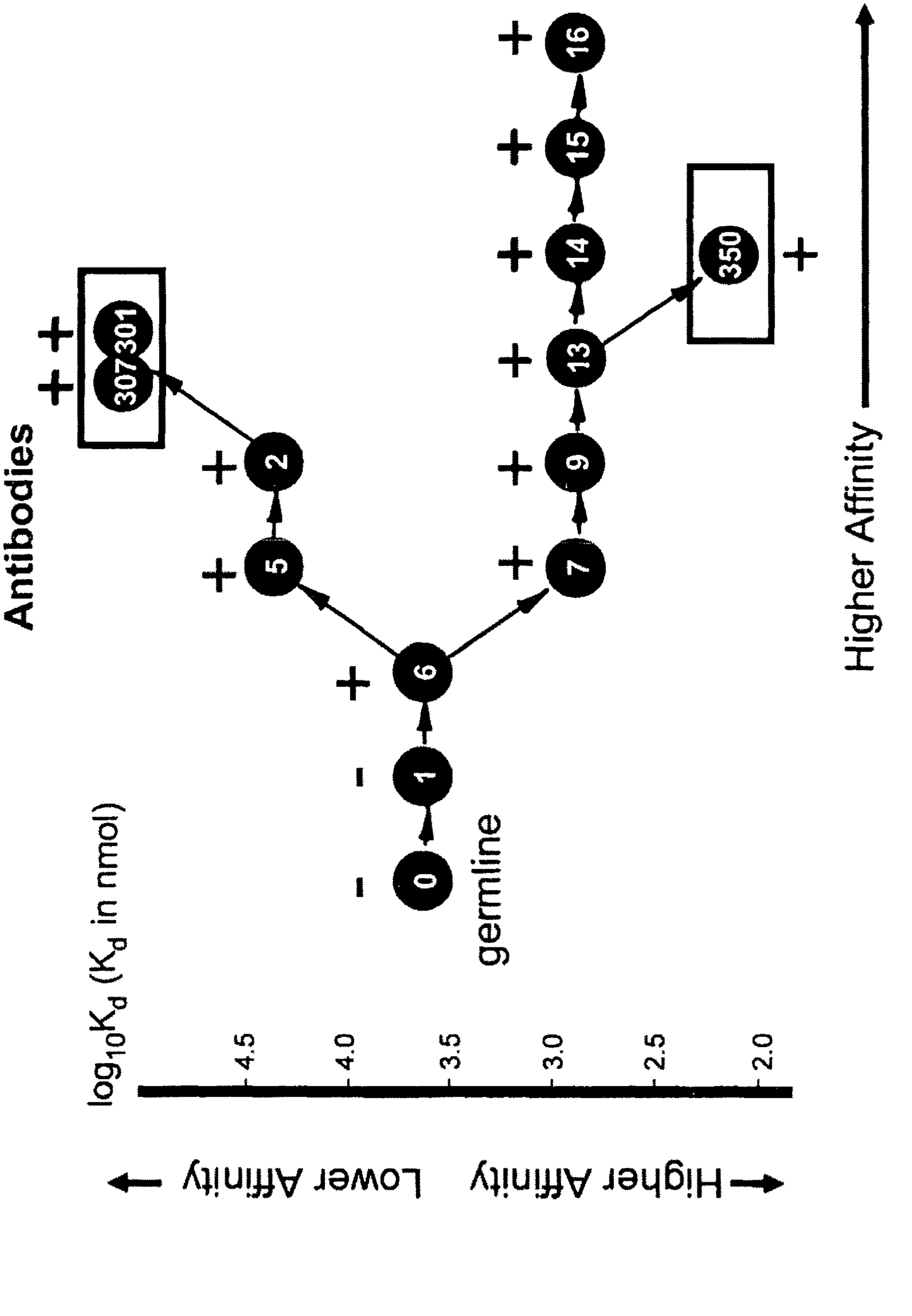
Figure 29:
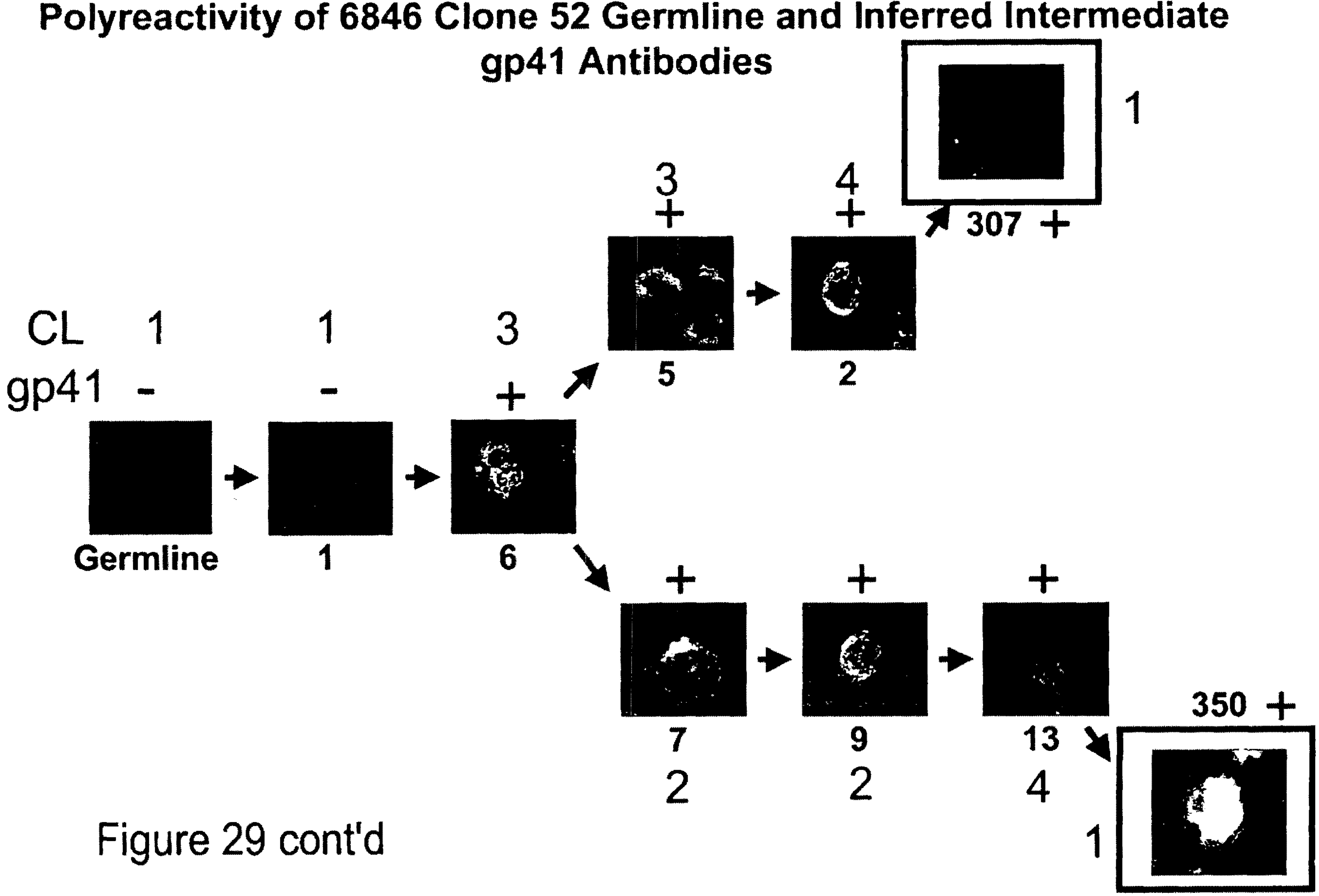
Figure 29:
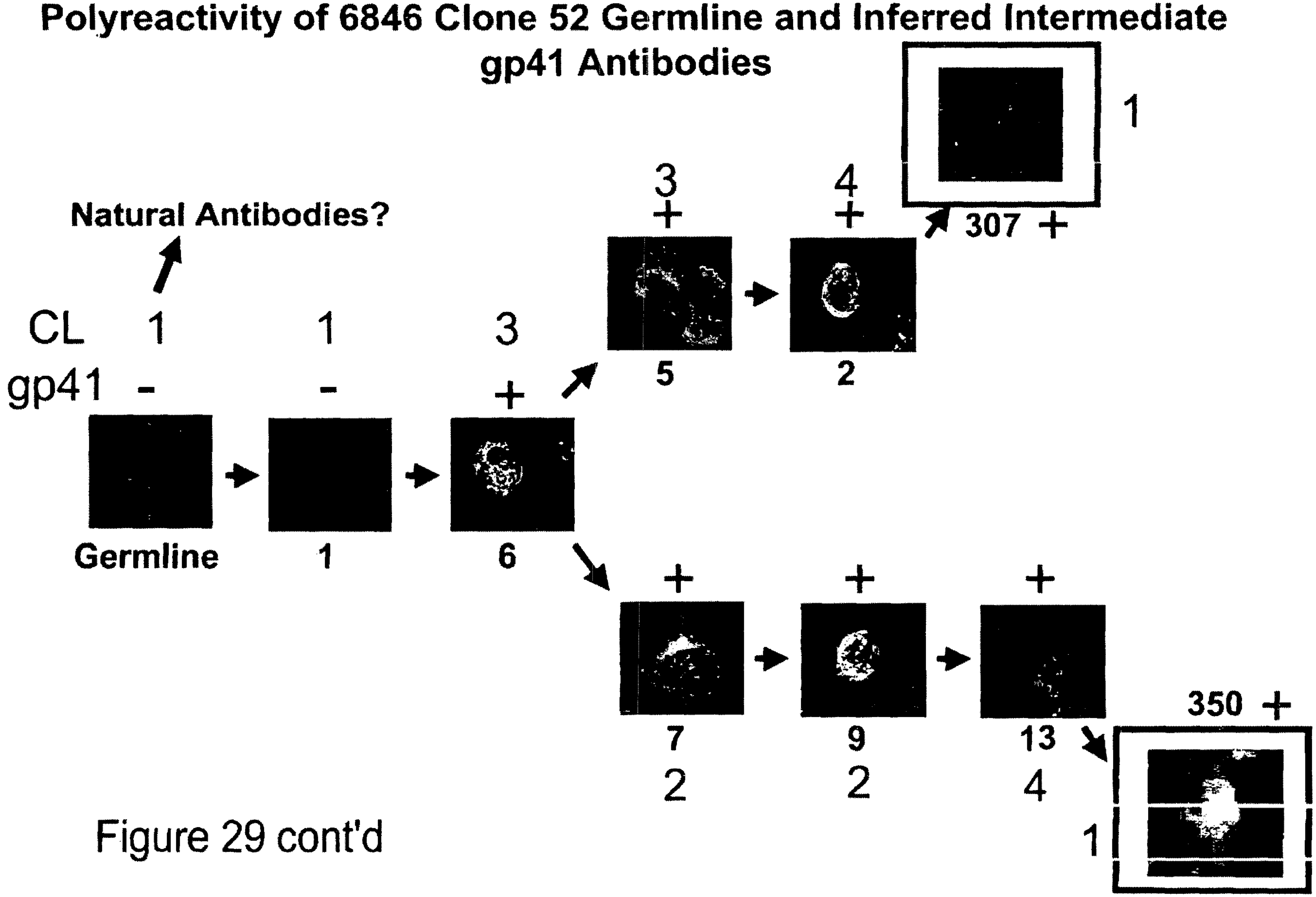
Figure 29:
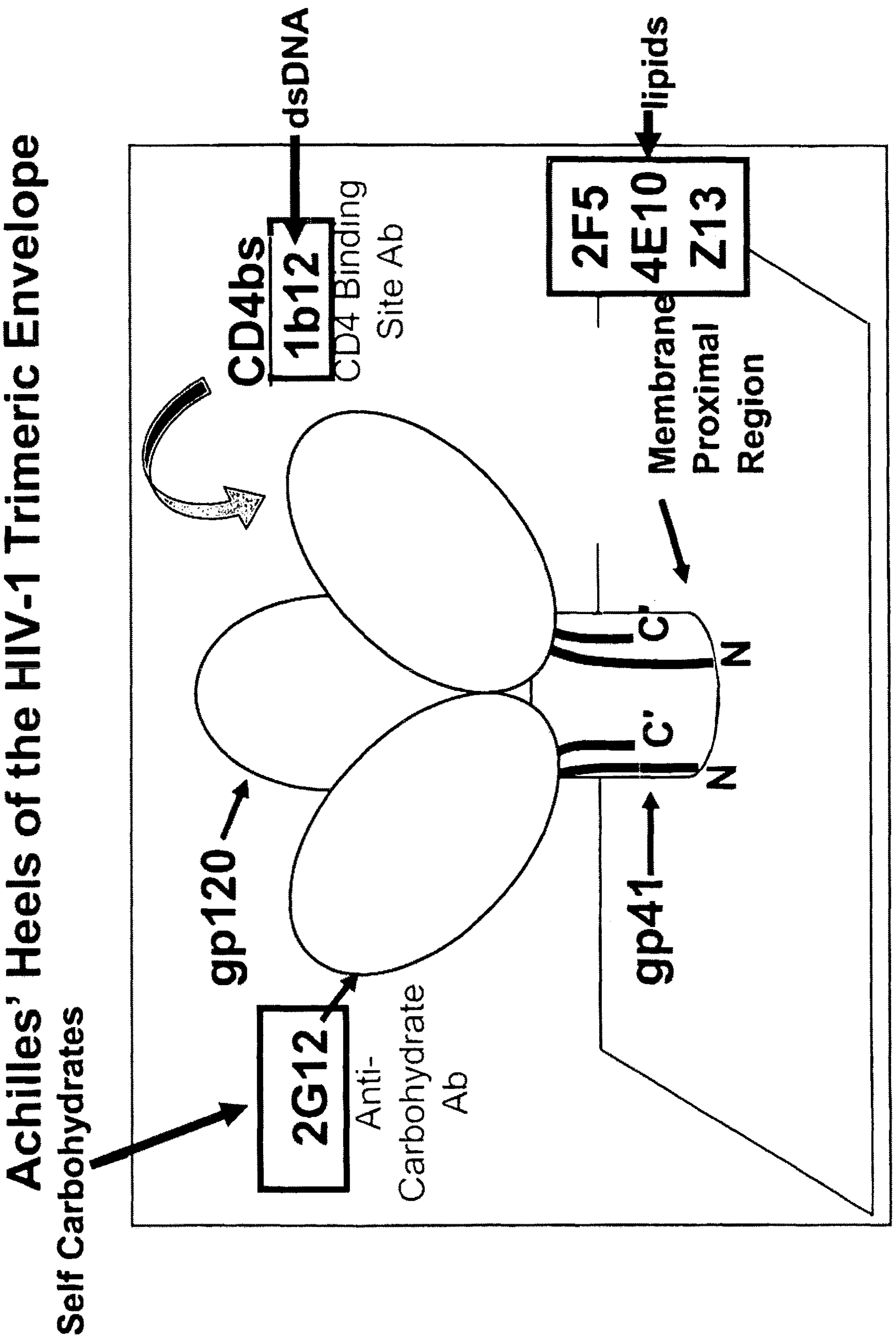
Figure 29:
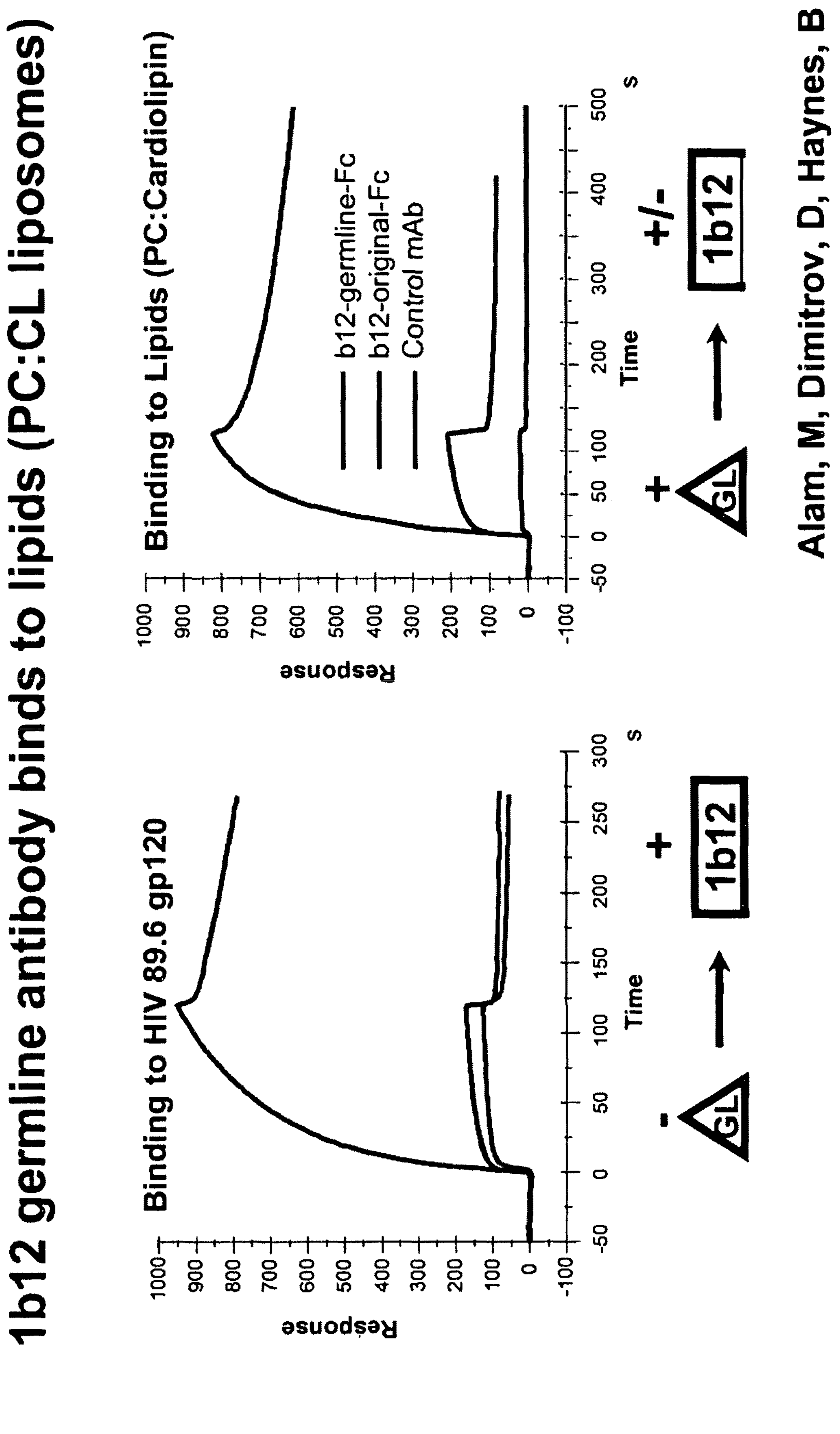
Figure 29:
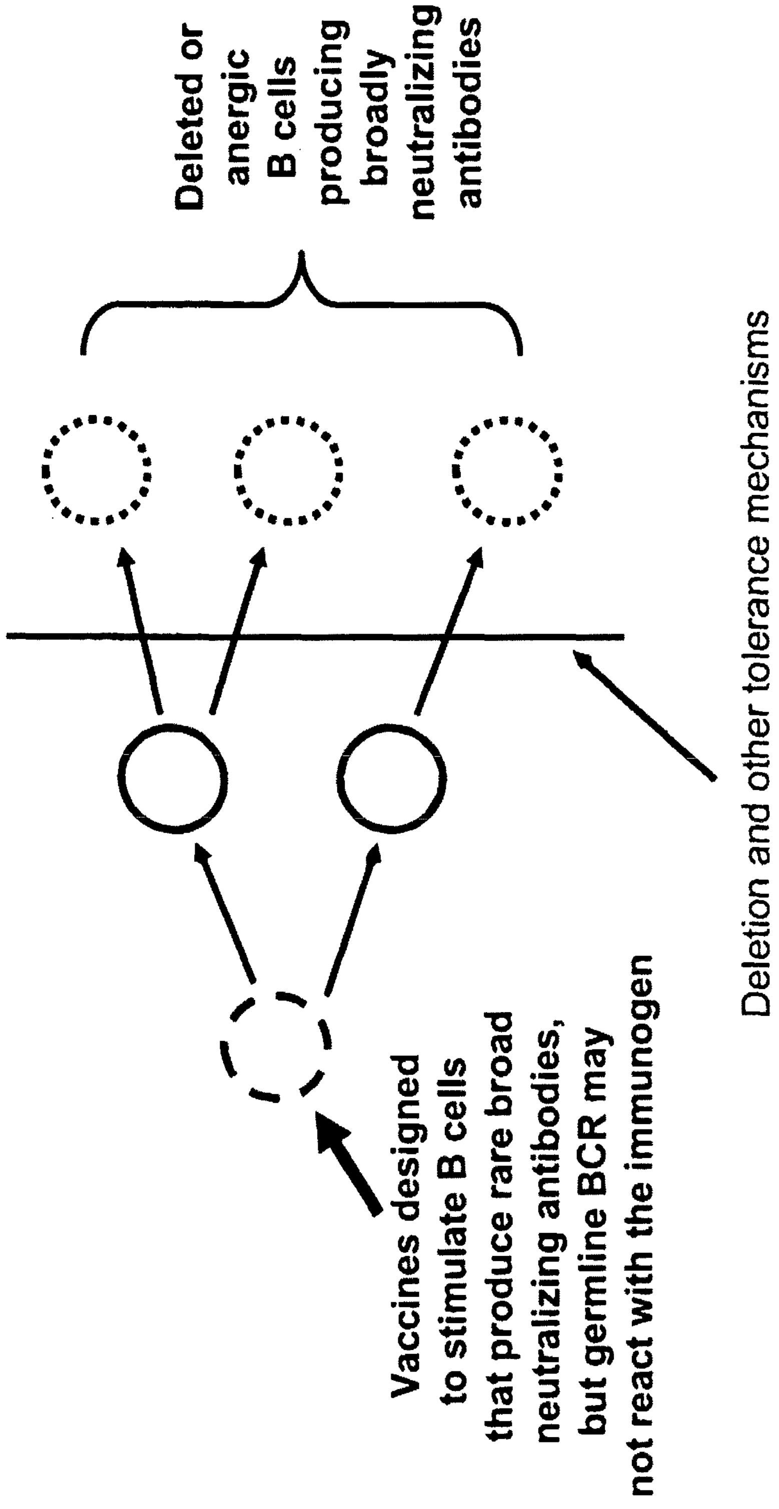
Figure 29:
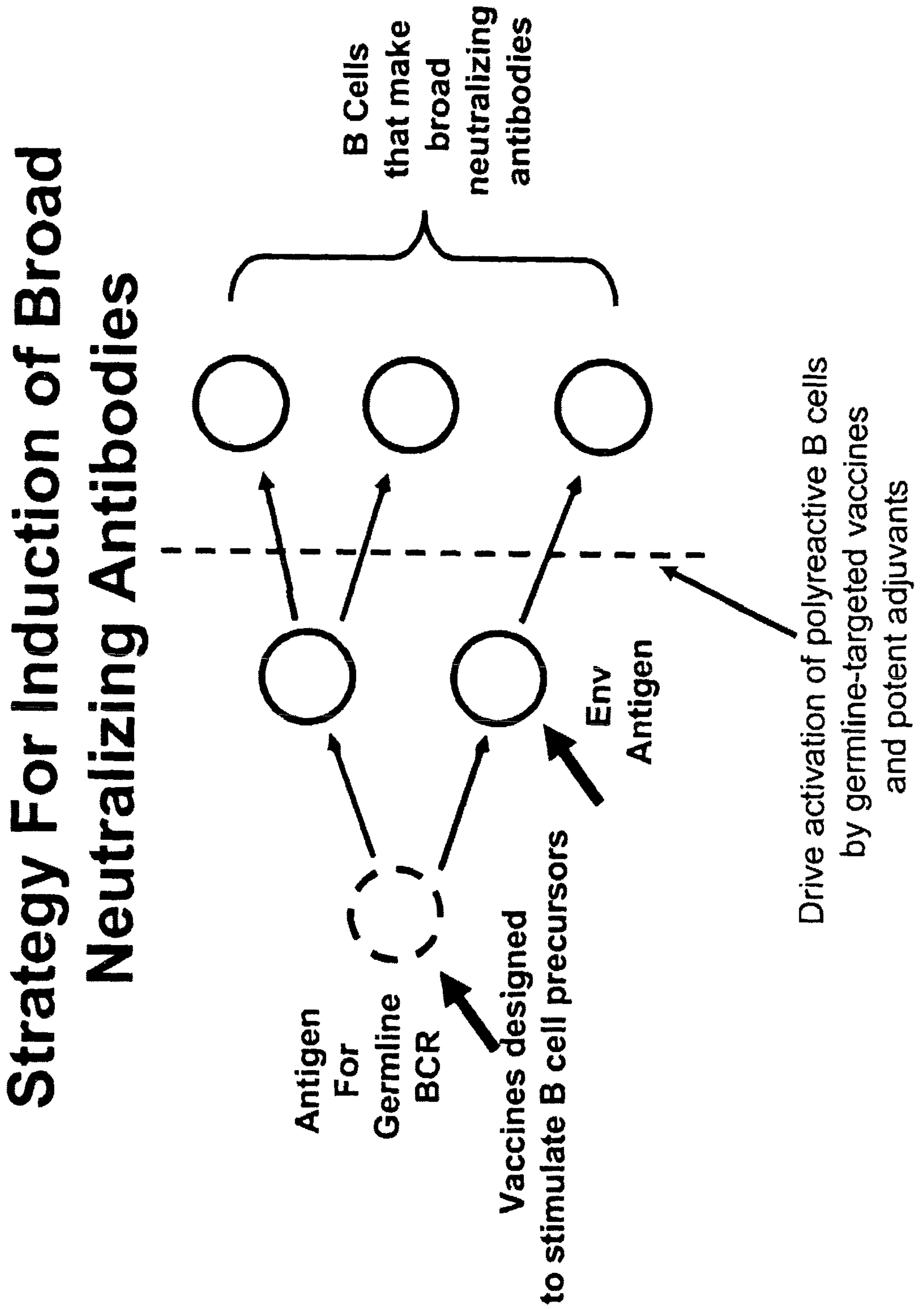

Liposomes expressing MPER antigens (Dennison, et al, J. Virology 83:10211-23 (2009)) with or without Toll Like Receptor (TLR) agonists have been described (see, for example, WO 2008/127651). Gp41 intermediate state protein (FIG. 23) has been described by (Frey et al, Proc. Natl. Acad. Sci. USA 105-3739-44 (2008)). The gp41 intermediates can be formulated with liposomes (FIGS. 24A and 24B) to form a stable immunogens that bind well to 2F5 and 4E10 (FIG. 25). Gp41 MPER immunogens of the invention can be adjuvanted by incorporating, for example, monophosphorylipid A (MPL-A) (Avanti Polar Lipids, Alabaster, Ala.) and a TLR 9 agonist, such as oCpGs 10103 (5'-TCGTCGTTTTTCGGTCGTTTT-3') (SEQ ID NO: 4) and R848 TLR 7 agonist (Enzo Life Sciences, Farmingdale, N.Y.) (FIG. 26). In addition, cytokine stimulators of B cell class switching, such as BAFF (BLYS) and/or APRIL (He et al, Immunity 26:812-26 (2007); Cerutti and Rescigno, Immunity 28: 740-50 (2008)) can be incorporated into the liposomes for optimal B cell stimulation.

Liposomes suitable for use in the invention include, but are not limited to, those comprising POPC, POPE, DMPA (or sphingomyelin (SM)), lysophosphorylcholine, phosphatidylserine, and cholesterol (Ch). While optimum ratios can be determined by one skilled in the art, examples include POPC:POPE (or POPS):SM:Ch or POPC:POPE (or POPS): DMPA:Ch at ratios of 45:25:20:10. Alternative formulations of liposomes that can be used include DMPC (1,2-dimyristoyl-sn-glycero-3-phosphocholine) (or lysophosphorylcholine), cholesterol (Ch) and DMPG (1,2-dimyristoyl-sn-glycero-3-phoshpho-rac-(1-glycerol) formulated at a molar ratio of 9:7.5:1 (Wassef et al, ImmunoMethods 4:217-222 (1994); Alving et al, G. Gregoriadis (ed.), Liposome technology 2nd ed., vol. III CRC Press, Inc., Boca Raton, Fla. (1993); Richards et al, Infect. Immun. 66(6):285902865 (1998)). The above-described lipid compositions can be complexed with lipid A and used as an immunogen to induce antibody responses against phospholipids (Schuster et al, J. Immunol. 122:900-905 (1979)). A preferred formulation comprises POPC:POPS:Ch at ratios of 60:30:10 complexed with lipid A according to Schuster et al, J. Immunol. 122:900-905 (1979). The optimum ratio of peptide to total lipid can vary, for example, with the peptide and the liposome.

A variety of adjuvants can be used in the present invention (including those noted above). The peptide-liposome immunogens and the conjugates described above can be formulated with, and/or administered with, adjuvants such as squalene-based adjuvants (Kaldova, Biochem. Biophys. Res. Communication, Dec. 16, 2009 E-pub ahead of print) and/or TLR agonists (e.g., a TRL 3, TRL 5, TRL4, TRL9 or TRL7/8 agonst, or combination thereof) that facilitate robust antibody responses (Rao et al, Immunobiol. Cell Biol. 82(5):523 (2004)). Other adjuvants that can be used include alum and Q521. Oligo CpGs in an oil emulsion such as Emulsigen (an oil in water emulsion) (Tran et al, Clin. Immunol. 109(3):278-287 (2003)) can also be used. Additional suitable adjuvants include those described in Ser. No. 11/302,505, filed Dec. 14, 2005, including the TRL agonists disclosed therein. (See also Tran et al, Clin. Immunol. 109:278-287 (2003), US Appln Nos. 20030181406, 20040006242, 20040006032, 20040092472, 20040067905, 20040053880, 20040152649, 20040171086, 20040198680, 200500059619). Immune response enhancing TLR ligands, such as Lipid A, oligo CpG and R-848 can be formulated individually or in combination into liposomes that have HIV-1 Env conjugated in them.

Liposomes loaded with strong adjuvants (e.g., potent TLR agonists) are examples of immunogens that can be used to overcome peripheral deletion and/or anergy of B cells that do get driven to make polyreactive neutralizing antibodies.

Transmembrane domain anchoring of HIV-1 gp4 peptides to liposomes can be used to achieve functional epitope display. The transmembrane domain of HIV-1 gp41 can be used to anchor the peptide into liposomes comprising synthetic lipids. Induction of trimerization of the TMD can facilitate formation of trimeric forms of gp41 MPER. Alternatively, His-tagged (c-terminus end) versions of the Env gp140 can be anchored into liposomes as described for an intermediate form of HIV-1 gp41 (gp41-inter).

The mode of administration of the non-HIV-1 immunogen and/or HIV-1 protein/polypeptide/peptide, or encoding sequence, can vary with the immunogen, the patient and the effect sought, similarly, the dose administered. Typically, the administration route will be intramuscular, intravenous, intraperitoneal or subcutaneous injection. Additionally, the formulations can be administered via the intranasal route, or intrarectally or vaginally as a suppository-like vehicle. Generally, the liposomes are suspended in an aqueous liquid such as normal saline or phosphate buffered saline pH 7.0. Optimum dosing regimens can be readily determined by one skilled in the art. The immunogens are preferred for use prophylactically, however, their administration to infected individuals may reduce viral load.

The human monoclonal antibodies (hu mAb) 2F5 and 4E10 bind with high specificity and nanomolar (nM) affinities to polypeptides that correspond to the HIV-1 gp41 MPER. Both hu mAb also react with discrete human and mouse cellular antigens as determined by immunofluorescence microscopy and western blotting. These properties indicate that 2F5 and 4E10 are ideal for the isolation of cellular proteins, including denatured forms and polypeptides, biochemically extracted from mammalian cells and recovered by standard immunoprecipitation methods. The same properties of 2F5 and 4E10 make them suitable for the identification of extracted cellular proteins/polypeptides by the standard methods of mass spectroscopy. Briefly, immunoprecipitated cellular proteins/polypeptides specifically bound to 2F5 or 4E10 can be subjected to enzymatic digestion and the mass and charge of the resulting fragments used to identify the parental molecule(s).

Certain aspects of the invention are described in greater detail in the non-limiting Examples that follow (see also Maksyutov et al, J. Clin. Virol. December; 31 Suppl 1:S26-38 (2004), Haynes et al, Science 308:1906 (2005), Gurgo et al, Virology 164:531-536 (1988), U.S. Pat. No. 7,611,704, U.S. application Ser. No. 11/812,992, filed Jun. 22, 2007, U.S. application Ser. No. 11/785,077, filed Apr. 13, 2007, PCT/US2006/013684, filed Apr. 12, 2006, PCT/US04/30397 (WO2005/028625), WO 2006/110831, WO 2008/127651, U.S. Published Application Nos. 2008/0031890 and 2008/0057075, U.S. application Ser. No. 11/918,219, filed Dec. 22, 2008, U.S. Prov. Appln. No. 60/960,413, filed Feb. 28, 2007, and U.S. Prov. Appln. Nos. 61/166,625, 61/166,648 and 61/202,778, all filed Apr. 3, 2009, U.S. Prov. Appln. No. 61/282,526, filed Feb. 25, 2010, U.S. Prov. Appln. No. 61/344,457, filed Jul. 27, 2010, U.S. Prov. Appln. Client File No. 01579-1597, filed Aug. 25, 2010, PCT/US2010/01018, PCT/US2010/030011, and PCT/US2010/01017 the entire contents of which are incorporated herein by reference).

Example 1

Experimental Details

Acute HIV-1 Infected Patients.

The patients selected for study were from 17 to 30 days following transmission with the dates of transmission estimated from patient history and Fiebig classification (Fiebig et al, AIDS 17:1871-1879 (2003)). Patients 065-0 and FIKE were Fiebig Stage 1, while patients 068-9, 684-6 and MCER were Fiebig stage 2.

Control Subjects.

Single plasmablast/plasma cell sorts were performed on bone marrow, leukapheresis or peripheral blood mononuclear cells (PBMC) of uninfected subjects as well as those vaccinated with trivalent inactivated (TVI) influenza vaccine (FLUZONE® 2007 or 2008). Those immunized with TVI were studied 7 days after immunization (Liao et al, J. Virologic Methods 158:171-9, (2009); Wrammert et al, Nature 453:667-71 (2008); Smith et al, Nature Protocols 4:372-84 (2009)).

Flow Sorting Strategy.

PBMC, leukapheresis or bone marrow samples were reacted with anti-B cell antibodies as previously described (Liao et al, J. Virologic Methods 158:171-9 (2009)). Wrammert et al (Nature 453:667-71 (2008)) have shown that the cells that are antibody secreting cells in human PBMC are those that are within the CDI9$^{+}$, CD38$^{hi+}$, IgD$^{-}$, CD20$^{lo+/-}$ B cells. Thus, in both acute HIV infection (AHI) and in influenza vaccine vaccinated controls, to isolate single antibody secreting plasmablasts/plasma cells, CD19$^{+}$, CD38$^{hi+}$, IgD$^{-}$, CD20$^{lo+/-}$ cells were sorted by flow cytometry into single 96 well plates containing RNA extraction buffer as described (Liao et al, J. Virologic Methods 158:171-9 (2008); Wrammert et al, Nature 453:667-71 (2008)). As positive controls for definition of successful isolation of the correct plasmablast/plasma cell population, the same population was isolated from day 7 after trivalent influenza vaccine (FLUZONE® 2007 or 2008) vaccines. It was demonstrated that, as expected, 75% of those sorted cells were indeed influenza specific antibodies (Wrammert et al, Nature 453:667-71 (2008)).

Identification and Expression of the Transmitted/Founder Envelope.

The transmitted/founder Env of patients 684-6 and FIKE were identified by single genome amplification and Env gene sequencing as previously described (Keele et al, Proc. Natl. Acad. Sci. USA 105:7552-7 (2008)). Env gp140C (gp120/41 cleavage site mutated), gp120 and gp41 proteins were expressed by transient transfections of 293T cells as described (Liao et al, J. Virologic Methods 158:171-9 (2008)).

PCR Amplification of Plasmablast/Plasma Cell Immunoglobulin VH and VL Genes.

The VH and VL Ig chains of sorted B plasmablast/plasma cells were isolated by single cell PCR and recombinant antibodies produced as described (Liao et al, J. Virologic Methods 158:171-9 (2009); Wrammert et al, Nature 453:667-71 (2008); Smith et al, Nature Protocols 4:372-84 (2009)).

Sequencing, Sequence Annotation, Quality Control, and Data Management Of Ig VH and VL Sequences.

All PCR products of Ig VH and VL genes were purified using a Qiagen (Valencia, Calif.) PCR purification kit and sequenced in forward and reverse directions using an ABI 3700 instrument and BigDye® sequencing kit (Applied Biosystems, Foster City, Calif.). Base calling for each sample is done using Phred (Ewing et al, Genome Res. 8:175-85 (1998); Ewing and Green, Genome Res. 8:186-94 (1998)). The forward and reverse strands of the antibody genes are assembled to one final nucleotide sequence using a novel assembly algorithm based on the quality scores at each position (Kepler et al, submitted). The estimated PCR artifact rate was 0.28 or approximately 1 PCR artifact per 5 genes amplified. The isotype of the immunoglobulin is determined by a local alignment algorithm (Smith and Waterman, J. Mol. Biol. 147:195-7 (1981)). The germline rearrangement of the quality assured antibody sequence is determined using SoDA (Volpe et. al, Bioinformatics 22:438-44 (2006)). Genomic information derived from SoDA, such as gene segment usage, somatic mutations and CDR3 regions, are stored in an ORACLE database for easy access.

To determine if antibodies from the same subject are clonally related, the following 3 criteria were utilized. First, the heavy chain of the antibodies in question must use the same VH and JH gene segments. Due to the length and high mutation in the D segment, these are more difficult to identify. Thus, similarity of D segments is not used as criteria for clonal relatedness. Similarly, both light chains must use the same Vκ/Vλ and Jκ/Jλ. Second, the heavy chains of the antibodies in question must have the same CDR3 length. This also applies to light chains. Third, the nucleotide sequence of the CDR3 of the heavy chains must be 70% identical. The same applies to the CDR3 of the light chain. Antibodies that adhere to these three criteria are labeled as being clonally related. Maximum Likelihood trees were constructed to determine the phylogenetic relationship between the clones using the PHYLIP 3.63 package (Felsenstein, Philos. Trans. R. Soc. Lond. B. Biol. Sci. 360:1427-34 (2005)) using the inferred germline from SoDA as the root. The ancestral sequences were also inferred using the same package.

Design and Generation of Inferred Germline and Intermediate Antibodies.

For each member of an antibody clonal family, Maximum Likelihood analysis was used to infer the germline antibody precursor as well as multiple antibody intermediate forms (Felsenstein, J. Mol. Evol. 17: 368-76 (1981); Volpe et al, Bioinformatics 22:438-44 (2006)). These VH and VL genes were synthesized (GeneScript, Piscataway, N.J.) and expressed as IgG1 mAbs by recombinant techniques as above.

Expression of $V_H$ and $V_L$ as Recombinant mAbs.

The isolated Ig $V_H$ and $V_L$ gene pairs were assembled by PCR into the linear full-length Ig heavy- and light-chain gene expression cassettes for production of recombinant mAbs by transfection in human embryonic kidney cell line, 293T (ATCC, Manassas, Va.) using the methods as described (Liao et al, J. Virol. Methods 158:171-9 (2009)). The purified PCR products of the paired Ig heavy- and light-chain gene expression cassettes were co-transfected into 80-90% confluent 293T cells grown in 6-well (2 μg of each per well) tissue culture plates (Becton Dickson, Franklin Lakes, N.J.) using PolyFect (Qiagen, Valencia, Calif.) and the protocol recommended by the manufacturer. Six to eight hours after transfection, the 293T cells were fed with fresh culture medium supplemented with 2% fetal calf serum (FCS) and were incubated at 37° C. in a 5% $CO_2$ incubator. Culture supernatants were harvested three days after transfection and quantified for IgG levels expressed and screened for antibody specificity. For future characterization of select antibodies identified through screening assays, the linear Ig heavy and light chain gene constructs were cloned into pcDNA 3.3 for production of purified recombinant mAbs using standard molecular protocols.

For production of purified recombinant mAbs derived from the isolated VH and VL genes and the inferred germline and intermediate precursor antibody sequences, 293T cells cultured in T175 flasks were co-transfected with the heavy and light chain Ig gene-containing plasmids using PolyFect (Qiagen, Valencia, Calif.), cultured in DMEM supplemented with 2% FCS. Recombinant mAbs were purified from culture supernatants of the transfected-293T cells using anti-human Ig heavy chain specific antibody-agarose beads (Sigma, St. Louis, Mo.).

Screening for Antibody Specificity by ELISA and Luminex Assays.

Concentration of recombinant mAbs in the supernatants were determined using the method as described (Liao et al, J. Virol. Meth. 158:171-179 (2009)). Specificity of the expressed recombinant mAb were assayed for antibody reactivity to HIV-1 antigens and to a panel of non-HIV-1 antigens. HIV antigens included Env peptides gp41 immunodominant region (RVLAVERYLRDQQLLGIWGC-SGKLICTTAVPWNASWSNKSLNK) (SEQ ID NO: Q, gp41 MPER region (QQEKNEQELLELDKWASLWN) (SEQ ID NO: 6), HIV-1 MN gp41 (Immunodiagnostics, Woburn, Mass.), HIV-1 group M consensus gp120 (Liao et al, Virology 353:268-82 (2006)), HIV-1 group M consensus gp140 CFI (Liao et al, Virology 353:268-82 (2006)), p66 (Worthington Biochemical, Lakewood, N.J.), p55 (Protein Sciences, Meriden, Conn.), p31 (Genway, San Diego, Calif.), nef (Genway, San Diego, Calif.), tat (Advanced BioScience, Kensington, Md.) and AT-2 inactivated HIV-1 ADA virions (Rutebemberwa et al, AIDS Res. Human Retrovirol. 23:532-42 (2007)); gift of Jeffrey Lifson, NIH, NCI, Frederick Cancer Research Facility). In addition, 684-6 mAbs were assayed against autologous gp140, gp120 and gp41, and FIKE mAbs were assayed against autologous gp140 and gp120. Non-HIV-1 antigens included trivalent influenza vaccine 2007 (FLUZONE® 2007), recombinant influenza HA protein from H1 A/Solomon Islands/03/2006 (Protein Sciences Corp. Meriden, Conn.), tetanus toxiod (Calbiochem, San Diego, Calif.), HEP-2 cells (Inverness Medical Professional Diagnostics, Princeton, N.J.), cardiolipin (Avanti Polar Lipids, location (Alabaster, Ala.) (Haynes et al, Science 308:1906-8 (2005)) and lipid A (Avanti Polar Lipids, Alabaster, Ala.). Whole cell lysates of anaerobic and aerobic bacterial extracts termed as gut flora were prepared as described below. Briefly, bacteria were inoculated from 4 stool specimens from patients and grown on agar plates under anaerobic or aerobic conditions at 30° C. Confluent bacteria were harvested, washed twice with phosphate-buffered saline (PBS) and treated with a commercially available bacterial protein extraction reagent (Pierce, Rockford, Ill.). The resulting extracts were filtered with a 0.22:m filter and stored at −80° C. until use (Kawatsu et al, J. Clin. Microbiol. 46:1226-31 (2008)). Assays against FLUZONE®, influenza HA, gp41 immunodominant and MPER regions, as well as gut flora whole cell lysates, were performed by both ELISA (Tomaras et al, J. Virology 82:12449-63 (2008)) and Luminex bead assays (Tomaras et al, J. Virology 82:12449-63 (2008)). Assays against tetanus toxoid, cardiolipin (Sigma, St Louis, Mo.), killed *Cryptococcus* and *Candida albicans* were ELISA Assays for reactivity with Hep-2 epithelial cells were indirect immunofluoresence assays (Mietzner et al, Proc. Natl. Acad. Sci. USA 105:9727-32 (2009)).

Surface Plasmon Reasonance (SPR) Analysis of Antibody Reactivity.

SPR binding assays were performed on a BIAcore 3000 (BIAcore Inc, Piscataway, N.J.) maintained at 20° C. HIV-1 gp41 or oligomeric gp140 proteins (Con S gp140, autologous Env gp140) were immobilized on a CM5 sensor chip by standard amine coupling as previously described (Alam et al, J. Immunol. 178:4424-35 (2007)). Human mAbs were captured on anti-human Fc antibody coupled surfaces and then each human mAbs were captured to about 200-500 RU. Specific binding responses of mAb binding were obtained following subtraction of non-specific binding on control surfaces (HIV-1 gp120 for Env immobilized surfaces and human IgG, IS6, for mAb captured surfaces). Rate constants were measured using the bivalent analyte model (to account for the avidity of bivalent Ig molecules) and global curve fitting to binding curves obtained from mAb titrations. MAbs were injected at 30 μL/min for 2-6 min and glycine-HCl pH 2.0 and surfactant P20 (0.01%) were used as the regeneration buffer.

Results

Influenza Vaccination.

Figure 1:
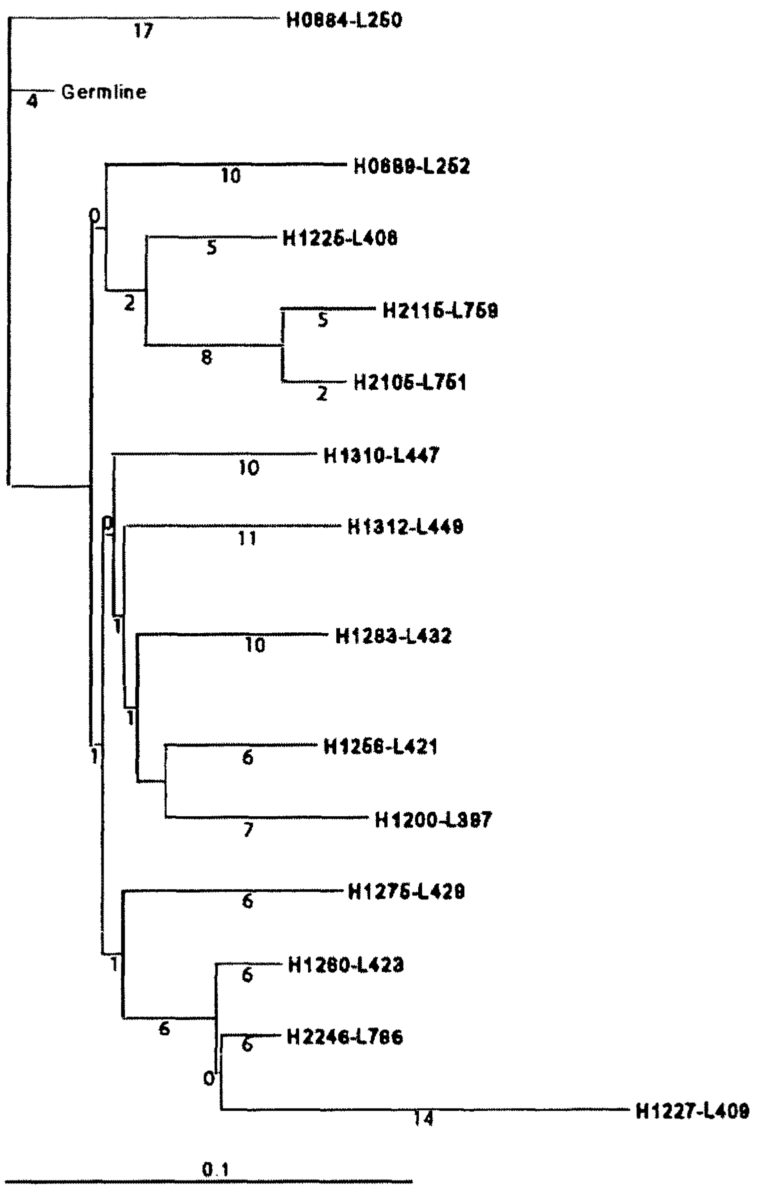
FIG. 1. A representative influenza antibody clone against H1 Soloman Islands hemagglutinin.

Clones of antibodies from influenza vaccinated subjects derived from single cell sorted plasma cells/plasmablasts were studied and the response was found to be highly clonal. The clones members almost all reacted with the influenza antigen tested. FIG. 1 shows a representative influenza antibody clone against H1 Soloman Islands hemagglutinin. A total of 450 antibodies were isolated from plasma cells/plasmblasts of three influenza vaccinated subjects and, of these, 57.7% were influenza-specific. Of all the 265 antibodies isolated from influenza infected subjects, twenty independent clones of clonally related antibodies were identified, among which, 115 antibodies (92%) reacted with influenza antigens.

Clonal Antibody Response in Acute HIV Infection.

In contrast to influenza vaccination, where ~75% of plasma cells/plasmablasts were influenza specific, out of a total of 1074 recombinant antibodies that have been isolated from plasmablasts/plasma cells of 5 AHI patients, 89 or 8.3% expressed antibodies (range 3.3% to 13.4%) were HIV-1 specific, while the majority of the remainder of the mAbs either were against non-HIV antigens (~6%) or had unknown specificity (882 or 82.1%). With the panel of non-HIV-1 related antigen assays, it was possible to demonstrate high affinity antibodies to Hep-2 epithelial cells (27 or 2.5%), gut flora (5 or 0.5%), cardiolipin (4 or 0.4%), influenza (9 or 0.8%), *Cryptococcus* (4 or 0.4%), *Candida albicans* (2 or 0.2%), and tetanus toxoid (8 or 0.7%). An additional 38 or 3.5% reacted with at least 2 of these antigens. Three of the patients had lipid A and one patient had gut flora antibodies suggesting the very early onset of gut damage, microbial translocation and induction of anti-lipid A and gut flora antibodies. Remarkably, none of these early AHI patients had any mAbs detected with HIV-1 specificities other than gp41 within days 17-30 after HIV transmission.

It was previously reported that consensus Envs were equal to autologous Envs in detecting the AHI response to gp41 (Tomaras et al, J. Virology 82: 12449-63 (2008)). However, to rule out the possibility that responses were being missed in AHI B cell analysis, the mAbs from 684-6 and FIKE were screened with their autologous recombinant gp140 Envs. In general, the response to the autologous gp140 envs was much less than to the clade B gp41.

Thus, the initial plasmablast/plasma cell repertoire response to the transmitted/founder virus, like the plasma antibody response (Tomaras et al, J. Virol. 82:12440-63 (2008)), was focused on Env gp41 epitopes. In addition, HIV-1 activates and drives to terminal differentiation pre-existing memory B cells from previous vaccination or infectious agent antigens, such as *Cryptococcus, Candida albicans*, and tetanus toxoid. Moreover, in the course of AHI, polyreactive clones of Hep-2 cell autoreactive B cells are triggered to join the initial plasmablast/plasma cell response.

Analysis of Antibody Clones within the AHI Plasmablast/Plasma Cell Repertoire.

In general, there few clones isolated from the AHI plasmablast/plasma cell repertoire compared to the reported plasmablast/plasma cell repertoires induced by influenza vaccination (Wrammert et al, Nature 453:667-72 (2009)) or the memory B cell repertoire of gp140+B cells in subjects with broad neutralizing antibody activity in plasma (Scheid et al, Nature 458:636-40 (2009)). In chronic HIV-1 infection in six patients with broad neutralizing antibodies, Scheid et al (Nature 458:636-40 (2009)) found the number of B-cell clones varied among patients from 22 to 50 in 502 antibodies isolated from those six patients.

In the study of AHI, only 8 clones of antibodies were found in 1074 mAbs isolated from 5 AHI patients. These included three clones of antibodies that reacted with gp41 among 6 independent clones of antibodies identified in one of AHI patients. Of interest, of all 52 clonal members of the 3 AHI gp41 clones, only 17 (37%) reacted with gp41. This is in contrast to 94% of influenza-reactive influenza clone members.

Figure 2:
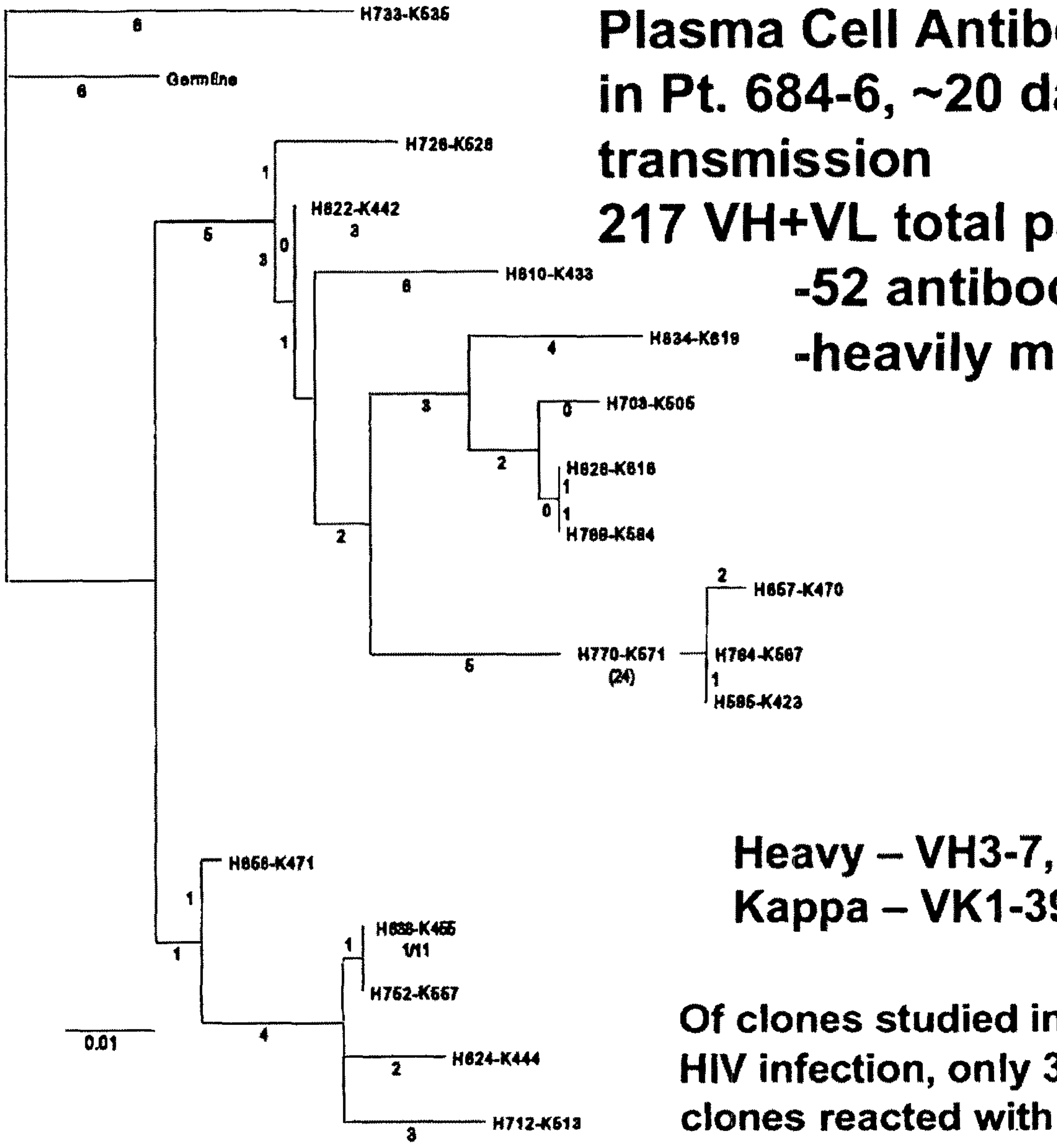
FIG. 2. Plasma cell antibody repertoire in patient 684-6, ~20 days after HIV-1 transmission.

FIG. 2 shows AHI clone 684-6B—a remarkable VH3-7, DH1-26, JH5, VKI-39, JK4, IgG3 mutated clone with 52 members, with no unmutated members. Out of the 57 antibodies, only 4 (8%) reacted with gp41.

Analysis of the Gp41 Reactivity with Clone Inferred Germline and Intermediate Antibodies.

Figure 3:
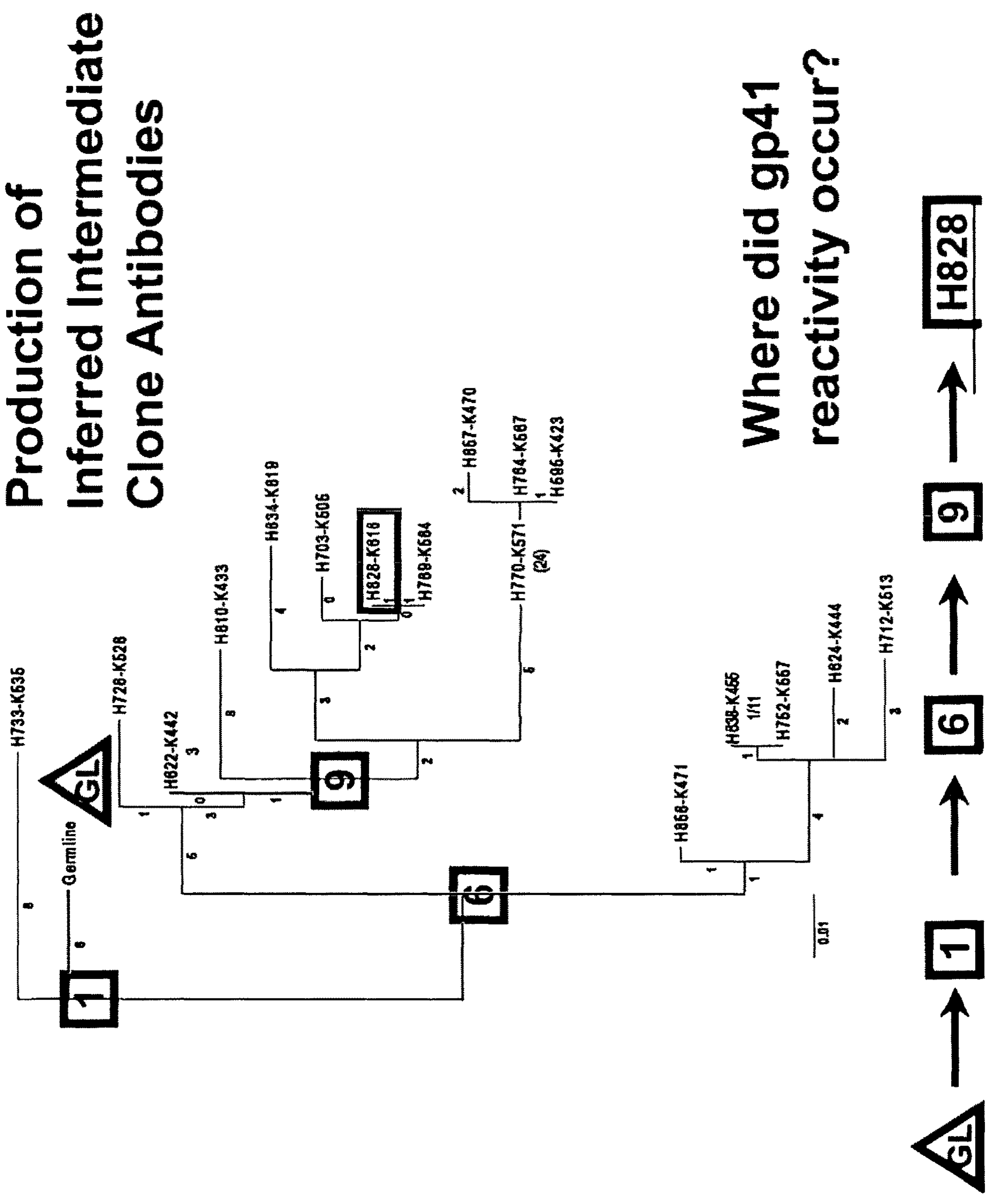
FIG. 3. Production of inferred intermediate clone antibodies.
Figure 4:
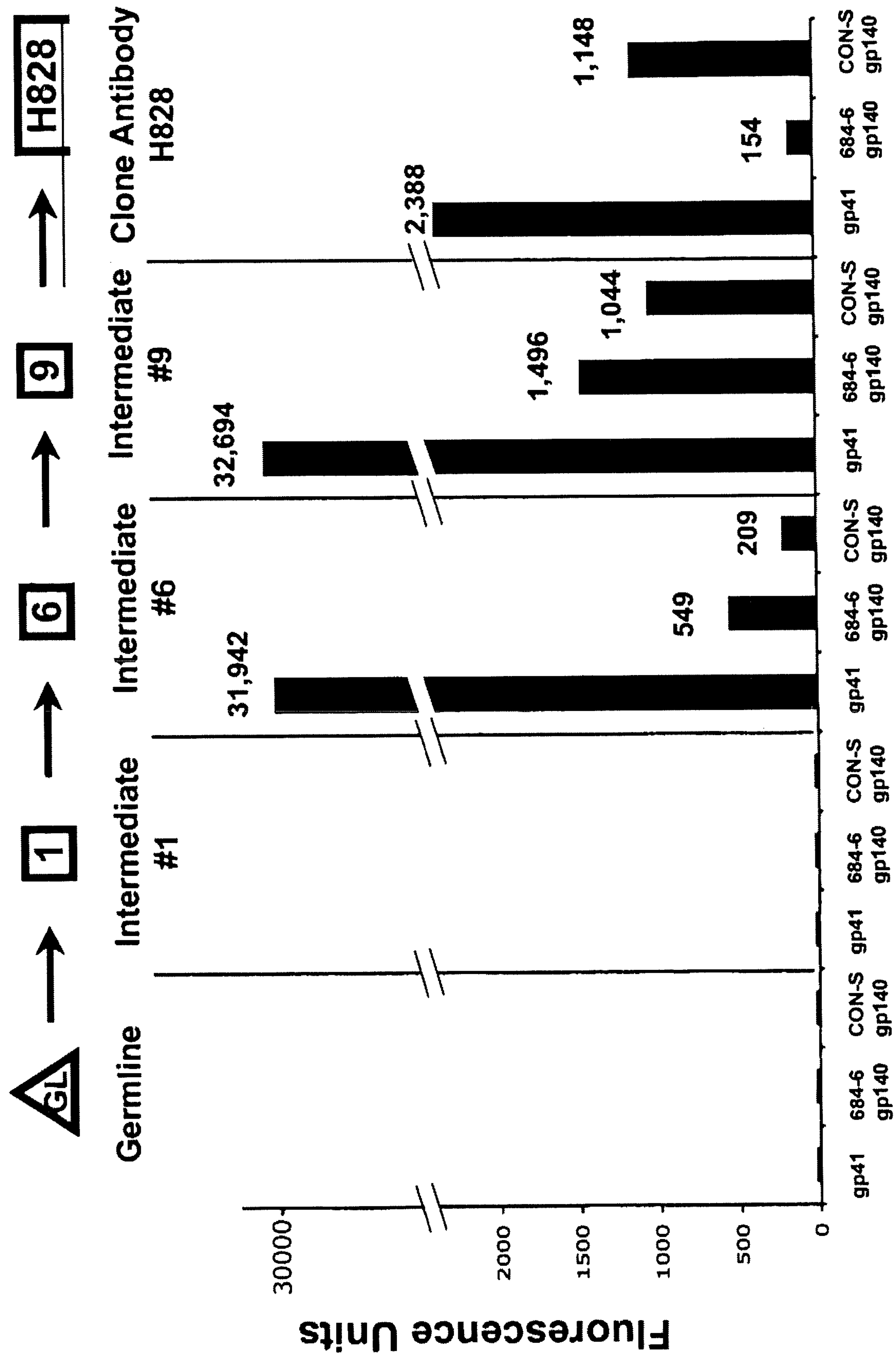
FIG. 4. Inferred germline and clone member intermediates assayed for reactivity with clade B gp41, autologous gp1140 and group M consensus gp140 to determine where in the clone development reactivity with gp41 was acquired.
Figure 5:
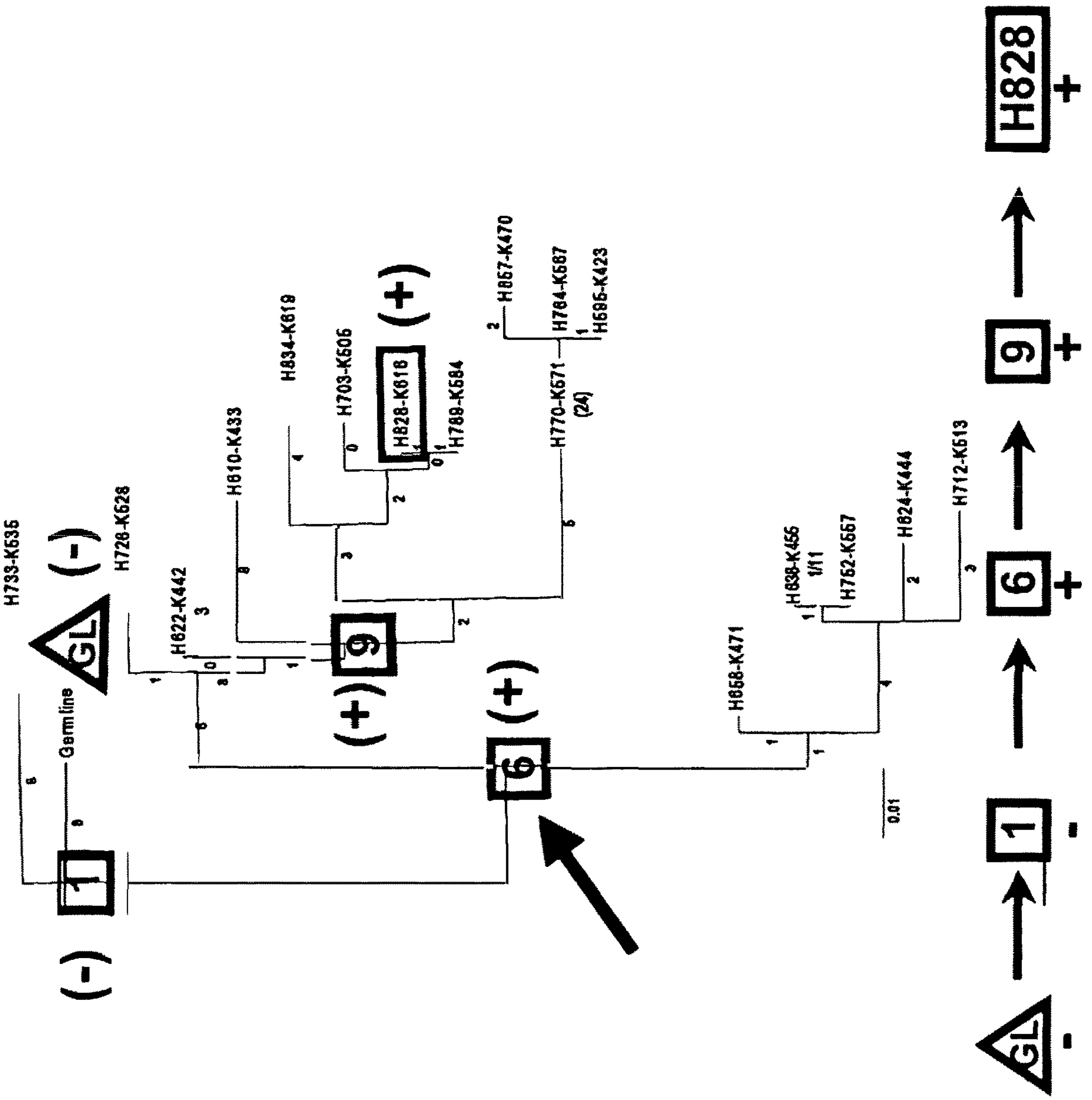
FIG. 5. Reactivity of clone 684-6B acquired at the second intermediate precursor antibody (see also FIG. 4).

It was reasoned that either HIV-1 gp41 was reacting with the germline B cell receptor of naïve B cells and was stimulating low affinity clones with poor antigen drive, or that gp41 may cross-react with pre-existing clones of memory B cells and enjoin clonal members to undergo simultaneous gp41 and self antigen drive. To distinguish between these two possibilities, Maximum Likehood analysis was used to infer the germline unmutated antibody and partially mutated clone intermediates were used to determine their reactivity with gp41 (FIG. 3). To determine where in the clone development reactivity with gp41 was acquired (i.e., germline VH+VL or later intermediates), inferred germline and clone member intermediates were assayed for reactivity with clade B gp41, autologous gp140 and group M consensus gp140 (FIG. 4). It was found that reactivity of clone 684-6B was acquired at the second intermediate precursor antibody (FIGS. 4 and 5).

Figure 6:
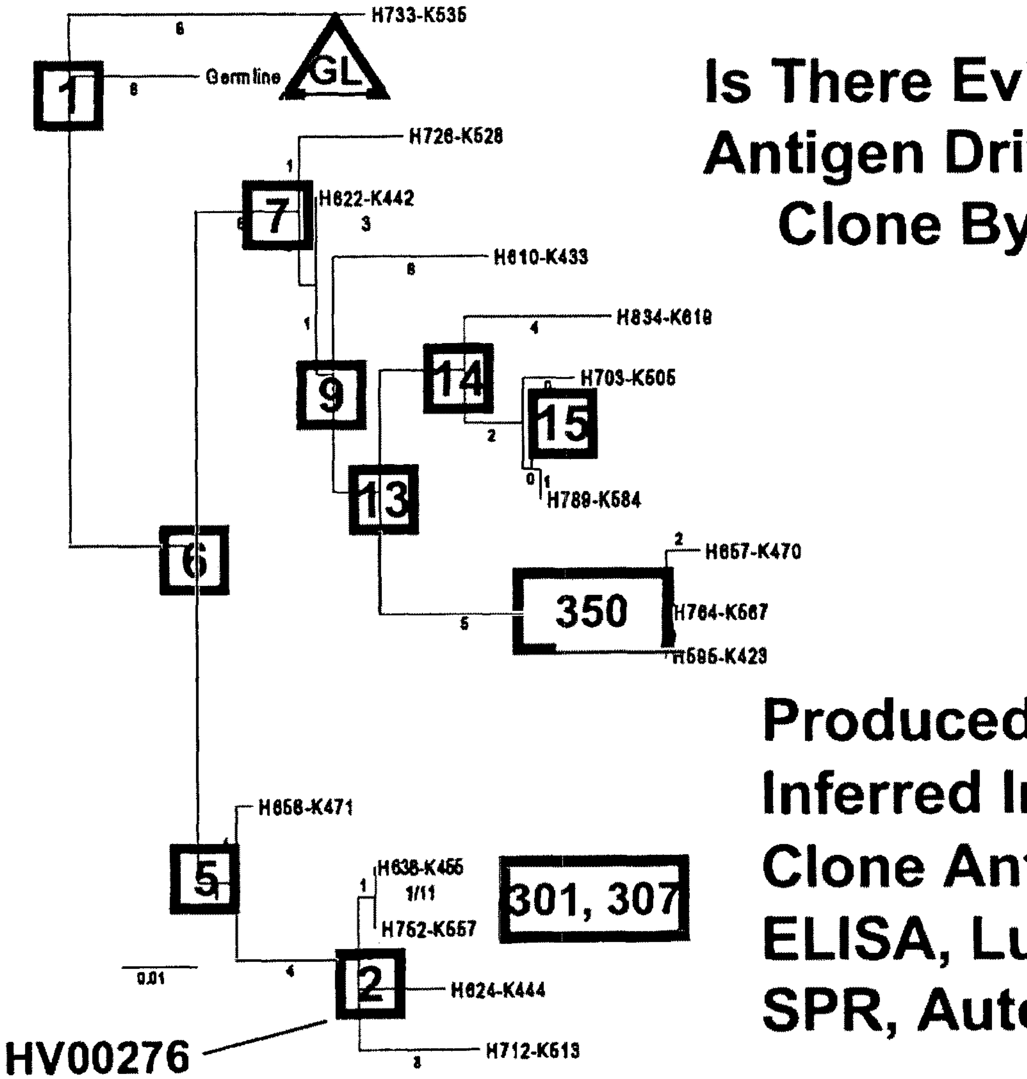
FIG. 6. Additional inferred intermediate antibody clones produced in mg quantities and analyzed for the dissociation constants (Kd) of antibody binding to gp41.
Figure 7:
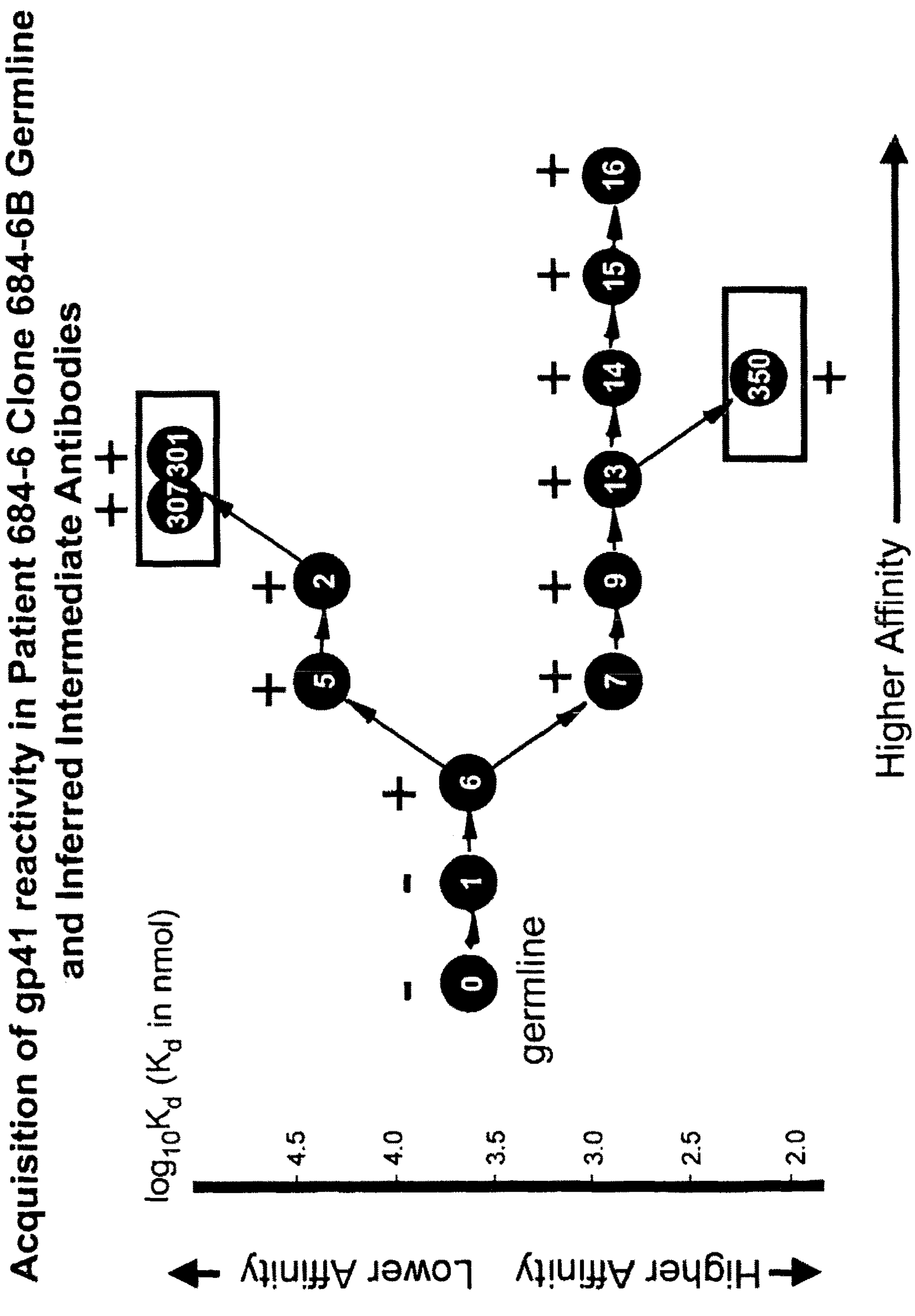
FIG. 7. Acquisition of gp41 reactivity in patient 684-6 clone 684-6B germline and inferred intermediate antibodies.

The next question asked was whether the reactivity with gp41 represented antigen drive by gp41. FIG. 6 shows more inferred intermediate antibody clones were produced in mg quantities and analyzed for the dissociation constants (Kd) of antibody binding to gp41. FIG. 7 shows a heat map plot with the dissociation constants plotted as log 10 of the Kds, and demonstrates that, indeed, as the intermediates progress to actual isolated antibodies, there is progression of affinity maturation for binding to gp41.

Figure 8:
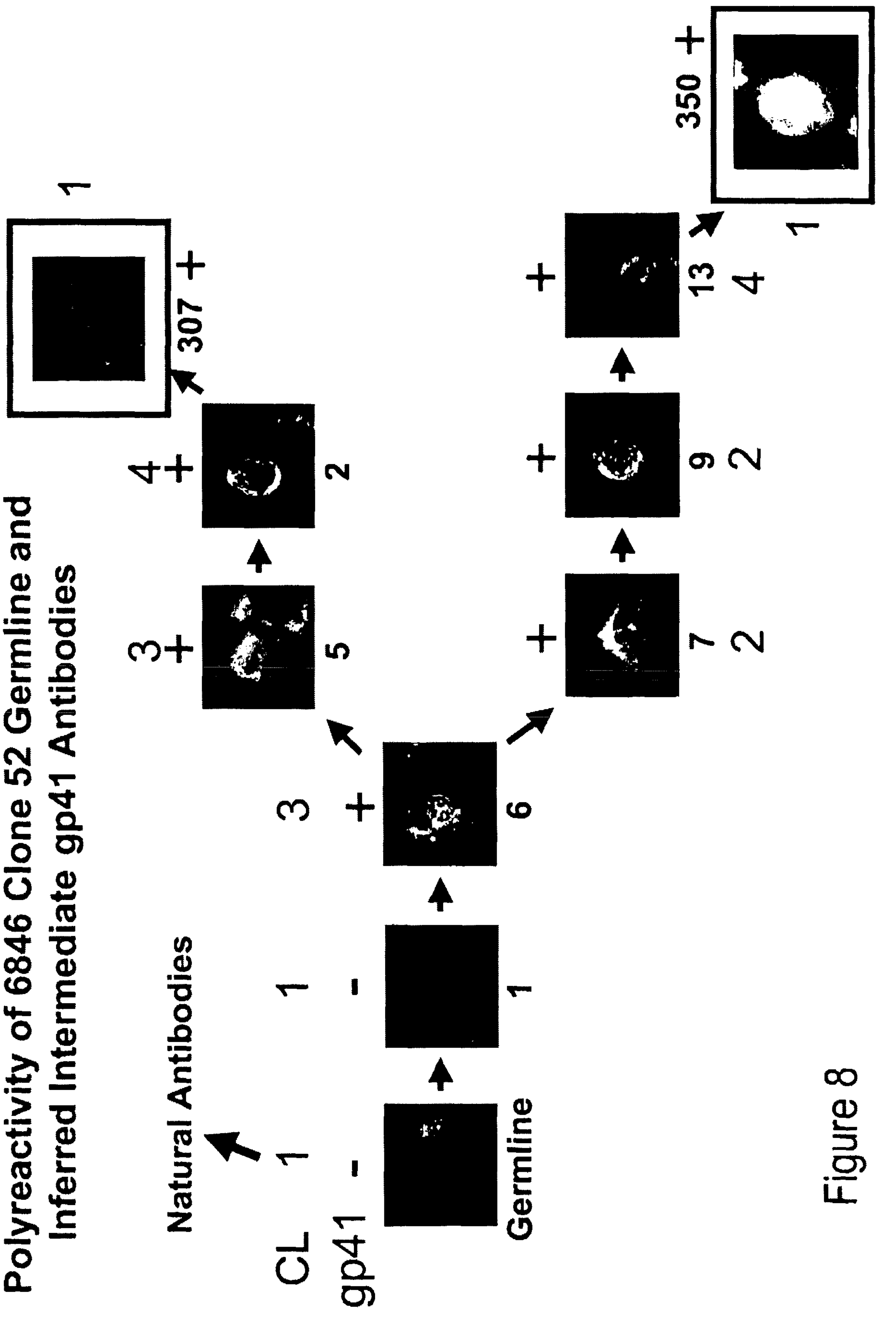
FIG. 8. Polyreactivity of 6846 clone 52 germline and inferred intermediate gp41 antibodies.

Given the induction of polyreactive non-HIV-1 gp41 clones during AHI, the next question asked was whether clone 684-6B members were polyreactive by reactivity with cardiolipin and Hep-2 epithelial cells. In the Hep-2 indirect immunofluoresence assay, reactivity of clone 684-6B was acquired at the same inferred intermediate precursor stage as gp41 reactivity (FIG. 8). All clone members of 684-6B reacted with cardiolipin, including the germline unmutated antibody, and while Hep-2 reactivity waxed and waned during clone development, reactivity with cardiolipin was relatively stable throughout the intermediates until the end clones 307 and 350. The polyreactivity of the germline and other clone members with cardiolipin stongly suggests that the initial antibody response to HIV is derived from HIV gp41 stimulating a preexisting, polyreactive clone of natural antibodies and gp41 recruits clones of B cells to become polyreactive gp41 clones as soon as the original clone acquires cross reactivity to gp41 by somatic hypermutations. This finding has considerable ramifications to HIV vaccine design.

The Nature of the Germline Reactivity to Non-HIV-1 Antigens.

Given the surprising result of the acquisition of reactivity of the 684-6B clone not in the germline antibody of each clone but in inferred clone intermediates, an effort was made to identify host antigens against which the germline might react to identify likely origins of the antibody clones activated in HIV.

It was hypothesized that because there is early gut microbial translocation in the gut due to AHI and because much of the initial antigenic stimulation in AHI comes at mucosal surfaces, the initial antibody response may in some manner be tied to or related to the gut microbial antibody response. To study this, a determination was made as to whether there were measurable reactivity of the clonal antibodies and inferred germline and inferred intermediates from 684-6B clone to the whole cell lysates of anerobic and aerobic gut flora. In addition, EBV transformation was used to isolate a panel of pentameric IgM mAbs from intestine, bone marrow or blood of AHI or uninfected subjects.

First, a series of IgM antibodies was isolated from AHI and two from uninfected subjects that were either gp41 reactive or gp41 non-reactive. The question asked was whether the IgMs that were reactive with gp41 also were reactive with gut flora. Table 1 shows that, indeed, all the mAbs that were gp41 reactive were also reactive with gut flora antigens while those mAbs that were not reactive with gp41 were not gut flora reactive.

TABLE 1

All HIV-1 Env gp41 IgM Mabs Isolated from Infected or Uninfected also Bind to Either Anerobic or Aerobic Gut Bacterial Whole Cell Lysates

| MAb | HIV-1 Env gp41 | Anerobic Gut Bacteria WCL | Aerobic Gut Bacteria WCL | Source of Mab |
|---|---|---|---|---|
| | Reactivity in Luminex Units | | | |
| 21B10 | 173 | 272 | 1012 | AHI intestine |
| 2C3 | 148 | 210 | 591 | AHI intestine |
| F3 | 177 | 671 | 2237 | AHI intestine |
| F8 | 1023 | 372 | 5433 | AHI intestine |
| 1E7 | 17153 | 259 | 133 | AHI bone marrow |
| 2B9 | 24886 | 742 | 847 | AHI bone marrow |
| ALL8 | 13031 | 1816 | 1584 | AHI intestine |
| C14-2 | 2500 | 172 | >80 | uninfected intestine |
| C08 | 3673 | 241 | >80 | uninfected blood |
| XM-1 | <80 | <80 | <80 | uninfected blood |
| XM-2 | <80 | <80 | <80 | AHI intestine |
| XM-3 | <80 | <80 | <80 | AHI Intestine |

AHI = acute/early HIV-1 infection.
Mab = monoclonal antibody.
WCL = whole cell lysate.
<80 = no reactivity over background in Luminex assay with gp41 or gut flora whole cell lysates.

Figure 9:
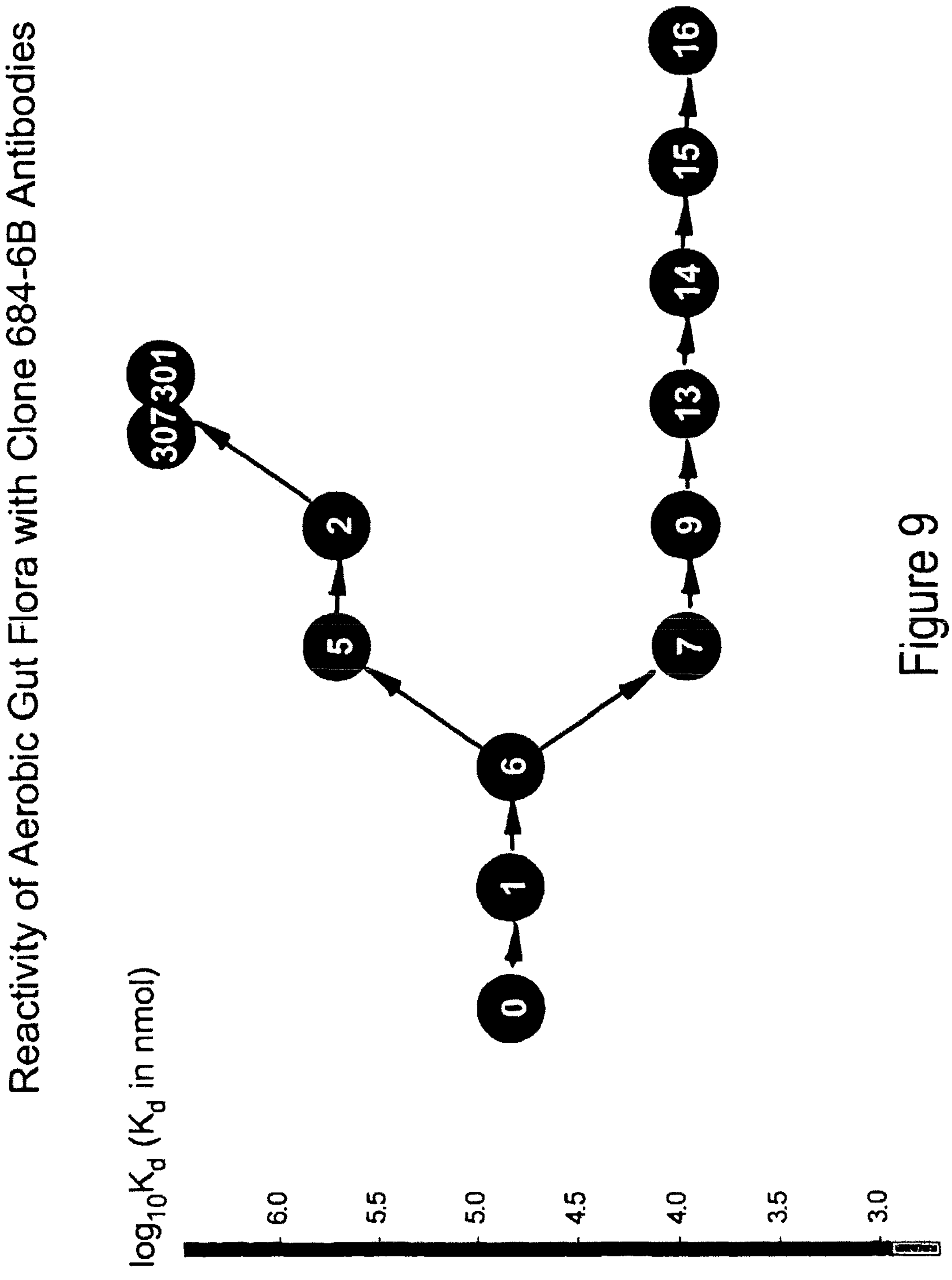
FIG. 9. Reactivity of aerobic gut flora with clone 684-6B antibodies.

Remarkably, when the germline and intermediate precursors from all clones tested were assayed with whole cell lysate of aerobic and anerobic gut flora, all of the antibodies in all of the clones reacted with gut flora whole cell lysate. FIG. 9 shows a heat map of the 684-6B clone reacting at each mAb with aerobic whole cell lysate (WCL). Similar results were obtained with anerobic WCL. When analyses were performed to determine antigen drive mediated by gut flora, it was found that, indeed, there were increases in antibody affinity coincident with progressive somatic hypermutation in the AHI clones, though less so than for gp41.

Western Blot of AHI Gp41 mAbs with Anerobic and Aerobic Gut Flora Whole Cell Lysates.

Figure 10A:
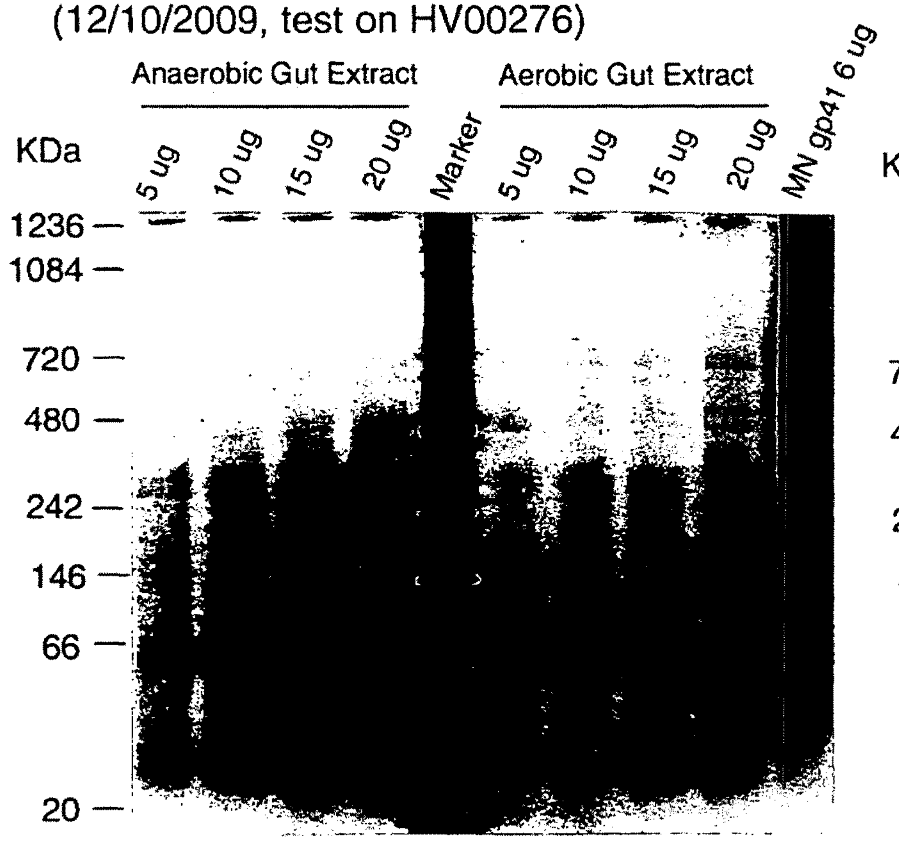
FIGS. 10A and 10B. Blue Native-PAGE and western blot images of gut extract vs Mojo antibody.
Figure 10B:
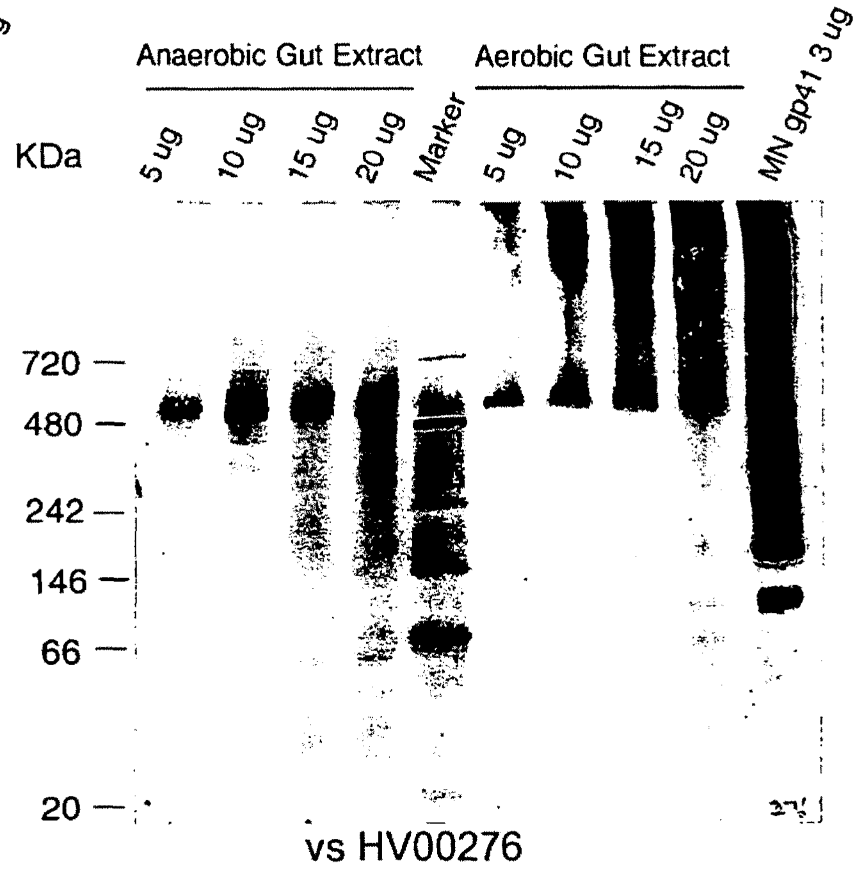
Figure 11:
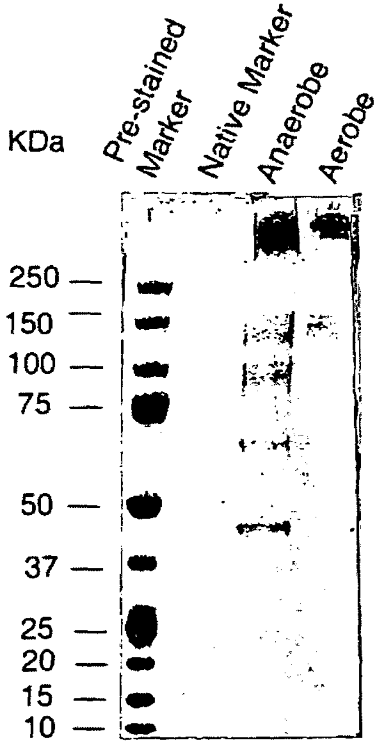
FIG. 11. Western blot image of gut extract vs Mojo antibody—non-reducing vs HV00276.
Figure 12:
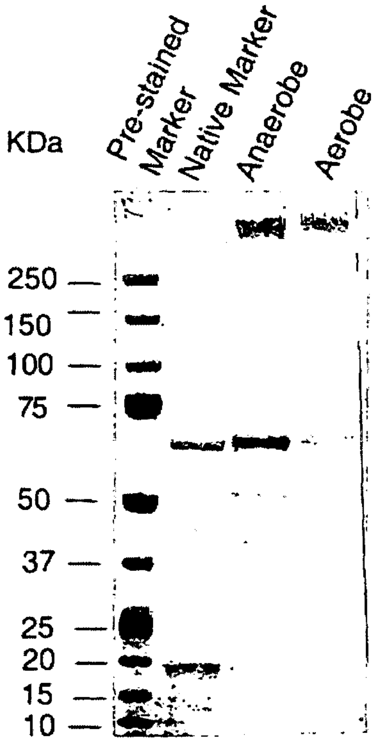
FIG. 12. Western blot image of gut extract vs Mojo antibody—reducing vs HV00276.

Next, the reactivity of the inferred intermediate #2 in FIG. 6 (HV00276) was determined with both anerobic and aerobic WCL in blue native PAGE (FIGS. 10A and B) and in SDS-PAGE (FIGS. 11 and 12). In blue native gel analysis, the 684-6B clone mAb reacted with a 520,000 Da molecule in both aerobic and anerobic gut samples (FIGS. 10 A and 10B). Moreover, mAb 276 also reacted with the 480 KDa MW marker that is phycoerthryn (FIGS. 10A and 10B). FIGS. 11 and 12 show that under SDS-PAGE non-reducing (FIG. 11) and reducing (FIG. 12) conditions, strong bands are seen again at ~520,000 Da. Also smaller band is seen at approx 60 and 50 Kd as well as in the native marker under reducing conditions (FIG. 12). The native marker is again phycoerythrin (PE) showing polyreactivity against PE by the 684-6B clone mabs.

Importantly, the somatically mutated original 2F5 and 4E10 broad neutralizing antibodies also reacted with protein bands in gut flora WCL with 2F5 reacting with ~300,000 Da molecule and ~80,000 Da molecules in aerobic WCL and 4E10 reacting with ~80,000 and 100,000 Da molecules in aerobic WCL. In FIG. 12 (SDS-PAGE under reducing conditions), it is seen that HV00276 (intermediate 684-6 ab #2) binds to an ~520,000 Da band in aerobic and anerobic WCL while 2F5 reacts with an ~80,000 Da band and 4E10 with an approximately 60,000 da band in aerobic WCL.

It has been shown previously that the broad neutralizing antibodies 2F5, 4E10 and 1b12 are polyreactive antibodies that bind to multiple host antigens. Thus, the question is, if the initial response to HIV is by a polyreactive antibody response, why are not polyreactive antibodies made that broadly neutralize? Two possibilities have been considered.

Figure 13:
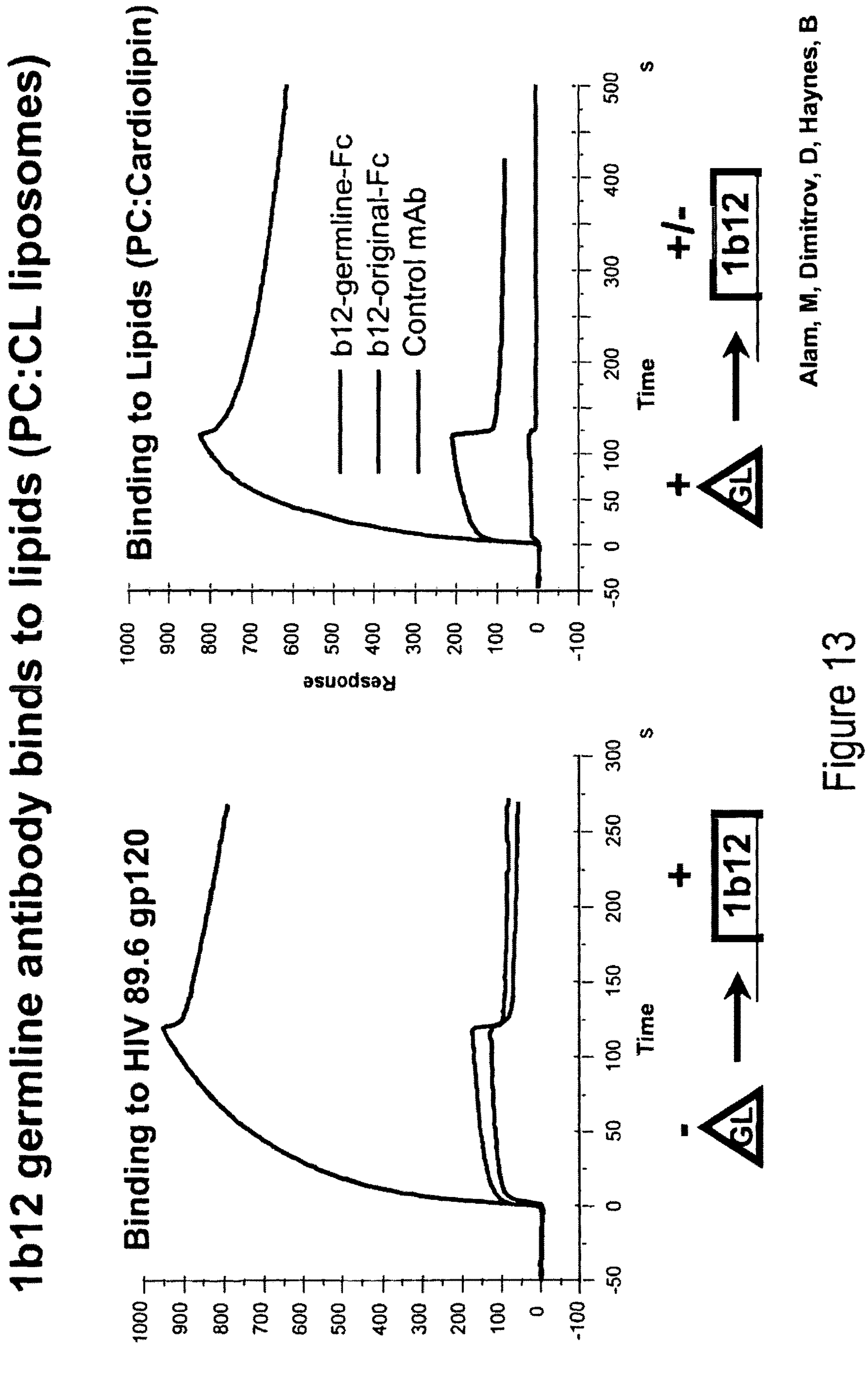
FIGS. 13A and 13B. 1b12 germline antibody binds to lipids (PC:CL liposomes).

First, it has been shown that the germline of 1b12, 2F5 and 2G12 do not bind to HIV gp120 or gp41 while the somatically hypermutated antibodies do bind (Xiao et al, Biochem. Biophys. Res. Commun. 390:404-9 (2009)). Thus, the notion is for many of the epitopes of broad neutralizing antibodies, the immunogens the field has been using do not target the B cell receptors of the naïve B cells they are targeting. The germline of the 1b12 has now been studied for lipid reactivity and for gut flora whole cell lysate activity and it has been found that, indeed, the germline 1b12 reactivity is negative to HIV gp120 envelope while the reactivity of the somatically mutated 1b12 is very high to HIV gp120 (FIG. 13). In contrast, the reactivity of the germline of 1b12 is very high to cardiolipin while the somatically mutated polyreactive original 1b12 mAb reactivity to cardiolipin is very low though not negative (FIG. 13). Moreover, the germline of 1b12 is reactive as well with gut flora whole cell lysate, while the mature original somatically mutated 1 B12 mAb is only weakly reactive (Table 2).

TABLE 2

Reactivity of Broadly Neutralizing Monoclonal Antibodies 2F5, 4E10, 1612, and 2G12 with Gut Flora and Their Germline Antibodies With Gut Flora

| MAb | gp41 | gp120 | Anerobic Gut Flora WCL | Aerobic Gut Flora WCL |
|---|---|---|---|---|
| | Reactivity in Luminex Units | | | |
| 1b12 original | NA | 5106 | 148 | 384 |
| 1b12 germline | NA | <80 | 524 | 1127 |
| 2F5 original | 32717 | 9237 | 103 | 100 |
| 2F5 germline | NA | NA | NA | NA |
| 4E10 original | | | | |
| 4E10 germline | NA | NA | NA | NA |
| 2612 original | | | | |
| 2612 germline | <80 | <80 | <80 | <80 |
| 17b original | 1433 | <80 | <80 | <80 |
| CCR5 binding site antibody | | | | |

Figure 14:
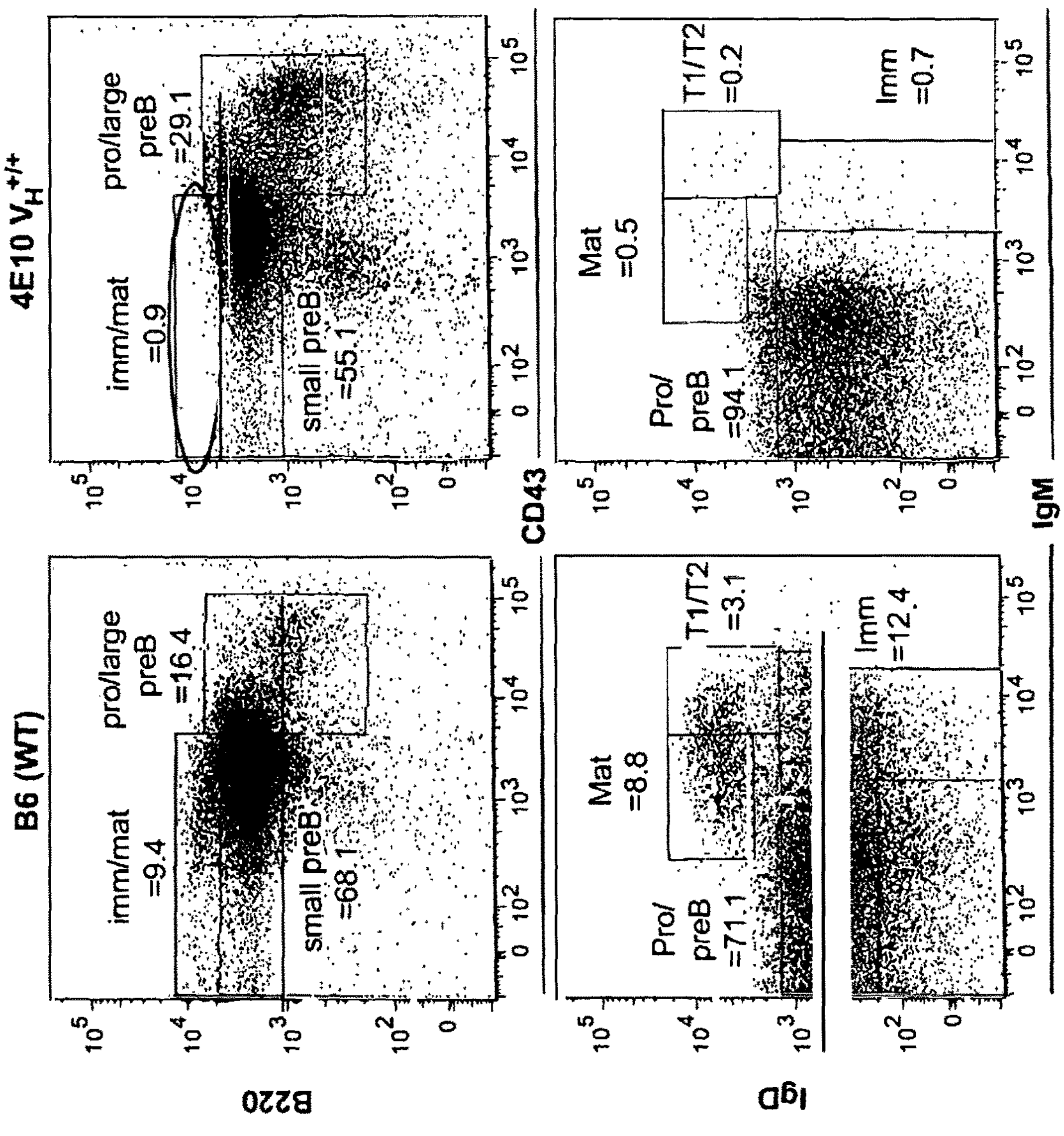
FIG. 14. A large fraction of B cells expressing 4E10 $V_H$ are deleted in bone marrow at the pre-B to immature B cell stage in 4E10 $V_H$ knock-in mice.

Second, it has been hypothesized that the polyreactivity of 2F5, 4E10 and 1b12 target the B cells making these types of antibodies for deletion or anergy (Haynes et al, Science 308:1906-8 (2005); Haynes et al, Human Antibodies 14:59-67 (2005); Alam et al, J. Immunol. 178:4424-35 (2007)). This hypothesis has recently been proven for the 2F5 VH in 2F5 FH homozygous knock-in mice (Verkoczy et al, Proc. Natl. Acad. Sci. USA 107:181-6 (2010)) and now in 4E10 VH homozygous mice (FIG. 14). In both animal models of knock-in of the broadly reactive somatically mutated VHs, the mutated VHs are sufficiently autoreactive to cause deletion in the bone marrow and to invoke multiple tolerance mechanisms in the periphery.

In summary, the results described above demonstrate:

The initial antibody response to HIV is focused on non-neutralizing Env gp41 epitopes.

The initial gp41 antibody response arises from preexisting somatically mutated, polyreactive "natural" antibody clones whose germline Ab do not react with gp41 but whose inferred intermediate Abs do react with gp41.

While the antibody members of gp41 antibody-reactive clones are polyreactive and cross-react with lipids and other self cellular antigens, the affinity of anti-gp41 antibodies increases as somatic hypermutation occurs, indicating gp41 antigen drive.

Initial HIV-induce clonal development however is not efficient nor high affinity—perhaps due to self mimicry, leading to a mixture of HIV Env-reactive and non-reactive antibody clone members.

The germline of broad neutralizing antibodies 1b12, 2F5 and 2G12 do not appear to react with their inferred germline antibodies.

IgM antibodies isolated from AHI or uninfected subjects that bind to gp41 also bind to gut flora whereas gp41 negative IgMs do not bind gut flora antigens The germline of 1b12 reacted with lipids and gut flora, implying origin from pre-existing polyreactive natural antibody producing naïve B cells that likely originated from B cell clones originally targeted against gut flora.

The somatically mutated 2F5, 4E10 and 1b12 broadly neutralizing antibodies all react with antigens in gut flora whole cell lysates, indicating that these antibodies likely derived from clones of naïve B cells originally targeted to gut flora.

Example 2

The enrichment and identification of a protein band in intestinal bacterial lysate reactive with mAb HV00276 is shown in FIG. 52. Western blot analysis following a Native PAGE gel run shows that mAb HV00276 binds to a ~520 kDa protein band in an anaerobe and aerobe intestinal bacterial lysate. Protein fractions from the bacterial lysate having a molecular weight of ~500 kDa were collected following size exclusion chromatography (SEC). SEC fractions show enrichment of the 520 kDa protein by Coomassie Blue (1), silver staining (2) and western blotting (3, arrow) with mAb HV00276. Isoelectric zoom fractionation shows migration of the mAb reactive protein to gel compartment A4 with pH6.2-7.

The 520 kDa band from the enriched fractions was subjected to LC-MS analysis for protein identification. RNA polymerase β, β' and α subunits were identified (see FIG. 53).

*E. coli* RNA polymerase core protein and holoenzyme (core protein+σ subunit) (Epicentre Biotechnologies, Madison, Wis.) were run on a NativePAGE gel, and the reactivity of mAb HV00276 was detected using western blotting. Reactivity to both core and holoenzyme was detected indicating that mAb HV00276 binds to RNA polymerase core protein.

*E. coli* RNA polymerase core protein (Epicentre Biotechnologies, Madison, Wis.) was run on a denaturing SDS-PAGE gel under both reducing (Red) and non-reducing (NR) conditions (left panel). On denaturing SDS-PAGE, the individual subunits (β, β', α and ω) of the core protein can be resolved and visualized following Coomassie Blue staining (right panel). Western blot analysis of the transferred gel shows that the 276 mAb binds only to the 37 kDa α-subunit of the RNA polymerase core protein. No reactivity of HV00503 mAb, which was negative for intestinal bacterial lysate proteins, was observed with any of the core protein subunits.

Example 3

Figure 31:
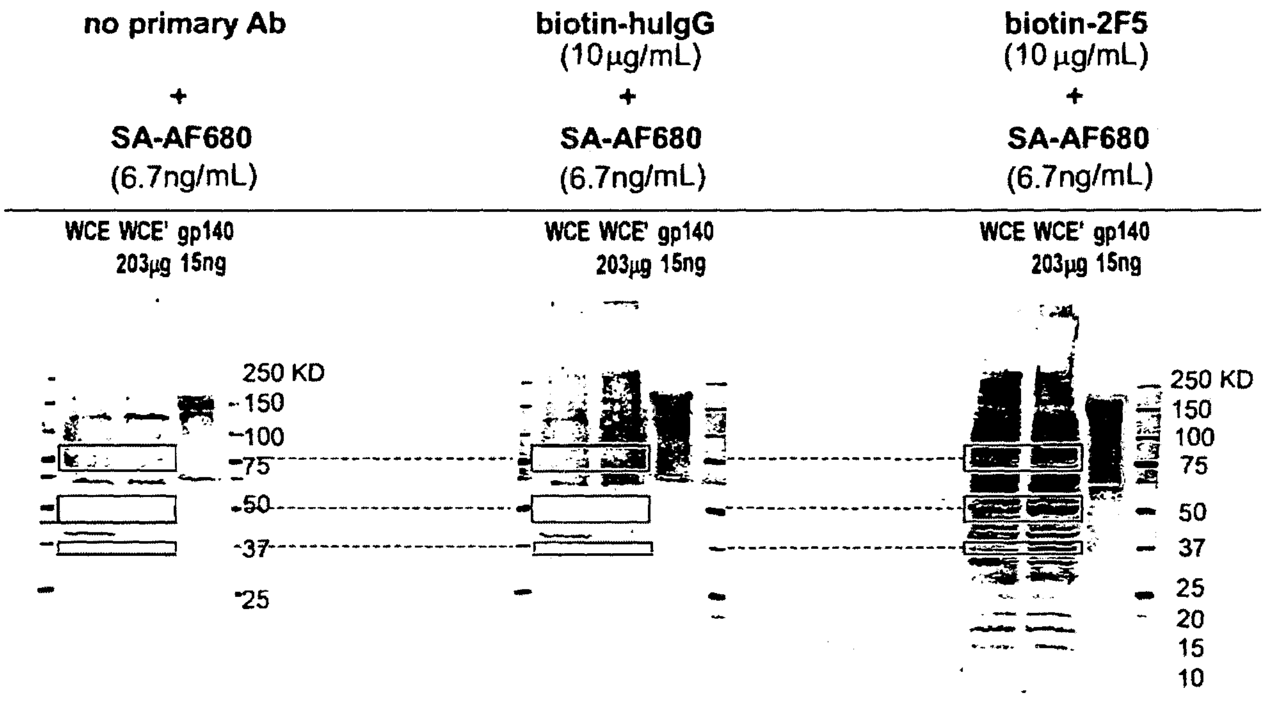

To understand how self tolerance may influence protective humoral responses to HIV-1, it is crucial to determine which self antigens are mimicked by HIV-1 epitopes and where/when these self antigens are exposed to T- and B lymphocytes. It is shown in FIG. 30 that monoclonal human antibodies specific for epitopes of the HIV-1 gp41 MPER also react with self-antigens present in acetone fixed mouse 3T3 cells. As shown in FIG. 31, at least four discrete molecules can be immunoprecipitated from mouse 3T3 cells by biotinylated 2F5 antibody. The dominant species precipitated has an apparent molecular mass of approximately 50-54 kDa.

Figure 34:
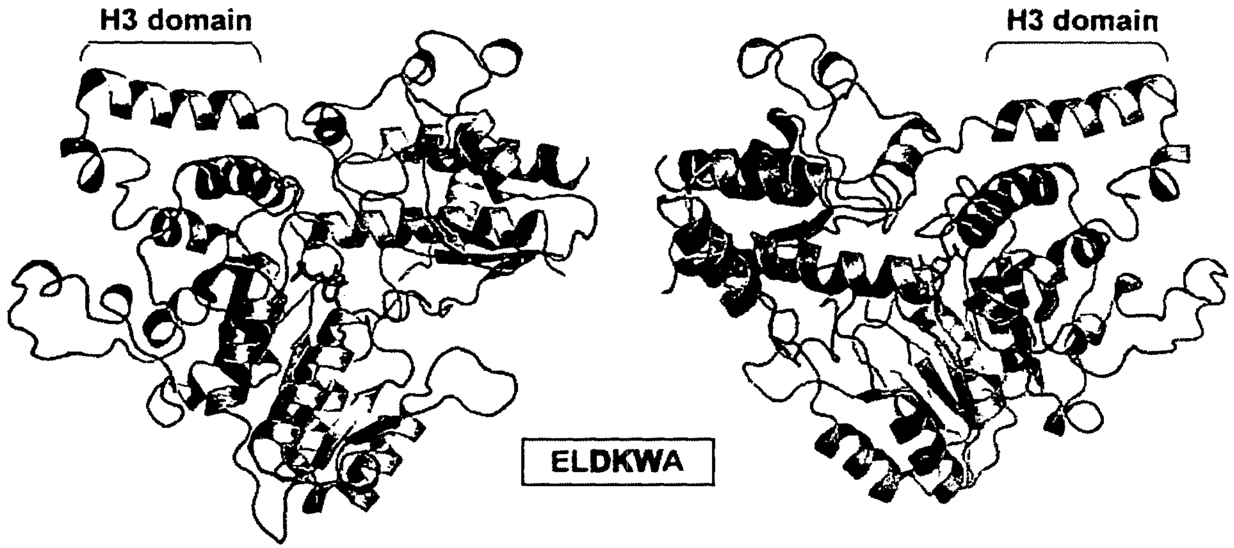
FIG. 34. Structure of human KYNU (PDB 2HZP) and location of ELDKWA (SEQ ID NO: 2) motif.

A conserved mammalian protein, KYNU, carries the core 2F5 epitope and has a molecular mass of 51 kDa (FIG. 32). The 2F5 core epitope is present in the KYNU of many vertebrate species (FIG. 33) and is present in the conserved H3 domain of KYNU (FIG. 34). As shown in FIG. 35, the ELDKWA (SEQ ID NO: 2) region is in a well-ordered alpha helix. The DKW motif is not surface-exposed.

Binding of the 2F5 antibody to human KYNU may require a distortion of the H3 domain, potentially resulting in a slowed $K_{on}$. As shown in FIG. 36, in H3, the D and W residues likely have exposed side chains but K is buried. The 2F5 antibody may necessarily "distort" the H3 helix to bind the ELDKWA (SEQ ID NO: 2) epitope. Under physiological conditions, KYNU is thought to be a homodimer. The ELDKWA (SEQ ID NO: 2) motif may be available to KYNU monomers but is unlikely to be accessible when KYNU forms dimers (FIGS. 37 and 38).

Figure 40:
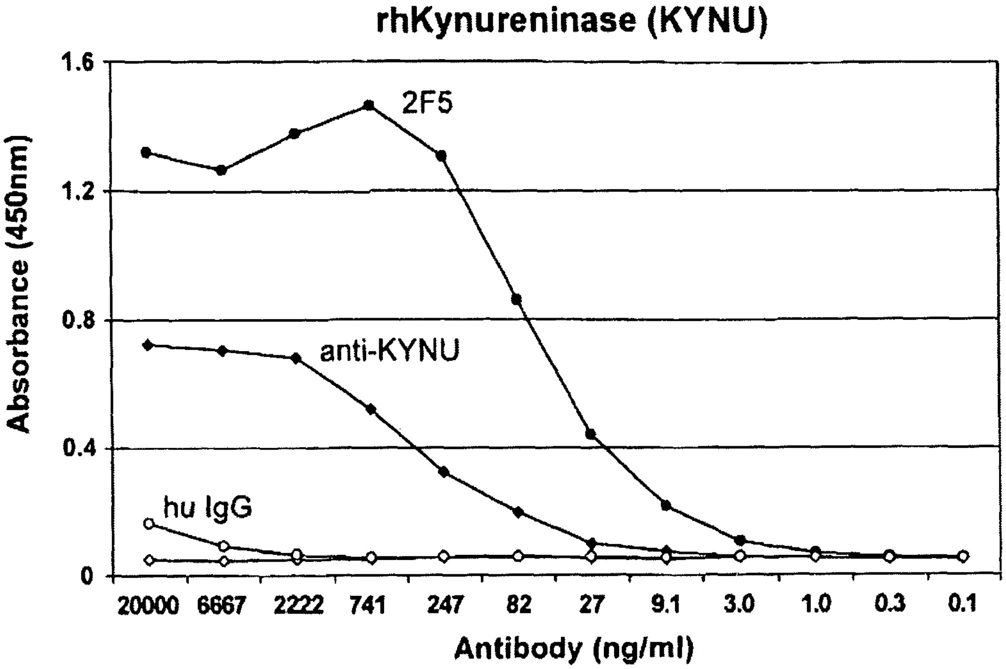
FIG. 40. 2F5 antibody avidly reacts with rhKYNU in a standard ELISA.
Figure 41:
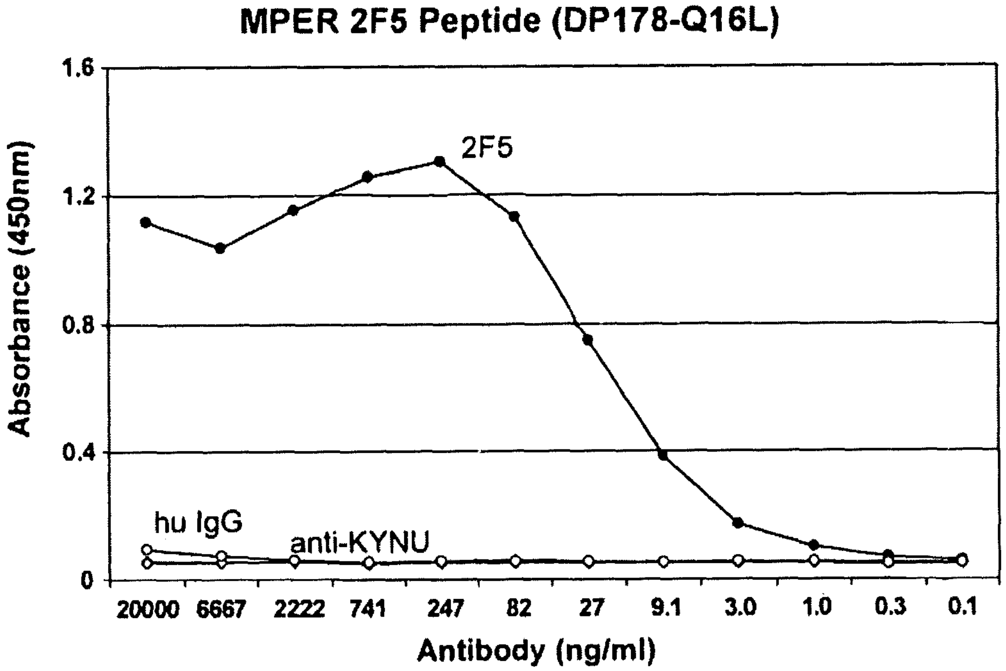
FIG. 41. 2F5 antibody reacts with a peptide (DP178-Q16L) containing 2F5 epitope—anti-KYNU antibody does not.
Figure 42:
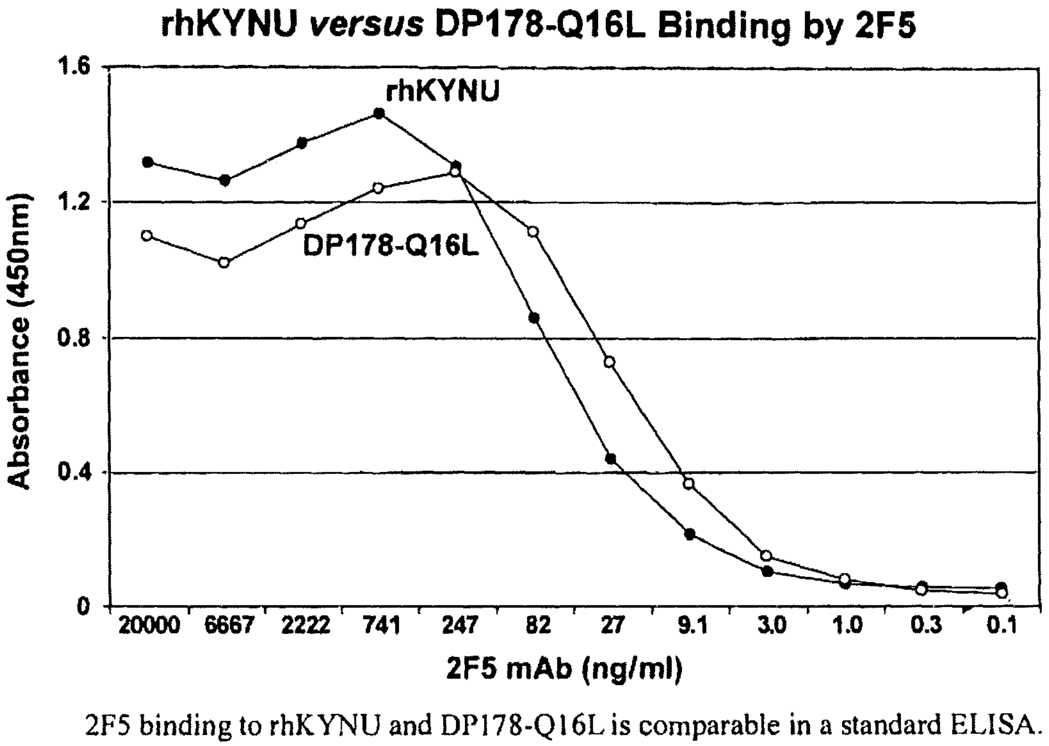
FIG. 42. 2F5 binding to rhKYNU and DP178-Q16L is comparable in a standard ELISA.
Figure 43:
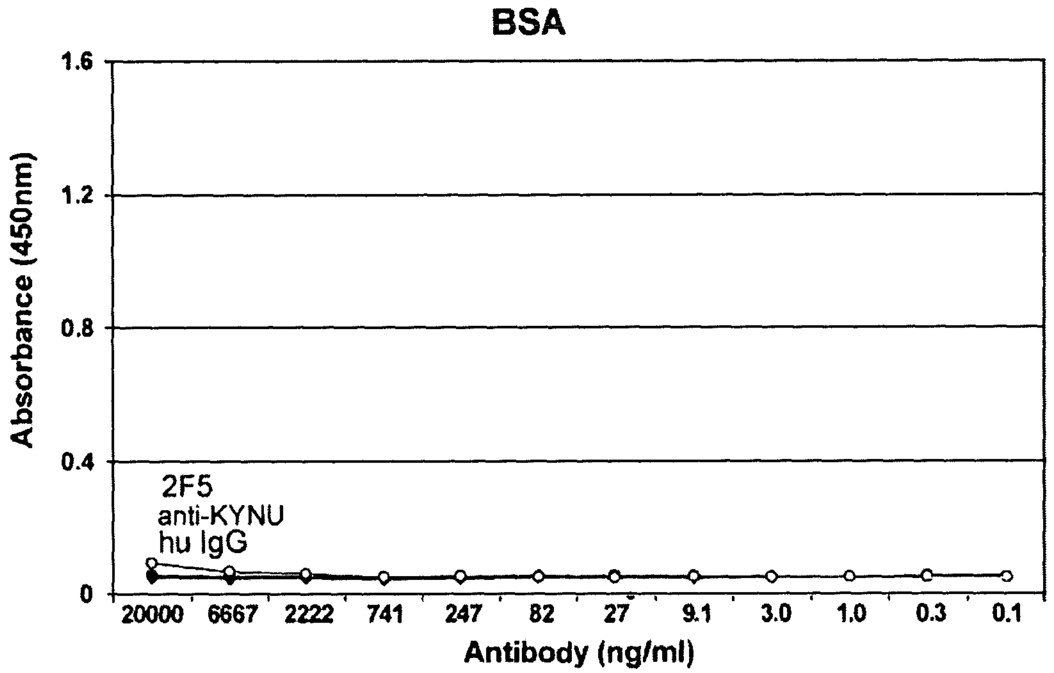
FIG. 43. Antibody binding in ELISA plates is antigen specific.

Putative germline 2F5 antibodies also react with rhKYNU (FIGS. 39 and 40). This is an important point in that it demonstrates that KYNU could be the original ligand of B cells that eventually produced the mutated, high affinity 2F5 antibody. As shown in FIG. 41,/the 2F5 antibody avidly reacts with a peptide (DP178-Q16L) containing the 2F5 epitope whereas anti-KYNU antibody does not (see also FIGS. 42 and 43).

Figure 44:
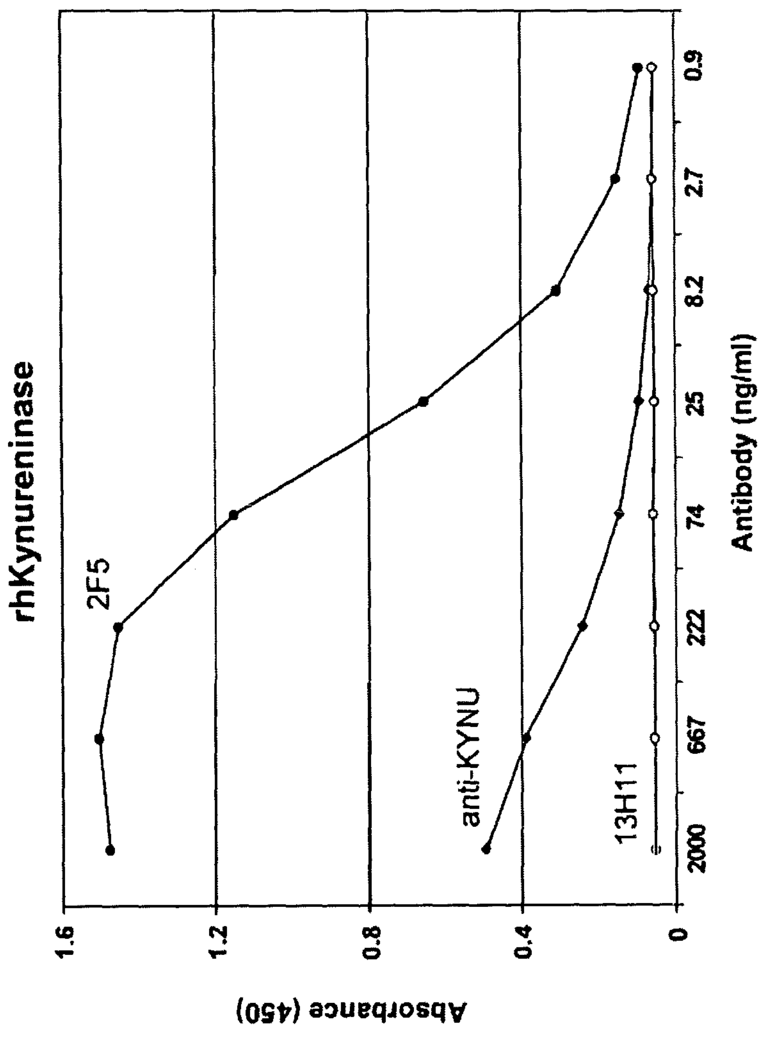
FIG. 44. 13H11 does not bind rhKYNU.
Figure 45:
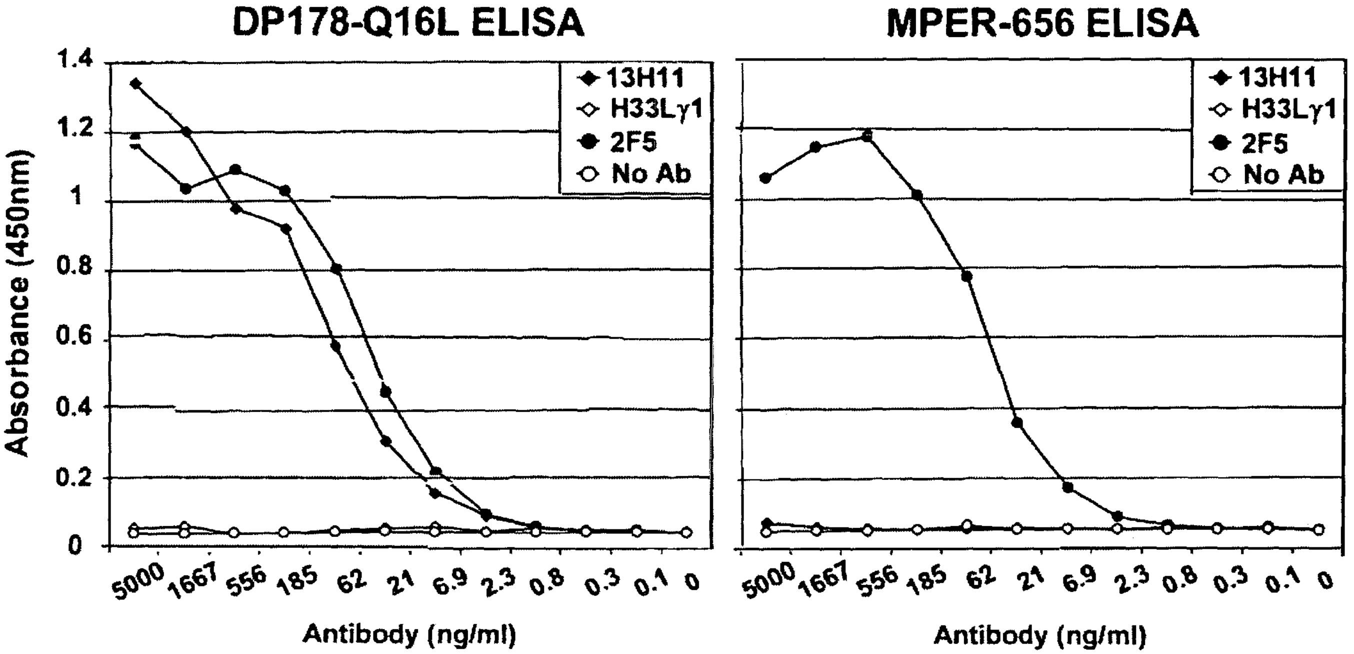
FIG. 45. 13H11 reacts with DP178-Q16L but not MPER-656.
Figure 46:
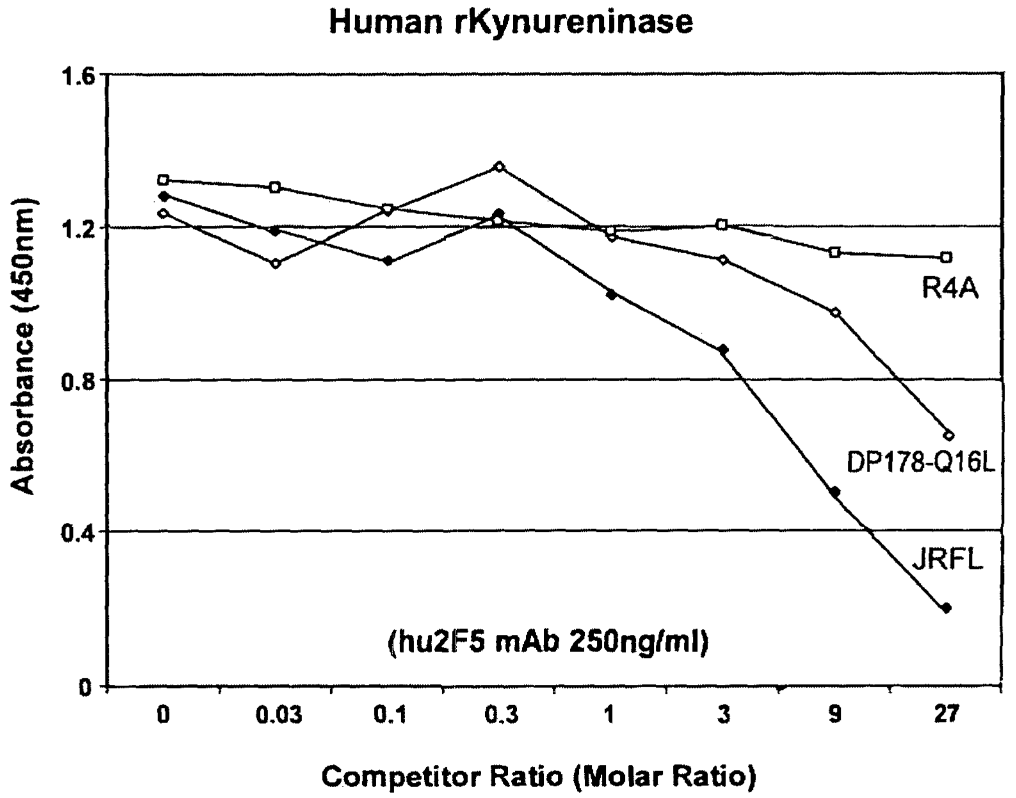
FIG. 46. Competitive inhibition of 2F5 binding to rhKYNU by JRFL, DP178-Q16L and R4A.

13H11, a non-neutralizing mouse HIV-1 MPER monoclonal antibody that recognizes an epitope proximal to the 2F5 determinant, does not bind rhKYNU (FIG. 44). FIG. 45 provides a mapping of residues that distinguish the binding sites of 2F5 and 13H11 monoclonal antibodies to the HIV-1 gp41 MPER. The data shown in FIG. 46 demonstrate competitive inhibition of 2F5 binding to rhKYNU by recombinant HIV-1 gp140 env (JRFL), DP178-Q16L, and an irrelevant peptide antigen, R4A.

Figure 47:
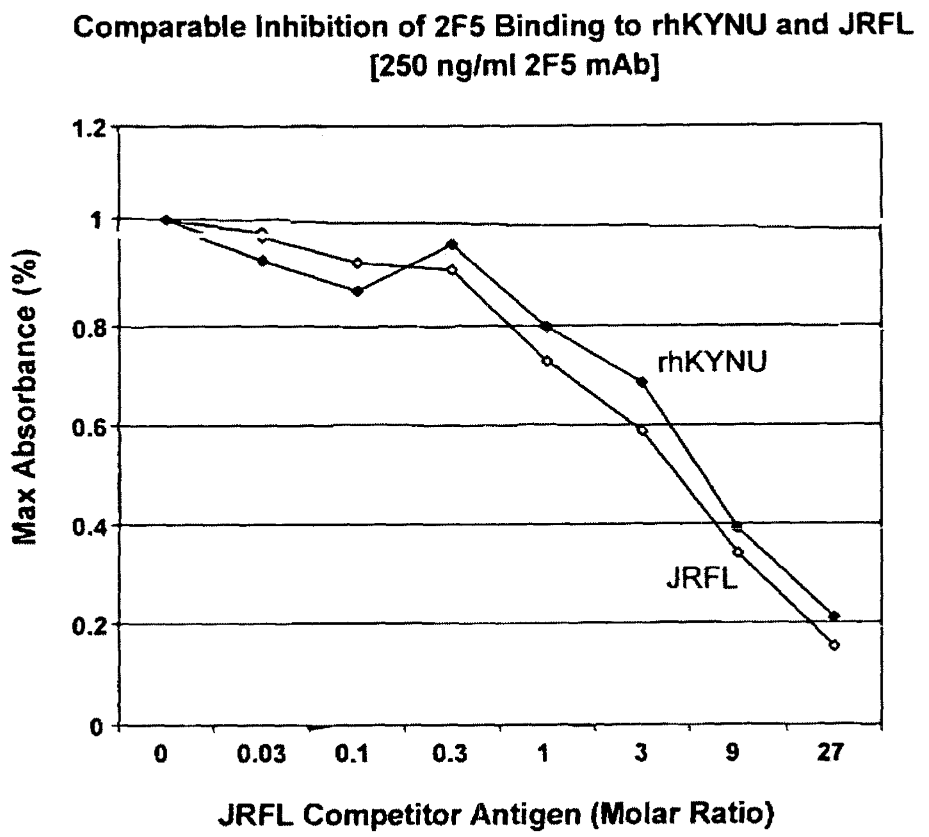
FIG. 47. Comparable inhibition of 2F5 binding to rhKYNU and JRFL.

JRFL recombinant HIV-1 gp140 comparably inhibits the binding of 2F5 to JRFL (homologous inhibition) and to rhKYNU (heterologous inhibition) (FIG. 47). The similarity of the inhibition curves indicates that a single, common epitope is responsible for 2F5 binding to both JRFL and rhKYNU.

As shown in FIG. 48, 2F5 monoclonal antibody binds both plate-bound and soluble rhKYNU comparably. Surface plasmon resonance studies demonstrate that both 2F5 and its unmutated precursors are capable of binding avidly to rhKYNU (FIG. 49). The slower $K_{on}$ is consistent with the 2F5 antibodies distorting the native KYNU structure in order to achieve maximal interaction. $K_{off}$ rates are very slow indicating that the bound KYNU interacts stably with all 2F5 types.

SPR binding analysis shows that the 2F5 mAb and its RUA (2F5-GL1 and 2F5-GL3) bind to KYNU (FIG. 50). Each of the antibodies was captured on a human anti-Fc immobilized sensor surface and soluble KYNY was injected at concentrations 50, 30, 20, and 10 μg/mL. Overlay of the binding curves show specific binding of KYNU to each antibody. Non-specific binding was measured using a control mAb (Synagis, anti-RSV) which showed no binding to KYNU.

Example 4

To determine whether 2F5 reactivity to fixed 3T3 cells could be inhibited by proteins/polypeptides containing the 2F5 MPER core epitope (ELDKWA) (SEQ ID NO: 2), 2F5 monoclonal (10 μg/ml) antibody was reacted with increasing molar concentrations of homologous (JRFL and DP178) or heterologous (R4A) inhibitors (1 hr, 25° C.). These mixtures were subsequently added to hydrated/blocked slides covered with methanol/acetone fixed 3T3 cells for (2 hr, 25° C.). Slides were rinsed and then washed overnight in 250 ml (PBS with 0.1% Tween-20 and 0.5% BSA). Washed slides were overlayed with goat anti-human IgG-FITC (1:400 in PBS with 0.1% Tween-20 and 0.5% BSA). After 1 hr., slides were washed, coversliped in Fluoromount-G. Twenty-four hr. later, fluorescence images were acquired using a Zeiss Axiovert 200M confocal microscope at 200× magnification and a fixed 300 msec exposure time.

Figure 51:
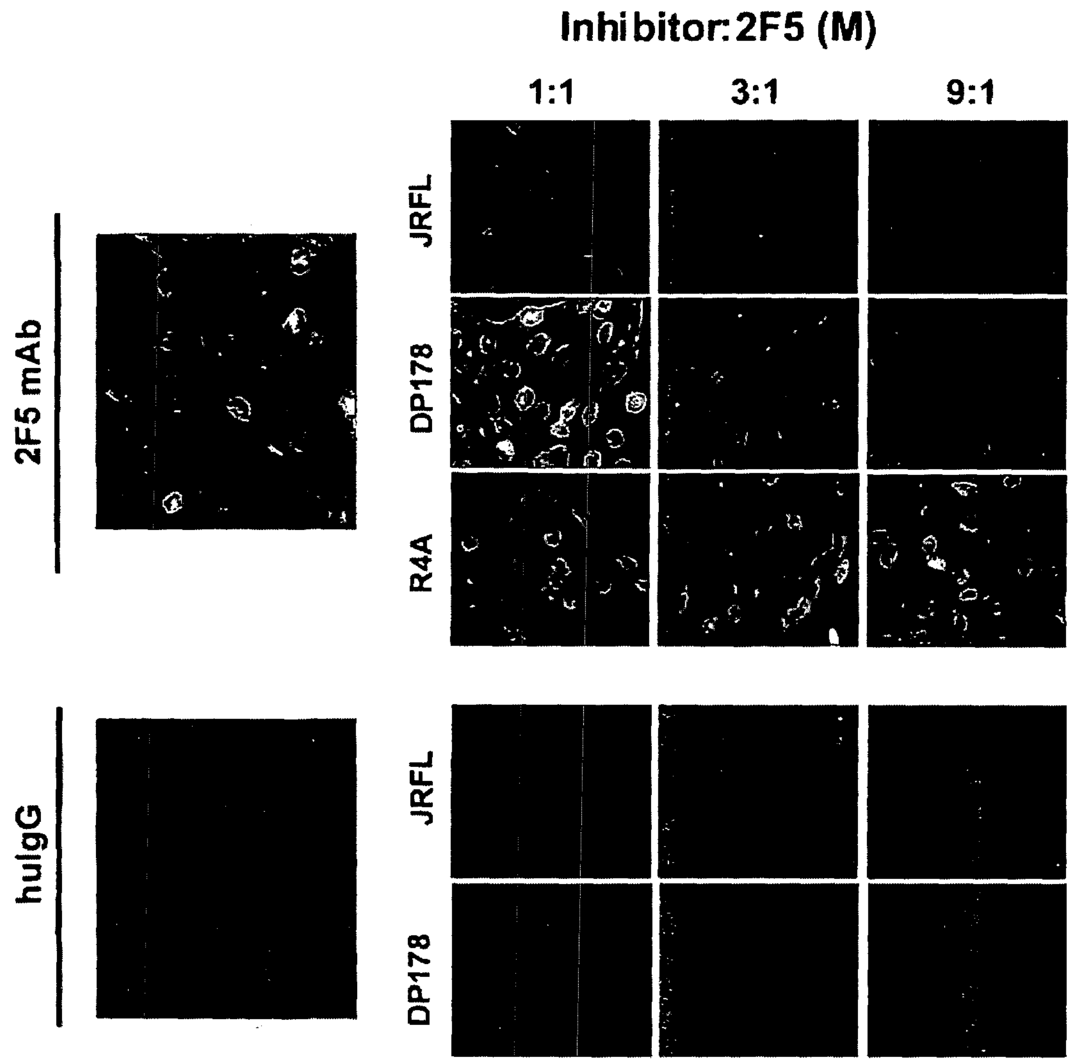
FIG. 51. Inhibition of 2F5 binding to 3T3 cells by recombinant HIV-1 gp140 (JRFL), and the DP178 and R4A peptides.

Homologous inhibitors, the JRFL protein and, to a lesser extent, DP178 polypeptide, inhibited 2F5 binding to 3T3 cells. An irrelevant polypeptide, R4A, showed no inhibition. (See FIG. 51.) These data demonstrate that a substantial amount of 2F5 reactivity to fixed 3T3 cells is determined by protein-protein interaction rather than un-specific lipid binding. Thus, proteins, like KYNU, may be primary autoligands for 2F5.

Example 5

As described above, the present invention relates to a vaccine strategy that comprises administering HIV envelope proteins (peptides or polypeptides) to, first, target B cells that express unmutated ancestor antibodies that are able to give rise to broadly neutralizing matured antibodies and, then, drive maturation of the B cell clones toward the desired breadth of neutralization by boosting the B cells that are undergoing somatic maturation with selected HIV envelope proteins (peptides or polypeptides). The development of the strategy involved reconstruction of this maturation pathway. Desired final (mature) antibodies were isolated from a patient who produces broadly neutralizing antibodies and the antibodies were characterized. The respective putative ancestral antibodies were inferred and expressed as real antibodies and a determination was made as to what they bind. The notion is that the B cells expressing unmutated "ancestral" and intermediate antibodies will affinity mature when triggered with the appropriate proteins (peptides or polypeptides) to yield the broadly neutralizing antibody-secreting B cells observed in the patient.

Selection and Isolation of Cross-Clade Neutralizing Monoclonal Antibodies CH01, CH02, CH03, CH04 and CH05

Approximately 30,000 memory B cells obtained from frozen PBMCs of subject 707-01-021-9 were screened and 28 cultures were found that neutralized >50% of CAP45 infectivity (FIG. 56). Monoclonal antibodies CH01, CH02, CH03, CH04 and CH05 (CH01-CH05) were isolated from four of these culture wells (1-27-G2, 1-27-G11, 1-19-F10 and 1-19-B7) (FIG. 56).

Amplification and sequencing were carried out of the V-heavy and V-light chains obtained from the RNA-later-treated memory B cells frozen at the time of screening. Cultures 1-27-G2 and 1-19-F10 contained only one pair (3~20/κ3~20; CH01 and CH02 monoclonal antibodies, respectively), which indicates that the cultures were monoclonal and that the CH01 and CH02 are natural antibodies. Conversely, 1-27-G11 and 1-19-B7 contained multiple V-heavy and V-light chains, indicating that the cultures were oligoclonal.

To identify the natural pairs from these latter cultures, single-cell sorted memory B cells, collected at the time of initial screening, were amplified and sequenced. CH03 and CH04 (both 3~20/κ3~20) were natural pairs isolated from cultures 1-27-G11 and 1-19-B7, respectively.

Human B-cell hybridomas were generated from culture 1-19-B7 by further expanding and cloning by sequential limiting dilutions the memory B cells for approximately 4 weeks. By this means; the CH04 natural antibody was obtained and CH05 was identified, which was produced by a lesser population of expanded memory B cells and expressed the same 3-20 V-heavy of CH04 but paired with a different κ1~6 V-light chain.

The CH01-CH03 monoclonal antibodies were obtained by transfecting the V-heavy and V-light pairs into 293T cells and expressed in an IgG1 backbone as previously described (Liao et al, J Virol Methods. 158(1-2):171-9 (2009)). Monoclonal antibodies CH04 and CH05 were instead purified from the hybridoma B cell lines.

These data demonstrate that the strategy allows quick identification of neutralizing monoclonal antibodies in approximately 2 weeks and production of natural moroclonal antibodies as early as one month. Furthermore, this method resolves the uncertainties of the classic phage display libraries related to the precise characterization of a monoclonal antibody being true to the natural antibodies that are represented in the in vivo repertoire. Finally, reported for the first time is the production of two natural human B-cell hybridomas that broadly neutralize HIV-1.

Genomic Characterization of the CH01-CH05 Antibodies

It was determined that the CH01-CH05 antibodies are all member of the same clonal family based on the following factors: (1) V(D)J families; (2) length of the HCDR3; (3) nucleotide sequences of the HCDR3 region and of the n-insertions.

The analysis of the heavy chains showed that CH01-CH05 are IgG1 antibodies, sharing the same V 3~20*1/J 2*01 rearrangement (Table 3). They also share the same D region which resulted from the D-D fusion of the 3~10*1 and the 2OF15*2/inv regions (Table 3). The HCDR3 is 26 amino acids long (Table 3). N-insertions were also of the same length and shared a nucleotide makeup compatible with the notion that CH01-CH05 monoclonal antibodies are clonally related (FIG. 57A). The V-heavy sequences of CH04 and CH05 are identical (FIG. 57A), which suggests that the moment in which the V-light chain peripheral editing occurred was intercepted.

TABLE 3

Main characteristics of the CH01-CH05 VH and VL sequences

| | V-heavy chain | | | | | | V-light chain | | | | |
|---|---|---|---|---|---|---|---|---|---|---|---|
| | V | D | J | HCDR3 length | Mutation rate* | Isotype | V | J | k/l | LCDR3 length | Mutation rate |
| CH01 | 3~20 | 3~3, 2OF15/inv | 2 | 26 | 0.120 | IgG1 | 3~20 | 1 | k | 9 | 0.091 |
| CH02 | 3~20 | 3~3, 2OF15/inv | 2 | 26 | 0.118 | IgG1 | 3~20 | 1 | k | 9 | 0.116 |

TABLE 3-continued

Main characteristics of the CH01-CH05 VH and VL sequences

| | V-heavy chain | | | | | | V-light chain | | | | |
|---|---|---|---|---|---|---|---|---|---|---|---|
| | V | D | J | HCDR3 length | Mutation rate* | Isotype | V | J | k/l | LCDR3 length | Mutation rate |
| CH03 | 3~20 | 3~3, 2OF15/inv | 2 | 26 | 0.152 | IgG1 | 3~20 | 1 | k | 9 | 0.138 |
| CH04 | 3~20 | 3~3, 2OF15/inv | 2 | 26 | 0.153 | IgG1 | 3~20 | 1 | k | 9 | 0.110 |
| CH05 | 3~20 | 3~3, 2OF15/inv | 2 | 26 | 0.153 | IgG1 | 1~6 | 2 | k | 9 | — |

*Mutation rates are calculated from putative reverted unmutated ancestor variable heavy and variable light chains inferred from the sequences of each individual monoclonal antibody independently.

Seemingly to the V-heavy chains, CH01-CH04 shared the same VLκ3~20/JLκ1 rearrangement (FIG. 57B), an LCDR3 of the same length (9 aminoacids) and similar n-insertions (FIG. 57B). The V-light chain of monoclonal antibody CH05 was instead unrelated (FIG. 57C), with a different VLκ1/JLκ2 rearrangment, LCDR3 length and n-insertions. It is contemplated that the biology underlying the pairing of the V-light chains to the VH3~20 chain is that the VH3~20/VLκ3~20 chain pairs (CH01-CH04) preceded the VH3~20/VLκ1~6 pairing (CH05) because higher VLκ numbers are closer to the Jκ locus and, therefore, ancestor antibodies would have had to rearrange VLκ3 first and then VLκ1. Furthermore, the low-numbered Jκ loci have to come before the high-numbered. Therefore, the transition from VLκ3/JLκ1 to VLκ1/JLκ2 is consistent with simple editing. Finally, the phylogenetic tree shown in FIG. 58, and discussed below, provides further very strong evidence that the VLκ3/JLκ2 rearrangement happened first.

Figure 58:
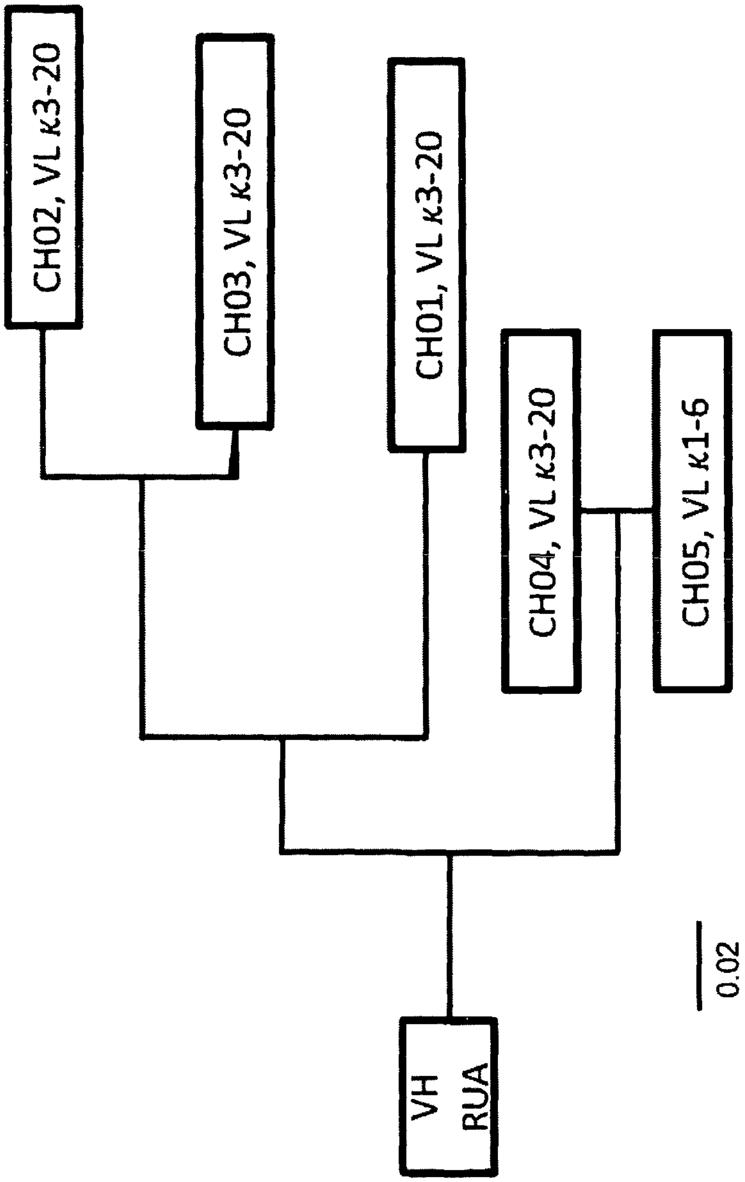
FIG. 58. Phylogenetic tree of the V-heavy chains of the CH01-CH05 monoclonal antibodies.

Next, a determination was made of the genetic relationship of the CH01-CH05 monoclonal antibodies by constructing the phylogenetic tree of the V-heavy chains (FIG. 58). To do so, the putative reverted unmutated ancestors of the CH01-CH05 antibodies were inferred by applying the maximum likelihood analysis on the observed antibodies as a whole. Using this method, two possible RUAs (0219-RUA1 and 0219-RUA2) were predicted that differed only for a single silent nucleotide substitution (G or T) in position 329 (FIG. 59). The putative RUAs were also predicted by analyzing each observed monoclonal antibody independently. With this method, 9 RUA antibody candidates were identified: one for CH01 (CH01-RUA1), two for CH02 (CH02-RUA1 and CH02-RUA2), four for CH03 (CH03-RUA1, CH03-RUA2, CH03-RUA3 and CH03-RUA4) and two for CH04 (CH04-RUA1 and CH04-RUA2). The alignment of all the computed putative RUAs is shown in FIG. 59.

The phylogenetic tree of the V-heavy chains (FIG. 58) shows that CH02 and CH03 are genetically close to each other and that CH03 is the most somatically mutated monoclonal antibody of the family.

Taken together, these data demonstrate that CH01-CH05 are clonally-related heavily somatically mutated monoclonal antibodies that share a long HCDR3 and harbor a D-D fusion rearrangement. Moreover, this is the first description of peripheral light chain editing in humans.

CH01-CH05 Monoclonal Antibodies Broadly Neutralize Tier 2 HIV-1 Isolates and Bind to a Limited Set of Monomeric gp120/gp140 HIV-1 Envelope Proteins.

The neutralization breadth of the CH01-CH05 antibodies was tested against a panel of 96 HIV-1 primary isolates. The panel comprised 4 tier 1A isolates, 3 tier 1B isolates (2 clade B and 1 clade AE) and 89 tier 2 isolates which included 10 clade A, 21 clade B, 27 clade C, 4 clade D, 7 clade G, 1 clade AE, 1 clade AD, 9 CRF01_AE and 9 CRF02_AG viruses.

As predicted by the genetic analysis, CH01-CH05 shared a very similar pattern of neutralization (Table 4). All the antibodies neutralized viruses from multiple clades and the breadth of neutralization ranged from 44.9% (43/96 isolates) of CH01 to 34.7% (33/95 isolates) of CH02. CH03, CH04 and CH05 neutralized 43.2% (41/95), 43.2% (41/95) and 44.2% (42/95) isolates, respectively. None of the antibodies neutralized tier 1A isolates. Tier 1B isolates were neutralized only by CH01 (2 out of 3), CH02 and CH03 (1 out of 3) but not by CH04 or CH05. Conversely, CH01-CH05 showed larger breadth of neutralization against tier 2 viruses. CH01 preferentially neutralized CRF02_AG isolates (7/9; 77.8%), followed by clade A (7/10; 70%), CRF01_AE (5/9; 55.6%), clade B (9/21; 42.9%), clade C (11/27; 40.7%), and clade G (1/7; 14.3%) isolates. Clade D viruses were not neutralized. Conversely, it is important to note that the CH01-CH05 monoclonal antibodies strongly neutralized AE.CM244.ec1

In comparison, the recently described PG9 and PG16 quaternary antibodies, shown in the table, neutralized 73/83 (88%) and 69/83 (83.1%) tier 2 isolates, respectively. Interestingly, with only one exception (T251-18), PG16 neutralizes a subset of the isolates neutralized by PG 9 and the CH01-CH05 broadly neutralizing antibodies neutralize a subset of viruses neutralized by PG16. This finding is compatible with the hypothesis that the CH01-CH05 epitope is related to that of PG9/PG16.

Next, the potency of the CH01-CH05 antibodies against the neutralization-sensitive isolates was evaluated. Overall, the median IC50 was approximately 1 μg/ml with an average 1050 ranging from 2.4 to 5.6 μg/ml. CH03 showed the strongest potency among the CH01-CH05 antibodies with a mean IC50 of 2.4 μg/ml and a median IC50 of 0.46 μg/ml, comparable to those of PG9 (mean IC50=2.1 μg/ml; median IC50=0.11 μg/ml) but weaker than those of PG16 (mean=0.67 μg/ml; median <0.02 μg/ml). CH01, the broadest neutralizer, showed a mean and median IC50s of 3.7 and 1.1 μg/ml, respectively. CH02, CH04 and CH05 mean IC50s were 4.9, 4.7 and 4.3 μg/ml, and median IC50s were 0.97, 0.8 and 0.79 μg/ml, respectively.

The ability to neutralize transmitted founder viruses is another critical parameter to evaluate. As shown in Table 4, CH01-CH05 bNabs were able to neutralize 3/3 (100%) clade A, 2/9 (22.2%) clade B and 2/3 (66.7%) clade C transmitted founder viruses.

Taken together, these data indicate that the clonal family of CH01-CH05 antibodies broadly neutralize tier 2 isolate from multiple clades, including transmitted founder viruses. This is the first report of a clonal family of broadly neutralizing antibodies. Since there was no significant differences in the pattern of neutralization of CH05 compared to that of the other broadly neutralizing antibodies of the clonal family, these results also indicate that the edited VLκ1~6 chain permitted the neutralization of the tested isolates at comparable levels to the VLκ3~20 chain.

In contrast to the mature antibodies, the inferred putative RUAs did not show such breadth of neutralization. Yet, few isolates were potently neutralized. The neutralization profile of 6 inferred RUAs tested on a panel of 24 isolates is shown in Table 5. It is important to note that CH03-RUA1, CH03-RUA4 and CH03-RUA3 neutralized AE. CM244.ec1 isolate with IC50 of 4.45, 5.26 and 18.8 µg/ml, respectively. Also, B.WITO4160.33 was potently neutralized by all the RUAs tested (IC50s from 0.06 to 0.47 µg/ml). A.Q23.17 isolate was also neutralized very potently by CH01-RUA1, CH03-RUA1, CH03-RUA3 and CH03-RUA4 with IC50s<0.02 µg/ml. Conversely, CH02-RUA1 and CH03-RUA2 neutralized A.Q23.17 at IC50s three orders of magnitude higher, showing the same pattern of neutralization of C.ZM233M.PB6.

Binding of CH01-CH05 Antibodies to Monomeric Gp120/Gp140 HIV-1 Envelopes.

To determine which monomeric envelope could be used in a vaccine formulation to bind to B cells and trigger the production of CH01-CH05-like antibodies, CH01-CH05 monoclonal antibodies and RUAs were tested for binding to a panel of 32 monomeric envelopes. Table 6 shows the EC50s expressed in µM.

Figure 60:
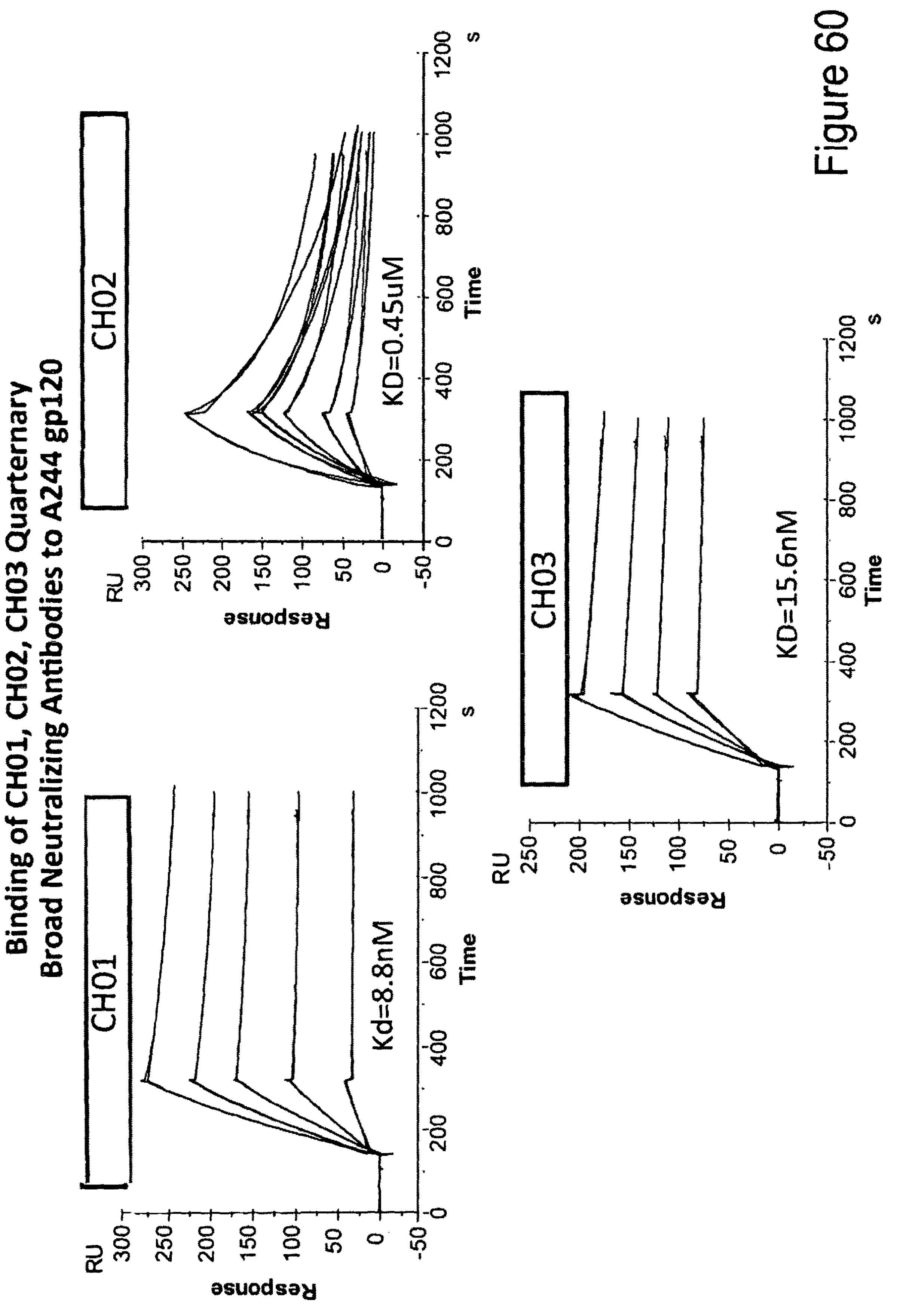
FIG. 60. Binding of CH01, CH02, CH03 quarternary broad neutralizing antibodies to A244 gp120.
Figure 61:
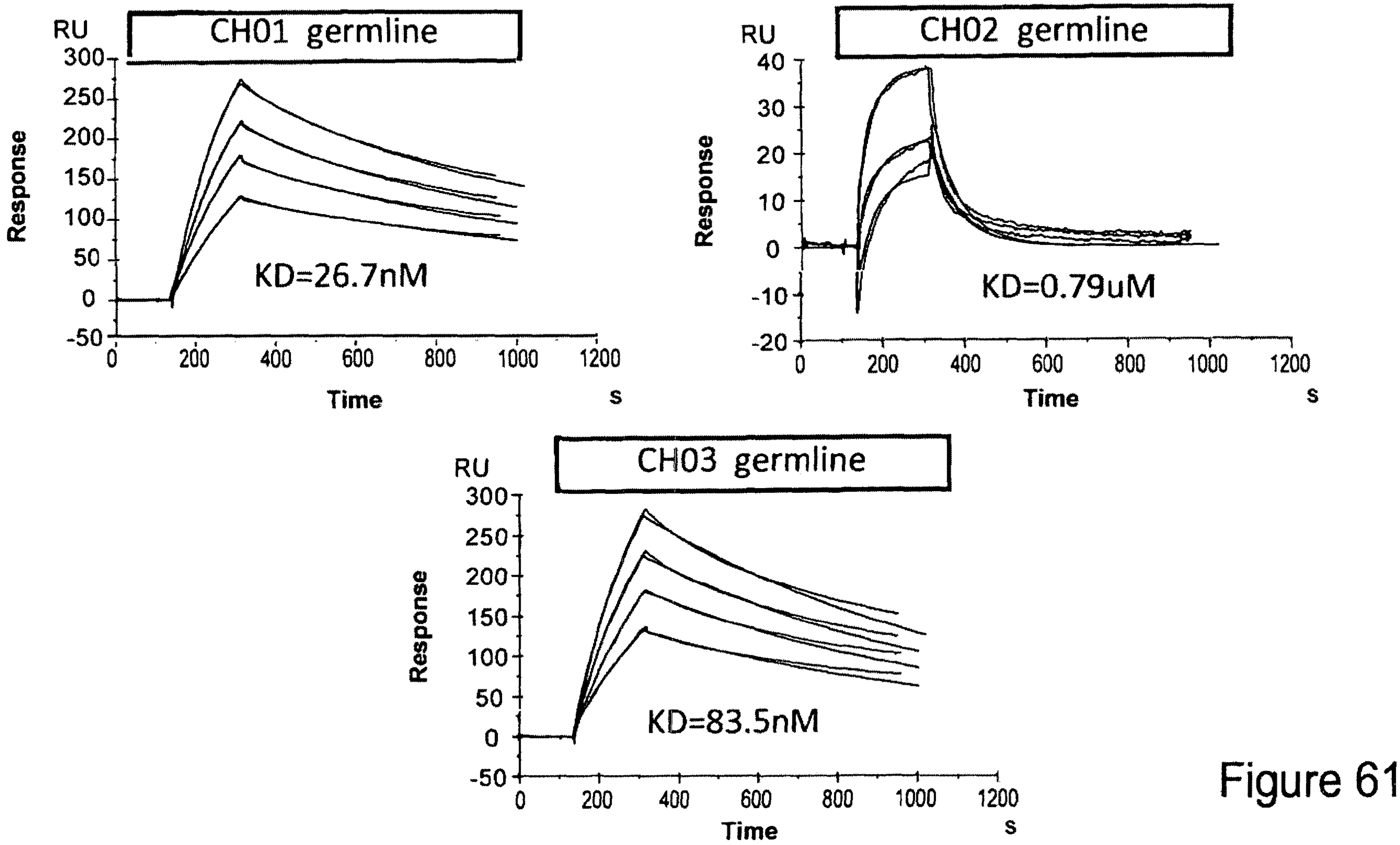
FIG. 61. Binding of reverted unmutated ancestors of CH01, CH02, CH03 quarternary broad neutralizing antibodies to A244 gp120.
Figure 62:
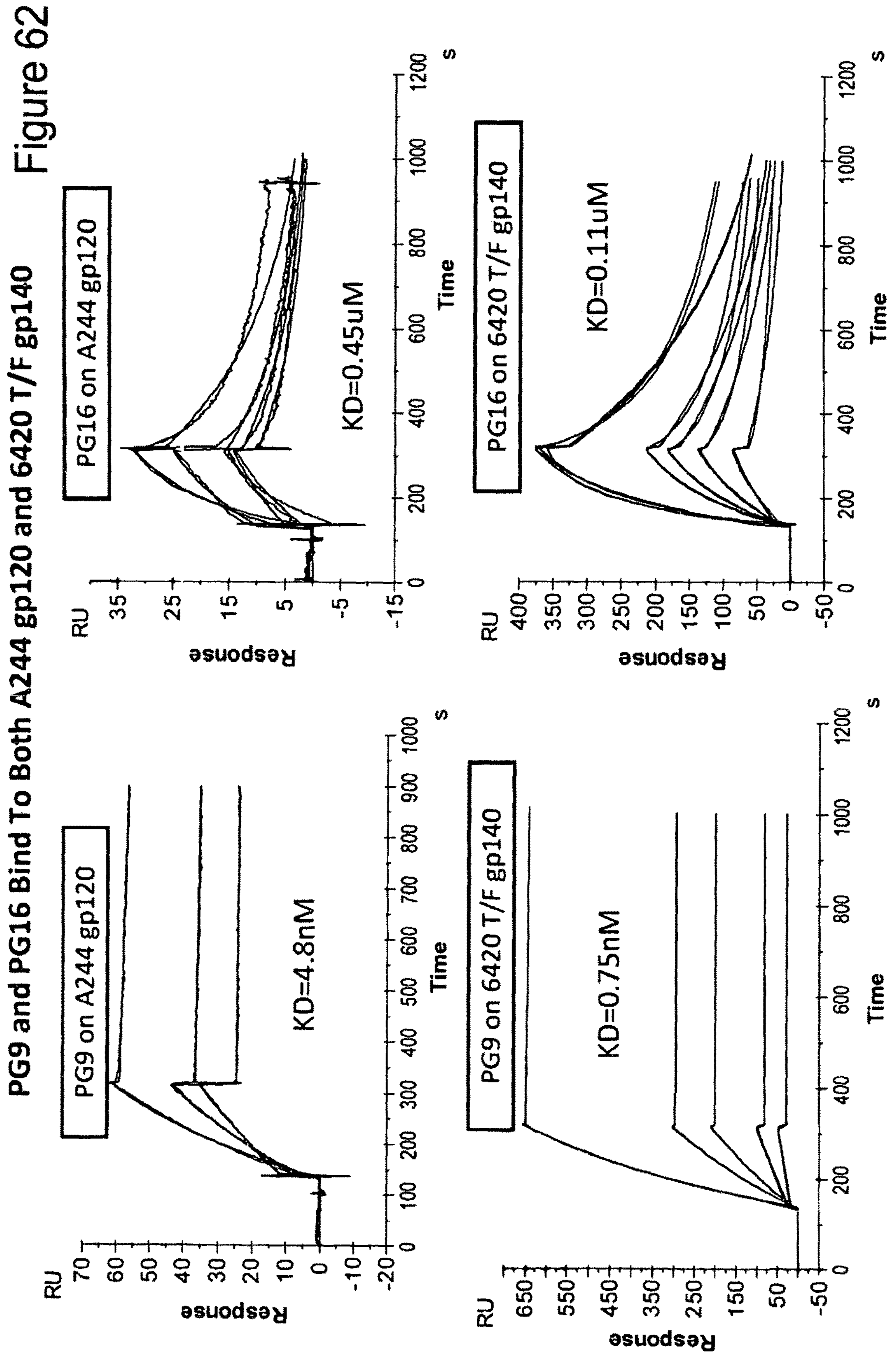
FIG. 62. PG9 and PG16 bind to both A244 gp120 and 6420 T/F gp140.
Figure 63:
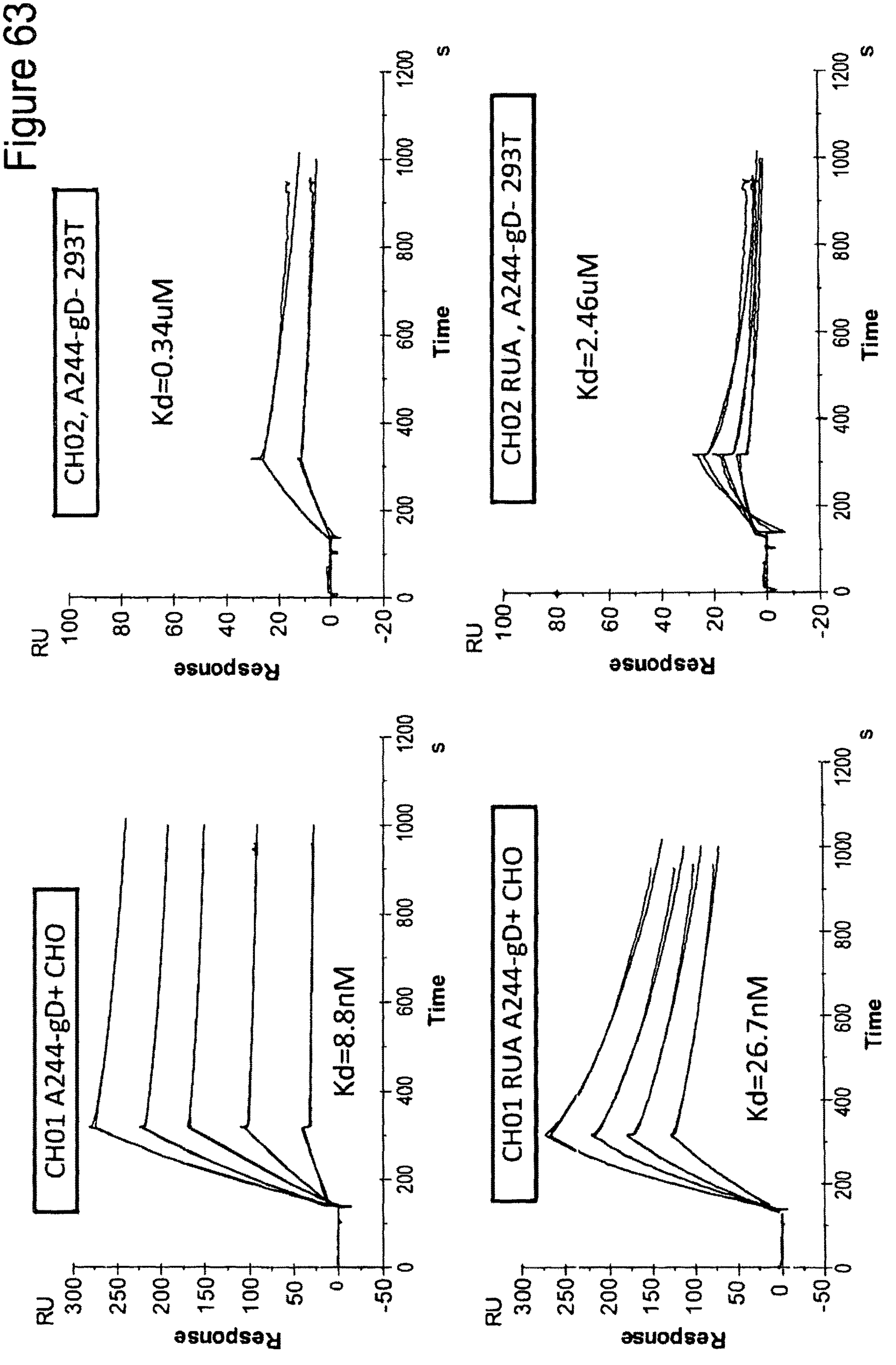
FIG. 63. CH01 monoclonal antibodies decreased by binding affinity to A244gD− gp120 envelope compared to A244gD+ gp120 envelopes.
Figure 64:
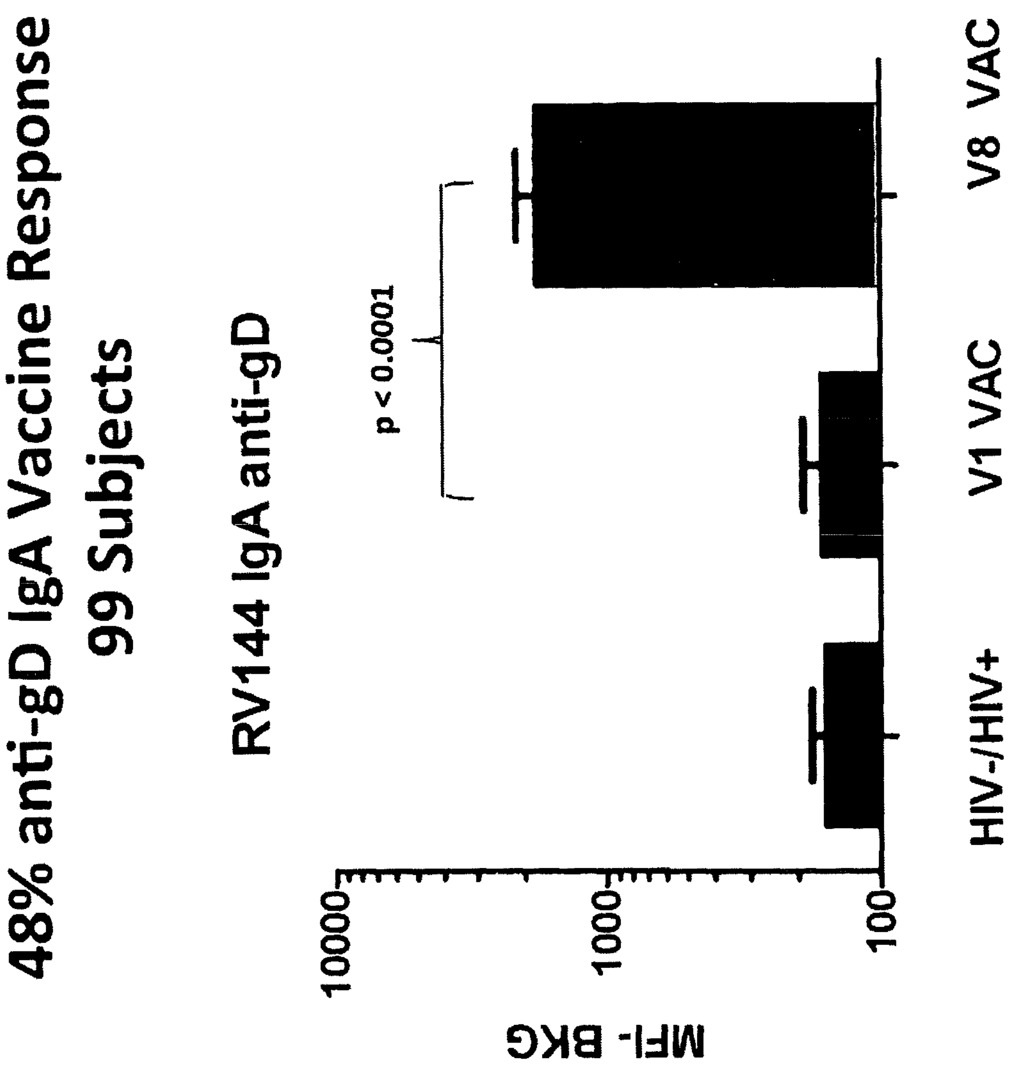
FIG. 64. Forty-eight percent anti-gD IgA vaccine response (99 subjects).
Figure 65:
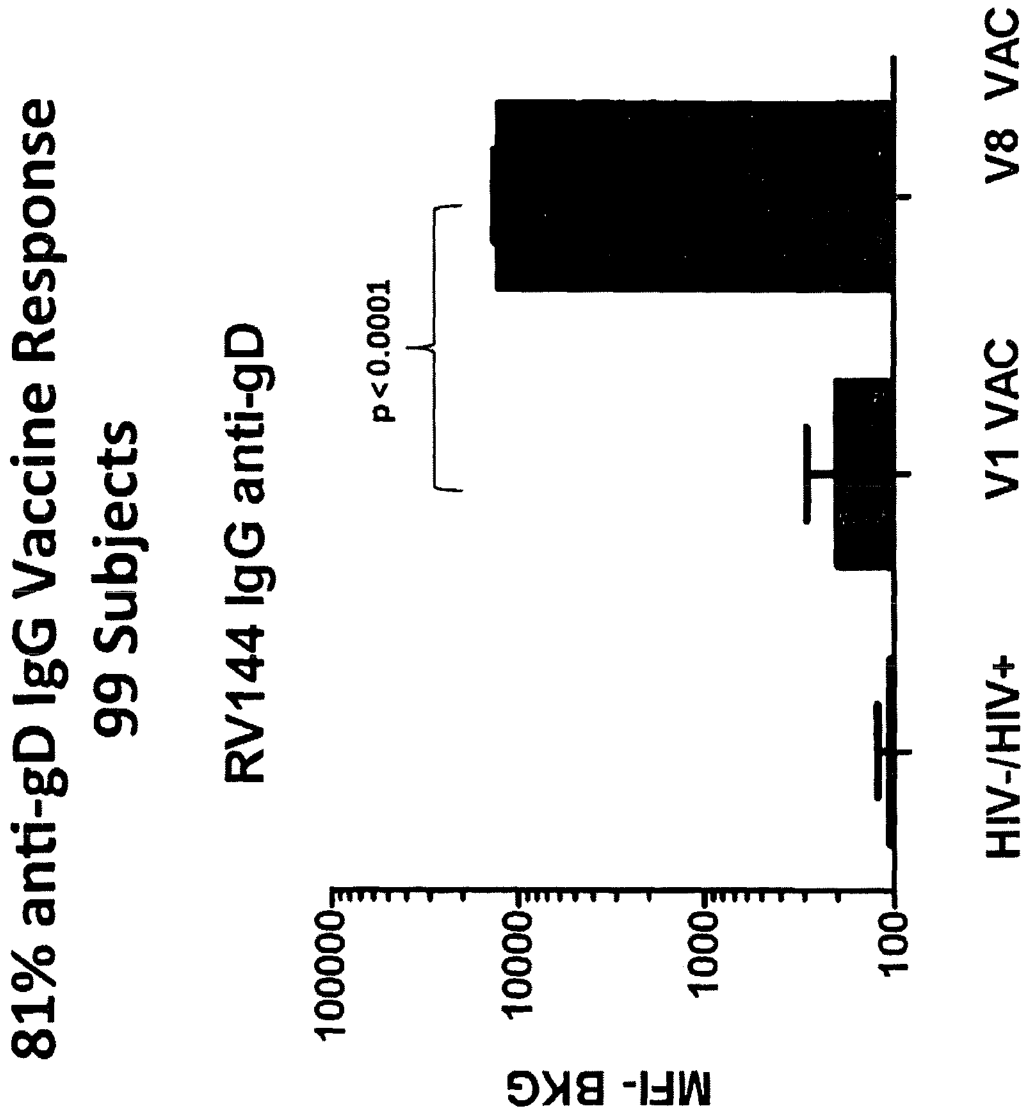
FIG. 65. Eight-one percent anti-gD IgG vaccine response (99 subjects).

Binding to monomeric envelope was weak with the exception of gp120 A244gD$^+$, which was bound by the CH01-CH05 antibodies with EC50s ranging from 7.8 µM (CH01) to 150 µM (CH02). In addition, and of extreme relevance for the selective targeting of precursors of B cells capable of secreting broadly neutralizing antibodies, also two putative RUAs showed some binding (Table 6). The other HIV-1 envelope that was bound by all the five mature antibodies was gp120 CM243, even though the mean EC50 was higher. The sequence of the A244 (CM244) Envelope is from McCutchan et al (AIDS Res. Hum. Retrovir. 8(11): 1887-1895 (1992)) with the exception of aa substitutions of L124P, N196S, K198E, A212P and D284 N. In addition, there is a 30AA sequence from the gD protein of herpes simplex virus KYALVDASLKMADPNRFRGKDLPVLDQ (SEQ ID NO: 7) at the N-terminus of gp120 A144 (CM244). This sequences comprises the receptor binding sites of the gD protein required for HSV entry and infection (Yoon et al, J. Virol. 77:9221 (2003), Connolly et al, J. Virol. 79:1282-1295 (2005), Campadelli-Fiume et al, Rev. Med. Virol. 17: 313-326 (2007)). In the RV144 Thai vaccine trial where this A244 gp120 was used as an immunogen, the subjects responded to the gD protein in both the MN gp120 and the A244 gp120 with both IgA (FIG. 60) and IgG (FIG. 61) gD antibodies. FIG. 62 shows that there are two potential sites of interest in the gD peptide that may mimic the alpha 4 beta 7 binding site of gp120 LPV and LDQ. Thus this raises three possibilities:

1. Motif for gp120 binding to a4b7 is LDV and LDI
   HSV gD LPV and LDQ

This raises the question whether antibodies to gD can block binding of HIV gp120 to a4b7.

2. LDQ of HSV-gD is a receptor binding site for host cellular receptor heparan sulfate (Yoon et al, J. Virol. 77:9221 (2003)).

This raises the question whether antibodies to gD can block binding HIV Env to heparan sulfate.

3. The LDQ is also the receptor binding site for the second HSV receptor HVEM. The anti-HSV antibody response to LDQ could be protective against HSV (Yoon et al, J. Virol. 77:9221 (2003)).

Therefore, an anti-gD response could be protective for HIV by reducing active infection.

Lack of binding to most monomeric gp120/gp140 envelopes indicates that CH01-CH05 bind to a conformation-sensitive, quaternary antibody, preferentially expressed on trimeric envelopes. Similar findings have been reported for PG9 and PG16 antibodies (Walker et al, Science 326(5950): 285-9 (2009)). Conversely, the strong binding to the A244gD$^+$ gp120 envelopes strongly suggested that the co-expression of the HSV-1 glycoprotein D restored the functional epitope.

To investigate the role of HSV-1 glycoprotein D in enhancing the binding of the CH01-CH05 antibodies and to detect binding of the RUAs to envelopes at levels that can be below the threshold of detection of standard ELISAs but still physiologically relevant, the constant of dissociation ($k_d$) of the CH01-CH05 antibodies and RUAs to A244gD$^+$ and A244gD$^-$ gp120 envelopes was measured using surface plasmon resonance (Table 7). A244gD$^+$ consistently showed a $k_d$ at least an order of magnitude lower than A244gD$^-$ but, even more importantly, all the RUAs bound to A244gD$^+$ gp120 with $k_d$'s ranging from 790 nM to 26.7 nM. The surface plasmon resonance patterns for these data are shown in FIGS. 63-66. Also seen in FIG. 66 is that the transmitted founder virus 6240 bound with sub-nanomolar Kd to PG9. Taken together these data demonstrate that the A244 gD+ envelope as well as the 6240 transmitted founder envelope were in a similar conformation as the gp120 found in the native Env trimer, and thus should be in the correct confirmations for use as immunogens.

TABLE 7

Constant of dissociation of the CH01-CH05 monoclonal antibodies and RUAs detected by surface plasmon resonance

| | | | Constant of dissociation $K_d$ (nM) | | | | | | | | | | |
|---|---|---|---|---|---|---|---|---|---|---|---|---|---|
| | Env | Clade | CH01 | CH02 | CH03 | CH04 | CH05 | PG9 | PG16 | CH01-RUA1 | CH02-RUA1 | CH02-RUA2 | CH03-RUA1 |
| A244 gD$^+$ | gp120 | E | 8.8 | 450 | 15.6 | 25.5 | 26.1 | 4.8 | 450 | 26.7 | 790 | 410 | 83.5 |
| A244 gD$^-$ | gp120 | E | 340 | N/A | 728 | 410 | 340 | N/A | N/A | 2460 | N/A | N/A | 270 |
| 63521 TC21 | gp140 | B (T/F) | N/A | N/A | N/A | N/A | N/A | 0.75 | 160 | N/A | N/A | N/A | N/A |
| 624008 TA5 | gp140 | B (T/F) | 300 | N/A | 1060 | 360 | 1450 | 210 | 110 | N/A | N/A | N/A | N/A |

Autoreactivity and Polyreactivity Profile of CH01-CH05 Broadly Neutralizing Antibodies.

Figure 67:
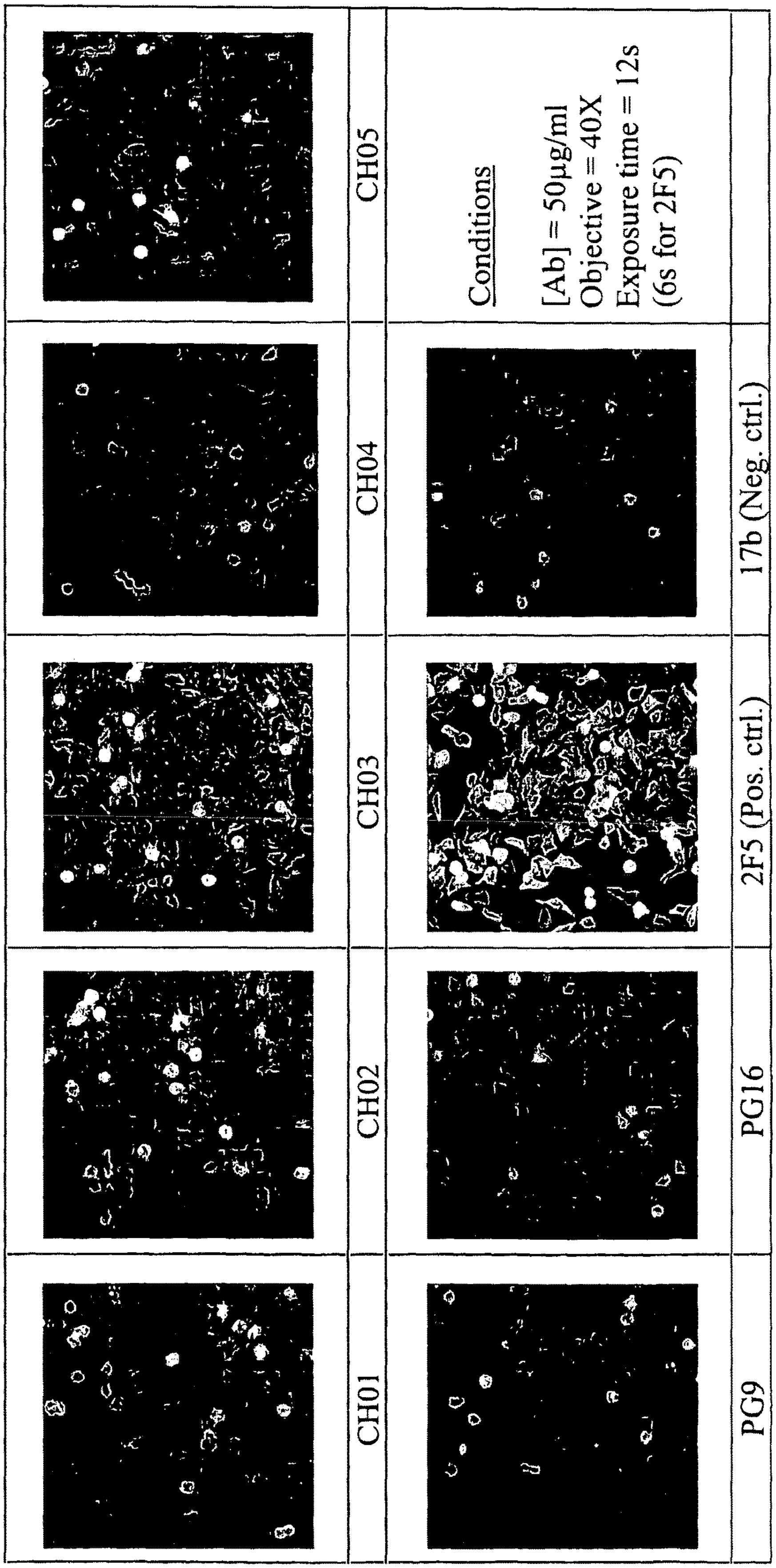
FIG. 67. HEP-2 binding

Table 8 shows that CH03 is autoreactive with RNP, histone and centromere B autoantigens. Presence of antibodies binding to centromere in CH03 was also found using indirect fluorescent antibody staining on HEp-2 cells (FIG. 67). Table 12 reports the binding (measured by Luminex assay) of CH01-CH05 to 4 non-HIV antigens. The data show that CH01-CH-3 are strongly polyreactive. CH04 and CH05 polyreactivity is still detectable even through at a much lower level. Conversely, PG9 and PG16 showed no polyreactive abilities. These data point out a potentially relevant difference on the biology of the respective developments between the CH01-CH05 and PG9 and PG16 antibodies.

TABLE 8

| Autoreactivity (Athena) Criteria for positive: >50 | | | | | | | | | | |
|---|---|---|---|---|---|---|---|---|---|---|
| | Conc. ug/ml | SSA | SSB | Sm | RNP | Scl 70 | Jo 1 | dsDNA | Cent B | Histone |
| Neg Control | — | — | — | — | — | — | — | — | — | — |
| Pos Control 1 | — | | | | | | | | 397 | |
| Pos Control 2 | — | 631 | 699 | | | | | 1073 | | 441 |
| Pos Control 3 | — | | | 544 | 458 | 402 | 575 | | | |
| 4E10 | 50 | 306 | 254 | 9 | 20 | 3 | 156 | 19 | 31 | 333 |
| | 25 | 247 | 206 | 7 | 15 | 4 | 138 | 8 | 19 | 274 |
| | 12.5 | 169 | 124 | 5 | 9 | 3 | 87 | 6 | 13 | 160 |
| | 6.25 | 115 | 93 | 4 | 6 | 2 | 65 | 3 | 9 | 113 |
| CH01 | 50 | 8 | 5.5 | 4 | 8 | 4 | 3.5 | 32 | 22 | 25 |
| | 25 | 6.5 | 5.5 | 4 | 5.5 | 3 | 2.5 | 17 | 14 | 17.5 |
| | 12.5 | 5 | 5 | 3 | 4.5 | 2 | 2 | 9.5 | 10 | 13.5 |
| | 6.25 | 5.5 | 5.5 | 2.5 | 4 | 1.5 | 2 | 6.5 | 7 | 10 |
| CH02 | 50 | 5.5 | 4.5 | 3.5 | 12.5 | 2.5 | 2 | 16 | 12.5 | 15.5 |
| | 25 | 6 | 4.5 | 3 | 9 | 2 | 1.5 | 10 | 9.5 | 11.5 |
| | 12.5 | 5 | 3.5 | 2.5 | 6 | 1.5 | 1 | 5 | 7 | 8.5 |
| | 6.25 | 5 | 5 | 2.5 | 5 | 2 | 1.5 | 3 | 6 | 7 |
| CH03 | 50 | 9 | 7 | 24 | 132 | 12 | 5 | 0 | 98 | 844 |
| | 25 | 6 | 4 | 10 | 70 | 7 | 4 | 38 | 34 | 386 |
| | 12.5 | 6 | 6 | 9 | 74 | 8 | 4 | 0 | 30 | 359 |
| | 6.25 | 5 | 5 | 7 | 51 | 4 | 3 | 0 | 19 | 231 |
| CH05 | 50 | 27 | 13 | 2.5 | 9 | 2 | 9 | 5.5 | 14.5 | 21.5 |
| | 25 | 12.5 | 5.5 | 3 | 4.5 | 1.5 | 3.5 | 5.5 | 9 | 14 |
| | 12.5 | 8 | 5 | 3.5 | 3.5 | 1.5 | 2.5 | 1.5 | 6.5 | 11 |
| | 6.25 | 7 | 6 | 2.5 | 3 | 1.5 | 2.5 | 2 | 6 | 10 |
| CH04 | 50 | 19 | 11 | 3 | 9 | 3 | 5 | 7 | 18 | 26 |
| | 25 | 11 | 8 | 2 | 6 | 2 | 3 | 6 | 13 | 16 |
| | 12.5 | 7 | 4.5 | 2.5 | 4 | 2 | 2.5 | 2.5 | 8 | 11 |
| | 6.25 | 6 | 6 | 3 | 3 | 1.5 | 2 | 5 | 6.5 | 9.5 |
| PG9 | 50 | 5 | 5 | 2 | 3 | 2 | 1 | 2 | 5 | 7 |
| | 25 | 5 | 6 | 3 | 2 | 1 | 2 | 1 | 5 | 9 |
| | 12.5 | 5 | 4 | 3 | 2 | 2 | 2 | 3 | 4 | 6 |
| | 6.25 | 4 | 4 | 2 | 3 | 2 | 2 | 3 | 4 | 5 |
| PG16 | 50 | 4 | 2 | 0 | 2 | 1 | 0 | 1 | 3 | 2 |
| | 25 | — | — | — | — | — | — | — | — | — |
| | 12.5 | 4 | 4 | 2 | 3 | 1 | 1 | 5 | 4 | 8 |
| | 6.25 | 5 | 5 | 2 | 2 | 2 | 2 | 6 | 5 | 8 |

TABLE 12

| Evaluation of the polyreactivity of the CH01-CH05 antibodies measured by Luminex assay. | | | | |
|---|---|---|---|---|
| | HCV E2 | Anaerobic Gut Flora | Aerobic Gut Flora | Influenza HA (Wisconsin) |
| CH01 | 17.5 | 196.7 | 19.2 | 0 |
| CH02 | 333.3 | 258.8 | 28.5 | 0.3 |
| CH03 | 2909.5 | 286.3 | 97.5 | 1 |
| CH04 | 0.5 | 17 | 3.5 | 2.5 |
| CH05 | 1.3 | 23.5 | 9 | 5.5 |
| PG9 | 0 | 0 | 0 | 0 |
| PG16 | 0 | 0 | 0 | 0 |
| 4E10 | 89.2 | 83 | 96.2 | 0 |
| Synegis | 0.5 | 2.5 | 1.5 | 1 |

Results are expressed as background substracted RFUs using an antibody concentration of 50 μg/ml Characterization of the Epitope Targeted by the CH01-CH05 Broadly Neutralizing Antibodies. PG16-Like Phenotype It was determined that the CH01-CH05 antibodies share unique characteristics with the quaternary broadly neutralizing PG9 and PG16 antibodies recently described by Walker et al (PLoS Pathog. 6(8).pii:e1001028 (Aug. 5, 2010)). In particular, the CH01-CH05 bNabs were characterized as "PG-like" antibodies based on the following four criteria: (1) the point mutation of the asparagine into a lysine at position 160 (N160K) of the gp120 protein abrogates the neutralization of an otherwise neutralization-sensitive isolate, (2) neutralization of otherwise neutralization-sensitive isolates is abrogated when the virus is partially deglycosilated due to its production in cells treated with the mannosidase 1-inhibitor kifunensine, (3) the epitopes are preferentially displayed in the context of envelope trimers but are not found on monomeric gp120 or gp140 envelopes, and (4) threading shows a high similarity with PG9 or PG16 bNAbs. As a representative of the CH01-CH05 clonal family of bNabs, CH01 was tested to determine if it met all the four criteria.

Table 9 shows the effect of the N160K point mutation on the CH01 neutralizing activity (IC50 and IC80) compared to that of PG9 and PG16 against a panel of wild-type and mutated isolates: clade A Q23.17 and clade B JR-CSF JRFL and 7165.18 isolates. CH01, PG9 and PG16 all strongly neutralize the wild-type Q23.17 (IC50s=0.014, 0.002 and 0.001 μg/ml, respectively) and JR-CSF (IC50s=0.07, 0.003 and 0.003 μg/ml, respectively) isolates. The introduction of the N160K mutation in the gp120 protein of Q23.17 and JR-CSF equally leads to complete abrogation of neutralizing activity by the three antibodies (IC50>50 μg/ml). CH01, PG9 and PG16 also share the same neutralization pattern against JRFL and its mutants. Neither of them neutralizes wild-type JRFL. A single mutation at position 168 (E168K)

reconstitutes a properly conformed epitope and results in potent neutralization (IC50s=0.044, 0.008 and 0.003 μg/ml for CH01, PG9 and PG16, respectively) but the subsequent introduction of the N160K mutation reverts the effect of the E168K mutation, making the JRFL/E168K/N160K isolate neutralization resistant (IC50>50 μg/ml) to all the three bNabs. Finally, 7165.18 is neutralized by CH01 (IC50=5.82 μg/ml) and PG16 (IC50=11.8 μg/ml) but not PG9 (IC50>50 μg/ml) and, again, the N160K mutation abrogates neutralization by both CH01 and PG16. Taken together, these data indicate that the neutralization activity of CH01 is similarly affected by the signature N160K mutation in gp120 as PG9 and PG16.

Broadly neutralizing antibodies with a limited breadth of binding to monomeric gp120 and gp140 envelopes described above is typical of quaternary antibodies, whose epitope is correctly exposed in the context of the trimeric envelope.

Figure 69:
Figure 69:
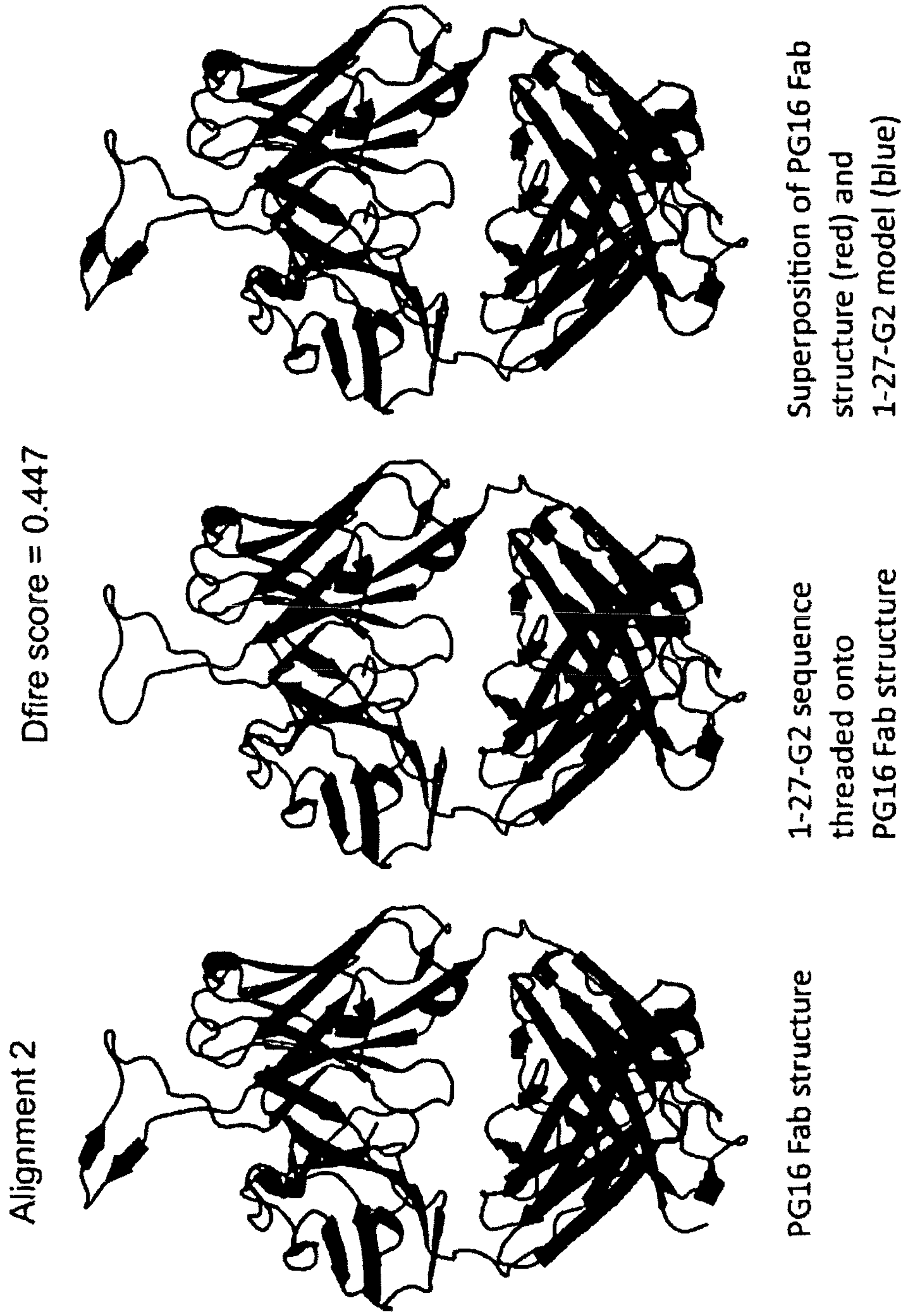
Figure 70:
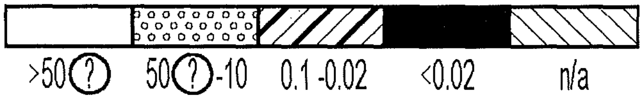
FIG. 70. The preferential neutralization of tier 2 viruses over tier 1 viruses is important in that previous work demonstrated that broad neutralization of easy-to-neutralize tier 1 isolates does not translate into breadth against more difficult-to-neutralize tier 2 isolates and, therefore, those kinds of antibodies could be of limited help in preventing or controlling HIV-1 infection.
Figure 71:
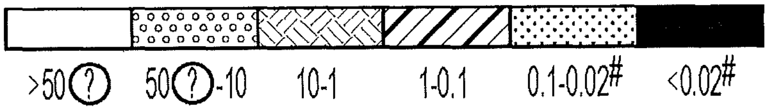
FIG. 71. Neutralization profile of the inferred putative reverted unmutated ancestors.

Superimposition of CH01 onto threads of 7 distinct monoclonal antibodies showed that the structure of PG 6 was the best fit to predict the 3D conformation of HC01 (Table 10). FIG. 69 shows the superimposition of CH01 onto the PG16 thread. PG9 and PG 16 are characterized by a unique shape of the HCDR3 region that protrudes from the tip of the antibody structure in a "hammer-like" shape (Pancera et al, J. Virol. 84(16):8098-110 (2010)). No other antibody had been previously described with such characteristics. Notably, CH01 structure is very similar and the "head" of the "hammer" superimposes well with that of PG16 (FIG. 69). Being the HCDR3 shorter than PG9 and PG16, the sequence differs in some parts and this might be the structural explanation of the different breadth of reactivities between the CH01-CH05 antibodies and PG9/PG16.

TABLE 9

Effect of point mutations on sensitive glycosilation sites for PG9/PG16-like antibodies

| | | IC50 ug/ml | | | IC80 ug/ml | | |
|---|---|---|---|---|---|---|---|
| Clade | Virus | PG9 | PG16 | 27G2 | PG9 | PG16 | 27G2 |
| A | Q23.17 | 0.002 | 0.001 | 0.014 | 0.005 | 0.003 | 0.035 |
| | Q23.17.N160K | >50 | >50 | >50 | >50 | >50 | >50 |
| B | JRCSF | 0.003 | 0.003 | 0.070 | 0.008 | 0.012 | >50* |
| | JRCSF.N160K | >50 | >50 | >50 | >50 | >50 | >50 |
| | JRFL | >50 | >50 | >50 | >50 | >50 | >50 |
| | JRFL.E168K | 0.008 | 0.003 | 0.044 | 0.055 | 0.015 | 0.382 |
| | JRFL.N160K.E168K | >50 | >50 | >50 | >50 | >50 | >50 |
| | 7165.18 | >50 | 11.8** | 5.82** | >50 | >50** | >50** |
| | 7165.18.N160K | >50 | >50 | >50 | >50 | >50 | >50 |

*curve reached plateau at 78%.

**curve reached plateau at 50-55%.

Figure 68:
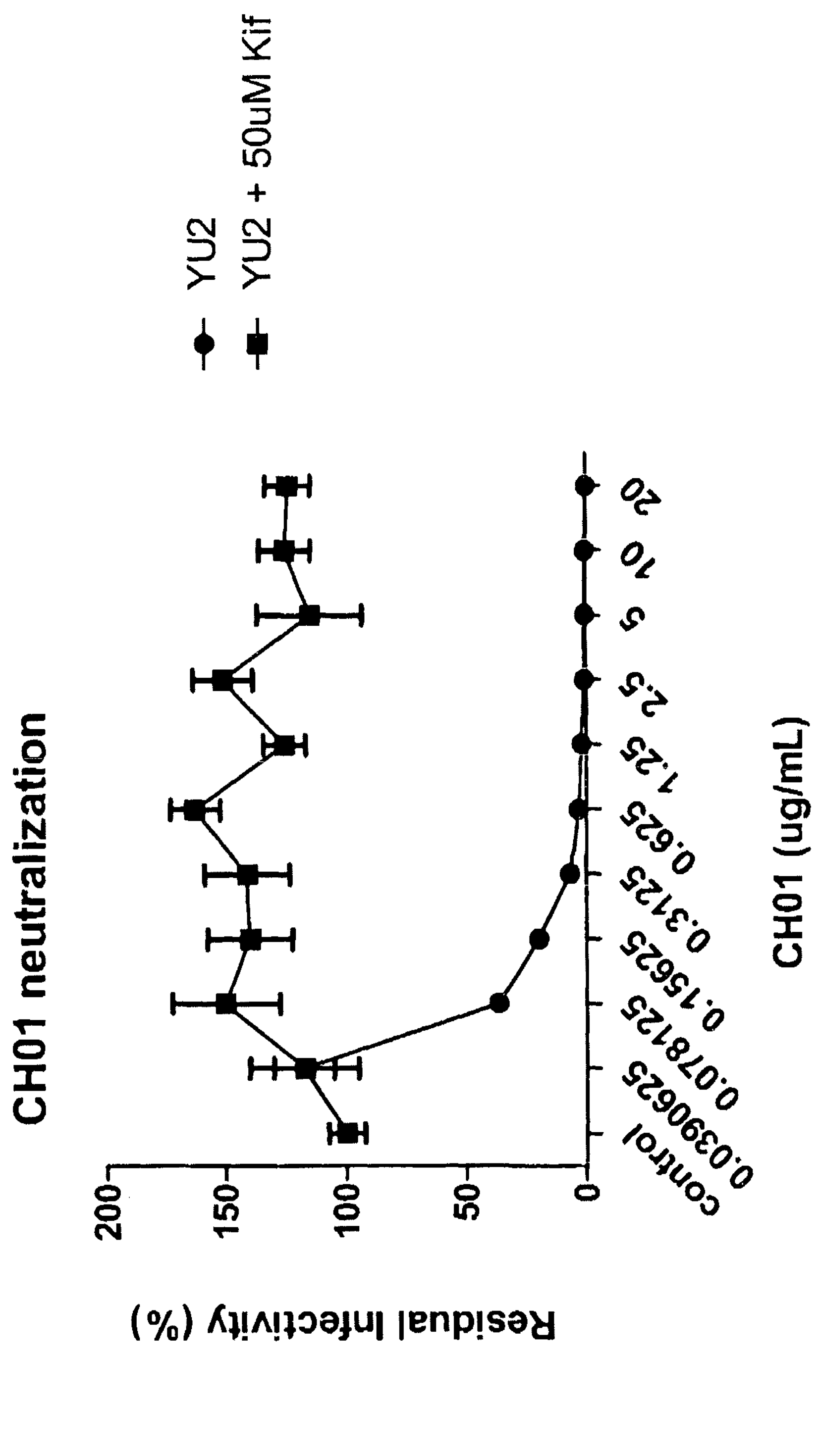
FIG. 68. Effect of kifunensine treatment on the ability of CH01 to mediate neutralization FIG. 69. Superimposition of the sequence of CH01 (here called 1-27-G2) with the PG16 Fab.

Another characteristic of PG9 and PG16 is that otherwise neutralization-sensitive viruses become resistant when 293T cells used to produce the virus are treated with kifunensine. FIG. 68 shows that CH01 neutralization of YU2 produced in 293T cells is seemingly negated by treatment with 50 μM of kifunensine.

TABLE 10

Threading of 9 antibody sequences onto 7 antibody structures with the resulting models evaluated by normalized DFIRE score.[c]

| | Sequences | | | | | | | | |
|---|---|---|---|---|---|---|---|---|---|
| Structures | PG16[a] | 47e[a] | 412d[a] | 17b[a] | 48d[a] | x5[a] | e51[a] | 27G2[a] | PG9[a] |
| PG16[b] | 1.0 | | | 2.0 | | 2.2 | | 1.7 | 1.0 |
| 47e[b] | | 1.0 | | 2.0 | 1.0 | | 1.4 | | 3.8 |
| 412d[b] | 3.6 | | 1.0 | | 1.3 | 2.8 | 2.4 | 2.5 | 3.5 |
| 17b[b] | 5.0 | 2.0 | | 1.0 | 2.5 | 3.0 | 3.3 | 2.6 | 3.2 |
| 48d[b] | 4.4 | 2.9 | 4.0 | 2.7 | 1.0 | 3.0 | 4.5 | 4.6 | 3.2 |
| x5[b] | 4.1 | 2.7 | | 2.5 | | 1.0 | 3.5 | | 4.0 |
| e51[b] | 3.1 | | 2.0 | 2.1 | 1.4 | 2.1 | 1.0 | 2.3 | 4.0 |

[a]Antibody sequences to be threaded, including PG16, 47e, 412d, 17b, 48d, x5, e51, 27G2 and PG9.

[b]Antibody structures used as template, including PG16, 47e, 412d, 17b, 48d, x5 and e51.

[c]After threading the variable region sequences of both heavy chain and light chain, the resulting model was evaluated using a normalized statistical potential (DFIRE). The smaller the score is, the better the sequence fits the template structure.

Values are normalized; the Dfire score obtained after threading the sequences onto the structures are divided by the Dfire score of sequence threaded onto the matched structure (i.e PG16 sequence onto PG16 structure).

1. to 1.4 values are colored in green as they will probably be correct.

1.5 to 1.9 values are colored in orange 2.0 and above are colored in red as they are unlikely to be correct.

An interesting feature of quarternary antibodies is that they may be tyrosine sulfated in the same way as the CD4i antibodies (Huang et al, PNAS 101(9):2706-2711 (2004) Epub 2004 Feb. 23 and Pejchal et al, PNAS 107(25): 11483-8 (2010)). Sequence analysis of CH01 performed with "sulfinator", a tyrosine sulfation prediction program, predicted one tyrosine that is likely to be sulfated (ARGT-DYTIDDAGIHYQGSGTFWYFDL) (SEQ ID NO: 8) (Table 11). (Note that CH01 is called 1-27-G2.). Table 11 discloses SEQ ID NOS 81-85, 85-87, 86, 88-94, 94-95, 95-96 and 96, respectively, in order of appearance.

TABLE 11

Tyrosine sulfation prediction for 1-27-G2, PG9, PG16 and CD4i antibodies.

| | Heavy variable sequence | | | | CDR H3 sequence |
|---|---|---|---|---|---|
| | Sulfinator[a] | | Sulfosite[b] | | Sulfinator[a] |
| Antibody | Sequence | E-value[c] | Sequence | SVM[d] | Sequence |
| 1-27-G2 | none | | RGTDYTIDD | 0.86 | TDYTID |
| PG9 | DYRNGYNYYDF | 45 | AFIKYDGSE | 0.5 | none |
| | | | YYDFYDGYY | 0.5 | |
| PG16 | none | | none | | none |
| 47e | none | | EDGDYLSDP | 0.85 | DGDYLSDPFY |
| | | | | | DGDYLSDPFYYNHGMDV |
| 412d | PYPNDYNDYAPE | 24 | | | NDYNDYAPEE |
| | NDYNDYAP | 14 | DYNDYAPEE | 0.59 | DYAPEEG |
| 17b | none | | none | | none |
| 48d | none | | none | | none |
| X5 | none | | none | | none |
| 23e | none | | none | | none |
| e51 | none | | AAGDYADYD | 0.69 | none |
| | | | DYADYDGGY | 0.95 | |
| | | | YDGGYYYDM | 0.54 | |

| | CDR H3 sequence | | | |
|---|---|---|---|---|
| | Sulfinator[a] | Sulfosite[b] | | |
| Antibody | E-value[c] | Sequence | SVM[d] | Experimental Data |
| 1-27-G2 | 33 | none | | |
| PG9 | | YYDFYDGYY | 0.5 | 2 Tyr sulfated<br>10-fold down neutralization<br>Pejchal et al, PNAS, 2010 |
| PG16 | | none | | 1 Tyr sulfated<br>10-fold down neutralization<br>Pejchal et al, PNAS, 2010 |
| 47e | 7.8 | EDGDYLSDP | 0.85 | 1 Tyr sulfated |
| | 38 | | | Role in binding to gp120<br>Huang CC et al, PNAS, 2004 |
| 412d | 4.2 | | | 2 Tyr sulfated |
| | 40 | same | | Role in binding to gp120 |
| 17b | | none | | Huang CC et al, PNAS, 2004 |
| 48d | | none | | Choe, H et al, Cell, 2003 |
| X5 | | none | | Sulfated but no impact on binding<br>Huang CC et al, PNAS, 2004 |
| 23e | | none | | |
| e51 | | AAGDYADYD | 0.69 | 3 Tyr sulfated |
| | | DYADYDGGY | 0.95 | Loss in binding |
| | | YDGGYYYDM | 0.54 | Huang CC et al, PNAS, 2004<br>Choe, H et al, Cell, 2003 |

[a]Sulfinator: http://ca.expasy.org/1ools/sulfinator/
[b]Sulfosite: http://sulfosite.mbc.nctu.edu.tw/
[c]statistical value of the match (smaller number are best)
[d]SVM: support vector machine Taken together these data strongly support the notion that CH01-CH05 bNabs are PG-like antibodies that recognize a quaternary epitope involving the V2 region of gp120.

In summary, the data presented above demonstrate: (1) a strategy has been developed that allows the rapid identification and isolation of natural antibodies without the need of generating phage display libraries; (2) a family of five clonally related broadly neutralizing antibodies has been described and their development tracked; (3) preliminary evidence of peripheral receptor editing in humans has been provided; (4) novel members of broadly neutralizing antibodies of the PG-like family have been described that are not genetically related to the previously described PG9 and PG16 broadly neutralizing antibodies; and (5) a method has been developed to increase accuracy of predicting putative reverted unmutated ancestors when more than a single monoclonal antibody is available.

For immunogen design for induction of quaternary V2, V3 antibodies, it is demonstrated in Example 5 that the gp120 Env A244 with a herpes simplex gD sequence can both bind well to the V2, V3 conformational determinant broad neutralizing Abs PG9, PG16, CH01-CH05, and also bind to reverted unmutated ancestors of CH01, 02 and 03 antibodies. Moreover, the 6240 transmitted founder Env can bind well to PG9, and PG16 mabs. Thus, a potent immunization regimen for induction of V2, V3 broad neutralizing antibodies is to prime several times (for example, from 1-3) with the A244 gp120 envelope with the gD sequence at the N-terminus and then boost, for example, with the 6240 transmitted founder gp140 (for example, from 1-3 times) either systemically (e.g., IM or subcutaneously) or mucosally (e.g., intranasally, sublingually, intravaginally or rectally). Given the immunogenicity of the HSV receptor binding region in the A244 gp120, this construct containing the gD peptide can also be used for a HSV vaccine construct. Similarly, the gD peptide inserted at the N-terminus of any HIV-1 envelope in a similar manner can be used for inducing protective antibodies to herpes simplex virus types 1 and 2.

All documents and other information sources cited above are hereby incorporated in their entirety by reference.

What is claimed is:

1. A recombinant protein comprising all consecutive amino acids immediately after the signal peptide MRVRGIWKNWPQWLIWSILGFWIGNMEGS in the amino acid sequence of SEQ ID NO: 12.

2. A recombinant protein comprising all consecutive amino acids immediately after the signal peptide MRVRGIWKNWPQWLIWSILGFWIGNMEGS in the amino acid sequence of the gp120 envelope from SEQ ID NO: 12.

3. A recombinant protein comprising all consecutive amino acids immediately after the signal peptide MRVRGIWKNWPQWLIWSILGFWIGNMEGS in the amino acid sequence of the gp140CF envelope from SEQ ID NO: 12.

4. A recombinant protein comprising all consecutive amino acids immediately after the signal peptide MRVRGIWKNWPQWLIWSILGFWIGNMEGS in the amino acid sequence of the gp140CFI envelope from SEQ ID NO: 12.

5. An immunogenic composition comprising the protein of claim 1.

6. The immunogenic composition of claim 5, further comprising an adjuvant.

7. The immunogenic composition of claim 6, wherein the adjuvant is a squalene based adjuvant, a TLR agonist, or alum.

8. The immunogenic composition of claim 7, wherein the adjuvant is an oligonucleotide (oCpGs) or R848.

9. An immunogenic composition comprising the protein of claim 2.

10. The immunogenic composition of claim 9, further comprising an adjuvant.

11. The immunogenic composition of claim 10, wherein the adjuvant is a squalene based adjuvant, a TLR agonist, or alum.

12. The immunogenic composition of claim 11, wherein the adjuvant is an oligonucleotide (oCpGs) or R848.

13. An immunogenic composition comprising the protein of claim 3.

14. The immunogenic composition of claim 13, further comprising an adjuvant.

15. The immunogenic composition of claim 14, wherein the adjuvant is a squalene based adjuvant, a TLR agonist, or alum.

16. The immunogenic composition of claim 15, wherein the adjuvant is an oligonucleotide (oCpGs) or R848.

17. An immunogenic composition comprising the protein of claim 4.

18. The immunogenic composition of claim 17, further comprising an adjuvant.

19. The immunogenic composition of claim 18, wherein the adjuvant is a squalene based adjuvant, a TLR agonist, or alum.

20. The immunogenic composition of claim 19, wherein the adjuvant is an oligonucleotide (oCpGs) or R848.

* * * * *